United States Patent
Baasov et al.

(10) Patent No.: US 11,613,551 B2
(45) Date of Patent: *Mar. 28, 2023

(54) AMINOGLYCOSIDE DERIVATIVES AND USES THEREOF IN TREATING GENETIC DISORDERS

(71) Applicant: ELOXX PHARMACEUTICALS LTD., Rehovot (IL)

(72) Inventors: Timor Baasov, Haifa (IL); Shmuel Tuvia, Natania (IL)

(73) Assignee: ELOXX PHARMACEUTICALS LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/126,007

(22) Filed: Dec. 17, 2020

(65) Prior Publication Data

US 2021/0300958 A1 Sep. 30, 2021

Related U.S. Application Data

(63) Continuation of application No. 15/756,691, filed as application No. PCT/IL2016/050968 on Sep. 2, 2016, now Pat. No. 10,899,785.

(60) Provisional application No. 62/213,143, filed on Sep. 2, 2015, provisional application No. 62/213,187, filed on Sep. 2, 2015, provisional application No. 62/274,915, filed on Jan. 5, 2016.

(51) Int. Cl.
C07H 15/23 (2006.01)
C07H 15/224 (2006.01)

(52) U.S. Cl.
CPC .......... *C07H 15/224* (2013.01); *C07H 15/23* (2013.01)

(58) Field of Classification Search
None
See application file for complete search history.

(56) References Cited

U.S. PATENT DOCUMENTS

| | | | |
|---|---|---|---|
| 3,978,214 A | 8/1976 | Mallams et al. | |
| 9,821,001 B2 | 11/2017 | Baasov et al. | |
| 10,159,689 B2 | 12/2018 | Baasov et al. | |
| 10,899,785 B2 * | 1/2021 | Baasov | A61P 27/02 |
| 2009/0093418 A1 | 4/2009 | Baasov et al. | |

FOREIGN PATENT DOCUMENTS

| | | |
|---|---|---|
| CN | 104540521 A | 4/2015 |
| JP | 2009-532461 A | 9/2009 |
| JP | 2013-542981 A | 11/2013 |
| JP | 6862428 B2 | 4/2021 |
| WO | 2007113841 A2 | 10/2007 |
| WO | 2011044538 A1 | 4/2011 |
| WO | 2012066546 A1 | 5/2012 |

OTHER PUBLICATIONS

CNIPA, Decision of Rejection for Chinese Patent Application No. 201680062161.0. dated Oct. 9, 2021. 8 pages with English translation.
USPTO, Notice of Allowance for U.S. Appl. No. 15/756,665. dated Oct. 14, 2021.
CNIPA, Office Action for Chinese Patent Application No. 201680062161.0. dated Aug. 3, 2020. 9 pages with English translation.
EPO, Examination Report for European Patent Application No. 16840986. dated Sep. 10, 2020. 4 pages.
IPA, First Examination Report for Australian Patent Application No. 2016314379. dated Mar. 25, 2020. 4 pages.
IPA, Second Examination Report for Australian Patent Application No. 2016314379. dated Jul. 15, 2020. 8 pages.
IPI, First Examination Report for Indian Patent Application No. 201827011427. dated Feb. 25, 2020. 7 pages.
IPO, Office Action for Israeli Patent Application No. 257820. dated Feb. 23, 2020. 9 pages with English translation.
JPO, Notice of Reasons for Rejection for Japanese Patent Application No. 2018-511473. dated May 26, 2020. 15 pages with English translation.
JPO, Final Notice of Reasons for Rejection for Japanese Patent Application No. 2018-511473. dated Sep. 18, 2020. 5 pages with English translation.
USPTO, Final Office Action for U.S. Appl. No. 15/756,591. dated Nov. 25, 2019. 12 pages.
USPTO, Advisory Action for U.S. Appl. No. 15/756,591. dated Apr. 3, 2020. 3 pages.
USPTO, Notice of Allowance for U.S. Appl. No. 15/756,591. dated Apr. 30, 2020. 7 pages.
USPTO, Notice of Allowance for U.S. Appl. No. 15/756,591. dated Jul. 30, 2020. 10 pages.
USPTO, Non-Final Office Action for U.S. Appl. No. 15/756,665. dated Jan. 27, 2020. 12 pages.
USPTO, Final Office Action for U.S. Appl. No. 15/756,665. dated Aug. 6, 2020. 9 pages.
Daniels, P. J. L., Semisynthetic Aminoglycoside Antibacterials. Part 11. Solution Conformations of Semisynthetic and Naturally Occurring Aminoglycoside Antibiotics, Journal of the Chemical Society, Perkins Transactions 1: Organic and Bio-Organic Chemistry, 1981, vol. 8, p. 2209-2227.
Davies, D. H., et al, "Semisynthetic aminoglycoside antibacterials. 6. Synthesis of sisomicin, antibiotic G-52, and novel 6'-substituted analogs of sisomicin from aminoglycoside 66-40C", Journal of medicinal chemistry,(Feb. 1, 1978), pp. 189-193.
Hanessian, S., Hybrid Aminoglycoside Antibiotics via Tsuji Palladium-Catalyzed Allylic Deoxygeneration, Org. Lett., 2011, vol. 13, No. 24, 6476-6479.

(Continued)

*Primary Examiner* — Traviss C McIntosh, III
(74) *Attorney, Agent, or Firm* — Perkins Coie LLP

(57) ABSTRACT

Novel aminoglycosides, represented by Formulae Ia and Ib, as defined in the instant specification, designed to exhibit stop codon mutation readthrough activity, are provided. Also provided are pharmaceutical compositions containing the same, and uses thereof in the treatment of genetic diseases and disorders, such as diseases and disorders associated with stop codon mutations.

11 Claims, 12 Drawing Sheets

Specification includes a Sequence Listing.

(56) References Cited

OTHER PUBLICATIONS

O'Connor, S., et al., Apramycin, a Unique Aminocyclitol Antibiotic, Journal of Organic Chemistry, 1976, vol. 41, No. 12, p. 2087-2092.
Registry [online], Dec. 9, 2011, [Searched on Apr. 28, 2020], Retrieved from: STN, CAS Registration No. 1350556-52-3.
Registry [online], Nov. 16, 1984, [Searched on Apr. 28, 2020], Retrieved from: STN, CAS Registration No. 79504-04-4.
Registry [online], Dec. 9, 2011, [Searched on Apr. 28, 2020], Retrieved from: STN, CAS Registration No. 1350556-51-2.
CNIPA, Second Office Action for Chinese Patent Application No. 201680062161.0. dated Mar. 1, 2021. 9 pages with English translation.
EPO, Examination Report for European Patent Application No. 16840987.8. dated Dec. 17, 2020. 4 pages.
EPO, Examination Report for European Patent Application No. 16840988.6. dated Jan. 21, 2021. 4 pages.
EPO, Examination Report for European Patent Application No. 16840988.6. dated May 17, 2021. 4 pages.
IPO, Office Action for Israeli Patent Application No. 257820. dated Apr. 19, 2021. 7 pages with English translation.
JPO, Notice of Decision to Grant a Patent for Japanese Patent Application No. 2018-511473. dated Mar. 2, 2021. 4 pages with English translation.
USPTO, Non-Final Office Action for U.S. Appl. No. 15/756,665. dated Feb. 18, 2021.
EPO, Examination Report for European Application No. 16840986.0. dated Dec. 15, 2021. pages.
INPI, Office Action for Brazilian Application No. BR112018004257-9. dated Nov. 23, 2020. 5 pages with English translation.
IP Australia, Examination Report No. 1 for Australian Application No. 2021203691. Dated Feb. 8, 2022. 2 pages.
IPO, Notice of Allowance for Israeli Application No. 257820. dated May 16, 2022. 4 pages with English machine translation.
JPO, Notice of Reasons for Rejection for Japanese Application No. 2021-060982. dated Apr. 19, 2022. 6 pages with English translation.
USPTO, Non-Final Office Action for U.S. Appl. No. 17/032,954. dated Dec. 8, 2021. 11 pages.
USPTO, Final Office Action for U.S. Appl. No. 17/032,954. dated Jun. 21, 2022. 8 pages.
USPTO, Notice of Allowance for U.S. Appl. No. 15/756,665. dated Feb. 3, 2022. 10 pages.
Nudelman, I. et al. "Repairing faulty genes by aminoglycosides: Development of new derivatives of geneticin (G418) with enhanced suppression of diseases-causing nonsense mutations" Bioorganic & Medicinal Chemistry, 2010, vol. 18, pp. 3735-3746.
CIPO, Examination Report for Canadian Application No. 2996763. dated Oct. 13, 2022. 6 pages.
Duscha et al., Identification and Evaluation of Improved 4=-O-(Alkyl) 4,5-Disubstituted 2-Deoxystreptamines as Next-Generation Aminoglycoside Antibiotics, mBio, Sep./Oct. 2014, vol. 5, Issue 5, e01827-14.
Huth et al., Designer Aminoglycosides Prevent Cochlear Hair Cell Loss and Hearing Loss, The Journal of Clinical Investigation, Feb. 2015, vol. 125, No. 2, pp. 583-592.

* cited by examiner

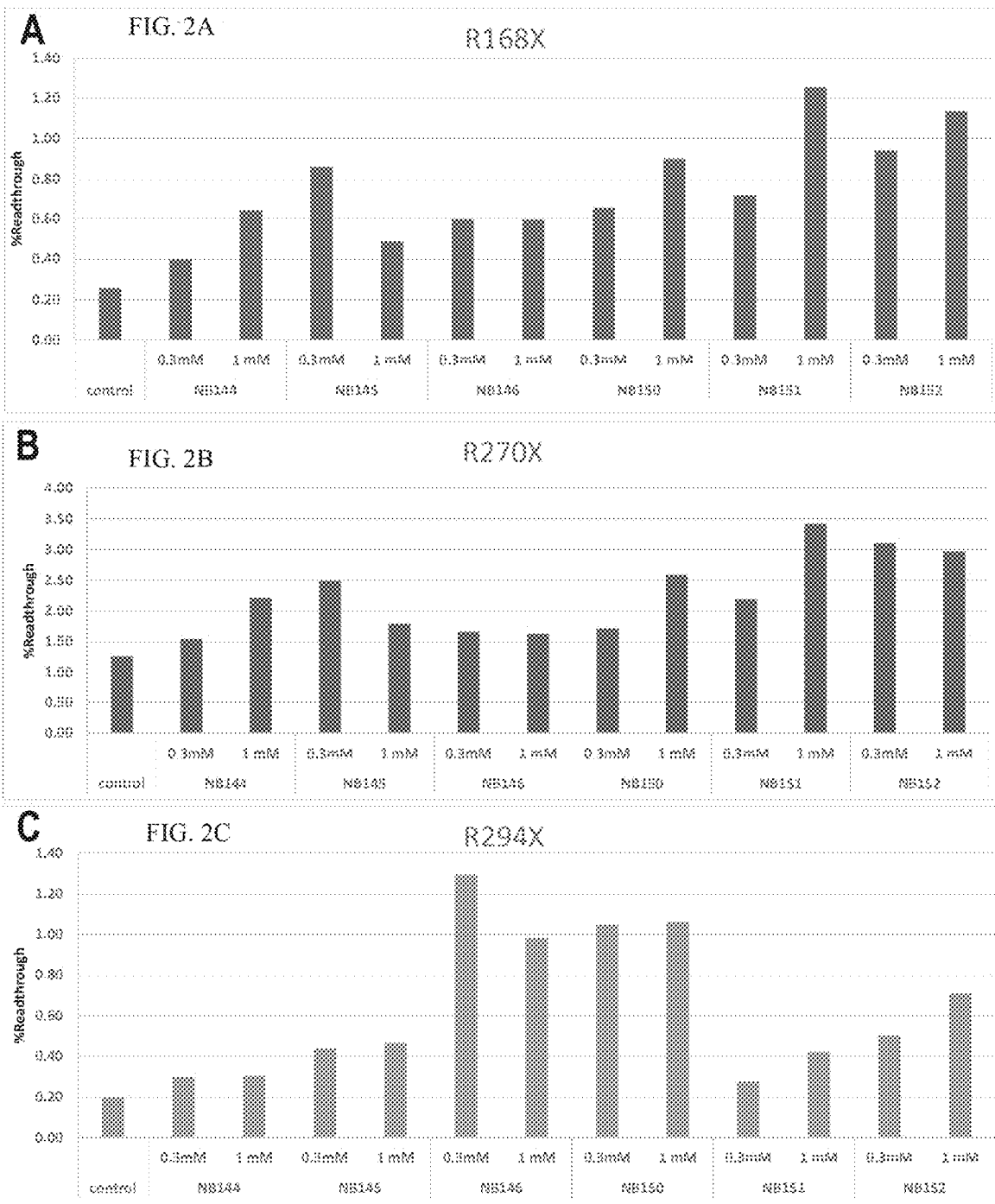

SEQUENCE LISTING

```
<160> NUMBER OF SEQ ID NOS: 8

<210> SEQ ID NO 1
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: n is T or C

<400> SEQUENCE: 1
gatcccagaa gatgtttnga cagttttatc tctggacaga gct          43

<210> SEQ ID NO 2
<211> LENGTH: 33
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: n is A or G

<400> SEQUENCE: 2
ctgtcagaga taaaactgtc naaacatctt ctg                           33

<210> SEQ ID NO 3
<211> LENGTH: 48
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: n is T or C

<400> SEQUENCE: 3
gatccaaaat ctgaatgaga ggngaaccac caccaccacc ctcgagct           48

<210> SEQ ID NO 4
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: n is G or A

<400> SEQUENCE: 4
cgagggtggt ggtggttgtt cncctctcat tcagattttg                    40

<210> SEQ ID NO 5
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: n is T or G

<400> SEQUENCE: 5
tcgaccaata tagttcttng agaaggtgga atcgagct                      38

<210> SEQ ID NO 6
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: n is A or G

<400> SEQUENCE: 6
cgattccacc ttctcnaaga actatattgg                               30

<210> SEQ ID NO 7
```

```
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: n is T or C

<400> SEQUENCE: 7
tcgaccctca gctgggacna gcagctcaac ctcgagct                           38

<210> SEQ ID NO 8
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: n is A or G

<400> SEQUENCE: 8
cgaggttgag ctgctngtcc cagctgagg                                     29
```

AMINOGLYCOSIDE DERIVATIVES AND USES THEREOF IN TREATING GENETIC DISORDERS

This patent document is a continuation of U.S. patent application Ser. No. 15/756,691, filed on Mar. 1, 2018 which is a 371 filing of International Application No. PCT/IL2016/050968, filed on Sep. 2, 2016, which claims the benefits and priority of U.S. Provisional Patent Application No. 62/213,143, filed on Sep. 2, 2015, U.S. Provisional Patent Application No. 62/213,187, filed on Sep. 2, 2015 and U.S. Provisional Patent Application No. 62/274,915, filed on Jan. 5, 2016. The entire contents of the aforementioned patent applications are incorporated by reference as part of the disclosure of this application.

REFERENCE TO SEQUENCE LISTING SUBMITTED VIA EFS-WEB

This application includes an electronically submitted sequence listing in .txt format. The .txt file contains a sequence listing entitled "128570-8004.US08_ST25.txt" created on Mar. 3, 2021 and is 2,566 bytes in size. The sequence listing contained in this .txt file is part of the specification and is hereby incorporated by reference herein in its entirety.

FIELD AND BACKGROUND OF THE INVENTION

The present invention, in some embodiments thereof, relates to aminoglycosides and more particularly, but not exclusively, to novel aminoglycoside derivatives and their use in increasing an expression of a gene having a stop codon mutation and/or in the treatment of genetic disorders.

Many human genetic disorders result from nonsense mutations, where one of the three stop codons (UAA, UAG or UGA) replaces an amino acid-coding codon, leading to premature termination of the translation and eventually to truncated inactive proteins. Currently, hundreds of such nonsense mutations are known, and several were shown to account for certain cases of fatal diseases, including, for example, cystic fibrosis (CF), Duchenne muscular dystrophy (DMD), ataxia-telangiectasia, Hurler syndrome, hemophilia A, hemophilia B, Tay-Sachs, Rett Syndrome, Usher Syndrome, Severe epidermolysis bullosa and more. For many of those diseases there is presently no effective treatment.

Some aminoglycoside compounds have been shown to have therapeutic value in the treatment of several genetic diseases because of their ability to induce ribosomes to read-through stop codon mutations, generating full-length proteins from part of the mRNA molecules.

Aminoglycosides are highly potent, broad-spectrum antibiotics commonly used for the treatment of life-threatening infections. It is accepted that the mechanism of action of aminoglycoside antibiotics, such as paromomycin (see, FIG. 1), involves interaction with the prokaryotic ribosome, and, more specifically, involves binding to the decoding A-site of the 16S ribosomal RNA, which leads to protein translation inhibition and interference with the translational fidelity.

Several achievements in bacterial ribosome structure determination, along with crystal and NMR structures of bacterial A-site oligonucleotide models, have provided useful information for understanding the decoding mechanism in prokaryote cells and understanding how aminoglycosides exert their deleterious misreading of the genetic code. These studies and others have given rise to the hypothesis that the affinity of the A-site for a non-cognate mRNA-tRNA complex is increased upon aminoglycoside binding, preventing the ribosome from efficiently discriminating between non-cognate and cognate complexes.

The enhancement of termination suppression by aminoglycosides in eukaryotes is thought to occur in a similar mechanism to the aminoglycosides' activity in prokaryotes of interfering with translational fidelity during protein synthesis, namely the binding of certain aminoglycosides to the ribosomal A-site probably induce conformational changes that stabilize near-cognate mRNA-tRNA complexes, instead of inserting the release factor. Aminoglycosides have been shown to suppress various stop codons with notably different efficiencies (UGA>UAG>UAA), and the suppression effectiveness has been found to be further dependent upon the identity of the fourth nucleotide immediately downstream from the stop codon (C>U>A≥grams) as well as the local sequence context around the stop codon.

The desired characteristics of an effective read-through drug would be oral administration and little or no effect on bacteria. Antimicrobial activity of read-through drug is undesirable as any unnecessary use of antibiotics, particularly with respect to the gastrointestinal (GI) biota, due to the adverse effects caused by upsetting the GI biota equilibrium and the emergence of resistance. In this respect, in addition to the abovementioned limitations, the majority of clinical aminoglycosides are greatly selective against bacterial ribosomes, and do not exert a significant effect on cytoplasmic ribosomes of human cells.

In an effort to circumvent the abovementioned limitations, the biopharmaceutical industry is seeking new stop codon mutations suppression drugs by screening large chemical libraries for nonsense read-through activity.

The first experiments of aminoglycoside-mediated suppression of cystic fibrosis transmembrane conductance regulator protein (CFTR) stop codon mutations demonstrated that premature stop codon mutations found in the CFTR gene could be suppressed by members of the gentamicin family and Geniticin® (G-418) (see, FIG. 1), as measured by the appearance of full-length, functional CFTR in bronchial epithelial cell lines.

Suppression experiments of intestinal tissues from CFTR−/−transgenic mice mutants carrying a human CFTR-G542X transgene showed that treatment with gentamicin, and to lesser extent tobramycin, have resulted in the appearance of human CFTR protein at the glands of treated mice. Most importantly, clinical studies using double-blind, placebo-controlled, crossover trails have shown that gentamicin can suppress stop codon mutations in affected patients, and that gentamicin treatment improved transmembrane conductance across the nasal mucosa in a group of 19 patients carrying CFTR stop codon mutations. Other genetic disorders for which the therapeutic potential of aminoglycosides was tested in in-vitro systems, cultured cell lines, or animal models include DMD, Hurler syndrome, nephrogenic diabetes insipidus, nephropathic cystinosis, retinitis pigmentosa, and ataxia-telangiectasia.

However, one of the major limitations in using aminoglycosides as pharmaceuticals is their high toxicity towards mammals, typically expressed in kidney (nephrotoxicity) and ear-associated (ototoxicity) illnesses. The origin of this toxicity is assumed to result from a combination of different factors and mechanisms such as interactions with phospholipids, inhibition of phospholipases and the formation of free radicals. Although considered selective to bacterial ribosomes, most aminoglycosides bind also to the eukaryotic A-site but with lower affinities than to the bacterial A-site.

The inhibition of translation in mammalian cells is also one of the possible causes for the high toxicity of these agents. Another factor adding to their cytotoxicity is their binding to the mitochondrial ribosome at the 12S rRNA A-site, whose sequence is very close to the bacterial A-site.

Many studies have been attempted to understand and offer ways to alleviate the toxicity associated with aminoglycosides, including the use of antioxidants to reduce free radical levels, as well as the use of poly-L-aspartate and daptomycin, to reduce the ability of aminoglycosides to interact with phospholipids. The role of megalin (a multiligand endocytic receptor which is especially abundant in the kidney proximal tubules and the inner ear) in the uptake of aminoglycosides has recently been demonstrated. The administration of agonists that compete for aminoglycoside binding to megalin also resulted in a reduction in aminoglycoside uptake and toxicity. In addition, altering the administration schedule and/or the manner in which aminoglycos ides are administered has been investigated as means to reduce toxicity.

Despite extensive efforts to reduce aminoglycoside toxicity, few results have matured into standard clinical practices and procedures for the administration of aminoglycosides to suppress stop codon mutations, other than changes in the administration schedule. For example, the use of sub-toxic doses of gentamicin in the clinical trials probably caused the reduced read-through efficiency obtained in the in-vivo experiments compared to the in-vitro systems. The aminoglycoside Geneticin® (also known as G-418 sulfate or simply G-418, see, FIG. 1) showed the best termination suppression activity in in-vitro translation-transcription systems, however, its use as a therapeutic agent is not possible since it is lethal even at very low concentrations. For example, the $LD_{50}$ of G-418 against human fibroblast cells is 0.04 mg/ml, compared to 2.5-5.0 mg/ml for gentamicin, neomycin and kanamycin.

The increased sensitivity of eukaryotic ribosomes to some aminoglycoside drugs, such as G-418 and gentamicin, is intriguing but up to date could not be rationally explained because of the lack of sufficient structural data on their interaction with eukaryotic ribosomes. Since G-418 is extremely toxic even at very low concentrations, presently gentamicin is the only aminoglycoside tested in various animal models and clinical trials. Although some studies have shown that due to their relatively lower toxicity in cultured cells, amikacin and paromomycin can represent alternatives to gentamicin for stop codon mutation suppression therapy, no clinical trials with these aminoglycos ides have been reported yet.

To date, nearly all suppression experiments have been performed with clinical, commercially available aminoglycosides, however, only a limited number of aminoglycosides, including gentamicin, amikacin, and tobramycin, are in clinical use as antibiotics for internal administration in humans. Among these, tobramycin do not have stop codon mutations suppression activity, and gentamicin is the only aminoglycoside tested for stop codon mutations suppression activity in animal models and clinical trials. Recently, a set of neamine derivatives were shown to promote read-through of the SMN protein in fibroblasts derived from spinal muscular atrophy (SPA) patients; however, these compounds were originally designed as antibiotics and no conclusions were derived for further improvement of the read-through activity of these derivatives.

WO 2007/113841 and WO 2012/066546 disclose classes of paromomycin-derived aminoglycosides, designed to exhibit high premature stop codon mutations readthrough activity while exerting low cytotoxicity in mammalian cells and low antimicrobial activity, and can thus be used in the treatment of genetic diseases. This class of paromomycin-derived aminoglycosides was designed by introducing certain manipulations to the paromamine core, which lead to enhanced readthrough activity and reduced toxicity and antimicrobial activity. The manipulations were made on several positions of the paromamine core.

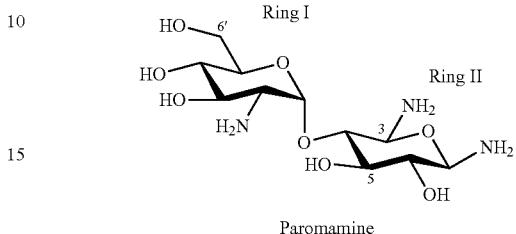

Paromamine

Exemplary such manipulations of the paromamine core which have been taught in these publications include a hydroxyl group at position 6' of the aminoglycoside core; introduction of one or more monosaccharide moieties or an oligosaccharide moiety at position 3', 5 and/or 6 of the aminoglycoside core; introduction of an (S)-4-amino-2-hydroxybutyryl (AHB) moiety at position 1 of the paromamine core; substitution of hydrogen at position 6' by an alkyl such as a methyl substituent; and an introductions of an alkyl group at the 5" position.

Additional background art includes Nudelman, I., et al., Bioorg Med Chem Lett, 2006. 16(24): p. 6310-5; Hobbie, S. N., et al., Nucleic Acids Res, 2007. 35(18): p. 6086-93; Kondo, J., et al., Chembiochem, 2007. 8(14): p. 1700-9; Rebibo-Sabbah, A., et al., Hum Genet, 2007. 122(3-4): p. 373-81; Azimov, R., et al., Am J Physiol Renal Physiol, 2008. 295(3): p. F633-41; Hainrichson, M., et al., Org Biomol Chem, 2008. 6(2): p. 227-39; Hobbie, S. N., et al., Proc Natl Acad Sci USA, 2008. 105(52): p. 20888-93; Hobbie, S. N., et al., Proc Natl Acad Sci USA, 2008. 105(9): p. 3244-9; Nudelman, I., et al., Adv. Synth. Catal., 2008. 350: p. 1682-1688; Nudelman, I., et al., J Med Chem, 2009. 52(9): p. 2836-45; Venkataraman, N., et al., PLoS Biol, 2009. 7(4): p. e95; Brendel, C., et al., J Mol Med (Berl), 2010. 89(4): p. 389-98; Goldmann, T., et al., Invest Ophthalmol Vis Sci, 2010. 51(12): p. 6671-80; Malik, V., et al., Ther Adv Neurol Disord, 2010. 3(6): p. 379-89; Nudelman, I., et al., Bioorg Med Chem, 2010. 18(11): p. 3735-46; Warchol, M. E., Curr Opin Otolaryngol Head Neck Surg, 2010. 18(5): p. 454-8; Lopez-Novoa, J. M., et al., Kidney Int, 2011. 79(1): p. 33-45; Rowe, S. M., et al., J Mol Med (Berl), 2011. 89(11): p. 1149-61; Vecsler, M., et al., PLoS One, 2011. 6(6): p. e20733; U.S. Pat. Nos. 3,897,412, 4,024,332, 4,029,882, and 3,996,205; Greenberg et al., J. Am. Chem. Soc., 1999, 121, 6527-6541; Kotra et al., antimicrobial agents and chemotherapy, 2000, p. 3249-3256; Haddad et al., J. Am. Chem. Soc., 2002, 124, 3229-3237; Kandasamy, J. et al., J. Med. Chem. 2012, 55, pp. 10630-10643; Duscha, S. et al., MBio, 2014, 5(5), p. e01827-14; Huth, M. E. et al., J Clin Invest., 2015, 125(2), pp. 583-92; Shulman, E. et al., J Biol Chem., 2014, 289(4), pp. 2318-30 and FR Patent No. 2,427,341, JP Patent No. 04046189. The teachings of all of these documents are incorporated by reference as if fully set forth herein.

SUMMARY OF THE INVENTION

The present invention relates to aminoglycosides, which can be beneficially used in the treatment of genetic diseases, by exhibiting high premature stop codon mutations readthrough activity, low toxicity in mammalian cells and low antimicrobial activity, as well as improved bioavailability and/or cell permeability. The presently disclosed aminoglycosides are characterized by a core structure based on Rings I, II and optionally III of paromomycin.

According to an aspect of some embodiments of the present invention there is provided a compound represented by Formula I:

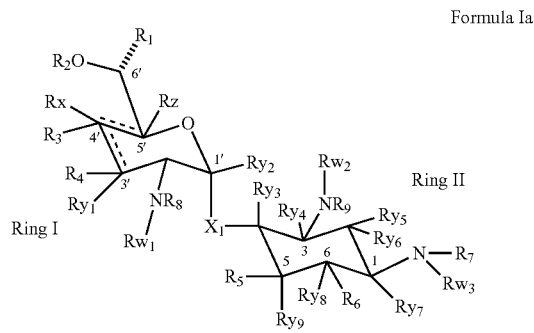

Formula Ia or a pharmaceutically acceptable salt thereof,
wherein:
the dashed line indicates a stereo-configuration of position 6' being an R configuration or an S configuration;
$X_1$ is O or S;
the dashed bond between C4' and C5' in Ring I represents a single bond or a double bond;
the dashed bond between C4' and C3' in Ring I represents a single bond or a double bond;
Rx, Ry1 and Rz are each independently hydrogen, alkyl or cycloalkyl, or absent, wherein at least Rz is absent in case the dashed bond between C4' and C5' is a double bond, and wherein at least Ry1 is absent in case the dashed bond between C4' and C3' is a double bond;
Ry2-Ry9 and Rw1-Rw3 are each independently selected from hydrogen, alkyl, alkenyl, alkynyl, aryl, heteroaryl and cycloalkyl, each being substituted or unsubstituted, or, alternatively, each can be as defined herein for $R_7$-$R_9$;
$R_1$ is selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl, a substituted or unsubstituted amine, a substituted or unsubstituted amide, an acyl, a carboxylate, and a saturated or unsaturated and/or substituted or unsubstituted hydroxy alkyl (e.g., —$CH_2$—OH);
$R_2$ is selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl and acyl;
$R_3$ and $R_4$ are each independently selected from the group consisting of hydrogen, alkyl, alkenyl, alkynyl, cycloalkyl, heteroalicyclic, aryl, heteroaryl, amine and $OR_{16}$, wherein $R_{16}$ is independently selected from hydrogen, a monosaccharide moiety, an oligosaccharide moiety, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl and acyl, or is absent, wherein $R_3$ is optionally absent in case the dashed bond between C4' and C5' is a double bond, and $R_4$ is optionally absent in case the dashed bond between C4' and C3' a double bond;
$R_5$ and $R_6$ are each independently selected from the group consisting of hydrogen, alkyl, alkenyl, alkynyl, cycloalkyl, heteroalicyclic, aryl, heteroaryl, amine and $OR_{16}$, wherein $R_{16}$ is independently selected from hydrogen, a monosaccharide moiety, an oligosaccharide moiety, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl and acyl; and
$R_7$-$R_9$ are each independently selected from the group consisting of hydrogen, acyl, an amino-substituted alpha-hydroxy acyl, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted alkaryl, carboxylate, sulfonyl (including alkyl sulfonyl and aryl sulfonyl) and a cell-permealizable group as defined herein.

It is to be noted that herein throughout, the stereoconfiguration of Rings I, II and III, if present, can be any possible, compatible configuration, and are therefore not to be limited to the illustration of these rings in the general Formulae presented herein. Exemplary stereroconfigurations are presented hereinunder.

According to some of any of the embodiments described herein, at least one of $R_3$, $R_4$, $R_5$ and $R_6$ is $OR_{16}$.

According to some of any of the embodiments described herein, $R_{16}$ is an aryl.

According to some of any of the embodiments described herein, at least one of $R_3$, $R_4$, $R_5$ and $R_6$ is selected from the group consisting of phenyloxy, 1-anthryloxy, 1-naphthyloxy, 2-naphthyloxy, 2-phenanthryloxy and 9-phenanthryloxy.

According to some of any of the embodiments described herein, $R_{16}$ is a substituted or unsubstituted heteroaryl, and at least one of $R_3$, $R_4$, $R_5$ and $R_6$ is independently a substituted or unsubstituted heteroaryloxy.

According to some of any of the embodiments described herein, at least one of $R_3$, $R_4$, $R_5$ and $R_6$ is independently selected from the group consisting of 2-anthryloxy, 2-furyloxy, 2-indolyloxy, 2-naphthyloxy, 2-pyridyloxy, 2-pyrimidyloxy, 2-pyrryloxy, 2-quinolyloxy, 2-thienyloxy, 3-furyloxy, 3-indolyloxy, 3-thienyloxy, 4-imidazolyloxy, 4-pyridyloxy, 4-pyrimidyloxy, 4-quinolyloxy, 5-methyl-2-thienyloxy and 6-chloro-3-pyridyloxy.

According to some of any of the embodiments described herein, $R_{16}$ is a substituted aryl.

According to some of any of the embodiments described herein, at least one of $R_3$, $R_4$, $R_5$ and $R_6$ is $OR_{16}$, and $R_{16}$ is independently selected from the group consisting of 2-(N-ethylamino)phenyl, 2-(N-hexylamino)phenyl, 2-(N-methylamino)phenyl, 2,4-dimethoxyphenyl, 2-acetamidophenyl, 2-aminophenyl, 2-carboxyphenyl, 2-chlorophenyl, 2-ethoxyphenyl, 2-fluorophenyl, 2-hydroxymethylphenyl, 2-hydroxyphenyl, 2-hydroxyphenyl, 2-methoxycarbonylphenyl, 2-methoxyphenyl, 2-methylphenyl, 2-N,N-dimethylaminophenyl, 2-trifluoromethylphenyl, 3-(N,N-dibutylamino)phenyl, 3-(N,N-diethylamino)phenyl, 3,4,5-trimethoxyphenyl, 3,4-dichlorophenyl, 3,4-dimethoxyphenyl, 3,5-dimethoxyphenyl, 3-aminophenyl, 3-biphenylyl, 3-carboxyphenyl, 3-chloro-4-methoxyphenyl, 3-chlorophenyl, 3-ethoxycarbonylphenyl, 3-ethoxyphenyl, 3-fluorophenyl, 3-hydroxymethylphenyl, 3-hydroxyphenyl, 3-isoamyloxyphenyl, 3-isobutoxyphenyl, 3-isopropoxyphenyl, 3-methoxyphenyl, 3-methylphenyl, 3-N,N-dimethylaminophenyl, 3-tolyl, 3-trifluoromethylphenyl, 4-(benzyloxy)phenyl, 4-(isopropoxycarbonyl)phenyl, 4-(N,N-diethylamino)phenyl, 4-(N,N-dihexylamino)phenyl, 4-(N,N-diisopropylamino)phenyl, 4-(N,N-dimethylamino)phenyl, 4-(N,N-di-n-pentylamino)phenyl, 4-(n-hexyloxycarbonyl)phenyl, 4-(N-methylamino)phenyl, 4-(trifluoromethyl)phenyl, 4-aminophenyl, 4-benzyloxyphenyl, 4-biphenylyl, 4-butoxyphenyl, 4-butyramidophenyl, 4-carboxyphenyl, 4-chlorophenyl, 4-ethoxycarbonylphenyl, 4-hexanamidophenyl, 4-hydroxymethylphenyl, 4-hydroxyphenyl, 4-iodophenyl, 4-isobutylphenyl, 4-isobutyramidophenyl, 4-isopropoxyphenyl, 4-isopropylphenyl, 4-methoxyphenyl, 4-methylphenyl, 4-n-hexanamidophenyl, 4-n-hexyloxyphenyl, 4-n-hexylphenyl, 4-nitrophenyl, 4-nitrophenyl, 4-propionamidophenyl, 4-tolyl, 4-trifluoromethylphenyl and 4-valeroyloxycarbonylphenyl.

According to some of any of the embodiments described herein, $R_3$ is $OR_{16}$ and $R_{16}$ is hydrogen.

According to some of any of the embodiments described herein, $R_3$ is $OR_{16}$ and $R_{16}$ is selected from the group consisting of methyl, ethyl, propyl, butyl, pentyl, propenyl, 2-hydroxyethyl, 3-hydroxypropyl, 2,3-dihydroxypropyl and methoxymethyl.

According to some of any of the embodiments described herein, at least one, or each, of $R_3$, $R_4$, $R_5$ and $R_6$ is $OR_{16}$ and $R_{16}$ is independently an acyl.

According to some of any of the embodiments described herein, each of $R_3$, $R_4$, $R_5$ and $R_6$ is $OR_{16}$ and $R_{16}$ is hydrogen.

According to some of any of the embodiments described herein, at least one of $R_3$, $R_4$, $R_5$ and —$R_6$ is $OR_{16}$ in which $R_{16}$ is the monosaccharide moiety.

According to some of any of the embodiments described herein, the monosaccharide moiety is represented by Formula II:

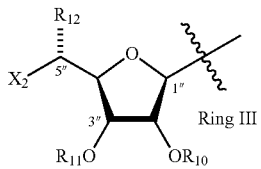

Formula II wherein:
the curved line denotes a position of attachment;
the dashed line indicates a stereo-configuration of position 5" being an R configuration or an S configuration;
$X_2$ is $OR_D$ or $NR_{14}R_{15}$;
each of $R_{10}$, $R_{11}$ and $R_{13}$ is independently selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl, and acyl;
$R_{12}$ is selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl, a substituted or unsubstituted amine, a substituted or unsubstituted amide, an acyl, a carboxylate, and a saturated or unsaturated and/or substituted or unsubstituted hydroxyalkyl;
each of $R_{14}$- and $R_{15}$ is independently selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl, acyl, and a cell-permealizable group, or, alternatively, $R_{14}$ and $R_{15}$, when present, form together a heterocyclic ring.

Substituents not shown in Formula II at positions such as 6', 1", 2", 3", 4" and 5" are typically hydrogen, although other substituents, such as, but not limited, as defined for Ry2-Ry9, are also contemplated.

According to some of any of the embodiments described herein, the compound is represented by Formula Ib:

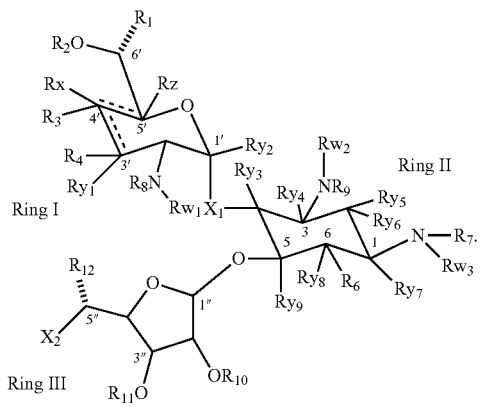

Formula Ib

Substituents not shown in Formula Ib at positions such as 6', 1", 2", 3", 4" and 5" are typically hydrogen, although other substituents, such as, but not limited, as defined for Ry2-Ry9, are also contemplated.

According to some of any of the embodiments described herein, $X_2$ is $OR_{13}$.

According to some of any of the embodiments described herein, $X_2$ is $NR_{14}R_{15}$.

According to some of any of the embodiments described herein, $R_{12}$ is other than hydrogen.

According to some of any of the embodiments described herein, at least one of $R_{10}$, $R_{11}$ and $R_{13}$ if present is an acyl.

According to some of any of the embodiments described herein, $X_1$ is O.

According to some of any of the embodiments described herein, the bond between C4' and C5' in Ring I is a single bond.

According to some of any of the embodiments described herein, the bond between C4' and C5' in Ring I is a double bond and Rx or $R_3$, and Rz, are absent.

According to some of any of the embodiments described herein, the bond between C4' and C3' in Ring I is a single bond.

According to some of any of the embodiments described herein, the bond between C4' and C3' in Ring I is a double bond and Rx or $R_4$, and Ry1, are absent.

According to some of any of the embodiments described herein, $R_1$ is other than hydrogen.

According to some of any of the embodiments described herein, $R_1$ is a hydroxyalkyl.

According to some of any of the embodiments described herein, $R_1$ is a hydroxymethyl.

According to some of any of the embodiments described herein, $R_1$ is or comprises a substituted or unsubstituted alkyl, a substituted or unsubstituted alkenyl or a substituted or unsubstituted alkynyl.

According to some of any of the embodiments described herein, $R_1$ is selected from the group consisting of methyl, ethyl, propyl, butyl and pentyl.

According to some of any of the embodiments described herein, $R_1$ is or comprises an aryl.

According to some of any of the embodiments described herein, $R_1$ is selected from the group consisting of phenyl, 1-anthryl, 1-naphthyl, 2-naphthyl, 2-phenanthryl and 9-phenanthryl.

According to some of any of the embodiments described herein, $R_1$ is or comprises a substituted or unsubstituted heteroaryl.

According to some of any of the embodiments described herein, $R_1$ is selected from the group consisting of 2-anthryl, 2-furyl, 2-indolyl, 2-naphthyl, 2-pyridyl, 2-pyrimidyl, 2-pyrryl, 2-quinolyl, 2-thienyl, 3-furyl, 3-indolyl, 3-thienyl, 4-imidazolyl, 4-pyridyl, 4-pyrimidyl, 4-quinolyl, 5-methyl-2-thienyl and 6-chloro-3-pyridyl.

According to some of any of the embodiments described herein, $R_1$ is or comprises a substituted aryl.

According to some of any of the embodiments described herein, $R_1$ is selected from the group consisting of 2-(N-ethylamino)phenyl, 2-(N-hexylamino)phenyl, 2-(N-methylamino)phenyl, 2,4-dimethoxyphenyl, 2-acetamidophenyl, 2-aminophenyl, 2-carboxyphenyl, 2-chlorophenyl, 2-ethoxyphenyl, 2-fluorophenyl, 2-hydroxymethylphenyl, 2-hydroxyphenyl, 2-hydroxyphenyl, 2-methoxycarbonylphenyl, 2-methoxyphenyl, 2-methylphenyl, 2-N,N-dimethylaminophenyl, 2-trifluoromethylphenyl, 3-(N,N-dibutylamino)phenyl, 3-(N,N-diethylamino)phenyl, 3,4,5-trimethoxyphenyl, 3,4-dichlorophenyl, 3,4-dimethoxyphenyl, 3,5-dimethoxyphenyl, 3-aminophenyl, 3-biphenylyl, 3-carboxyphenyl, 3-chloro-4-methoxyphenyl, 3-chlorophenyl, 3-ethoxycarbonylphenyl, 3-ethoxyphenyl, 3-fluorophenyl, 3-hydroxymethylphenyl, 3-hydroxyphenyl, 3-isoamyloxyphenyl, 3-isobutoxyphenyl, 3-isopropoxyphenyl, 3-methoxyphenyl, 3-methylphenyl, 3-N,N-dimethylaminophenyl, 3-tolyl, 3-trifluoromethylphenyl, 4-(benzyloxy)phenyl, 4-(isopropoxycarbonyl)phenyl, 4-(N,N-diethylamino)phenyl, 4-(N,N-dihexylamino)phenyl, 4-(N,N-diisopropylamino)phenyl, 4-(N,N-dimethylamino)phenyl, 4-(N,N-di-n-pentylamino)phenyl, 4-(n-hexyloxycarbonyl)phenyl, 4-(N-methylamino)phenyl, 4-(trifluoromethyl)phenyl, 4-aminophenyl, 4-benzyloxyphenyl, 4-biphenylyl, 4-butoxyphenyl, 4-butyramidophenyl, 4-carboxyphenyl, 4-chlorophenyl, 4-ethoxycarbonylphenyl, 4-hexanamidophenyl, 4-hydroxymethylphenyl, 4-hydroxyphenyl, 4-iodophenyl, 4-isobutylphenyl, 4-isobutyramidophenyl, 4-isopropoxyphenyl, 4-isopropylphenyl, 4-methoxyphenyl, 4-methylphenyl, 4-n-hexanamidophenyl, 4-n-hexyloxyphenyl, 4-n-hexylphenyl, 4-nitrophenyl, 4-nitrophenyl, 4-propionamidophenyl, 4-tolyl, 4-trifluoromethylphenyl and 4-valeroyloxycarbonylphenyl.

According to some of any of the embodiments described herein, $R_1$ is or comprises an amine.

According to some of any of the embodiments described herein, $R_1$ is selected from the group consisting of —$NH_2$, —$NHCH_3$, —$N(CH_3)_2$, —NH—$CH_2$—$CH_2$—$NH_2$, —NH—$CH_2$—$CH_2$—OH and —NH—$CH_2$—$CH(OCH_3)_2$.

According to some of any of the embodiments described herein, $R_2$ is hydrogen.

According to some of any of the embodiments described herein, $R_2$ is alkyl, preferably selected from the group consisting of methyl, ethyl and propyl.

According to some of any of the embodiments described herein, $R_2$ is acyl.

According to some of any of the embodiments described herein, $R_7$ is selected from the group consisting of hydrogen, (R/S)-4-amino-2-hydroxybutyryl (AHB), (R/S)-3-amino-2-hydroxypropionate (AHP), (R/S)-3-amino-2-hydroxypropionyl, 5-aminopentanoyl, 5-hydroxypentanoyl, formyl, —C(=O)—O-methyl, —C(=O)—O-ethyl, —C(=O)—O-benzyl, -β-amino-α-hydroxypropionyl, -δ-amino-α-hydroxyvaleryl, -β-benzyloxycarbonylamino-α-hydroxypropionyl, -δ-benzyloxy carbonylamino-α-hydroxyvaleryl, methylsulfonyl, phenylsulfonyl, benzoyl, propyl, isopropyl, —$(CH_2)_2NH_2$, —$(CH_2)_3NH_2$, —$CH_2CH(NH_2)CH_3$, —$(CH_2)_4NH_2$, —$(CH_2)_5NH_2$, —$(CH_2)_2NH$-ethyl, —$(CH_2)_2NH(CH_2)_2NH_2$, —$(CH_2)_3NH(CH_2)_3NH_2$, —$(CH_2)_3NH(CH_2)_4NH(CH_2)_3NH_2$, —CH(—$NH_2$)$CH_2$(OH), —CH(OH)$CH_2$($NH_2$), —CH(—OH)—$(CH_2)_2(NH_2)$, —CH(—$NH_2$)—$(CH_2)_2$(OH), —CH(—$CH_2NH_2$)—($CH_2$OH), —$(CH_2)_4NH(CH_2)_3NH_2$, —$(CH_2)_2NH(CH_2)_2NH(CH_2)_2NH_2$, —$(CH_2)_2N(CH_2CH_2NH_2)_2$, —$CH_2$—C(=O)$NH_2$, —CH($CH_3$)—C(=O)$NH_2$, —$CH_2$-phenyl, —CH(i-propyl)-C(=O)$NH_2$, —CH(benzyl)-C(=O)$NH_2$, —$(CH_2)_2$OH, —$(CH_2)_3$OH and —CH$(CH_2OH)_2$.

According to some of any of the embodiments described herein, each of $R_8$ and $R_9$ is independently selected from the group consisting of hydrogen, (R/S)-4-amino-2-hydroxybutyryl (AHB), (R/S)-3-amino-2-hydroxypropionate (AHP), (R/S)-3-amino-2-hydroxypropionyl, 5-aminopentanoyl, 5-hydroxypentanoyl, formyl, —COO-methyl, —COO-ethyl, —COO-benzyl, -β-amino-α-hydroxypropionyl, -δ-amino-α-hydroxyvaleryl, -β-benzyloxycarbonylamino-α-hydroxypropionyl, -δ-benzyloxycarbonylamino-α-hydroxyvaleryl, methylsulfonyl, phenylsulfonyl, benzoyl, propyl, isopropyl, —$(CH_2)_2NH_2$, —$(CH_2)_3NH_2$, —$CH_2CH(NH_2)CH_3$, —$(CH_2)_4NH_2$, —$(CH_2)_5NH_2$, —$(CH_2)_2NH$-ethyl, —$(CH_2)_2NH(CH_2)_2NH_2$, —$(CH_2)_3NH(CH_2)_3NH_2$, —$(CH_2)_3NH(CH_2)_4NH(CH_2)_3NH_2$, —CH(—$NH_2$)$CH_2$(OH), —CH(OH)$CH_2$($NH_2$), —CH(—OH)—$(CH_2)_2(NH_2)$, —CH(—$NH_2$)—$(CH_2)_2$(OH), —CH(—$CH_2NH_2$)—($CH_2$OH), —$(CH_2)_4NH(CH_2)_3NH_2$, —$(CH_2)_2NH(CH_2)_2NH(CH_2)_2NH_2$, —$(CH_2)_2N(CH_2CH_2NH_2)_2$, —$CH_2$—C(=O)$NH_2$, —CH($CH_3$)—C(=O)$NH_2$, —$CH_2$-phenyl, —CH(i-propyl)-C(=O)$NH_2$, —CH(benzyl)-C(=O)$NH_2$, —$(CH_2)_2$OH, —$(CH_2)_3$OH and —CH$(CH_2OH)_2$.

According to some of any of the embodiments described herein, the amino-substituted alpha-hydroxy acyl is (S)-4-amino-2-hydroxybutyryl (AHB).

According to some of any of the embodiments described herein, the cell-permealizable group is guanidyl.

According to some of any of the embodiments described herein, an unsubstituted aryl as described herein in any of the respective embodiments is selected from the group consisting of phenyl, 1-anthryl, 1-naphthyl, 2-naphthyl, 2-phenanthryl and 9-phenanthryl.

According to some of any of the embodiments described herein, a substituted or unsubstituted heteroaryl as described herein in any of the respective embodiments is selected from the group consisting of 2-anthryl, 2-furyl, 2-indolyl, 2-naphthyl, 2-pyridyl, 2-pyrimidyl, 2-pyrryl, 2-quinolyl, 2-thienyl, 3-furyl, 3-indolyl, 3-thienyl, 4-imidazolyl, 4-pyridyl, 4-pyrimidyl, 4-quinolyl, 5-methyl-2-thienyl and 6-chloro-3-pyridyl.

According to some of any of the embodiments described herein, a substituted aryl as described herein in any of the respective embodiments is selected from the group consisting of 2-(N-ethylamino)phenyl, 2-(N-hexylamino)phenyl, 2-(N-methylamino)phenyl, 2,4-dimethoxyphenyl, 2-acetamidophenyl, 2-aminophenyl, 2-carboxyphenyl, 2-chlorophenyl, 2-ethoxyphenyl, 2-fluorophenyl, 2-hydroxymethylphenyl, 2-hydroxyphenyl, 2-hydroxyphenyl, 2-methoxycarbonylphenyl, 2-methoxyphenyl, 2-methylphenyl, 2-N,N-dimethylaminophenyl, 2-trifluoromethylphenyl, 3-(N,N-dibutylamino)phenyl, 3-(N,N-diethylamino)phenyl, 3,4,5-trimethoxyphenyl, 3,4-dichlorophenyl, 3,4-dimethoxyphenyl, 3,5-dimethoxyphenyl, 3-aminophenyl, 3-biphenylyl, 3-carboxyphenyl, 3-chloro-4-methoxyphenyl, 3-chlorophenyl, 3-ethoxycarbonylphenyl, 3-ethoxyphenyl, 3-fluorophenyl, 3-hydroxymethylphenyl, 3-hydroxyphenyl, 3-isoamyloxyphenyl, 3-isobutoxyphenyl, 3-isopropoxyphenyl, 3-methoxyphenyl, 3-methylphenyl, 3-N,N-dimethylaminophenyl, 3-tolyl, 3-trifluoromethylphenyl, 4-(benzyloxy)phenyl, 4-(isopropoxycarbonyl)phenyl, 4-(N,N-diethylamino)phenyl, 4-(N,N-dihexylamino)phenyl, 4-(N,N-diisopropylamino)phenyl, 4-(N,N-dimethylamino)phenyl, 4-(N,N-di-n-pentylamino)phenyl, 4-(n-hexyloxycarbonyl)phenyl, 4-(N-methylamino)phenyl, 4-(trifluoromethyl)phenyl, 4-aminophenyl, 4-benzyloxyphenyl, 4-biphenylyl, 4-butoxyphenyl, 4-butyramidophenyl, 4-carboxyphenyl, 4-chlorophenyl, 4-ethoxycarbonylphenyl, 4-hexanamidophenyl, 4-hydroxymethylphenyl, 4-hydroxyphenyl, 4-iodophenyl, 4-isobutylphenyl, 4-isobutyramidophenyl, 4-isopropoxyphenyl, 4-isopropylphenyl, 4-methoxyphenyl, 4-methylphenyl, 4-n-hexanamidophenyl, 4-n-hexyloxyphenyl, 4-n-hexylphenyl, 4-nitrophenyl, 4-nitrophenyl, 4-propionamidophenyl, 4-tolyl, 4-trifluoromethylphenyl and 4-valeroyloxycarbonylphenyl.

According to some of any of the embodiments described herein, an acyl as described herein in any of the respective embodiments is selected from the group consisting of a hydrocarbon acyl radical having from 2 to 18 carbon atoms, optionally substituted by one or more of halo, nitro, hydroxy, amine, cyano, thiocyano, and alkoxy.

According to some of any of the embodiments described herein, the acyl is derived from an acid selected from the group consisting of a saturated or unsaturated and/or substituted or unsubstituted aliphatic carboxylic acid, acetic acid, propionic acid, butyric acid, isobutyric acid, tert-butylacetic acid, valeric acid, isovaleric acid, caproic acid, caprylic acid, decanoic acid, dodecanoic acid, lauric acid, tridecanoic acid, myristic acid, pentadecanoic acid, palmitic acid, margaric acid, stearic acid, acrylic acid, crotonic acid, undecylenic acid, oleic acid, hexynoic acid, heptynoic acid, octynoic acid, a saturated or unsaturated alicyclic carboxylic acid, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, a saturated or unsaturated, alicyclic aliphatic carboxylic acid, cyclopentaneacetic acid, cyclopentanepropionic acid, cyclohexaneacetic acid, cyclohexanebutyric acid, methylcyclohexaneacetic acid, a substituted or unsubstituted aromatic carboxylic acid, benzoic acid, toluic acid, naphthoic acid, ethylbenzoic acid, isobutylbenzoic acid, methylbutylbenzoic acid, an aromatic aliphatic carboxylic acid, phenylacetic acid, phenylpropionic acid, phenylvaleric acid, cinnamic acid, phenylpropiolic acid, naphthylacetic acid, a halo-alkoxyhydrocarbon carboxylic acid, a nitro-alkoxyhydrocarbon carboxylic acid, a hydroxy-alkoxyhydrocarbon carboxylic acid, an amino-alkoxyhydrocarbon carboxylic acid, a cyano-alkoxyhydrocarbon carboxylic acid, a thiocyano-alkoxyhydrocarbon carboxylic acid, mono-acetic acid, di-acetic acid, trichloroacetic acid, 1,2,3,4,5,6-hexachlorocyclohexanecarboxylic acid, 1,2-dibromo-4-methylcyclohexanecarboxylic acid, 1,6-dibromo-3-methylcyclohexanecarboxylic acid, 1-bromo-3,5-dimethylcyclohexanecarboxylic acid, 2-chlorocyclohexanecarboxylic acid, 4-chlorocyclohexanecarboxylic acid, 2,3-dibromo-2-methylcyclohexanecarboxylic acid, 2,4,6-trinitrobenzoic acid, 2,5-dibromo-2-methylcyclohexanecarboxylic acid, 2-bromo-4-methylcyclohexanecarboxylic acid, 2-nitro-1-methyl-cyclobutanecarboxylic acid, 3,4-dinitrobenzoic acid, 3,5-dinitrobenzoic acid, 3-bromo-2,2,3-trimethylcyclopentanecarboxylic acid, 3-bromo-2-methylcyclohexanecarboxylic acid, 3-bromo-3-methylcyclohexanecarboxylic acid, 4-bromo-2-methylcyclohexanecarboxylic acid, 5-bromo-2-methylcyclohexanecarboxylic acid, 4,4-dichlorobenzilic acid, 4,5-dibromo-2-methylcyclohexanecarboxylic acid, 5-bromo-2-methylcyclohexanecarboxylic acid, 6-bromo-2-methylcyclohexanecarboxylic acid, 5,6-dibromo-2-methylcyclohexanecarboxylic acid, 6-bromo-3-methylcyclohexanecarboxylic acid, anisic acid, cyanoacetic acid, cyanopropionic acid, ethoxyformic acid (ethyl hydrogen carbonate), gallic acid, homogentisic acid, o-, m-, and p-chlorobenzoic acid, lactic acid, mevalonic acid, o-, m-, p-nitrobenzoic acid, p-hydroxybenzoic acid, salicylic acid, shikimic acid, thiocyanoacetic acid, trimethoxybenzoic acid, trimethoxycinnamic acid, veratric acid, α- and β-chloropropionic acid, α- and γ-bromobutyric acid and α- and δ-iodovaleric acid, β-resorcylic acid.

According to an aspect of some embodiments of the present invention there is provided a pharmaceutical composition comprising the compound as described herein in any one of the embodiments and any combination thereof, and a pharmaceutically acceptable carrier.

According to some of any of the embodiments described herein, the pharmaceutical composition is packaged in a packaging material and identified in print, in or on the packaging material, for use in the treatment of a genetic disorder with a premature stop-codon truncation mutation and/or a protein truncation phenotype.

According to an aspect of some embodiments of the present invention there is provided a method for treating a genetic disorder with a premature stop-codon truncation mutation and/or a protein truncation phenotype, the method comprising administering to a subject in need thereof a therapeutically effective amount of the compound as described herein in any one of the embodiments and any combination thereof.

According to an aspect of some embodiments of the present invention there is provided a compound as described herein in any one of the embodiments and any combination thereof, for use in the treatment of a genetic disorder with a premature stop-codon truncation mutation and/or a protein truncation phenotype.

According to an aspect of some embodiments of the present invention there is provided a use of the compound as described herein in any one of the embodiments and any combination thereof, in the manufacture of a medicament for treating a genetic disorder with a premature stop-codon truncation mutation and/or a protein truncation phenotype.

According to some of any of the embodiments described herein, the genetic disorder is selected from the group consisting of cystic fibrosis (CF), Duchenne muscular dystrophy (DMD), ataxia-telangiectasia, Hurler syndrome, hemophilia A, hemophilia B, Usher syndrome, Tay-Sachs, Becker muscular dystrophy (BMD), Congenital muscular dystrophy (CMD), Factor VII deficiency, Familial atrial fibrillation, Hailey-Hailey disease, McArdle disease, Mucopolysaccharidosis, Nephropathic cystinosis, Polycystic kidney disease, Rett syndrome, Spinal muscular atrophy (SMA), cystinosis, Severe epidermolysis bullosa, Dravet syndrome, X-linked nephrogenic diabetes insipidus (XNDI), X-linked retinitis pigmentosa and cancer.

According to an aspect of some embodiments of the present invention there is provided a method of increasing the expression level of a gene having a premature stop-codon mutation, the method comprising translating the gene into a protein in the presence of a compound as described herein in any of the respective embodiments and any combination thereof.

According to an aspect of some embodiments of the present invention there is provided a compound as described herein in any of the respective embodiments and any combination thereof for use in increasing the expression level of a gene having a premature stop-codon mutation.

According to an aspect of some embodiments of the present invention there is provided a use of a compound as described herein in any of the respective embodiments and any combination thereof in the manufacture of a medicament for increasing the expression level of a gene having a premature stop-codon mutation.

According to some of any of the embodiments described herein, the premature stop-codon mutation has an RNA code selected from the group consisting of UGA, UAG and UAA.

According to some of any of the embodiments described herein, the protein is translated in a cytoplasmic translation system.

According to some of any of the embodiments described herein, the compound is used in a mutation suppression amount.

According to some of any of the embodiments described herein, an inhibition of translation $IC_{50}$ of the compound in a eukaryotic cytoplasmic translation system is greater that an inhibition of translation $IC_{50}$ of the compound in a ribosomal translation system.

According to some of any of the embodiments described herein, an inhibition of translation $IC_{50}$ of the compound in a eukaryotic cytoplasmic translation system is greater that an inhibition of translation $IC_{50}$ of the compound in a prokaryotic translation system.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-C present comparative bar plot showing read-through levels of the Rett syndrome causing premature stop codon mutations R168X (FIG. 2A), R270X (FIG. 2B) and R294X (FIG. 2C), as measured and calculated for exemplary compounds according to some embodiments of the present invention, being contacted with expression HEK293 cells at a concentration of 0.3 mM and 1 mM, as well as for a control sample (no added compound), based on the firefly/*renilla* expression ratios versus the expression ratios observed in the wild type (WT);

FIGS. 4A-F present the results of cystic fibrosis G542X nonsense mutation suppression dose-response cell-free assays conducted for exemplary compounds according to some embodiments of the present invention, NB144, NB145 and NB146, at a concentration range of 0-50 µM, wherein FIG. 4A shows the expression level of the firefly luciferase which is found downstream of the WT sequence, FIG. 4B shows the expression level of the firefly luciferase which is found downstream of the G542X mutant sequence, FIG. 4C shows the expression level of the *renilla* luciferase which is found upstream of the WT sequence, FIG. 4D shows the expression level of the *renilla* luciferase which is found upstream of the G542X mutant sequence, FIG. 4E shows the firefly/*renilla* expression ratio measured in the WT sequence, and FIG. 4F shows the firefly/*renilla* expression ratio measured in the G542X mutant sequence;

FIGS. 5A-B present the results of cystic fibrosis G542X nonsense mutation suppression dose-response cell-free assays conducted for exemplary compounds according to some embodiments of the present invention, NB144, NB145 and NB146, at a concentration rage of 0-50 µM, wherein FIG. 5A shows the expression level of the firefly luciferase, which is found downstream of the mutant sequence, as a fraction of the expression level exhibited in the control experiment (no added compound), and FIG. 5B shows the firefly/*renilla* expression ratio, down and upstream of the mutant sequence, as a fraction of the expression level in the control experiment;

FIGS. 6A-F present the results of cystic fibrosis G542X nonsense mutation suppression dose-response cell-free assays conducted for exemplary compounds according to some embodiments of the present invention, NB150, NB151 and NB152, at a concentration rage of 0-50 µM, wherein FIG. 6A shows the expression level of the firefly luciferase which is found downstream of the WT sequence, FIG. 6B shows the expression level of the firefly luciferase which is found downstream of the G542X mutant sequence, FIG. 6C shows the expression level of the *renilla* luciferase which is found upstream of the WT sequence, FIG. 6D shows the expression level of the *renilla* luciferase which is found upstream of the G542X mutant sequence, FIG. 6E shows the firefly/*renilla* expression ratio measured in the WT sequence, and FIG. 6F shows the firefly/*renilla* expression ratio measured in the G542X mutant sequence;

FIGS. 7A-B present the results of cystic fibrosis G542X nonsense mutation suppression dose-response cell-free assays conducted for exemplary compounds according to some embodiments of the present invention, NB150, NB151 and NB152, at a concentration rage of 0-50 µM, wherein FIG. 7A shows the expression level of the firefly luciferase, which is found downstream of the mutant sequence, as a fraction of the expression level exhibited in the control experiment (no added compound), and FIG. 7B shows the firefly/*renilla* expression ratio, down and upstream of the mutant sequence, as a fraction of the expression level in the control experiment;

DESCRIPTION OF SPECIFIC EMBODIMENTS OF THE INVENTION

Figure 1:
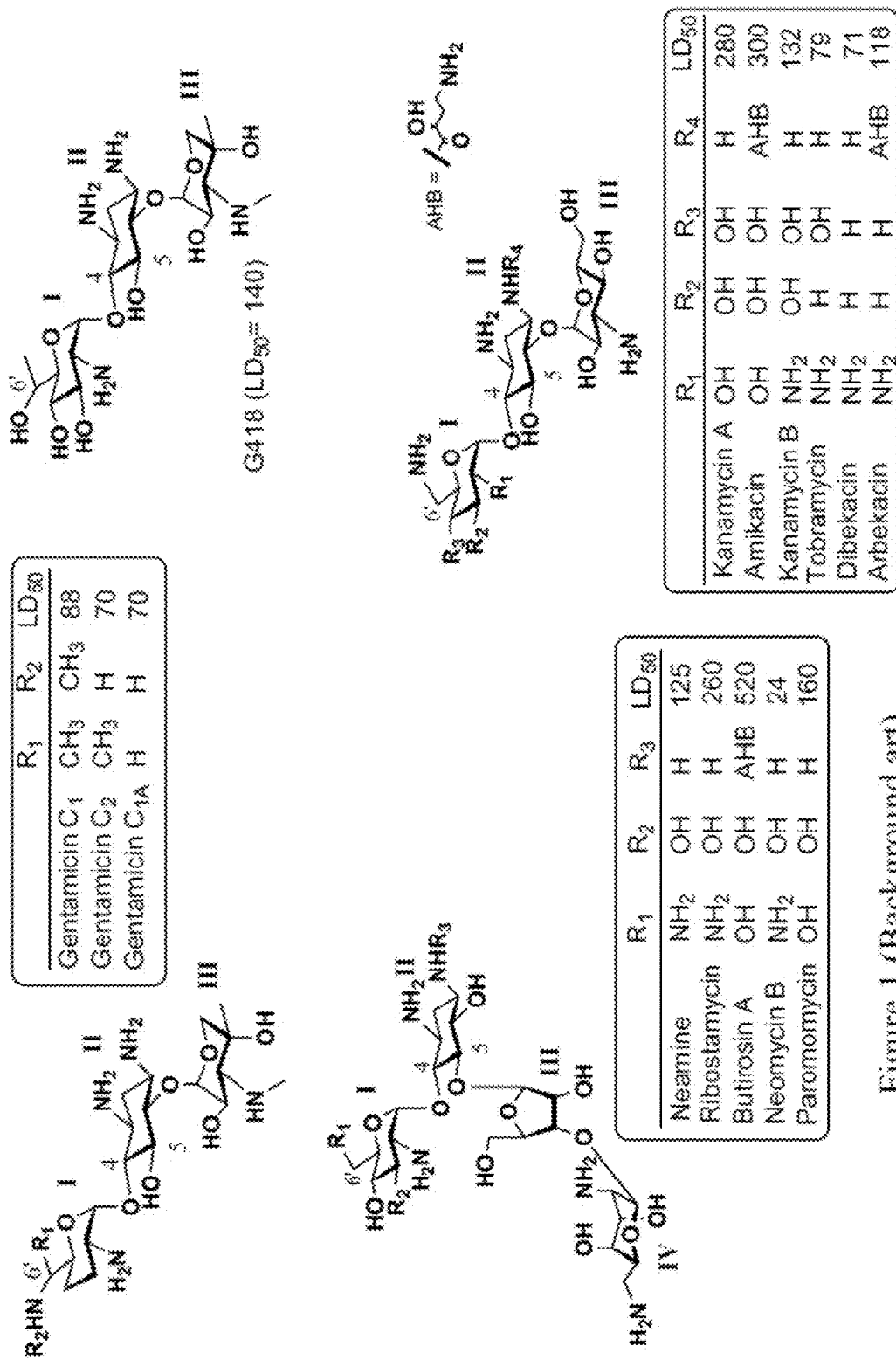
FIG. 1 (Background Art) presents the chemical structures of some known families of aminoglycosides.

The present invention, in some embodiments thereof, relates to aminoglycosides and more particularly, but not exclusively, to novel aminoglycoside derivatives and their use in increasing an expression of a gene having a stop codon mutation and/or in the treatment of genetic disorders.

Specifically, the present invention, in some embodiments thereof, relates to a novel aminoglycoside compounds, derived from paromomycin, which exhibit high premature stop codon mutations readthrough activity while exerting low toxicity in mammalian cells, and which are characterized by improved bioavailability and/or cell permeability. Embodiments of the present invention are further of pharmaceutical compositions containing these compounds, and of uses thereof in the treatment of genetic disorders. Embodiments of the present invention are further of processes of preparing these compounds.

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, the use aminoglycosides as therapeutic agents is limited primarily due to their high toxicity. In the context of treatment of genetic disorders, such a use is further limited by the antibacterial activity exhibited by the aminoglycosides, which can also translate into toxicity.

Additional limitations associated with aminoglycosides include low bioavailability, which typically requires an intravenous or subcutaneous administration, and poor permeability into eukaryotic cells, which typically requires administration of high doses which are associated with adverse side effected. It is assumed that the high water solubility and polarity of aminoglycosides limits their absorbance through intestinal tissues and their permeability through cell membranes.

As further discussed hereinabove, several structural manipulations on the structure of paromamine have given rise to synthetic aminoglycosides which have been shown to exert improved premature stop codon mutations readthrough activity while exerting low toxicity in mammalian cells. WO 2007/113841 and WO 2012/066546, which are incorporated by reference as if fully set forth herein, describe such aminoglycosides.

While further deciphering the structure-activity relationship of such aminoglycosides, in an attempt to further improve their therapeutic effect in the context of genetic disorders, the present inventor has designed numerous additional modifications, at varying positions of the paromamine structure, which are collectively represented herein by Formulae I and Ia.

While reducing the present invention to practice, exemplary novel aminoglycosides structures were prepared. As demonstrated in the Examples section that follows, these compounds were sown to exhibit high readthrough activity of disease-causing nonsense mutations as well as reduced toxicity.

The Compounds:

According to an aspect of some embodiments of the present invention, there are provided novel aminoglycoside (AMG) compounds (also referred to herein as "aminoglycoside derivatives"), which are collectively represented by Formula Ia:

Formula Ia

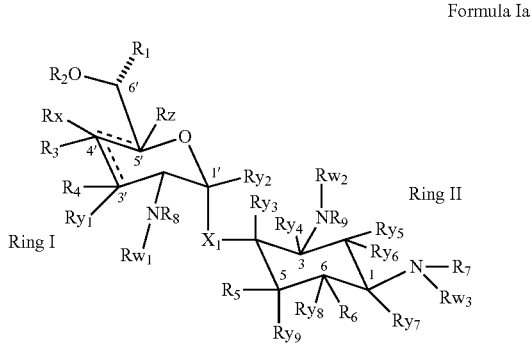

wherein:
the dashed line indicates a stereo-configuration of position 6' being an R configuration or an S configuration;
$X_1$ is O or S;
the dashed bond between C4' and C5' in Ring I represents a single bond or a double bond;
the dashed bond between C4' and C3' in Ring I represents a single bond or a double bond;
Rx, Ry1 and Rz are each independently selected from hydrogen, alkyl, alkenyl, alkynyl, alkaryl, aryl heteroaryl and cycloalkyl, or absent, wherein at least Rz is absent in case the dashed bond between C4' and C5' is a double bond, and at least Ry1 is absent in case the dashed bond between C4' and C3' is a double bond;
Ry2-Ry9 and Rw1-Rw3 are each independently selected from hydrogen, alkyl, alkenyl, alkynyl, alkaryl, aryl, heteroaryl and cycloalkyl, each being substituted or unsubstituted, or, alternatively, each can be as defined herein for $R_7$-$R_9$;
$R_1$ is selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl, a substituted or unsubstituted amine, a substituted or unsubstituted amide, an acyl, a carboxylate, and a saturated or unsaturated and/or a substituted or unsubstituted hydroxy alkyl (e.g., —$CH_2$—OH);
$R_2$ is selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl and acyl;
$R_3$ and $R_4$ are each independently selected from the group consisting of hydrogen, alkyl, alkenyl, alkynyl, cycloalkyl, heteroalicyclic, aryl, heteroaryl, amine and $OR_{16}$, wherein $R_{16}$ is independently (when 2 or more of $R_3$-$R_6$ is said $OR_{16}$) selected from hydrogen, a monosaccharide moiety, an oligosaccharide moiety, a substituted or unsubstituted alkyl, a substituted or unsubstituted alkenyl, a substituted or unsubstituted to alkynyl, a substituted or unsubstituted cycloalkyl, a substituted or unsubstituted aryl, a substituted or unsubstituted heteroaryl, a substituted or unsubstituted alkaryl and acyl, or is absent, wherein $R_3$ is optionally absent in case the dashed bond between C4' and C5' is a double bond, and $R_4$ is optionally absent in case the dashed bond between C4' and C3' is a double bond; and
$R_7$-$R_9$ are each independently selected from the group consisting of hydrogen, acyl, an amino-substituted alpha-hydroxy acyl, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted alkaryl, carboxylate, sulfonyl (including alkyl sulfonyl and aryl sulfonyl) and a cell-permealizable group.

In some of any of the embodiments described herein, the compound is a pseudo-disaccharide, having Ring I and Ring II as depicted in Formula Ia.

In these embodiments, none of $R_3$-$R_6$ is $OR_{16}$ in which $R_{16}$ is a monosaccharide or an oligosaccharide moiety.

In some of these embodiments, one or more, or all, of $R_3$-$R_6$ is $OR_{16}$.

In some of these embodiments, one or more, or all, of $R_3$-$R_6$ is $OR_{16}$ and $R_{16}$ is independently an aryl, which can be substituted or unsubstituted. In these embodiments, one or more, or all, of $R_3$-$R_6$ is an aryloxy, as defined herein.

In some of these embodiments, the aryl is unsubstituted such that one or more, or all of $R_3$-$R_6$, independently, can be, as non-limiting examples, phenyloxy, 1-anthryloxy, 1-naphthyloxy, 2-naphthyloxy, 2-phenanthryloxy and 9-phenanthryloxy.

In some of these embodiments, one or more of the aryls in one or more of $OR_{16}$ is a substituted aryl, such that one or more, or all of $R_3$-$R_6$, independently, can be, as non-limiting examples, an aryloxy in which the aryl is 2-(N-ethylamino)phenyl, 2-(N-hexylamino)phenyl, 2-(N-methylamino)phenyl, 2,4-dimethoxyphenyl, 2-acetamidophenyl, 2-aminophenyl, 2-carboxyphenyl, 2-chlorophenyl, 2-ethoxyphenyl, 2-fluorophenyl, 2-hydroxymethylphenyl, 2-hydroxyphenyl, 2-hydroxyphenyl, 2-methoxycarbonylphenyl, 2-methoxyphenyl, 2-methylphenyl, 2-N,N-dimethylaminophenyl, 2-trifluoromethylphenyl, 3-(N,N-dibutylamino)phenyl, 3-(N,N-diethylamino)phenyl, 3,4,5-trimethoxyphenyl, 3,4-dichlorophenyl, 3,4-dimethoxyphenyl, 3,5-dimethoxyphenyl, 3-aminophenyl, 3-biphenylyl, 3-carboxyphenyl, 3-chloro-4-methoxyphenyl, 3-chlorophenyl, 3-ethoxycarbonylphenyl, 3-ethoxyphenyl, 3-fluorophenyl, 3-hydroxymethylphenyl, 3-hydroxyphenyl, 3-isoamyloxyphenyI, 3-isobutoxyphenyl, 3-isopropoxyphenyl, 3-methoxyphenyl, 3-methylphenyl, 3-N,N-dimethylaminophenyl, 3-tolyl, 3-trifluoromethylphenyl, 4-(benzyloxy)phenyl, 4-(isopropoxycarbonyl)phenyl, 4-(N,N-diethylamino)phenyl, 4-(N,N-dihexylamino)phenyl, 4-(N,N-diisopropylamino)phenyl, 4-(N,N-dimethylamino)phenyl, 4-(N,N-di-n-pentylamino)phenyl, 4-(n-hexyloxycarbonyl)phenyl, 4-(N-methylamino)phenyl, 4-(trifluoromethyl)phenyl, 4-aminophenyl, 4-benzyloxyphenyl, 4-biphenylyl, 4-butoxyphenyl, 4-butyramidophenyl, 4-carboxyphenyl, 4-chlorophenyl, 4-ethoxycarbonylphenyl, 4-hexanamidophenyl, 4-hydroxymethylphenyl, 4-hydroxyphenyl, 4-iodophenyl, 4-isobutylphenyl, 4-isobutyramidophenyl, 4-isopropoxyphenyl, 4-isopropylphenyl, 4-methoxyphenyl, 4-methylphenyl, 4-n-hexanamidophenyl, 4-n-hexyloxyphenyl, 4-n-hexylphenyl, 4-nitrophenyl, 4-nitrophenyl, 4-propionamidophenyl, 4-tolyl, 4-trifluoromethylphenyl and/or 4-valeroyloxycarbonylphenyl.

In some of these embodiments, one or more, or all, of $R_3$-$R_6$ is $OR_{16}$ and $R_{16}$ is independently a heteroaryl, which can be substituted or unsubstituted. In these embodiments, one or more, or all, of $R_3$-$R_6$ is a heteroaryloxy, as defined herein.

In some embodiments, one or more, or all of $R_3$-$R_6$, independently, can be, as non-limiting examples, 2-anthryloxy, 2-furyloxy, 2-indolyloxy, 2-naphthyloxy, 2-pyridyloxy, 2-pyrimidyloxy, 2-pyrryloxy, 2-quinolyloxy, 2-thienyloxy, 3-furyloxy, 3-indolyloxy, 3-thienyloxy, 4-imidazolyloxy, 4-pyridyloxy, 4-pyrimidyloxy, 4-quinolyloxy, 5-methyl-2-thienyl oxy and 6-chloro-3-pyridyloxy.

In some of any of the embodiments described herein, $R_3$ is aryloxy or heteroaryloxy, as described herein.

In some of any of the embodiments described herein, $R_3$ is $OR_{16}$ and $R_{16}$ is a substituted or unsubstituted alkyl or alkenyl, for example, methyl, ethyl, propyl, butyl, pentyl, propenyl, 2-hydroxyethyl, 3-hydroxypropyl, 2,3-dihydroxypropyl and methoxymethyl.

In some of any of the embodiments described herein, $R_3$ is $OR_{16}$ and $R_{16}$ is hydrogen.

In some of any of the embodiments described herein, $R_4$ is $OR_{16}$ and $R_{16}$ is hydrogen.

In some of any of the embodiments described herein, each of $R_3$ and $R_4$ is $OR_{16}$ and $R_{16}$ is hydrogen.

In some of any of the embodiments described herein, one or more of, or all, of $R_3$-$R_6$ are $OR_{16}$.

In some of these embodiments, in each of $R_3$-$R_6$, $R_{16}$ is hydrogen.

In some of these embodiments, in one or more, or all, of $R_3$-$R_6$, $R_{16}$ is other than hydrogen.

In some of any of the embodiments described herein, when one or more, or all, of $R_3$-$R_6$ is $OR_{16}$ and when one or more, or all, of the $R_{16}$ moiety is other than hydrogen, $R_{16}$ can be the same or different for each of $R_3$-$R_6$.

In some of these embodiments, when in one or more, or all, of $R_3$-$R_6$, $R_{16}$ is other than hydrogen, $R_{16}$ can be, for example, independently, alkyl, alkenyl, alkynyl, cycloalkyl, aryl or heteroaryl, each being optionally substituted, as described herein.

In some of any of the embodiments described herein, in one or more, or all, of $R_3$-$R_6$, $R_{16}$ is independently an acyl, forming an ester (a carboxylate) at the respective position.

Herein throughout, the term "acyl" describes a —C(═O)—R' group, wherein R' is as described herein.

In some of any of the embodiments described herein, In some of any of the embodiments described herein, when $R_{16}$ is an acyl, R' is a hydrocarbon chain, as described herein, optionally substituted. In some embodiments, the hydrocarbon chain is of 2 to 18 carbon atoms in length. In some embodiments, the acyl is a hydrocarbon acyl radical having from 2 to 18 carbon atoms, optionally substituted by one or more of halo, nitro, hydroxy, amine, cyano, thiocyano, and alkoxy.

Herein, the term "hydrocarbon" or "hydrocarbon radical" describes an organic moiety that includes, as its basic skeleton, a chain of carbon atoms, also referred to herein as a backbone chain, substituted mainly by hydrogen atoms. The hydrocarbon can be saturated or non-saturated, be comprised of aliphatic, alicyclic and/or aromatic moieties, and can optionally be substituted by one or more substituents (other than hydrogen). A substituted hydrocarbon may have one or more substituents, whereby each substituent group can independently be, for example, alkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, amide, and hydrazine, and any other substituents as described herein.

The hydrocarbon moiety can optionally be interrupted by one or more heteroatoms, including, without limitation, one or more oxygen, nitrogen (substituted or unsubstituted, as defined herein for —NR'—) and/or sulfur atoms.

In some embodiments of any of the embodiments described herein relating to a hydrocarbon, the hydrocarbon is not interrupted by any heteroatom, nor does it comprise heteroatoms in its backbone chain, and can be an alkylene chain, or be comprised of alkyls, cycloalkyls, aryls, alkenes and/or alkynes, covalently attached to one another in any order.

In some of any of the embodiments described herein, when $R_{16}$ is an acyl, the acyl can be derived from a carboxylic acid, such that the ester formed at the respective position is derived from, for example, a saturated or unsaturated and/or substituted or unsubstituted aliphatic carboxylic acid, including, but not limited to, acetic acid, propionic acid, butyric acid, isobutyric acid, tert-butylacetic acid, valeric acid, isovaleric acid, caproic acid, caprylic acid, decanoic acid, dodecanoic acid, lauric acid, tridecanoic acid, myristic acid, pentadecanoic acid, palmitic acid, margaric acid, stearic acid, acrylic acid, crotonic acid, undecylenic acid, oleic acid, hexynoic acid, heptynoic acid, octynoic acid; a saturated or unsaturated alicyclic carboxylic acid, including, but not limited to, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid; a saturated or unsaturated, alicyclic aliphatic carboxylic acid, including, but not limited to, cyclopentaneacetic acid, cyclopentanepropionic acid, cyclohexaneacetic acid, cyclohexanebutyric acid, methylcyclohexaneacetic acid, a substituted or unsubstituted aromatic carboxylic acid, benzoic acid, toluic acid, naphthoic acid, ethylbenzoic acid, isobutylbenzoic acid, methylbutylbenzoic acid; an aromatic carboxylic acid, including, but not limited to, phenylacetic acid, benzoic acid, phenylpropionic acid, phenylvaleric acid, cinnamic acid, phenylpropiolic acid, naphthylacetic acid; a halo-alkoxyhydrocarbon carboxylic acid; a nitro-alkoxyhydrocarbon carboxylic acid; a hydroxy-alkoxyhydrocarbon carboxylic acid; an amino-alkoxyhydrocarbon carboxylic acid; a cyano-alkoxyhydrocarbon carboxylic acid; a thiocyano-alkoxyhydrocarbon carboxylic acid; as well as mono-acetic acid; di-acetic acid, trichloroacetic acid; 1,2,3,4,5,6-hexachlorocyclohexanecarboxylic acid, 1,2-dibromo-4-methylcyclohexanecarboxylic acid, 1,6-dibromo-3-methylcyclohexanecarboxylic acid, 1-bromo-3,5-dimethylcyclohexanecarboxylic acid, 2-chlorocyclohexanecarboxylic acid, 4-chlorocyclohexanecarboxylic acid, 2,3-dibromo-2-methylcyclohexanecarboxylic acid, 2,4,6-trinitrobenzoic acid, 2,5-dibromo-2-methylcyclohexanecarboxylic acid, 2-bromo-4-methylcyclohexanecarboxylic acid, 2-nitro-1-methyl-cyclobutanecarboxylic acid, 3,4-dinitrobenzoic acid, 3,5-dinitrobenzoic acid, 3-bromo-2,2,3-trimethylcyclopentanecarboxylic acid, 3-bromo-2-methylcyclohexanecarboxylic acid, 3-bromo-3-methylcyclohexanecarboxylic acid, 4-bromo-2-methylcyclohexanecarboxylic acid, 5-bromo-2-methylcyclohexanecarboxylic acid, '4,4-dichlorobenzilic acid, 4,5-dibromo-2-methylcyclohexanecarboxylic acid, 5-bromo-2-methylcyclohexanecarboxylic acid, 6-bromo-2-methylcyclohexanecarboxylic acid, 5,6-dibromo-2-methylcyclohexanecarboxylic acid, 6-bromo-3-methylcyclohexanecarboxylic acid, anisic acid, cyanoacetic acid, cyanopropionic acid, ethoxyformic acid (ethyl hydrogen carbonate), gallic acid, homogentisic acid, o-, m-, and p-chlorobenzoic acid, lactic acid, mevalonic acid, o-, m-, p-nitrobenzoic acid, p-hydroxybenzoic acid, salicylic acid, shikimic acid, thiocyanoacetic acid, trimethoxybenzoic acid, trimethoxycinnamic acid, veratric acid, α- and β-chloropropionic acid, α- and γ-bromobutyric acid and α- and δ-iodovaleric acid, β-resorcylic acid.

In some of any of the embodiments described herein, when one or more of $R_7$-$R_9$ is acyl, the acyl is such that R' is an alkyl or alkaryl or aryl, each of which being optionally substituted by one or more amine substituents.

In some embodiments, R is a substituted alkyl, and in some embodiments, R is substituted by hydroxy at the α position with respect to the carbonyl group, such that the acyl is α-hydroxy-acyl.

In some embodiments, the α-hydroxy-acyl is further substituted by one or more amine groups, and is an amino-substituted α-hydroxy-acyl.

In some of the embodiments of an acyl group as described herein, the amine substituents can be, for example, at one or more of positions β, γ, δ, and/or ω of the moiety R, with respect to the acyl.

Exemplary amino-substituted α-hydroxy-acyls include, without limitation, the moiety (S)-4-amino-2-hydroxybutyryl, which is also referred to herein as AHB. According to some embodiments of the present invention, an alternative to the AHB moiety can be the α-hydroxy-β-aminopropionyl (AHP) moiety. Additional exemplary amino-substituted α-hydroxy-acyls include, but are not limited to, L-(-)-γ-amino-α-hydroxybutyryl, L(-)-δ-amino-α-hydroxyvaleryl, L-(-)-β-benzyloxycarbonylamino-α-hydroxypropionyl, a L-(-)-δ-benzyloxycarbonylamino-α-hydroxyvaleryl It is noted herein that according to some embodiments of the present invention, other moieties which involve a combination of carbonyl(s), hydroxyl(s) and amino group(s) along a lower alkyl exhibiting any stereochemistry, are contemplated as optional substituents in place of AHB and/or AHP, including, for example, 2-amino-3-hydroxybutanoyl, 3-amino-2-hydroxypentanoyl, 5-amino-3-hydroxyhexanoyl and the likes.

In some of any of the embodiments described herein, one or more of $R_3$-$R_6$ is other than $OR_{16}$. In some of any of the embodiments described herein, one or more of $R_3$-$R_6$ is hydrogen.

In some of any of the embodiments described herein $R_3$ is hydrogen.

In some of any of the embodiments described herein $R_4$ is hydrogen.

In some of any of the embodiments described herein $R_3$ and $R_4$ are each hydrogen.

In some of any of the embodiments described herein, one or more of $R_3$-$R_6$ is $OR_{16}$ and $R_{16}$ is independently a monosaccharide moiety or an oligosaccharide moiety, as defined herein, such that the compound is a pseudo-trisaccharide, a pseudo-tetrasaccharide, a pseudo-pentasaccharide, a pseudo hexasaccharide, etc.

Whenever one or more of $R_3$-$R_6$ is $OR_{16}$ and $R_{16}$ is a monosaccharide moiety or an oligosaccharide moiety and one or more of $R_3$-$R_6$ is not $OR_{16}$ in which $R_{16}$ is a monosaccharide moiety or an oligosaccharide moiety, the one or more of $R_3$-$R_6$ is not $OR_{16}$ in which $R_{16}$ is a monosaccharide moiety or an oligosaccharide moiety can be as described herein for any of the respective embodiments for $R_3$-$R_6$.

The term "monosaccharide", as used herein and is well known in the art, refers to a simple form of a sugar that consists of a single saccharide molecule which cannot be further decomposed by hydrolysis. Most common examples of monosaccharides include glucose (dextrose), fructose, galactose, and ribose. Monosaccharides can be classified according to the number of carbon atoms of the carbohydrate, i.e., triose, having 3 carbon atoms such as glyceraldehyde and dihydroxyacetone; tetrose, having 4 carbon atoms such as erythrose, threose and erythrulose; pentose, having 5 carbon atoms such as arabinose, lyxose, ribose, xylose, ribulose and xylulose; hexose, having 6 carbon atoms such as allose, altrose, galactose, glucose, gulose, idose, mannose, talose, fructose, psicose, sorbose and tagatose; heptose, having 7 carbon atoms such as mannoheptulose, sedoheptulose; octose, having 8 carbon atoms such as 2-keto-3-deoxy-manno-octonate; nonose, having 9 carbon atoms such as sialose; and decose, having 10 carbon atoms. Monosaccharides are the building blocks of oligosaccharides like sucrose (common sugar) and other polysaccharides (such as cellulose and starch).

The term "oligosaccharide" as used herein refers to a compound that comprises two or more monosaccharide units, as these are defined herein, linked to one another via a glycosyl bond (—O—). Preferably, the oligosaccharide comprises 2-6 monosaccharides, more preferably the oligosaccharide comprises 2-4 monosaccharides and most preferably the oligosaccharide is a disaccharide moiety, having two monosaccharide units.

In some of any of the embodiments described herein, the monosaccharide is a pentose moiety, such as, for example, represented by Formula II. Alternatively, the monosaccharide moiety is hexose. Further alternatively, the monosaccharide moiety is other than pentose or hexose, for example, a hexose moiety as described in U.S. Pat. No. 3,897,412.

In some of any of the embodiments described herein, the monosaccharide moiety is a ribose, represented by Formula II:

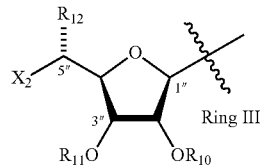

Formula II wherein:
the curved line denotes a position of attachment;
the dashed line indicates a stereo-configuration of position 5" being an R configuration or an S configuration;
$X_2$ is $OR_{13}$ or $NR_{14}R_{15}$;
each of $R_{10}$, $R_{11}$ and $R_{13}$ is independently selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl, and acyl;
$R_{12}$ is selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl, a substituted or unsubstituted amine, a substituted or unsubstituted amide, an acyl, a carboxylate, and a saturated or unsaturated and/or substituted or unsubstituted hydroxyalkyl;
each of $R_{14}$ and $R_{15}$ is independently selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl, acyl, and a cell-permealizable group, or, alternatively, $R_{14}$ and $R_{15}$, when present, form together a heterocyclic ring.

In some embodiments, $X_2$ is $OR_{13}$.

In some embodiments, $X_2$ is $NR_{14}R_{15}$.

In some of any of the embodiments described herein, $R_{12}$ is other than hydrogen. In some of these embodiments, $R_{12}$ is alkyl, cycloalkyl or aryl, and in some embodiments, $R_{12}$ is alkyl, preferably a lower alkyl, for example, methyl.

In some embodiments, $R_{12}$ is as defined herein for $R_1$.

In some of any of the embodiments where one or more of $R_3$-$R_6$ is $OR_{16}$ and $R_{16}$ is a monosaccharide moiety or an oligosaccharide moiety, one or more of the hydroxy groups in the monosaccharide or oligosaccharide moiety/moieties are substituted by an acyl, forming an ester (a carboxylate), as described herein in any of the respective embodiments.

In some of any of the embodiments described herein, one of $R_3$-$R_6$ is $OR_{16}$ and $R_{16}$ is a monosaccharide moiety such that the compound is a pseudo-trisaccharide.

In some of any of the embodiments described herein for a pseudo-trisaccharide, one or more, or all, of $R_{10}$ and $R_{11}$, and $R_{13}$ if present, can be an acyl, as described herein.

In some of any of the embodiments described herein for a pseudo-trisaccharide, one or more, or all, of $R_3$-$R_6$ are $OR_{16}$, such that in one of $R_3$-$R_6$, $R_{16}$ is a monosaccharide moiety, and in the others, $R_{16}$ is as defined herein (e.g., hydrogen, acyl).

In some of any of the embodiments described herein, $R_5$ is $OR_{16}$ in which $R_{16}$ is a monosaccharide moiety.

In some of these embodiments, the compound is represented by Formula Ib:

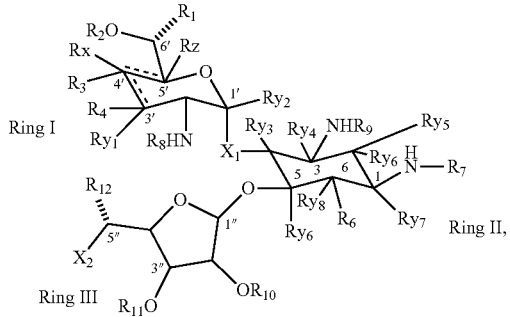

Formula Ib with the variables being as described herein for Formulae Ia and II, including any combination thereof.

In some of any of the embodiments described herein for Formulae Ia and Ib, $X_1$ is O.

In some of any of the embodiments described herein, the bond between C4' and C5' in Ring I is a single bond.

In some of any of the embodiments described herein, the bond between C4' and C5' in Ring I is a double bond. In some of these embodiments, Rx and Rz are absent. Alternatively, $R_3$ and Rz are absent.

In some of any of the embodiments described herein, the bond between C4' and C3' in Ring I is a single bond.

In some of any of the embodiments described herein, the bond between C4' and C3' in Ring I is a double bond. In some of these embodiments, Rx and Ry1 are absent. Alternatively, $R_4$ and Ry1 are absent.

In some of any of the embodiments described herein, one or more, or all, of Rx, Rz, Ry1, if present, and Ry2-Ry9 and Rw1-Rw3 is/are hydrogen.

In some of any of the embodiments described herein, $R_1$ is other than hydrogen.

In some of any of the embodiments described herein, $R_1$ is a hydroxyalkyl, wherein the alkyl can be further substituted or not.

In some of any of the embodiments described herein, $R_1$ is a hydroxymethyl.

In some of any of the embodiments described herein, $R_1$ is alkyl, alkenyl or alkynyl, each being substituted or unsubstituted.

In some of any of the embodiments described herein, $R_1$ is alkyl, preferably a lower alkyl, for example, methyl, ethyl, propyl, butyl or pentyl.

In some of any of the embodiments described herein, $R_1$ is or comprises an aryl which can be substituted or unsubstituted. In some embodiments, $R_1$ is an unsubstituted aryl and can be, as non-limiting examples, phenyl, 1-anthryl, 1-naphthyl, 2-naphthyl, 2-phenanthryl or 9-phenanthryl.

In some embodiments, $R_1$ is a substituted aryl, and can be, as non-limiting examples, 2-(N-ethylamino)phenyl, 2-(N-hexylamino)phenyl, 2-(N-methylamino)phenyl, 2,4-dimethoxyphenyl, 2-acetamidophenyl, 2-aminophenyl, 2-carboxyphenyl, 2-chlorophenyl, 2-ethoxyphenyl, 2-fluorophenyl, 2-hydroxymethylphenyl, 2-hydroxyphenyl, 2-hydroxyphenyl, 2-methoxycarbonylphenyl, 2-methoxyphenyl, 2-methylphenyl, 2-N,N-dimethylaminophenyl, 2-trifluoromethylphenyl, 3-(N,N-dibutylamino)phenyl, 3-(N,N-diethylamino)phenyl, 3,4,5-trimethoxyphenyl, 3,4-dichlorophenyl, 3,4-dimethoxyphenyl, 3,5-dimethoxyphenyl, 3-aminophenyl, 3-biphenylyl, 3-carboxyphenyl, 3-chloro-4-methoxyphenyl, 3-chlorophenyl, 3-ethoxycarbonylphenyl, 3-ethoxyphenyl, 3-fluorophenyl, 3-hydroxymethylphenyl, 3-hydroxyphenyl, 3-isoamyloxyphenyl, 3-isobutoxyphenyl, 3-isopropoxyphenyl, 3-methoxyphenyl, 3-methylphenyl, 3-N,N-dimethylaminophenyl, 3-tolyl, 3-trifluoromethylphenyl, 4-(benzyloxy)phenyl, 4-(isopropoxycarbonyl)phenyl, 4-(N,N-diethylamino)phenyl, 4-(N,N-dihexylamino)phenyl, 4-(N,N-diisopropylamino)phenyl, 4-(N,N-dimethylamino)phenyl, 4-(N,N-di-n-pentylamino)phenyl, 4-(n-hexyloxycarbonyl)phenyl, 4-(N-methylamino)phenyl, 4-(trifluoromethyl)phenyl, 4-aminophenyl, 4-benzyloxyphenyl, 4-biphenylyl, 4-butoxyphenyl, 4-butyramidophenyl, 4-carboxyphenyl, 4-chlorophenyl, 4-ethoxycarbonylphenyl, 4-hexanamidophenyl, 4-hydroxymethylphenyl, 4-hydroxyphenyl, 4-iodophenyl, 4-isobutylphenyl, 4-isobutyramidophenyl, 4-isopropoxyphenyl, 4-isopropylphenyl, 4-methoxyphenyl, 4-methylphenyl, 4-n-hexanamidophenyl, 4-n-hexyloxyphenyl, 4-n-hexylphenyl, 4-nitrophenyl, 4-nitrophenyl, 4-propionamidophenyl, 4-tolyl, 4-trifluoromethylphenyl or 4-valeroyloxycarbonylphenyl.

In some of any of the embodiments described herein, $R_1$ is or comprises a substituted or unsubstituted heteroaryl, and can be, as non-limiting examples, 2-anthryl, 2-furyl, 2-indolyl, 2-naphthyl, 2-pyridyl, 2-pyrimidyl, 2-pyrryl, 2-quinolyl, 2-thienyl, 3-furyl, 3-indolyl, 3-thienyl, 4-imidazolyl, 4-pyridyl, 4-pyrimidyl, 4-quinolyl, 5-methyl-2-thienyl and 6-chloro-3-pyridyl.

In some of any of the embodiments described herein, $R_1$ is or comprises an amine, as defined herein, and can be, as non-limiting examples, —$NH_2$, —$NHCH_3$, —$N(CH_3)_2$, —NH—$CH_2$—$CH_2$—$NH_2$, —NH—$CH_2$—$CH_2$—OH and —NH—$CH_2$—$CH(OCH_3)_2$.

In some of any of the embodiments described herein, $R_1$ is alkyl, and in some embodiments it is a lower alkyl, of 1 to 4 carbon atoms, including, but not limited to, methyl, ethyl, propyl, butyl, isopropyl, and isobutyl.

In some of any of the embodiments described herein, $R_1$ is a non-substituted alkyl.

In some of any of the embodiments described herein, $R_1$ is methyl.

Alternatively, in some of any of the embodiments described herein, $R_1$ is cycloalkyl, including, but not limited to, cyclopropyl, cyclobutyl, cyclopentyl and cyclohexyl.

Further alternatively, in some of any of the embodiments described herein, $R_1$ is aryl, such as substituted or unsubstituted phenyl. Non-limiting examples include unsubstituted phenyl and toluene.

Further alternatively, in some of any of the embodiments described herein, $R_1$ is alkaryl, such as, for example, a substituted or unsubstituted benzyl.

In some of any of the embodiments described herein, $R_1$ is other than alkyl, cycloalkyl and aryl.

In some of any of the embodiments described herein, $R_1$ is other than alkyl, cycloalkyl and aryl, wherein each is unsubstituted.

In some of any of the embodiments described herein, $R_1$ is other than methyl.

In some of any of the embodiments described herein, $R_2$ is hydrogen.

In some of any of the embodiments described herein, $R_2$ is other than hydrogen.

In some of any of the embodiments described herein, $R_2$ is an acyl, forming as ester at this position, as described herein.

In some embodiments, $R_2$ is alkyl, preferably selected from the group consisting of methyl, ethyl and propyl.

In some of any of the embodiments described herein, $R_2$ is alkyl, and in some of these embodiments $R_2$ is a substituted alkyl, for example, an alkyl substituted by one or more amine groups (aminoalkyl).

In some of any of the embodiments described herein, $R_2$ is a substituted or unsubstituted alkyl, as defined herein, or a substituted or unsubstituted cycloalkyl, as defined herein.

In some of any of the embodiments described herein, $R_2$ is a substituted or unsubstituted aryl, as defined herein.

In some of any of the embodiments described herein, $R_1$ is hydroxyalkyl and $R_2$ is hydrogen.

In some of any of the embodiments described herein, $R_1$ is hydroxyalkyl and $R_2$ is an acyl.

In some of any of the embodiments described herein, one or more of $R_7$-$R_9$ and of $R_{14}$ and $R_{15}$, if present, is independently an alkyl, a cell-permealizable group, as described herein, or an acyl, such as, for example, an alpha-hydroxy acyl or an amino-substituted alpha-hydroxy acyl, as described herein.

In some of any of the embodiments described herein, one or more of $R_7$-$R_9$ and of $R_{14}$ and $R_{15}$, if present, is a sulfonyl, for example, an alkyl sulfonyl or an aryl sulfonyl.

Exemplary moieties represented by one or more of $R_7$-$R_9$ and of $R_{14}$ and $R_{15}$, if present, include, but are not limited to, hydrogen, (R/S)-4-amino-2-hydroxybutyryl (AHB), (R/S)-3-amino-2-hydroxypropionyl (AHP), 5-aminopentanoyl, 5-hydroxypentanoyl, formyl, —C(=O)—O-methyl, —C(=O)—O-ethyl, —C(=O)-benzyl, -β-amino-α-hydroxypropionyl, -δ-amino-α-hydroxyvaleryl, -β-benzyloxycarbonylamino-α-hydroxypropionyl, -δ-benzyloxycarbonylamino-α-hydroxyvaleryl, methylsulfonyl, phenylsulfonyl, benzoyl, propyl, isopropyl, —(CH$_2$)$_2$NH$_2$, —(CH$_2$)$_3$NH$_2$, —CH$_2$CH(NH$_2$)CH$_3$, —(CH$_2$)$_4$NH$_2$, —(CH$_2$)$_5$NH$_2$, —(CH$_2$)$_2$NH-ethyl, —(CH$_2$)$_2$NH(CH$_2$)$_2$NH$_2$, —(CH$_2$)$_3$NH(CH$_2$)$_3$NH$_2$, —(CH$_2$)$_3$NH(CH$_2$)$_4$NH(CH$_2$)$_3$NH$_2$, —CH(—NH$_2$)CH$_2$(OH), —CH(OH)CH$_2$(NH$_2$), —CH(—OH)—(CH$_2$)$_2$(NH$_2$), —CH(—NH$_2$)—(CH$_2$)$_2$(OH), —CH(—CH$_2$NH$_2$)—(CH$_2$OH), —(CH$_2$)$_4$NH(CH$_2$)$_3$NH$_2$, —(CH$_2$)$_2$NH(CH$_2$)$_2$NH(CH$_2$)$_2$NH$_2$, —(CH$_2$)$_2$N(CH$_2$CH$_2$NH$_2$)$_2$, —CH$_2$—C(=O)NH$_2$, —CH(CH$_3$)—C(=O)NH$_2$, —CH$_2$-phenyl, —CH(i-propyl)-C(=O)NH$_2$, —CH(benzyl)-C(=O)NH$_2$, —(CH$_2$)$_2$OH, —(CH$_2$)$_3$OH and —CH(CH$_2$OH)$_2$.

In some of any of the embodiments described herein, $R_7$ is hydrogen, (R/S)-4-amino-2-hydroxybutyryl (AHB), (R/S)-3-amino-2-hydroxypropionyl, 5-aminopentanoyl, 5-hydroxypentanoyl, formyl, —C(=O)—O-methyl, —C(=O)—O-ethyl, —C(=O)—O-benzyl, —O-amino-α-hydroxypropionyl, -δ-amino-α-hydroxyvaleryl, -β-benzyloxycarbonylamino-α-hydroxypropionyl, -δ-benzyloxycarbonylamino-α-hydroxyvaleryl, methylsulfonyl, phenylsulfonyl, benzoyl, propyl, isopropyl, —(CH$_2$)$_2$NH$_2$, —(CH$_2$)$_3$NH$_2$, —CH$_2$CH(NH$_2$)CH$_3$, —(CH$_2$)$_4$NH$_2$, —(CH$_2$)$_5$NH$_2$, —(CH$_2$)$_2$NH-ethyl, —(CH$_2$)$_2$NH(CH$_2$)$_2$NH$_2$, —(CH$_2$)$_3$NH(CH$_2$)$_3$NH$_2$, —(CH$_2$)$_3$NH(CH$_2$)$_4$NH(CH$_2$)$_3$NH$_2$, —CH(—NH$_2$)CH$_2$(OH), —CH(OH)CH$_2$(NH$_2$), —CH(—OH)—(CH$_2$)$_2$(NH$_2$), —CH(—NH$_2$)—(CH$_2$)$_2$(OH), —CH(—CH$_2$NH$_2$)—(CH$_2$OH), —(CH$_2$)$_4$NH(CH$_2$)$_3$NH$_2$, —(CH$_2$)$_2$NH(CH$_2$)$_2$NH(CH$_2$)$_2$NH$_2$, —(CH$_2$)$_2$N(CH$_2$CH$_2$NH$_2$)$_2$, —CH$_2$—C(=O)NH$_2$, —CH(CH$_3$)—C(=O)NH$_2$, —CH$_2$-phenyl, —CH(i-propyl)-C(=O)NH$_2$, —CH(benzyl)-C(=O)NH$_2$, —(CH$_2$)$_2$OH, —(CH$_2$)$_3$OH or —CH(CH$_2$OH)$_2$.

In some of any of the embodiments described herein, $R_7$ is other than hydrogen, (R/S)-4-amino-2-hydroxybutyryl (AHB), and (R/S)-3-amino-2-hydroxypropionyl (AHP).

In some of any of the embodiments described herein, $R_7$ is other than hydrogen, and in some of these embodiments, $R_7$ is other than an amino-substituted alpha-hydroxy acyl, as defined herein.

In some of any of the embodiments described herein, $R_7$ is other than alkyl, cycloalkyl, aryl and a cell-permealizable group, as described herein.

In some of any of the embodiments described herein, one or both of $R_8$ and $R_9$ is independently hydrogen, (R/S)-4-amino-2-hydroxybutyryl (AHB), (R/S)-3-amino-2-hydroxypropionate (AHP), (R/S)-3-amino-2-hydroxypropionyl, 5-aminopentanoyl, 5-hydroxypentanoyl, formyl, —COO-methyl, —COO-ethyl, —COO-benzyl, -β-amino-α-hydroxypropionyl, -δ-amino-α-hydroxyvaleryl, —O-benzyloxycarbonylamino-α-hydroxypropionyl, -δ-benzyloxycarbonylamino-α-hydroxyvaleryl, methylsulfonyl, phenylsulfonyl, benzoyl, propyl, isopropyl, —(CH$_2$)$_2$NH$_2$, —(CH$_2$)$_3$NH$_2$, —CH$_2$CH(NH$_2$)CH$_3$, —(CH$_2$)$_4$NH$_2$, —(CH$_2$)$_5$NH$_2$, —(CH$_2$)$_2$NH-ethyl, —(CH$_2$)$_2$NH(CH$_2$)$_2$NH$_2$, —(CH$_2$)$_3$NH(CH$_2$)$_3$NH$_2$, —(CH$_2$)$_3$NH(CH$_2$)$_4$NH(CH$_2$)$_3$NH$_2$, —CH(—NH$_2$)CH$_2$(OH), —CH(OH)CH$_2$(NH$_2$), —CH(—OH)—(CH$_2$)$_2$(NH$_2$), —CH(—NH$_2$)—(CH$_2$)$_2$(OH), —CH(—CH$_2$NH$_2$)—(CH$_2$OH), —(CH$_2$)$_4$NH(CH$_2$)$_3$NH$_2$, —(CH$_2$)$_2$NH(CH$_2$)$_2$NH(CH$_2$)$_2$NH$_2$, —(CH$_2$)$_2$N(CH$_2$CH$_2$NH$_2$)$_2$, —CH$_2$—C(=O)NH$_2$, —CH(CH$_3$)—C(=O)NH$_2$, —CH$_2$-phenyl, —CH(i-propyl)-C(=O)NH$_2$, —CH(benzyl)-C(=O)NH$_2$, —(CH$_2$)$_2$OH, —(CH$_2$)$_3$OH or —CH(CH$_2$OH)$_2$.

In some of any of the embodiments described herein, an amino-substituted alpha-hydroxy acyl is (S)-4-amino-2-hydroxybutyryl (AHB).

In some of any of the embodiments described herein, each of $R_7$-$R_9$ is other than hydrogen, (R/S)-4-amino-2-hydroxybutyryl (AHB), and (R/S)-3-amino-2-hydroxypropionyl (AHP).

In some of any of the embodiments described herein, each of $R_7$-$R_9$ is other than hydrogen, and in some of these embodiments, each of $R_7$-$R_9$ is other than an amino-substituted alpha-hydroxy acyl, as defined herein.

In some of any of the embodiments described herein, each of $R_7$-$R_9$ is other than alkyl, cycloalkyl, aryl and a cell-permealizable group, as described herein.

Herein throughout, an amine which bears a substituent other than hydrogen is referred to herein as a "modified amine substituent" or simply as a "modified amine".

According to some embodiments of the present invention, one or both of the amine substituents at positions 1 ($R_7$), 2' ($R_8$), 3 ($R_9$) or 5'' ($R_{14}$ or $R_{15}$), if present, of the aminoglycoside structure represented by Formulae Ia and Ib, is modified to include a hydrophobic moiety such as alkyl, cycloalkyl, alkaryl and/or aryl, or a group which is positively-charged at physiological pH and which can increase cell permeability of the compound (also referred to herein interchangeably as "cell-permealizable group" or "cell-permealizing group"), such as guanine or guanidine groups, as defined herein, or, alternatively, hydrazine, hidrazide, thiohydrazide, urea and thiourea.

In some of any of the embodiments described herein, one or more $R_7$-$R_9$ and $R_{14}$ and $R_{15}$, if present, is a cell-permealizable group as defined herein, and in some embodiments, it is a guanidyl, as defined herein.

In some of any of the embodiments described herein, one or more $R_7$-$R_9$ and $R_{14}$ and $R_{15}$, if present, is a hydrophobic moiety such as alkyl, cycloalkyl, alkaryl and/or aryl.

In some of any of the embodiments described herein, none of $R_7$-$R_9$ and $R_{14}$ and $R_{15}$, if present, is a hydrophobic moiety such as alkyl, cycloalkyl, alkaryl and/or aryl.

In some of any of the embodiments described herein, none of $R_7$-$R_9$ and $R_{14}$ and $R_{15}$, if present, is a cell-permealizable group, as defined herein.

In some of any of the embodiments described herein, none of $R_7$-$R_9$ and $R_{14}$ and $R_{15}$, if present, is a modified amine as described herein.

In some of any of the embodiments described herein, one or more $R_7$-$R_9$ and $R_{14}$ and $R_{15}$, if present, is an acyl, as defined herein, and in some of these embodiments, the acyl can independently be an amino-substituted alpha-hydroxy acyl, as defined herein.

In some of any of the embodiments described herein, whenever a variable is defined as an unsubstituted aryl, the unsubstituted aryl can be, for example, phenyl, 1-anthryl, 1-naphthyl, 2-naphthyl, 2-phenanthryl and/or 9-phenanthryl.

In some of any of the embodiments described herein, whenever a variable is defined as a substituted or unsubstituted heteroaryl, the heteroaryl can be, for example, 2-anthryl, 2-furyl, 2-indolyl, 2-naphthyl, 2-pyridyl, 2-pyrimidyl, 2-pyrryl, 2-quinolyl, 2-thienyl, 3-furyl, 3-indolyl, 3-thienyl, 4-imidazolyl, 4-pyridyl, 4-pyrimidyl, 4-quinolyl, 5-methyl-2-thienyl and/or 6-chloro-3-pyridyl.

In some of any of the embodiments described herein, whenever a variable is defined as a substituted aryl, the aryl can be, for example, 2-(N-ethylamino)phenyl, 2-(N-hexylamino)phenyl, 2-(N-methylamino)phenyl, 2,4-dimethoxyphenyl, 2-acetamidophenyl, 2-aminophenyl, 2-carboxyphenyl, 2-chlorophenyl, 2-ethoxyphenyl, 2-fluorophenyl, 2-hydroxymethylphenyl, 2-hydroxyphenyl, 2-hydroxyphenyl, 2-methoxycarbonylphenyl, 2-methoxyphenyl, 2-methylphenyl, 2-N,N-dimethylaminophenyl, 2-trifluoromethylphenyl, 3-(N,N-dibutylamino)phenyl, 3-(N,N-diethylamino)phenyl, 3,4,5-trimethoxyphenyl, 3,4-dichlorophenyl, 3,4-dimethoxyphenyl, 3,5-dimethoxyphenyl, 3-aminophenyl, 3-biphenylyl, 3-carboxyphenyl, 3-chloro-4-methoxyphenyl, 3-chlorophenyl, 3-ethoxycarbonylphenyl, 3-ethoxyphenyl, 3-fluorophenyl, 3-hydroxymethylphenyl, 3-hydroxyphenyl, 3-isoamyloxyphenyl, 3-isobutoxyphenyl, 3-isopropoxyphenyl, 3-methoxyphenyl, 3-methylphenyl, 3-N,N-dimethylaminophenyl, 3-tolyl, 3-trifluoromethylphenyl, 4-(benzyloxy)phenyl, 4-(isopropoxycarbonyl)phenyl, 4-(N,N-diethylamino)phenyl, 4-(N,N-dihexylamino)phenyl, 4-(N,N-diisopropylamino)phenyl, 4-(N,N-dimethylamino)phenyl, 4-(N,N-di-n-pentylamino)phenyl, 4-(n-hexyloxycarbonyl)phenyl, 4-(N-methylamino)phenyl, 4-(trifluoromethyl)phenyl, 4-aminophenyl, 4-benzyloxyphenyl, 4-biphenylyl, 4-butoxyphenyl, 4-butyramidophenyl, 4-carboxyphenyl, 4-chlorophenyl, 4-ethoxycarbonylphenyl, 4-hexanamidophenyl, 4-hydroxymethylphenyl, 4-hydroxyphenyl, 4-iodophenyl, 4-isobutylphenyl, 4-isobutyramidophenyl, 4-isopropoxyphenyl, 4-isopropylphenyl, 4-methoxyphenyl, 4-methylphenyl, 4-n-hexanamidophenyl, 4-n-hexyloxyphenyl, 4-n-hexylphenyl, 4-nitrophenyl, 4-nitrophenyl, 4-propionamidophenyl, 4-tolyl, 4-trifluoromethylphenyl and/or 4-valeroyloxycarbonylphenyl.

In some of any of the embodiments described herein, the amine substituent at position 1 ($R_7$, Ring II) in Formula Ia or Ib, is a modified amine, as described herein, such that $R_7$ is other than hydrogen.

In some of these embodiments, $R_7$ can be alkyl, cycloalkyl, alkaryl, aryl, an acyl, or an amino-substituted α-hydroxy acyl, as defined herein, such as, for example, (S)-4-amino-2-hydroxybutyryl (AHB), or (S)-4-amino-2-hydroxy propionyl (AHP).

In some of the embodiments where $R_7$ is alkyl, the alkyl can be, for example, a lower alkyl, of 1-4 carbon atoms, such as, but not limited to, methyl, ethyl, propyl, butyl, isopropyl, and isobutyl, each being optionally substituted, as described herein.

In some of these embodiments, the alkyl is independently a non-substituted alkyl, such as, but not limited to, ethyl, propyl and isopropyl.

In some of these embodiments, the alkyl is independently a substituted methyl, such as, but not limited to, an alkaryl such as benzyl.

Alternatively, $R_7$ is cycloalkyl, and the cycloalkyl can be, for example, cyclopropyl, cyclobutyl, cyclopentyl and cyclohexyl.

Further alternatively, $R_7$ is aryl, and the aryl can be, for example, a substituted or unsubstituted phenyl. Non-limiting examples include unsubstituted phenyl and toluene.

In some of any of the embodiments described herein, $R_7$ is alkyl, cycloalkyl or aryl, as described herein.

In some of these embodiments, $R_1$ is alkyl, cycloalkyl or aryl, and is preferably alkyl, as defined herein.

In some of these embodiments, $R_1$ is alkyl, cycloalkyl or aryl, and is preferably alkyl, as defined herein, $R_3$ is $OR_{16}$ and $R_{16}$ is hydrogen (such that $R_3$ is hydroxy).

In some of any of the embodiments described herein, $R_7$ is alkyl and in some embodiments it is a lower alkyl, of 1-4 carbon atoms.

In some embodiments, $R_7$ is an alkyl such as ethyl, propyl, butyl, isopropyl, isobutyl, tert-butyl, each being optionally substituted.

In some embodiments, $R_7$ is methyl or ethyl, and is preferably a substituted methyl or ethyl. In some of these embodiments, the methyl or ethyl is substituted by, for example, a cycloalkyl or aryl. Such substituents are also referred to in the art as alkylcycloalkyl and alkaryl, respectively. An exemplary alkaryl is benzyl (—$CH_2$-Phenyl).

In some embodiments, $R_7$ is propyl or isopropyl.

In some embodiments, $R_7$ is benzyl.

In some of any of the embodiments described herein, $R_7$ is a cell-permealizable group, as defined herein, and in some embodiments, $R_7$ is guanidyl.

In some of any of the embodiments described herein, $R_1$ is alkyl, cycloalkyl or aryl, and is preferably alkyl, as defined herein, and $R_7$ is alkyl, as defined herein, preferably, ethyl, propyl, isopropyl or benzyl.

In some of any of the embodiments described herein, $R_1$ is alkyl, cycloalkyl or aryl, and is preferably alkyl, as defined herein; $R_7$ is alkyl, as defined herein, preferably, ethyl, propyl, isopropyl or benzyl; and $R_3$ is hydrogen.

In some of any of the embodiments described herein, $R_1$ is alkyl, cycloalkyl or aryl, and is preferably alkyl, as defined herein; $R_7$ is a cell-permealizing group, as defined herein, preferably, guanidine or guanine; and $R_3$ is hydrogen.

In some of any of the embodiments described herein, $R_1$ is alkyl, cycloalkyl or aryl, and is preferably alkyl, as defined herein; $R_7$ is a cell-permealizing group, as defined herein, preferably, guanidine or guanine, more preferably guanidine (guanidinyl).

Exemplary pseudo-disaccharide compounds are Compounds NB144, NB145, NB146 and NB150 (see, Table 1).

In some of any of the embodiments described herein, $R_7$ is hydrogen or a moiety such as (S)-4-amino-2-hydroxybutyryl (AHB), or (S)-4-amino-2-hydroxypropionyl (AHP).

In some of these embodiments, a modified amine is introduced to the compound within a third saccharide moiety (Ring III; e.g., as $R_5$ in Formula Ia).

Any of the embodiments described herein for Formula Ia, and any combination thereof, are included within the embodiments relating to Formula Ib.

In some of any of the embodiments of Formula Ib, $R_1$ is alkyl, as defined herein.

In some of any of the embodiments of Formula Ib, $R_2$ and $R_7$ are as described in any of the respective embodiments for Formula Ia.

In some of any of the embodiments of Formula Ib, $R_3$, $R_4$ and $R_6$ are each hydrogen.

In some of these embodiments, $R_7$ is alkyl, cycloalkyl or aryl, and is preferably alkyl, as described herein.

In some embodiments, $R_1$ is alkyl, cycloalkyl or aryl, and is preferably alkyl, as defined herein; $R_7$ is alkyl, as defined herein, preferably, ethyl, propyl, isopropyl or benzyl; and $R_5$ is a monosaccharide moiety of Formula II, wherein $R_{14}$ and $R_{15}$ are both hydrogen.

An exemplary compound is NB147 (see, Table 1).

In some of any of the embodiments of Formula Ib, $R_7$ is hydrogen, acyl or amino-substituted α-hydroxy-acyl, as defined herein.

In some of these embodiments, X is $NR_{14}R_{15}$; and one of $R_{14}$ and $R_{15}$ is other than hydrogen. In some of these embodiments, one of $R_{14}$ and $R_{15}$ is a cell-permealizable group such as, for example, a guanidine group. Alternatively, one of $R_{14}$ and $R_{15}$ is alkyl, cycloalkyl or aryl, as defined, for example, for any of the embodiments of $R_7$.

In some of any of the embodiments described herein, $R_1$ is alkyl, cycloalkyl or aryl, and is preferably alkyl, as defined herein; $R_7$ is hydrogen or amino-substituted α-hydroxy-acyl, as defined herein; $R_5$ is a monosaccharide moiety of Formula II; X is $NR_{14}R_{15}$; and $R_{15}$ is a guanidine group (guanidinyl; guanidyl).

In some of these embodiments, $R_{14}$ is hydrogen.

Exemplary compounds are NB 151 and NB 152 (see, Table 1).

In some of any of the embodiments described herein for Formula Ib, X is $NR_{14}R_{15}$; and $R_{14}$ is hydrogen or methyl, unless specifically indicated otherwise.

In some of any of the embodiments described herein for Formula Ib, X is $NR_{14}R_{15}$; and $R_{14}$ is hydrogen.

In some of any of the embodiments described herein for Formula Ib, X is $NR_{14}R_{15}$; and $R_{15}$ is acyl, as defined herein.

In some of any of the embodiments described herein for Formula Ib, X is $NR_{14}R_{15}$; and one or both of $R_{14}$ and $R_{15}$ is a substituted or unsubstituted alkyl, a substituted or unsubstituted cycloalkyl, a substituted or unsubstituted aryl, a substituted or unsubstituted alkaryl, or a substituted or unsubstituted heteroaryl, or an acyl, as these terms are defined herein.

In some of any of the embodiments described herein for Formula Ib, X is $NR_{14}R_{15}$; and $R_{14}$ and $R_{15}$ form together a nitrogen-containing heterocyclic ring, such as, but not limited to, morpholine, piperidine, and piperazine.

In some of any of the embodiments described herein for Formula Ib, X is $OR_{13}$; and $R_{13}$ is as defined herein for $R_{16}$, in any of the respective embodiments. In some of these embodiments, $R_{13}$ is an acyl, forming an ester at the 5" position, as described herein in any of the respective embodiments.

In some of any one of the embodiments described herein for Formulae Ia and Ib, and any combination thereof, the stereoconfiguration at position 6' is an R configuration.

In some of any one of the embodiments described herein for Formula Ib, and any combination thereof, the stereoconfiguration at position 5" is an S configuration.

Table 1 below presents exemplary compounds according to some embodiments of the present invention.

TABLE 1

| Compound | Structure |
|---|---|
| NB144 | 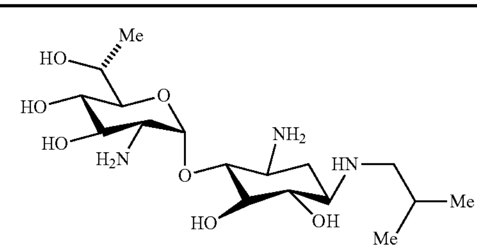 |

TABLE 1-continued

| Compound | Structure |
|---|---|
| NB145 | (structure image) |
| NB146 | (structure image) |
| NB147 | (structure image) |
| NB150 | (structure image) |
| NB151 | (structure image) |

TABLE 1-continued

| Compound | Structure |
|---|---|
| NB152 | (structure image) |

Additional exemplary compounds include compounds referred to herein as NB153, NB155, NB156, NB157, NB154, NB158, and NB159, the structures of which are presented in the Examples section that follows.

Additional exemplary compounds include compounds referred to herein as multi-esterified compounds, in which one or more, or two or more, of $R_3$-$R_6$ is $OR_{16}$, and one or more of the $R_{16}$, $R_2$ and $R_{13}$, if present, is independently an acyl, forming an ester at the respective position, such that the compound comprises at least two esters. The structures of exemplary such are presented in Scheme 14 in the Examples section that follows.

According to some of any of the embodiments of the present invention, excluded from the scope of the present invention are compounds known in the art, including any of the documents cited in the Background section of the instant application, which are encompassed by Formula Ia or Ib.

Exemplary compounds which are excluded from the scope of the present embodiments include, but are not limited to, gentamicin, geneticin, fortimycin, apramycin, arbekacin, dibekacin, geneticin (G-418, G418), habekacin, kanamycin, Lividomycin, paromomycin, streptomycin and tobramycin.

Additional exemplary compounds which are excluded from the scope of the present embodiments include compounds represented by Formula Ia, in which $R_2$ is hydrogen, and $R_7$ is hydrogen, AHB or AHP, or equivalents of AHB and AHP, as defined in WO 2007/113841 and WO 2012/066546; and compounds represented by Formula Ib, in which $R_2$ is hydrogen, $R_7$ is hydrogen, AHB or AHP, or equivalents of AHB and AHP, as defined in WO 2007/113841 and WO 2012/066546, and $R_{14}$ and $R_{15}$ are each hydrogen.

According to some embodiments of the present invention, when $R_2$ is hydrogen, then $R_7$ is not hydrogen, AHB or AHP, or equivalents of AHB and AHP, as defined in WO 2007/113841 and WO 2012/066546, and/or one or both of $R_{14}$ and $R_{15}$, if present, is not hydrogen.

According to some embodiments of the present invention, one or both of the amine substituents at positions 1 or 5" of the aminoglycoside structure is a modified amine, as defined herein, such that $R_7$ and/or one or both of $R_{14}$ and $R_{15}$ is not hydrogen.

The chemical structures of exemplary compounds which are excluded from the scope of the present invention are presented in Table 2 below.

TABLE 2

| Number | Structure |
|---|---|
| n/a | (structure image) |
| NB30 | (structure image) |

TABLE 2-continued

| Number | Structure |
|---|---|
| n/a | (structure) |
| n/a | (structure) |
| n/a | (structure) |
| n/a | (structure) |
| n/a | (structure) |
| n/a | (structure) |

TABLE 2-continued
| Number | Structure |
|---|---|
| n/a | 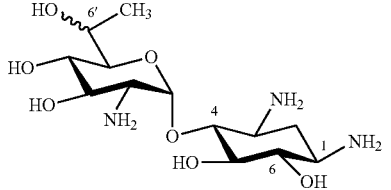 |
| n/a | 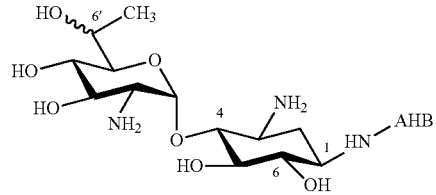 |
| NB54 | 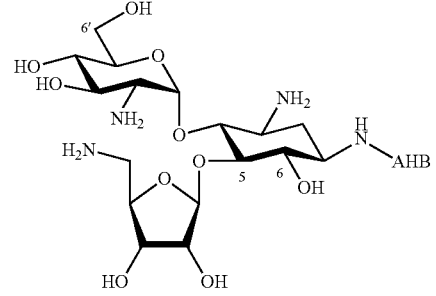 |
| NB74 | 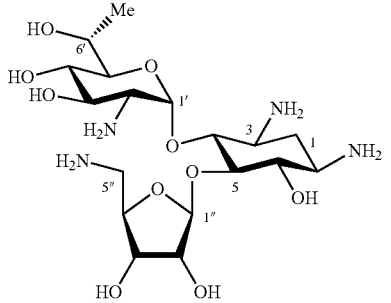 |
| NB84 | 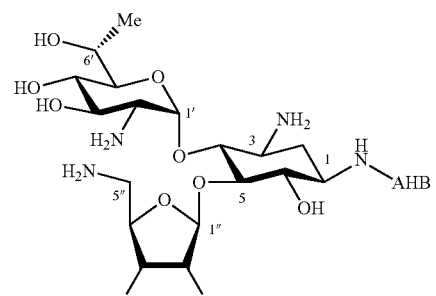 |

TABLE 2-continued

| Number | Structure |
|---|---|
| NB118 | *(structure)* |
| NB119 | *(structure)* |
| NB122 | *(structure)* |
| NB123 | *(structure)* |
| NB124 | *(structure)* |

TABLE 2-continued

| Number | Structure |
|---|---|
| NB125 | 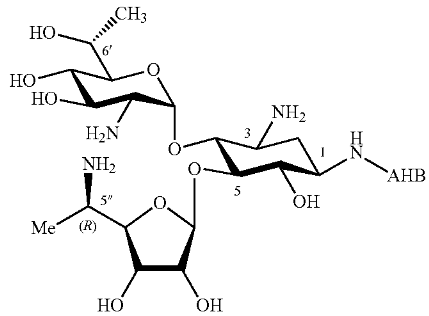 |
| NB127 | 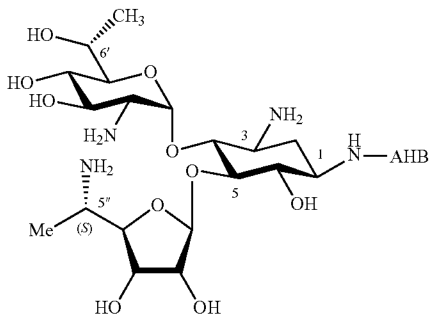 |
| NB128 | 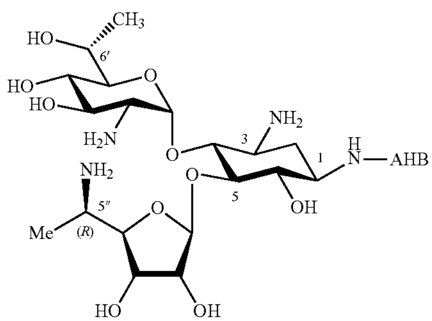 |

According to some embodiments of the present invention, excluded from the scope of the present embodiments are also compounds represented by Formulae I' a as follows:

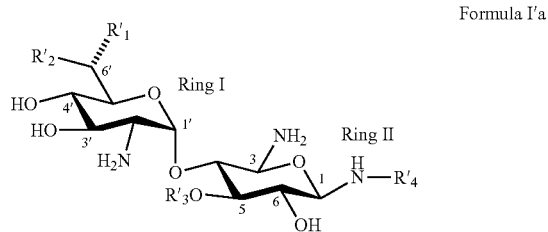

Formula I'a wherein:
the dashed line indicates a stereo-configuration of position 6' being an R configuration or an S configuration;
R'$_1$ is alkyl, cycloalkyl, alkaryl or aryl;
R'$_2$ is OR', wherein R' is selected from hydrogen, a substituted or unsubstituted alkyl, a substituted or unsubstituted cycloalkyl, a substituted or unsubstituted aryl, a substituted or unsubstituted heteroaryl, a substituted or unsubstituted alkaryl, and an acyl, as defined herein;

R'$_4$ is selected from hydrogen, acyl, an amino-substituted alpha-hydroxy acyl, a substituted or unsubstituted alkyl, a substituted or unsubstituted cycloalkyl, a substituted or unsubstituted aryl, a substituted or unsubstituted alkaryl and a cell-permealizable group, such as guanyl or guanidyl; and R'$_3$ is hydrogen or a monosaccharide moiety represented by Formula II':

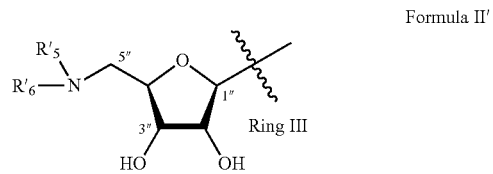

Formula II' wherein the curved line denotes a position of attachment; and

R'$_5$ and R'$_6$ are each independently selected from hydrogen, a substituted or unsubstituted alkyl, a substituted or unsubstituted cycloalkyl, a substituted or unsubstituted aryl, a substituted or unsubstituted alkaryl, a substituted or unsubstituted heteroaryl, acyl, and a cell-permealizable group such as guanyl and guanidinyl, or, alternatively, $R'_5$ and $R'_6$ form together a heterocyclic ring, wherein when $R'_2$ is hydrogen, $R'_4$ is not hydrogen, AHB or AHP, and/or at least one of $R'_5$ and/or $R'_6$, if present, is not hydrogen.

According to some embodiments of the present invention, excluded from the scope of the present embodiments are also compounds represented by Formulae I'b as follows:

Formula I'b or a pharmaceutically acceptable salt thereof, wherein:

the dashed line indicates a stereo-configuration of position 6' being an R configuration or an S configuration;

$R'_1$ is selected from hydrogen, alkyl, cycloalkyl or aryl; $R_2$ is OR', wherein R' is selected from hydrogen, a substituted or unsubstituted alkyl, a substituted or unsubstituted cycloalkyl, a substituted or unsubstituted aryl, a substituted or unsubstituted heteroaryl, a substituted or unsubstituted alkaryl, and an acyl;

$R'_4$ is selected from hydrogen, acyl, an amino-substituted alpha-hydroxy acyl, a substituted or unsubstituted alkyl, a substituted or unsubstituted cycloalkyl, a substituted or unsubstituted aryl, a substituted or unsubstituted alkaryl, and a cell-permealizable group;

$R'_6$ and $R'_7$ are each independently selected from hydrogen, a substituted or unsubstituted alkyl, a substituted or unsubstituted cycloalkyl, a substituted or unsubstituted aryl, a substituted or unsubstituted alkaryl, a substituted or unsubstituted heteroaryl, acyl, and a cell-permealizable group, or, alternatively, $R'_5$ and $R'_6$ form together a heterocyclic ring; and $R'_8$ is alkyl, cycloalkyl or aryl, wherein when $R'_2$ is hydrogen, $R'_4$ is not hydrogen, AHB or AHP, and/or at least one of $R'_6$ and/or $R'_7$, if present, is not hydrogen.

In some of any of the embodiments described herein, excluded from the scope of the present invention are the compounds presented in Table 1.

According to some of any of the embodiments described herein, a compound as described herein is represented by Formula Ic:

Formula Ic or a pharmaceutically acceptable salt thereof, wherein:

the dashed line indicates a stereo-configuration of position 6' being an R configuration or an S configuration;

$X_1$ is O or S;

Rx, Ry1 and Rz are each independently hydrogen, alkyl or cycloalkyl;

Ry2-Ry9 and Rw1-Rw3 are each independently selected from hydrogen, alkyl, alkenyl, alkynyl, aryl, heteroaryl and cycloalkyl, each being substituted or unsubstituted, or, alternatively, each can be as defined herein for $R_7$-$R_9$;

$R_1$ is a substituted or unsubstituted hydroxy alkyl (e.g., —$CH_2$—OH);

$R_2$ is selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl and acyl, as described herein for Formula Ia;

$R_3$-$R_6$ are each independently selected from the group consisting of hydrogen, alkyl, alkenyl, alkynyl, cycloalkyl, heteroalicyclic, aryl, heteroaryl, amine and $OR_{16}$, wherein $R_{16}$ is independently selected from hydrogen, a monosaccharide moiety, an oligosaccharide moiety, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl and acyl, as described herein for any of the respective embodiments of Formula Ia; and $R_7$-$R_9$ are each independently selected from the group consisting of hydrogen, acyl, an amino-substituted alpha-hydroxy acyl, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted alkaryl, carboxylate, sulfonyl (including alkyl sulfonyl and aryl sulfonyl) and a cell-permealizable group, as described herein for any of the respective embodiments of Formula Ia.

In some of these embodiments, one or more $R_3$-$R_6$ is a monosaccharide or an oligosaccharide, as described herein for any of the respective embodiments of Formulae Ia and Ib.

In some of any of the embodiments of Formula Ic:

$X_1$ is O;

Rx, Ry1 and Rz are each hydrogen;

Ry2-Ry9 and Rw1-Rw3 are each hydrogen;

$R_2$ is selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl and acyl, as described herein for Formula Ia or Ib;

$R_3$-$R_6$ are each independently $OR_{16}$, wherein $R_{16}$ is independently selected from hydrogen, a monosaccharide moiety, an oligosaccharide moiety, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl and acyl, as described herein for any of the respective embodiments of Formula Ia; and $R_7$-$R_9$ are each independently selected from the group consisting of hydrogen, acyl, an amino-substituted alpha-hydroxy acyl, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted alkaryl, carboxylate, sulfonyl (including alkyl sulfonyl and aryl sulfonyl) and a cell-permealizable group, as described herein for any of the respective embodiments of Formula Ia or Ib.

In some of any of the embodiments of Formula Ic:
$X_1$ is O;
Rx, Ry1 and Rz are each hydrogen;
Ry2-Ry9 and Rw1-Rw3 are each hydrogen;
$R_2$ is hydrogen;
$R_3$-$R_6$ are each independently $OR_{16}$, wherein $R_{16}$ is hydrogen; and
$R_7$-$R_9$ are each independently selected from the group consisting of hydrogen, acyl, an amino-substituted alpha-hydroxy acyl, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted alkaryl, and a cell-permealizable group, as described herein for any of the respective embodiments of Formula Ia or Ib.

In some of any of the embodiments of Formula Ic:
$X_1$ is O;
Rx, Ry1 and Rz are each hydrogen;
Ry2-Ry9 and Rw1-Rw3 are each hydrogen;
$R_2$ is hydrogen;
$R_3$, $R_4$ and $R_6$ are each independently $OR_{16}$, wherein $R_{16}$ is hydrogen;
$R_5$ is a monosaccharide represented by Formula II as described herein, wherein $X_2$ is preferably $NR_{14}R_{15}$, as described herein for any of the respective embodiments of Formula Ia or Ib; and
$R_7$-$R_9$ are each independently selected from the group consisting of hydrogen, acyl, an amino-substituted alpha-hydroxy acyl, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted alkaryl, and a cell-permealizable group, as described herein for any of the respective embodiments of Formula Ia or Ib.

Compounds represented by Formula Ic are also referred to herein as "diol-containing" compounds.

Exemplary compounds encompassed by Formula Ic include NB153, NB155, NB156 and NB157, the structures of which are presented in the Examples section that follows.

According to some of any of the embodiments described herein, a compound as described herein is represented by Formula Id:

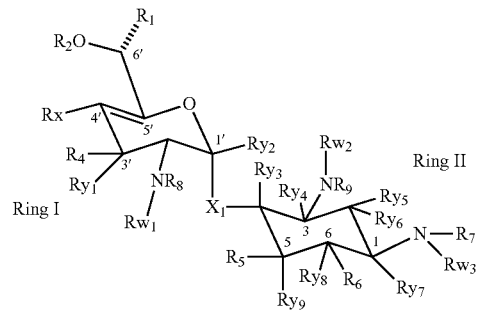

Formula Id or a pharmaceutically acceptable salt thereof,
wherein:
the dashed line indicates a stereo-configuration of position 6' being an R configuration or an S configuration;
$X_1$ is O or S;
Rx, Ry1-Ry9 and Rw1-Rw3 are each independently selected from hydrogen, alkyl, alkenyl, alkynyl, aryl, heteroaryl and cycloalkyl, each being substituted or unsubstituted, or, alternatively, each can be as defined herein for $R_7$-$R_9$;

$R_1$ is selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl, a substituted or unsubstituted amine, a substituted or unsubstituted amide, an acyl, a carboxylate, and a saturated or unsaturated and/or substituted or unsubstituted hydroxy alkyl (e.g., —$CH_2$—OH), as described herein in any of the respective embodiments of Formula Ia or Ib;

$R_2$ is selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl and acyl, as described herein in any of the respective embodiments of Formula Ia or Ib;

$R_4$-$R_6$ are each independently selected from the group consisting of hydrogen, alkyl, alkenyl, alkynyl, cycloalkyl, heteroalicyclic, aryl, heteroaryl, amine and $OR_{16}$, wherein $R_{16}$ is independently selected from hydrogen, a monosaccharide moiety, an oligosaccharide moiety, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl and acyl, as described herein in any of the respective embodiments of Formula Ia or Ib; and $R_7$-$R_9$ are each independently selected from the group consisting of hydrogen, acyl, an amino-substituted alpha-hydroxy acyl, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted alkaryl, carboxylate, sulfonyl (including alkyl sulfonyl and aryl sulfonyl) and a cell-permealizable group as defined herein, as described herein in any of the respective embodiments of Formula Ia or Ib.

In some of these embodiments, one or more $R_4$-$R_6$ is a monosaccharide or an oligosaccharide, as described herein for any of the respective embodiments of Formulae Ia and Ib.

In some of any of the embodiments of Formula Id:
$X_1$ is O;
Rx, Ry1-Ry9 and Rw1-Rw3 are each hydrogen;
$R_1$ is selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl, a substituted or unsubstituted amine, a substituted or unsubstituted amide, an acyl, a carboxylate, and a saturated or unsaturated and/or substituted or unsubstituted hydroxy alkyl (e.g., —$CH_2$—OH), as described herein in any of the respective embodiments of Formula Ia or Ib;
$R_2$ is selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl and acyl, as described herein for Formula Ia or Ib;
$R_4$-$R_6$ are each independently $OR_{16}$, wherein $R_{16}$ is independently selected from hydrogen, a monosaccharide moiety, an oligosaccharide moiety, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl and acyl, as described herein for any of the respective embodiments of Formula Ia; and
$R_7$-$R_9$ are each independently selected from the group consisting of hydrogen, acyl, an amino-substituted alpha-hydroxy acyl, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted alkaryl, carboxylate, sulfonyl (including alkyl sulfonyl and aryl sulfonyl) and a cell-permealizable group, as described herein for any of the respective embodiments of Formula Ia or Ib.

In some of any of the embodiments of Formula Id:
$X_1$ is O;
Rx, Ry1-Ry9 and Rw1-Rw3 are each hydrogen;
$R_1$ is hydrogen, alkyl, cycloalkyl or aryl, as described herein, and is preferably hydrogen or a lower alkyl, as described herein;
$R_2$ is hydrogen;
$R_4$-$R_6$ are each independently $OR_{16}$, wherein $R_{16}$ is hydrogen; and
$R_7$-$R_9$ are each independently selected from the group consisting of hydrogen, acyl, an amino-substituted alpha-hydroxy acyl, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted alkaryl, and a cell-permealizable group, as described herein for any of the respective embodiments of Formula Ia or Ib.

In some of any of the embodiments of Formula Id:
$X_1$ is O;
Rx, Ry1-Ry9 and Rw1-Rw3 are each hydrogen;
$R_1$ is hydrogen, alkyl, cycloalkyl or aryl, as described herein, and is preferably hydrogen or a lower alkyl, as described herein;
$R_2$ is hydrogen;
$R_4$ and $R_6$ are each independently $OR_{16}$, wherein $R_{16}$ is hydrogen;
$R_5$ is a monosaccharide represented by Formula II as described herein, wherein
$X_2$ is preferably $NR_{14}R_{15}$, as described herein for any of the respective embodiments of Formula Ia or Ib; and
$R_7$-$R_9$ are each independently selected from the group consisting of hydrogen, acyl, an amino-substituted alpha-hydroxy acyl, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted alkaryl, and a cell-permealizable group, as described herein for any of the respective embodiments of Formula Ia or Ib.

Compounds represented by Formula Id are also referred to herein as "unsaturated Glucosamine (Ring I)-containing" compound. Exemplary compounds encompassed by Formula Id include NB154, NB158 and NB159, the structures of which are presented in the Examples section that follows.

According to some of any of the embodiments described herein, a compound as described herein is represented by Formula Ie:

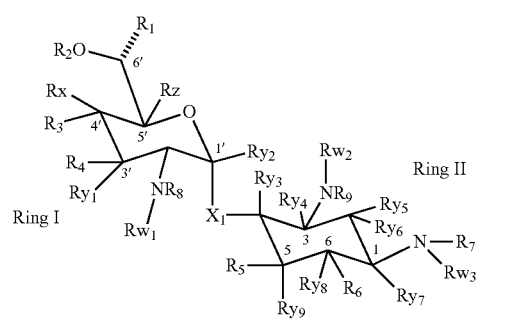

Formula Ie or a pharmaceutically acceptable salt thereof,
wherein:
the dashed line indicates a stereo-configuration of position 6' being an R configuration or an S configuration;
$X_1$ is O or S;
Rx, Ry1 and Rz are each independently hydrogen, alkyl or cycloalkyl;
Ry2-Ry9 and Rw1-Rw3 are each independently selected from hydrogen, alkyl, alkenyl, alkynyl, aryl, heteroaryl and cycloalkyl, each being substituted or unsubstituted, or, alternatively, each can be as defined herein for $R_7$-$R_9$;
$R_1$ is selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl, a substituted or unsubstituted amine, a substituted or unsubstituted amide, an acyl, a carboxylate, and a saturated or unsaturated and/or substituted or unsubstituted hydroxy alkyl (e.g., —$CH_2$—OH), as described herein in any of the respective embodiments of Formula Ia or Ib;
$R_2$ is selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl and acyl, as described herein for Formula Ia;

$R_3$-$R_6$ are each independently selected from the group consisting of hydrogen, alkyl, alkenyl, alkynyl, cycloalkyl, heteroalicyclic, aryl, heteroaryl, amine and $OR_{16}$, wherein $R_{16}$ is independently selected from hydrogen, a monosaccharide moiety, an oligosaccharide moiety, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl and acyl, as described herein for any of the respective embodiments of Formula Ia, wherein at least one of $R_3$-$R_6$ is $OR_{16}$; and $R_7$-$R_9$ are each independently selected from the group consisting of hydrogen, acyl, an amino-substituted alpha-hydroxy acyl, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted alkaryl, carboxylate, sulfonyl (including alkyl sulfonyl and aryl sulfonyl) and a cell-permealizable group, as described herein for any of the respective embodiments of Formula Ia or Ib, wherein at least two of $R_2$ and $OR_{16}$ in the one or more of $R_3$-$R_6$ which is/are $OR_{16}$ is an acyl.

In some of these embodiments, one or more $R_3$-$R_6$ is a monosaccharide or an oligosaccharide, as described herein for any of the respective embodiments of Formulae Ia and Ib.

In some of any of the embodiments of Formula Ie:
$X_1$ is O;
Rx, Ry1 and Rz are each hydrogen;
Ry2-Ry9 and Rw1-Rw3 are each hydrogen;
$R_1$ is selected from the group consisting of hydrogen, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl, a substituted or unsubstituted amine, a substituted or unsubstituted amide, an acyl, a carboxylate, and a saturated or unsaturated and/or substituted or unsubstituted hydroxy alkyl (e.g., —$CH_2$—OH), as described herein in any of the respective embodiments of Formula Ia or Ib;
$R_2$ is an acyl;
$R_3$-$R_6$ are each independently $OR_{16}$, wherein $R_{16}$ is independently selected from hydrogen, a monosaccharide moiety, an oligosaccharide moiety, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted heteroaryl, a substituted or unsubstituted alkaryl and acyl, as described herein for any of the respective embodiments of Formula Ia, at least one of $R_3$-$R_6$ is $OR_{16}$ in which $R_{16}$ is an acyl; and $R_7$-$R_9$ are each independently selected from the group consisting of hydrogen, acyl, an amino-substituted alpha-hydroxy acyl, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted alkaryl, carboxylate, sulfonyl (including alkyl sulfonyl and aryl sulfonyl) and a cell-permealizable group, as described herein for any of the respective embodiments of Formula Ia or Ib.

In some of any of the embodiments of Formula Ie:
$X_1$ is O;
Rx, Ry1 and Rz are each hydrogen;
Ry2-Ry9 and Rw1-Rw3 are each hydrogen;
$R_1$ is hydrogen, alkyl, cycloalkyl or aryl, and is preferably hydrogen or a lower alkyl, as described herein;
$R_2$ is acyl;
$R_3$, $R_5$ and $R_6$ are each independently $OR_{16}$, wherein $R_{16}$ is acyl;
$R_4$ is $OR_{16}$, wherein $R_{16}$ is hydrogen or acyl; and
$R_7$-$R_9$ are each independently selected from the group consisting of hydrogen, acyl, an amino-substituted alpha-hydroxy acyl, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted alkaryl, and a cell-permealizable group, as described herein for any of the respective embodiments of Formula Ia or Ib.

In some of any of the embodiments of Formula Ie:
$X_1$ is O;
Rx, Ry1 and Rz are each hydrogen;
Ry2-Ry9 and Rw1-Rw3 are each hydrogen;
$R_1$ is hydrogen, alkyl, cycloalkyl or aryl, and is preferably hydrogen or a lower alkyl, as described herein;
$R_2$ is acyl;
$R_3$ and $R_6$ are each independently $OR_{16}$, wherein $R_{16}$ is an acyl;
$R_4$ is $OR_{16}$, wherein $R_{16}$ is hydrogen or acyl; and
$R_5$ is a monosaccharide represented by Formula II as described herein, wherein $X_2$ is preferably $NR_{14}R_{15}$, as described herein for any of the respective embodiments of Formula Ia or Ib; and
$R_7$-$R_9$ are each independently selected from the group consisting of hydrogen, acyl, an amino-substituted alpha-hydroxy acyl, a substituted or unsubstituted alkyl, a substituted or unsubstituted alkenyl, a substituted or unsubstituted alkynyl, a substituted or unsubstituted cycloalkyl, a substituted or unsubstituted aryl, a substituted or unsubstituted alkaryl, and a cell-permealizable group, as described herein for any of the respective embodiments of Formula Ia or Ib.

Compounds represented by Formula Ie are also referred to herein as "multi-esterified" compounds.

Exemplary compounds encompassed by Formula Ie include the compounds presented in Scheme 14 in the Examples section that follows.

For any of the embodiments described herein, and any combination thereof, the compound may be in a form of a salt, for example, a pharmaceutically acceptable salt.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound. A pharmaceutically acceptable salt of a compound as described herein can alternatively be formed during the synthesis of the compound, e.g., in the course of isolating the compound from a reaction mixture or re-crystallizing the compound.

In the context of some of the present embodiments, a pharmaceutically acceptable salt of the compounds described herein may optionally be an acid addition salt comprising at least one basic (e.g., amine and/or guanidine) group of the compound which is in a positively charged form (e.g., wherein the basic group is protonated), in combination with at least one counter-ion, derived from the selected base, that forms a pharmaceutically acceptable salt.

The acid addition salts of the compounds described herein may therefore be complexes formed between one or more basic groups of the compound and one or more equivalents of an acid.

Depending on the stoichiometric proportions between the charged group(s) in the compound and the counter-ion in the salt, the acid additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

An example, without limitation, of a pharmaceutically acceptable salt would be an ammonium cation or guanidinium cation and an acid addition salt thereof.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

The present embodiments further encompass any enantiomers, diastereomers, prodrugs, solvates, hydrates and/or pharmaceutically acceptable salts of the compounds described herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems. In the context of the present embodiments, a compound may exhibit one or more chiral centers, each of which exhibiting an R- or an S-configuration and any combination, and compounds according to some embodiments of the present invention, can have any their chiral centers exhibit an R- or an S-configuration.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers. Each stereo-center (chiral center) gives rise to two different configurations and thus to two different stereoisomers. In the context of the present invention, embodiments of the present invention encompass compounds with multiple chiral centers that occur in any combination of stereo-configuration, namely any diastereomer.

According to some of any of the embodiments described herein, a stereo-configuration of each of position 6' and position 5" (if present) is independently an R configuration or an S configuration.

According to some of any of the embodiments described herein, a stereo-configuration of position 6' is an R configuration.

According to some of any of the embodiments described herein, a stereo-configuration of position 5", if present, is an S configuration.

According to some of any of the embodiments described herein, a stereo-configuration of position 6' is an R configuration and a stereo-configuration of position 5", if preset, is an R configuration or an S configuration.

According to some of any of the embodiments described herein, a stereo-configuration of position 6' is an R configuration and a stereo-configuration of position 5", if present, is an S configuration.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The terms "hydroxyl" or "hydroxy", as used herein, refer to an —OH group.

As used herein, the term "amine" describes a —NR'R" group where each of R' and R" is independently hydrogen, alkyl, alkenyl, alkynyl, cycloalkyl, heteroalicyclic, aryl, heteroaryl, alkaryl, alkheteroaryl, or acyl, as these terms are defined herein. Alternatively, one or both of R' and R" can be, for example, hydroxy, alkoxy, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

As used herein, the term "alkyl" describes an aliphatic hydrocarbon including straight chain and branched chain groups. The alkyl may have 1 to 20 carbon atoms, or 1-10 carbon atoms, and may be branched or unbranched. According to some embodiments of the present invention, the alkyl is a low (or lower) alkyl, having 1-4 carbon atoms (namely, methyl, ethyl, propyl and butyl).

Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. In some embodiments, the alkyl is a lower alkyl, including 1-6 or 1-4 carbon atoms.

An alkyl can be substituted or unsubstituted. When substituted, the substituent can be, for example, one or more of an alkyl (forming a branched alkyl), an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow. An alkyl substituted by aryl is also referred to herein as "alkaryl", an example of which is benzyl.

Whenever "alkyl" is described, it can be replaced also by alkenyl or alkynyl. The term "alkyl" as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond, e.g., allyl, vinyl, 3-butenyl, 2-butenyl, 2-hexenyl and i-propenyl. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" refers to an all-carbon monocyclic or fused ring (i.e., rings which share an adjacent pair of carbon atoms), branched or unbranched group containing 3 or more carbon atoms where one or more of the rings does not have a completely conjugated pi-electron system, and may further be substituted or unsubstituted. Exemplary cycloalkyl groups include, for example, cyclopropyl, cyclobutyl, cyclopentyl, cyclohexyl, or cyclododecyl. The cycloalkyl can be substituted or unsubstituted. When substituted, the substituent can be, for example, one or more of an alkyl, an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow.

The term "aryl" describes an all-carbon monocyclic or fused-ring polycyclic (i.e., rings which share adjacent pairs of carbon atoms) groups having a completely conjugated pi-electron system. The aryl group may be unsubstituted or substituted by one or more substituents. When substituted, the substituent can be, for example, one or more of an alkyl, an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. Representative examples are thiadiazole, pyridine, pyrrole, oxazole, indole, purine and the like. The heteroaryl group may be unsubstituted or substituted by one or more substituents. When substituted, the substituent can be, for example, one or more of an alkyl, an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow.

The term "heteroalicyclic", as used herein, describes a monocyclic or fused ring group having in the ring(s) one or more atoms such as nitrogen, oxygen and sulfur. The rings may also have one or more double bonds. However, the rings do not have a completely conjugated pi-electron system. Representative examples are morpholine, piperidine, piperazine, tetrahydrofurane, tetrahydropyrane and the like. The heteroalicyclic may be substituted or unsubstituted. When substituted, the substituent can be, for example, one or more of an alkyl, an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow.

The term "halide", as used herein, refers to the anion of a halo atom, i.e. $F^-$, $Cl^-$, $Br^-$ and $I^-$.

The term "halo" refers to F, Cl, Br and I atoms as substituents.

The term "alkoxide" refers to an R'—O$^-$ anion, wherein R' is as defined hereinabove.

The term "alkoxy" refers to an —OR' group, wherein R' is alkyl or cycloalkyl, as defined herein.

The term "aryloxy" refers to an —OR' group, wherein R' is aryl, as defined herein.

The term "heteroaryloxy" refers to an —OR' group, wherein R' is heteroaryl, as defined herein.

The term "thioalkoxy" refers to an —SR' group, wherein R' is alkyl or cycloalkyl, as defined herein.

The term "thioaryloxy" refers to an —SR' group, wherein R' is aryl, as defined herein.

The term "thioheteroaryloxy" refers to an —SR' group, wherein R' is heteroaryl, as defined herein.

The term "hydroxyalkyl," as used herein, refers to an alkyl group, as defined herein, substituted with one or more hydroxy group(s), e.g., hydroxymethyl, 2-hydroxyethyl and 4-hydroxypentyl.

The term "aminoalkyl," as used herein, refers to an alkyl group, as defined herein, substituted with one or more amino group(s).

The term "alkoxyalkyl," as used herein, refers to an alkyl group substituted with one or more alkoxy group(s), e.g., methoxymethyl, 2-methoxyethyl, 4-ethoxybutyl, n-propoxyethyl and t-butylethyl.

The term "trihaloalkyl" refers to —CX$_3$, wherein X is halo, as defined herein. An exemplary haloalkyl is CF$_3$.

A "guanidino" or "guanidine" or "guanidinyl" or "guanidyl" group refers to an —RaNC(=NRd)-NRbRc group, where each of Ra, Rb, Rc and Rd can each be as defined herein for R' and R".

A "guanyl" or "guanine" group refers to an RaRbNC(=NRd)-group, where Ra, Rb and Rd are each as defined herein for R' and R".

In some of any of the embodiments described herein, the guanidine group is —NH—C(=NH)—NH$_2$.

In some of any of the embodiments described herein, the guanyl group is H$_2$N—C(=NH)— group.

Any one of the amine (including modified amine), guanidine and guanine groups described herein is presented as a free base form thereof, but is meant to encompass an ionized form thereof at physiological pH, and/or within a salt thereof, e.g., a pharmaceutically acceptable salt thereof, as described herein.

Whenever an alkyl, cycloalkyl, aryl, alkaryl, heteroaryl, heteroalicyclic, acyl and any other moiety as described herein is substituted, it includes one or more substituents, each can independently be, but are not limited to, hydroxy, alkoxy, thiohydroxy, thioalkoxy, aryloxy, thioaryloxy, alkaryl, alkenyl, alkynyl, sulfonate, sulfoxide, thiosulfate, sulfate, sulfite, thiosulfite, phosphonate, cyano, nitro, azo, sulfonamide, carbonyl, thiocarbonyl, C-carboxylate, O-carboxylate, N-thiocarbamate, O-thiocarbamate, oxo, thiooxo, oxime, acyl, acyl halide, azo, azide, urea, thiourea, N-carbamate, O-carbamate, C-amide, N-amide, guanyl, guanidyl, hydrazine and hydrazide, as these terms are defined herein.

The term "cyano" describes a —C≡N group.

The term "nitro" describes an —NO$_2$ group.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O—group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfonate" describes a —S(=O)—OR' end group or an —S(=O)—O— group linking group, as these phrases are defined hereinabove, where R' is as defined hereinabove.

The term "sulfoxide" or "sulfonyl" describes a —S(=O)R' end group or an —S(=O)— linking group, as these phrases are defined hereinabove, where R' is as defined hereinabove.

The term "sulfonate" or "sulfonyl" describes a —S(=O)$_2$—R' end group or an —S(=O)$_2$-linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, with R' and R" are as defined herein.

The term "carbonyl" or "carbonate" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "oxo" as used herein, describes a (=O) group, wherein an oxygen atom is linked by a double bond to the atom (e.g., carbon atom) at the indicated position.

The term "thiooxo" as used herein, describes a (=S) group, wherein a sulfur atom is linked by a double bond to the atom (e.g., carbon atom) at the indicated position.

The term "oxime" describes a =N—OH end group or a =N—O— linking group, as these phrases are defined hereinabove.

The term "acyl halide" describes a —(C=O)R"" group wherein R"" is halide, as defined hereinabove.

The term "azo" or "diazo" describes an —N=NR' end group or an —N=N— linking group, as these phrases are defined hereinabove, with R' as defined hereinabove.

The term "azide" describes an —N$_3$ end group.

The term "carboxylate" as used herein encompasses C-carboxylate and O-carboxylate.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

A carboxylate can be linear or cyclic. When cyclic, R' and the carbon atom are linked together to form a ring, in C-carboxylate, and this group is also referred to as lactone. Alternatively, R' and O are linked together to form a ring in O-carboxylate. Cyclic carboxylates can function as a linking group, for example, when an atom in the formed ring is linked to another group.

The term "thiocarboxylate" as used herein encompasses C-thiocarboxylate and O-thiocarboxylate.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)-linking group, as these phrases are defined hereinabove, where R' is as defined herein.

A thiocarboxylate can be linear or cyclic. When cyclic, R' and the carbon atom are linked together to form a ring, in C-thiocarboxylate, and this group is also referred to as thiolactone. Alternatively, R' and O are linked together to form a ring in O— thiocarboxylate. Cyclic thiocarboxylates can function as a linking group, for example, when an atom in the formed ring is linked to another group.

The term "carbamate" as used herein encompasses N-carbamate and O-carbamate.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

A carbamate can be linear or cyclic. When cyclic, R' and the carbon atom are linked together to form a ring, in O-carbamate. Alternatively, R' and O are linked together to form a ring in N-carbamate. Cyclic carbamates can function as a linking group, for example, when an atom in the formed ring is linked to another group.

The term "carbamate" as used herein encompasses N-carbamate and O-carbamate.

The term "thiocarbamate" as used herein encompasses N-thiocarbamate and O-thiocarbamate.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)—NR'— linking group, as these phrases are defined hereinabove, with R' and R" as defined herein.

Thiocarbamates can be linear or cyclic, as described herein for carbamates.

The term "dithiocarbamate" as used herein encompasses S-dithiocarbamate and N-dithiocarbamate.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "amide" as used herein encompasses C-amide and N-amide.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "hydrazine" describes a —NR'—NR"R'" end group or a —NR'—NR"-linking group, as these phrases are defined hereinabove, with R', R", and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

Processes:

Further according to embodiments of the present invention, there are provided processes of preparing the compounds as described herein.

These processes are generally effected by providing a paromamine derivative and introducing thereto a desired modification to thereby obtain a pseudo-disaccharide compound as described herein.

Processes of preparing pseudo-trisaccharide compounds as described herein are generally effected by devising appropriate acceptor aminoglycoside molecules and corresponding donor molecules, as is known in the art of aminoglycosides.

Generally, the synthesis of pseudo-trisaccharide compounds according to some embodiments of the present invention is accomplished using suitable acceptor and donor molecules and reaction conditions which allow reacting a protected derivative of the donor and of the acceptor and removing the protecting group so as to obtain a desired pseudo-trisaccharide of Formula Ia.

The term "acceptor" is used herein to describe the skeletal structure derived from paromamine which has an available (unprotected) hydroxyl group at position C3', C4', C6 or C5, preferably C5, which is reactive during a glycosylation reaction, and can accept a glycosyl.

The term "donor" is used herein to describe the glycosyl that reacts with the acceptor to form the final pseudo-trisaccharide compound.

The term "glycosyl", as used herein, refers to a chemical group which is obtained by removing the hydroxyl group from the hemiacetal function of a monosaccharide.

The donors and acceptors are designed so as to form the desired compounds according to some embodiments of the present invention. The following describes some embodiments of this aspect of the present invention, presenting exemplary processes of preparing exemplary subsets of the compounds described herein. More detailed processes of preparing exemplary compounds according to some embodiments of the present invention, are presented in the Examples section that follows below.

The syntheses of pseudo-trisaccharide compounds according to some embodiments of the present invention, generally include (i) preparing an acceptor compound by selective protection of one or more hydroxyls and amines at selected positions present on the paromamine scaffold, leaving the selected position (e.g., C5) unprotected and therefore free to accept a donor (glycosyl) compound as defined herein; (ii) preparing a donor compound by selective protection of one or more hydroxyls and amines at selected positions present on the glycosyl, leaving one position unprotected and therefore free to couple with an acceptor compound as defined herein; (iii) subjecting the donor and the acceptor to a coupling reaction; and (iii) removing the protecting groups to thereby obtain the desired compound.

The phrase "protected group", as used herein, refers to a group that is substituted or modified so as to block its functionality and protect it from reacting with other groups under the reaction conditions (e.g., a coupling reaction as described herein). A protected group is re-generated by removal of the substituent or by being re-modified.

When an "amino-protected group" or "hydroxyl-protected group" are used, it is meant that a protecting group is attached or used to modify the respective group so as to generate the protected group.

The phrase "protecting group", as used herein, refers to a substituent or a modification that is commonly employed to block or protect a particular functionality while reacting other functional groups on the compound. The protecting group is selected so as to release the substituent or to be re-modified, to thereby generate the desired unprotected group.

For example, an "amino-protecting group" or "amine-protecting group" is a substituent attached to an amino group, or a modification of an amino group, that blocks or protects the amino functionality in the compound, and prevents it from participating in chemical reactions. The amino-protecting group is removed by removal of the substituent or by a modification that re-generates an amine group.

Suitable amino-protected groups include azide (azido), N-phthalimido, N-acetyl, N-trifluoroacetyl, N-t-butoxycarbonyl (BOC), N-benzyloxycarbonyl (CBz) and N-9-fluorenylmethylenoxycarbonyl (Fmoc).

A "hydroxyl-protecting group" or "hydroxyl-protecting group" refers to a substituent or a modification of a hydroxyl group that blocks or protects the hydroxyl functionality, and prevents it from participating in chemical reactions. The hydroxy-protecting group is removed by removal of the substituent or by a modification that re-generates a hydroxy group.

Suitable hydroxy protected groups include isopropylidene ketal and cyclohexanone dimethyl ketal (forming a 1,3-dioxane with two adjacent hydroxyl groups), 4-methoxy-1-methylbenzene (forming a 1,3-dioxane with two adjacent hydroxyl groups), O-acetyl, O-chloroacetyl, O-benzoyl and O-silyl.

For a general description of protecting groups and their use, see T. W. Greene, Protective Groups in Organic Synthesis, John Wiley & Sons, New York, 1991.

According to some embodiments, the amino-protected groups include an azido ($N_3$—) and/or an N-phthalimido group, and the hydroxyl-protecting groups include O-acetyl (AcO—), O-benzoyl (BzO—) and/or O-chloroacetyl.

It is noted herein that when applicable, a "protected group" refers to a moiety in which one reactive function on a compound is protected or more than one function are protected at the same time, such as in the case of two adjacent functionalities, e.g., two hydroxyl groups that can be protected at once by a isopropylidene ketal.

In some embodiments, the donor compound is a protected monosaccharide which can be represented by the general Formula III:

In some embodiments, the donor compound is a protected monosaccharide which can be represented by the general Formula III, having a leaving group at position 1" thereof, denoted L, and optionally a substituent $R_{12}$ at position 5", as defined herein:

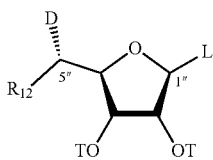

Formula III wherein:

L is a leaving group;

OT is a donor protected hydroxyl group;

$R_{12}$ is as defined herein for Formula Ib (the configuration at the 5" position as presented in Formula III being a non-limiting example); and D is a protected or unprotected form of $NR_{14}R_{15}$ as defined for Formula Ib, wherein when $R_{14}$ and $R_{15}$ in Formula Ib are both hydrogen, D is a donor protected amine group.

As used herein, the phrase "leaving group" describes a labile atom, group or chemical moiety that readily undergoes detachment from an organic molecule during a chemical reaction, while the detachment is typically facilitated by the relative stability of the leaving atom, group or moiety thereupon. Typically, any group that is the conjugate base of a strong acid can act as a leaving group. Representative examples of suitable leaving groups according to some of the present embodiments include, without limitation, trichloroacetimidate, acetate, tosylate, triflate, sulfonate, azide, halide, hydroxy, thiohydroxy, alkoxy, cyanate, thiocyanate, nitro and cyano.

According to some embodiments of the present invention, each of the donor hydroxyl-protecting groups is O-benzoyl and the donor amino-protecting group in either $R_{15}$ or $R_{17}$ is azido, although other protecting groups are contemplated.

It is to be noted that when one of $R_{14}$ and $R_{15}$ is other than hydrogen, it can be protected or unprotected. Typically, when one of $R_6$ and $R_7$ is guanine or guanidine, a protecting group suitable for the reaction conditions (e.g., of a coupling reaction with an acceptor) can be used. Optionally, the guanine or guanidine are unprotected. When one of $R_{14}$ and $R_{15}$ is an alkyl, aryl or cycloalkyl, typically D in Formula III is an unprotected form of $NR_{14}R_{15}$.

The structure of the donor compound sets the absolute structure of Ring III in the resulting compound according to some embodiments of the present invention, namely the stereo-configuration of the 5" position and the type of $R_{14}$, $R_{15}$ and $R_{12}$ in Formula Ib.

Exemplary acceptor molecules suitable for use in the preparation of the compounds described herein, are represented by Formula IV:

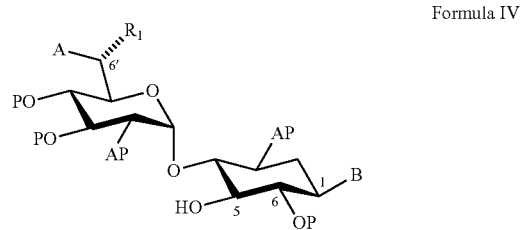

Formula IV wherein:

the dashed line represents an S-configuration or an R-configuration at position 6';

OP is an acceptor protected hydroxyl group;

AP is an acceptor protected amine group;

$R_1$ is as defined herein for Formula Ia or Ib;

A is an acceptor protected hydroxyl group (OP); or can otherwise be one of the other groups defining $OR_2$, either protected or unprotected, according to the chemical nature of these groups and the reaction conditions; and B is an acceptor protected amine group, in case $R_7$ is Formula Ia is hydrogen, or can otherwise be a protected or unprotected form of the groups defining $R_7$.

According to some embodiments of the present invention, the acceptor hydroxyl-protected group is O-acetyl.

According to some embodiments of the present invention, the donor amino-protecting group is azido, although other protecting groups are contemplated.

The acceptor hydroxyl-protected groups and the acceptor amino-protected groups at the various positions of the acceptors can be the same or different each position.

In some embodiments, for example, in case $R_7$ is other than H, the acceptor is prepared by generating the moiety B, prior to reacting it with the donor.

The structure of the acceptor compound sets the absolute structure of Ring I and Ring II in the resulting compound according to some embodiments of the present invention.

In some embodiments, the synthesis of pseudo-disaccharide compounds of Formula Ia, according to some embodiments of the present invention, is accomplished using an amino-protected compound of Formula V:

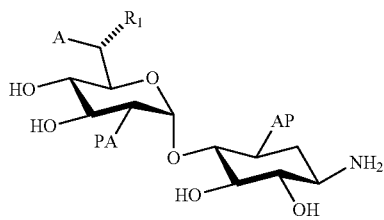

Formula V wherein:

the dashed line represents an S-configuration or an R-configuration at position 6';

AP is an acceptor protected amine group;

$R_1$ is as defined herein for Formula Ia;

A is an acceptor protected hydroxyl group (OP), as described herein; or can otherwise be one of the other groups defining $OR_2$, either protected or unprotected, according to the chemical nature of these groups and the reaction conditions.

Embodiments of the present invention further encompass any of the intermediate compounds described herein in the context of processes of preparing the compounds of the present embodiments.

Therapeutic Uses:

As known in the art, about a third of alleles causing genetic diseases carry premature termination (stop) codons (PTCs), which lead to the production of truncated proteins. One possible therapeutic approach involves the induction and/or promotion of readthrough of such PTCs to enable synthesis of full-length proteins. PTCs originate from either mutations, such as nonsense mutations, frame-shift deletions and insertions, or from aberrant splicing that generates mRNA isoforms with truncated reading frames. These mutations can lead to the production of truncated, nonfunctional or deleterious proteins, owing to dominant negative or gain-of-function effects.

In general, readthrough of PTCs can be achieved by suppressor transfer RNAs (tRNAs), factors that decrease translation-termination efficiency, such as small-interfering RNAs (siRNAs) directed against the translation-termination factors, and RNA antisense that targets the nonsense mutation region. One of the objectives of the present invention is to provide a pharmacological therapeutic approach aimed at achieving sufficient levels of functional proteins in a subject suffering from at least one genetic disorder associated with at least one premature stop-codon mutation. According to embodiments of the present invention, the provided therapeutic approach is aimed at inducing and/or promoting translational readthrough of the disease causing PTCs, to enable the synthesis and expression of full-length functional proteins.

As presented hereinabove, one extensively studied approach that has reached clinical trials, is based on readthrough by drugs affecting the ribosome decoding site, such as aminoglycoside antibiotics; however, aminoglycosides have severe adverse side effects when used at high concentrations and/or used long-term. The compounds presented herein were designed to exhibit an ability to induce and/or promote readthrough of a premature stop-codon mutation in an organism having such a mutation, while exhibiting minimal adverse effects. Such an activity renders these compounds suitable for use as therapeutically active agents for the treatment of genetic disorders associated with a premature stop-codon mutation.

As demonstrated in the Examples section that follows, exemplary compounds encompassed by the present embodiments were indeed shown to exhibit a premature stop-codon mutation suppression activity, and hence as useful in inducing readthrough of genes characterized by a disease-causing premature stop-codon mutation, and thus exhibit usefulness in treating respective genetic diseases or disorders associated with a premature stop-codon mutation.

According to an aspect of some embodiments of the present invention, any of the compounds presented herein having Formula Ia or Ib, including any of the respective embodiments of the compounds and any combinations thereof (and including compounds represented by Formula IC, Id and Ie), are for use in inducing and/or promoting readthrough of a premature stop codon mutation and/or for increasing an expression of a gene having a premature stop codon mutation, and/or are for use in the manufacture of a medicament for inducing and/or promoting readthrough of a premature stop codon mutation and/or for increasing an expression of a gene having a premature stop codon mutation.

According to an aspect of some embodiments of the present invention, any of the compounds presented herein having Formula Ia or Ib, including any of the respective embodiments of the compounds and any combinations thereof (and including compounds represented by Formula IC, Id and Ie), are for use in the treatment of a genetic disorder associated with a premature stop-codon mutation, or for use in the manufacture of a medicament for the treatment of a genetic disorder associated with a premature stop-codon mutation.

Any of the premature stop-codon mutations are contemplated. In some embodiments, the mutations are those having an RNA code of UGA, UAG or UAA.

According to some of any of the embodiments described herein, the protein is translated in a cytoplasmic translation system.

According to some of any of the embodiments described herein, the compound is used in a mutation suppression amount.

According to some of any of the embodiments described herein, an inhibition of translation $IC_{50}$ of the compound in a eukaryotic cytoplasmic translation system is greater that an inhibition of translation $IC_{50}$ of the compound in a ribosomal translation system.

According to some of any of the embodiments described herein, an inhibition of translation $IC_{50}$ of the compound in a eukaryotic cytoplasmic translation system is greater that an inhibition of translation $IC_{50}$ of the compound in a prokaryotic translation system.

According to an aspect of some embodiments of the present invention, any of the compounds presented herein having Formula Ia or Ib, including any of the respective embodiments of the compounds and any combinations thereof (and including compounds represented by Formula IC, Id and Ie), are for use in the treatment of a genetic disorder associated with a premature stop-codon mutation, or for use in the manufacture of a medicament for the treatment of a genetic disorder associated with a premature stop-codon mutation.

According to an aspect of some embodiments of the present invention there is provided a method of treating a genetic disorder associated with a premature stop-codon mutation. The method, according to this aspect of the present invention, is effected by administering to a subject in need thereof a therapeutically effective amount of one or more of the compounds presented herein having Formula Ia or Ib, including any of the respective embodiments of the compounds and any combinations thereof (and including compounds represented by Formula IC, Id and Ie).

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "therapeutically effective amount" describes an amount of the polymer being administered which will relieve to some extent one or more of the symptoms of the condition being treated.

The phrase "genetic disorder", as used herein, refers to a chronic disorder which is caused by one or more defective genes that are often inherited from the parents, and which can occur unexpectedly when two healthy carriers of a defective recessive gene reproduce, or when the defective gene is dominant. Genetic disorders can occur in different inheritance patterns which include the autosomal dominant pattern wherein only one mutated copy of the gene is needed for an offspring to be affected, and the autosomal recessive pattern wherein two copies of the gene must be mutated for an offspring to be affected.

The phrase "genetic disorder", as used herein, encompasses a genetic disorder, genetic disease, genetic condition or genetic syndrome.

According to some of any of the embodiments of the present invention, the genetic disorder, genetic disease, genetic condition or genetic syndrome, involves a gene having a premature stop-codon mutation, also referred to herein as a truncation mutation and/or a nonsense mutation, which leads to improper translation thereof. The improper translation produces a dysfunctional essential protein or causes a reduction or abolishment of synthesis of an essential protein. In the context of the some embodiments of the present invention, the genetic disorders which are contemplated within the scope of the present embodiments are referred to as genetic disorders associated with a premature stop-codon mutation and/or a protein truncation phenotype.

According to some of any of the embodiments of the present invention, a genetic disorder associated with a premature stop-codon mutation and/or a protein truncation phenotype is treatable by inducing and/or promoting readthrough of the mutation in the complete but otherwise defective transcript (mRNA), or in other words, by inducing and/or promoting suppression of the nonsense mutation (the premature stop-codon mutation and/or the truncation mutation). In the context of embodiments of the present invention, a genetic disorder is one that is treatable by readthrough-inducing and/or promoting compounds.

Methods for identification of a genetic disorder associated with a premature stop-codon mutation and/or a protein truncation phenotype are well known in the art, and include full or partial genome elucidation, genetic biomarker detection, phenotype classification and hereditary information analysis.

Such methods often result in pairs of mutant/wild type (WT) sequences, and these pairs can be used in known methodologies for identifying if the genetic disorder is associated with a premature stop-codon mutation and/or a protein truncation phenotype.

A readthrough-inducing/promoting activity of compounds for treating such genetic disorders can be established by methods well known in the art.

For example, a plasmid comprising two reporter genes interrupted by a sequence of the mutated gene (the genetic disorder-causing gene) is transected into a protein expression platform, either in full cells or in a cell-free systems, and the ratio between the expression level of the two genes in the presence of a tested compound is measured, typically in series of concentrations and duplications, and compared to the gene expression level ratio of the wild-type and/or to the expression level ratio measured in a control sample not containing the tested compound.

It is noted that the experimental model for readthrough activity, namely the nucleotide sequence of gene containing the premature stop-codon mutation, is a byproduct of the process of identifying a genetic disorder as associated with a premature stop-codon mutation and/or a protein truncation phenotype, and further noted that with the great advances in genomic data acquisition, this process is now well within the skills of the artisans of the art, and that once the mechanism of action of a drug candidate is established, as in the case of genetic disorders which have been shown to be associated with a premature stop-codon mutation and/or a protein truncation phenotype, it is well within the skills of the artisans of the art to identify, characterize and assess the efficacy, selectivity and safety of any one of the readthrough-inducing compounds presented herein. It is further well within the skills of the artisans of the art to take the readthrough-inducing compounds presented herein further though the routine processes of drug development.

Methodologies for testing readthrough of a premature stop-codon mutation and/or a truncation mutation, referred to herein as readthrough activity, are known in the art, and several exemplary experimental methods are provided in the Examples section that follows, by which the readthrough-inducing compounds, according to some embodiments of the present invention, can be characterized. It is to be understood that other methods can be used to characterized readthrough-inducing compounds, and such methods are also contemplated within the scope of the present invention. Methods such as provided herein can also be adapted for high throughput screening technology that can assay thousands of compounds in a relatively short period of time.

The skilled artisan would appreciate that many in vitro methodologies can be used to characterize readthrough-inducing compounds provided herein in terms of safety of use as drugs, and assess the drug candidates in terms of their cytotoxicity versus their efficacy. The skilled artisan would also appreciate that many in vitro methodologies can be used to characterize the readthrough-inducing compounds provided herein for eukaryotic versus prokaryotic selectivity, and such methodologies may also be adapted for high throughput screening technology that can assay thousands of compounds in a relatively short period of time.

Non-limiting examples of genetic disorders, diseases, conditions and syndromes, which are associated with the presence of at least one premature stop-codon or other nonsense mutations include cancer, Rett syndrome, cystic fibrosis (CF), Becker's muscular dystrophy (BMD), Congenital muscular dystrophy (CMD), Duchenne muscular dystrophy (DMD), Factor VII deficiency, Familial atrial fibrillation, Hailey-Hailey disease, hemophilia A, hemophilia B, Hurler syndrome, Louis-Bar syndrome (ataxia-telangiectasia, AT), McArdle disease, Mucopolysaccharidosis, Nephropathic cystinosis, Polycystic kidney disease, type I, II and III Spinal muscular atrophy (SMA), Tay-Sachs, Usher syndrome, cystinosis, Severe epidermolysis bullosa, Dravet syndrome, X-linked nephrogenic diabetes insipidus (XNDI) and X-linked retinitis pigmentosa.

Additional genetic disorders, diseases, conditions and syndromes, which are associated with the presence of at least one premature stop-codon or other nonsense mutations, are listed in "*Suppression of nonsense mutations as a therapeutic approach to treat genetic diseases*" by Kim M. Keeling, K. M Bedwell, D. M., *Wiley Interdisciplinary Reviews: RNA*, 2011, 2(6), p. 837-852; "*Cancer syndromes and therapy by stop-codon readthrough*", by Bordeira-Carriço, R. et al., *Trends in Molecular Medicine*, 2012, 18(11), p. 667-678, and any references cited therein, all of which are incorporated herewith by reference in their entirety.

In any of the methods and uses described herein, the compounds described herein can be utilized either per se or form a part of a pharmaceutical composition, which further comprises a pharmaceutically acceptable carrier, as defined herein.

According to an aspect of some embodiments of the present invention, there is provided a pharmaceutical composition which comprises, as an active ingredient, any of the novel compounds described herein and a pharmaceutically acceptable carrier.

As used herein a "pharmaceutical composition" refers to a preparation of the compounds presented herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the compounds presented herein into preparations which, can be used pharmaceutically. Proper formulation is dependent upon the route of administration chosen.

According to some embodiments, the administration is effected orally. For oral administration, the compounds presented herein can be formulated readily by combining the compounds with pharmaceutically acceptable carriers well known in the art. Such carriers enable the compounds presented herein to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the compounds presented herein may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For injection, the compounds presented herein may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active aminoglycoside compounds doses.

For buccal administration, the compositions may take the form of tablets or lozenges formulated in conventional manner.

For administration by inhalation, the compounds presented herein are conveniently delivered in the form of an aerosol spray presentation (which typically includes powdered, liquefied and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compounds presented herein and a suitable powder base such as, but not limited to, lactose or starch.

The compounds presented herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the compounds preparation in water-soluble form. Additionally, suspensions of the compounds presented herein may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilisers or agents, which increase the solubility of the compounds presented herein to allow for the preparation of highly concentrated solutions.

Alternatively, the compounds presented herein may be in powder form for constitution with a suitable vehicle, e.g., sterile, pyrogen-free water, before use.

The compounds presented herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of compounds presented herein effective to prevent, alleviate or ameliorate symptoms of the disorder, or prolong the survival of the subject being treated.

Determination of a therapeutically effective amount is well within the capability of those skilled in the art, especially in light of the detailed disclosure provided herein.

For any compounds presented herein used in the methods of the present embodiments, the therapeutically effective amount or dose can be estimated initially from activity assays in animals. For example, a dose can be formulated in animal models to achieve a circulating concentration range that includes the mutation suppression levels as determined by activity assays (e.g., the concentration of the test compounds which achieves a substantial read-through of the truncation mutation). Such information can be used to more accurately determine useful doses in humans.

Toxicity and therapeutic efficacy of the compounds presented herein can be determined by standard pharmaceutical procedures in experimental animals, e.g., by determining the $EC_{50}$ (the concentration of a compound where 50% of its maximal effect is observed) and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the compounds presented herein which are sufficient to maintain the desired effects, termed the minimal effective concentration (MEC). The MEC will vary for each preparation, but can be estimated from in vitro data; e.g., the concentration of the compounds necessary to achieve 50-90% expression of the whole gene having a truncation mutation, i.e. read-through of the mutation codon. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the chronic condition to be treated, dosing can also be a single periodic administration of a slow release composition described hereinabove, with course of periodic treatment lasting from several days to several weeks or until sufficient amelioration is effected during the periodic treatment or substantial diminution of the disorder state is achieved for the periodic treatment.

The amount of a composition to be administered will, of course, be dependent on the subject being treated, the severity of the affliction, the manner of administration, the judgment of the prescribing physician, etc. Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound according to the present embodiments, formulated in a compatible pharmaceutical carrier may also be prepared, placed in an appropriate container, and labeled for treatment of an indicated condition or diagnosis, as is detailed hereinabove.

Thus, in some embodiments, the pharmaceutical composition is packaged in a packaging material and identified in print, in or on the packaging material, for use in the treatment of a genetic disorder, as defined herein, and/or in any of the uses described herein.

In some embodiments, the pharmaceutical composition is for use in the treatment of a genetic disorder, as defined herein, and/or in any of the uses described herein.

In any of the composition, methods and uses described herein, the compounds can be utilized in combination with other agents useful in the treatment of the genetic disorder and/or in inducing or promoting readthrough activity of a premature stop codon mutation and/or in increasing expression of a gene having a premature stop codon mutation as described herein.

Being primarily directed at treating genetic disorders, which are chronic by definition, the compounds presented herein or pharmaceutical compositions containing the same are expected to be administered throughout the lifetime of the subject being treated. Therefore, the mode of administration of pharmaceutical compositions containing the compounds should be such that will be easy and comfortable for administration, preferably by self-administration, and such that will take the smallest toll on the patient's wellbeing and course of life.

The repetitive and periodic administration of the compounds presented herein or the pharmaceutical compositions containing the same can be effected, for example, on a daily basis, i.e. once a day, more preferably the administration is effected on a weekly basis, i.e. once a week, more preferably the administration is effected on a monthly basis, i.e. once a month, and most preferably the administration is effected once every several months (e.g., every 1.5 months, 2 months, 3 months, 4 months, 5 months, or even 6 months).

As discussed hereinabove, some of the limitations for using presently known aminoglycosides as truncation mutation readthrough drugs are associated with the fact that they are primarily antibacterial (used as antibiotic agents). Chronic use of any antibacterial agents is highly unwarranted and even life threatening as it alters intestinal microbial flora which may cause or worsen other medical conditions such as flaring of inflammatory bowel disease, and may cause the emergence of resistance in some pathological strains of microorganisms.

In some embodiments, the compounds presented herein have substantially no antibacterial activity. By "no antibacterial activity" it is meant that the minimal inhibition concentration (MIC) thereof for a particular strain is much higher than the concentration of a compound that is considered an antibiotic with respect to this strain. Further, the MIC of these compounds is notably higher than the concentration required for exerting truncation mutation suppression activity.

Being substantially non-bactericidal, the compounds presented herein do not exert the aforementioned adverse effects and hence can be administered via absorption paths that may contain benign and/or beneficial microorganisms that are not targeted and thus their preservation may even be required. This important characteristic of the compounds presented herein renders these compounds particularly effective drugs against chronic conditions since they can be administered repetitively and during life time, without causing any antibacterial-related adverse, accumulating effects, and can further be administered orally or rectally, i.e. via the GI tract, which is a very helpful and important characteristic for a drug directed at treating chronic disorders.

According to some embodiments, the compounds presented herein are selected and/or designed to be selective towards the eukaryotic cellular translation system versus that of prokaryotic cells, namely the compounds exhibit higher activity in eukaryotic cells, such as those of mammalian (humans) as compared to their activity in prokaryotic cells, such as those of bacteria. Without being bound by any particular theory, it is assumed that the compounds presented herein, which are known to act by binding to the A-site of the 16S ribosomal RNA while the ribosome is involved in translating a gene, have a higher affinity to the eukaryotic ribosomal A-site, or otherwise are selective towards the eukaryotic A-site, versus the prokaryotic ribosomal A-site, as well as the mitochondrial ribosomal A-site which resembles its prokaryotic counterpart.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is expected that during the life of a patent maturing from this application many relevant genetic diseases and disorders as defined herein will be uncovered and the scope of this term is intended to include all such new disorders and diseases a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Chemical Syntheses of Cell-Permealizing Group-Containing Exemplary Compounds According to Some of the Present Embodiments In general, aminoglycosides (AGs) antibiotic are charged at physiological pH, thus they may be limited in their absorption through the GI tract and are therefore typically administered by injection. In addition, AGs exhibit limited permeability into eukaryotic cells, which requires their administration in higher dosages in order to overcome the cellular uptake limitation, which in turn causes adverse effects and limits their use in translational therapy. The compounds described in this example were designed in order to solve these problems.

To mitigate the GI tract absorption problem, alkyl/aryl groups have been attached on the pseudo-disaccharide scaffold at the N1 position of a paromamine-derived aminoglycoside. Exemplary compounds NB 144, NB 145, NB 146 and NB 147 (see, Table 1 herein), were prepared so as to exhibit respectively an isopropyl, a benzyl, a propyl and a propyl substitution at the N-1 position.

To mitigate the cellular uptake limitation, a series of compounds was prepared with cell-permealizable groups so as to increase their cellular uptake. These compounds were prepared by introducing a cell-permealizable group, such as a guanidine group, at various positions on the scaffold.

The following are processes for preparing exemplary compounds according to some embodiments of the present invention, which are presented in Table 1 hereinabove.

The synthesis of compounds NB144, NB145 and NB146 was accomplished in two steps starting with Compound 1, (prepared as previously reported in Baasov et al., *Bioorg. Med. Chem.*, 2010, 18, pp. 3735-3746), as illustrated in a general Scheme 2 below (reagents and conditions: (i) RCHO, H$_2$O, 1M HCl, NaBCNH$_3$ or RCHO, MeOH, NaBH$_4$ 0° C.; PMe$_3$, NaOH, THF, room temperature).

Scheme 2

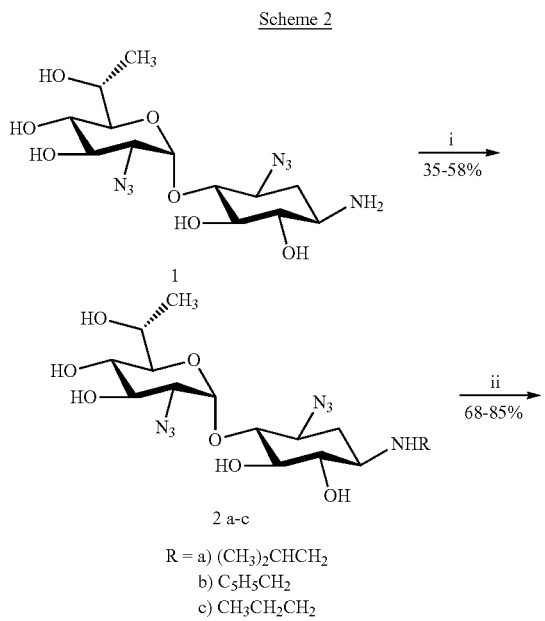

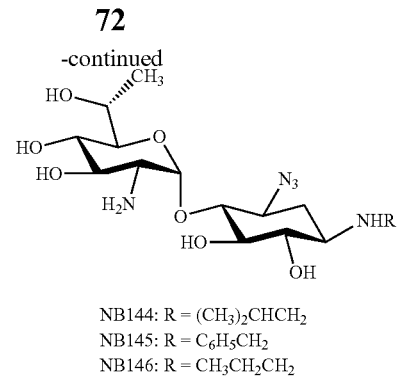

NB144: R = (CH$_3$)$_2$CHCH$_2$
NB145: R = C$_6$H$_5$CH$_2$
NB146: R = CH$_3$CH$_2$CH$_2$

Monoalkylation of primary amine with aliphatic aldehydes was performed in water with sodium borocyanohydride, while methanol/NaBH$_4$ was used in the case of benzaldehyde. The total yield of this step was 35-58% of monoalkylated/benzylated products 2a-c (Scheme 2). The Staudinger reaction was then performed to obtain the final compounds NB144, NB145 and NB146 in good yields of 68-85%.

Synthesis of NB144

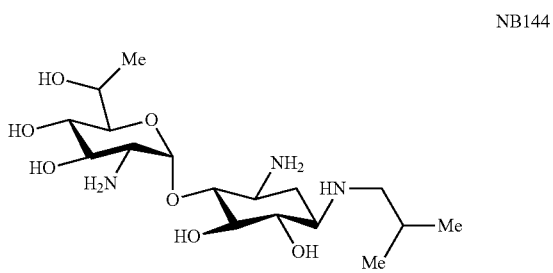

NB144 was prepared according to Scheme 2 hereinabove, starting with the precursor Compound 1. Compound 1 (0.5 grams, 1.2 mmol) was dissolved and stirred in water (15 mL) at 0° C. for 15 minutes, and 1 M solution of hydrochloric acid was added dropwise to adjust the pH of the reaction mixture to about 2-3. About 2 equivalents of isobutyraldehyde (0.2 mL) were added to the reaction mixture and stirred for 15 minutes at room temperature. The resulted solution was cooled to 0° C. and NaBCNH$_3$ (30 mg, 1.5 equivalents) was added and progress was monitored by TLC. After 1 hour of reaction, the similar process was repeated until starting material was consumed to desired product. After completion, the reaction mixture was evaporated and subjected to column chromatography to obtain the mono alkylated product, Compound 2a (0.2 grams, 35%). Compound 2a was dissolved in a mixture of THF (5 mL) and aqueous NaOH (1 mM, 5.0 mL). The mixture was stirred at room temperature for 10 minutes, after which PMe$_3$ (1 M solution in THF, 2.0 mL, 2.0 mmol) was added. The reaction progress was monitored by TLC [CH$_2$Cl$_2$/MeOH/H$_2$O/MeNH$_2$ (33% solution in EtOH) 10:15:6:15], which indicated completion after 1 hour. The product was purified by column chromatography on a short column of silica gel. The column was washed with the following solvents: THF (200 mL), CH$_2$Cl$_2$ (200 mL), EtOAc (100 mL), and MeOH (200 mL). The product was then eluted with a mixture of MeNH$_2$ (33% solution in EtOH) and MeOH (8:2). Fractions containing the product were combined and evaporated to dryness. The residue was re-dissolved in a small volume of water and evaporated again (2-3 repeats) to afford the free amine form of NB144. The analytically pure product was obtained by passing the above product through a short column of Amberlite CG50 ($NH_4^+$ form). The column was first washed with a mixture of MeOH/$H_2O$ (3:2), then the product was eluted with a mixture of MeOH/$H_2O$/$NH_4OH$ (8:1:1) to afford title compound NB144 (0.150 grams, 85%). For the storage and biological tests, NB144 was converted to its sulfate salt form: the free base was dissolved in water, the pH was adjusted around 7.0 with $H_2SO_4$ (0.1 N) and lyophilized.

$^1$H NMR (500 MHz, $CD_3OD$): "Ring I": $\delta_H$=1.21 (d, 3H, J=6.0 Hz, $CH_3$), 2.70 (dd, 1H, $J_1$=3.4, $J_2$=10.0 Hz, H-2'), 3.21 (t, 1H, J=10.0 Hz, H-4'), 3.48 (t, 1H, J=9.0 Hz, H-3'), 3.81 (dd, 1H, $J_1$=3.4, $J_2$=10.0 Hz, H-5'), 4.09 (m, 1H, H-6'), 5.16 (d, 1H, J=2.5 Hz, H-1'); "Ring II": $\delta_H$=1.11 (m, 1H, H-2$_{ax}$), 2.14 (td, 1H, $J_1$=4.5, $J_2$=12.5 Hz, H-2$_{eq}$), 2.46 (m, 1H, H-1), 2.71 (m, 1H, H-3), 3.19 (m, 2H, H-4 and H-6), 3.44 (t, 1H, J=9.1 Hz, H-5). The additional peaks in the spectrum were identified as follows: $\delta_H$=0.96 (t, 3H, J=3.1 Hz), 0.97 (t, 3H, J=3.2 Hz), 1.79 (m, 1H), 2.32 (m, 1H), 2.56 (m, 1H).

$^{13}$CNMR (125 MHz, $CD_3OD$): $\delta_C$=16.6, 20.8, 20.9, 29.0, 34.6, 51.5, 55.8, 57.4, 58.9, 67.8, 73.6, 75.8, 76.5 (2C), 77.8, 90.9, 103.2 (C-1').

MALDI TOFMS: calculated for $C_{17}H_{36}N_3O$ ([M+H]$^+$) m/e: 394.2; measured m/e: 394.1.

Synthesis of NB145

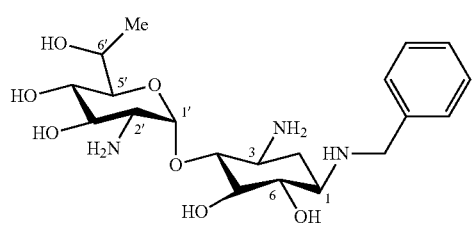

NB145

NB145 was prepared according to Scheme 2 presented hereinabove, starting with the precursor Compound 1. Compound 1 (0.5 grams, 1.2 mmol) and benzaldehyde (0.3 grams 4 mmol) were dissolved and stirred in methanol (15 mL) at room temperature for 15 minutes. The resulted solution was cooled to 0° C. and $NaBH_4$ (100 mg) was added and progress was monitored by TLC. After completion, the reaction mixture evaporated and subjected to column chromatography to obtain the mono benzylated Compound 2b in 0.3 grams, 50% yield. Compound 2b was dissolved in a mixture of THF (5 mL) and aqueous NaOH (1 mM, 5.0 mL). The mixture was stirred at room temperature for 10 minutes, after which $PMe_3$ (1 M solution in THF, 2.0 mL, 2.0 mmol) was added. The reaction progress was monitored by TLC [$CH_2Cl_2$/MeOH/$H_2O$/MeNH$_2$ (33% solution in EtOH) 10:15:6:15], which indicated completion after 1 hour. The product was purified by column chromatography on a short column of silica gel. The column was washed with the following solvents: THF (200 mL), $CH_2Cl_2$ (200 mL), EtOAc (100 mL), and MeOH (200 mL). The product was then eluted with a mixture of MeNH$_2$ (33% solution in EtOH) and MeOH (8:2). Fractions containing the product were combined and evaporated to dryness. The residue was re-dissolved in a small volume of water and evaporated again (2-3 repeats) to afford the free amine form of NB145. The analytically pure product was obtained by passing the above product through a short column of Amberlite CG50 ($NH_4^+$ form). The column was first washed with a mixture of MeOH/$H_2O$ (3:2), then the product was eluted with a mixture of MeOH/$H_2O$/$NH_4OH$ (8:1:1) to afford NB145 (0.200 grams, 75% yield). For the storage and biological tests, NB145 was converted to its sulfate salt form: the free base was dissolved in water, the pH was adjusted around 7.0 with $H_2SO_4$ (0.1 N) and lyophilized.

$^1$HNMR (500 MHz, $CD_3OD$): "Ring I": $\delta_H$=1.21 (d, 3H, J=6.0 Hz, $CH_3$), 2.73 (dd, 1H, $J_1$=4.6, $J_2$=10.3 Hz, H-2'), 3.23 (t, 1H, J=10.0 Hz, H-4'), 3.49 (t, 1H, J=9.0 Hz, H-3'), 3.82 (dd, 1H, $J_1$=3.4, $J_2$=10.0 Hz, H-5'), 4.12 (m, 1H, H-6'), 5.18 (d, 1H, J=2.5 Hz, H-1'); "Ring II": $\delta_H$=1.15 (m, 1H, H-2$_{ax}$), 2.23 (td, 1H, $J_1$=4.5, $J_2$=12.5 Hz, H-2$_{eq}$), 2.56 (m, 1H, H-1), 2.70 (m, 1H, H-3), 3.22 (t, 1H, J=9.2 Hz, H-6), 3.28 (t, 1H, J=9.0 Hz, H-4), 3.43 (t, 1H, J=9.1 Hz, H-5). The additional peaks in the spectrum were identified as follows: $\delta_H$=3.65 (d, 1H, J=12.5 Hz), 3.92 (d, 1H, J=12.5 Hz), 7.28-7.37 (m, 5H, Ar).

$^{13}$CNMR (125 MHz, $CD_3OD$): $\delta_C$=16.4, 34.2, 51.1, 51.6, 57.2, 57.8, 67.6, 73.2, 75.7, 76.3, 76.4, 77.7, 90.2, 102.9 (C-1'), 128.3 (Ar), 129.4 (Ar), 129.6 (Ar), 140.3 (Ar).

MALDI TOFMS calculated for $C_{20}H_{34}N_3O_7$ ([M+H]$^+$) m/e: 428.2; measured m/e: 428.1.

Synthesis of NB146

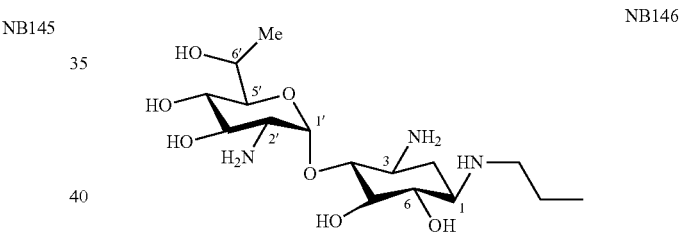

NB146

NB146 was prepared according to Scheme 2 presented hereinabove, starting with Compound 1. Compound 1 (0.5 grams, 1.2 mmol) was dissolved and stirred in water (15 mL) at 0° C. for 15 minutes and a 1 M solution of hydrochloric acid was added dropwise to adjust the pH of the reaction mixture to about 2-3. About 2 equivalents of propyl aldehyde (0.2 mL) were added to the reaction mixture and stirred for 15 minutes at room temperature. The resulted solution was cooled to 0° C. and $NaBCNH_3$ (30 mg, 1.5 equivalents) was added and progress was monitored by TLC. After 1 hour of reaction, the similar process was repeated until starting material was consumed to desired product. After completion, the reaction mixture was evaporated and subjected to column chromatography to obtain Compound 2c in 0.325 g (58%).

$^1$H NMR (500 MHz, $CD_3OD$): "Ring I": $\delta_H$=1.27 (d, 3H, J=6.0 Hz, $CH_3$), 3.09 (dd, 1H, $J_1$=4.2, $J_2$=10.5 Hz, H-2'), 3.39 (dd, 1H, $J_1$=8.7, $J_2$=10.0 Hz, H-4'), 3.94 (m, 2H, H-3' and H-5'), 4.04 (m, 1H, H-6'), 5.73 (d, 1H, J=3.5 Hz, H-1'); "Ring II": $\delta_H$=1.26 (m, 1H, H-2$_{ax}$), 2.31 (td, 1H, $J_1$=4.5, $J_2$=12.5 Hz, H-2$_{eq}$), 2.54 (m, 1H, H-1), 3.15 (m, 1H, H-3), 3.46-3.54 (m, 3H, H-4, H-5 and H-6). The additional peaks in the spectrum were identified as follows: $\delta_H$=0.98 (t, 3H, J=7.2 Hz), 1.56 (m, 2H), 2.53 (m, 1H), 2.72 (m, 1H).

$^{13}$CNMR (125 MHz, CD$_3$OD): $\delta_C$=11.9, 18.1, 23.6, 32.6 (C-2), 49.7, 57.9, 61.7, 64.7, 69.4, 72.3, 74.3, 75.2, 76.7, 78.6, 80.7, 98.6 (C-1').

MALDI TOFMS calculated for C$_{16}$H$_{30}$N$_7$O$_7$([M+H]$^+$) m/e: 432.2; measured m/e: 432.2.

Compound 2c (0.325 grams, 0.75 mmol) was dissolved in a mixture of THF (5 mL) and aqueous NaOH (1 mM, 5.0 mL). The mixture was stirred at room temperature for 10 minutes, after which PMe$_3$ (1 M solution in THF, 2.0 mL, 2.0 mmol) was added. The reaction progress was monitored by TLC [CH$_2$Cl$_2$/MeOH/H$_2$O/MeNH$_2$ (33% solution in EtOH) 10:15:6:15], which indicated completion after 1 hour. The product was purified by column chromatography on a short column of silica gel. The column was washed with the following solvents: THF (200 mL), CH$_2$Cl$_2$ (200 mL), EtOAc(100 mL), and MeOH (200 mL). The product was then eluted with a mixture of 20% MeNH$_2$ (33% solution in EtOH) in 80% MeOH. Fractions containing the product were combined and evaporated to dryness. The residue was re-dissolved in a small volume of water and evaporated again (2-3 repeats) to afford the free amine form of NB146. The analytically pure product was obtained by passing the above product through a short column of Amberlite CG50 (NH$_4$$^+$ form). The column was first washed with a mixture of MeOH/H$_2$O (3:2), then the product was eluted with a mixture of MeOH/H$_2$O/NH$_4$OH (8:1:1) to afford NB146 (0.175 grams, 68% yield). For the storage and biological tests, compound was converted to its sulfate salt form: the free base was dissolved in water, the pH was adjusted around 7.0 with H$_2$SO$_4$ (0.1 N) and lyophilized.

$^1$HNMR (500 MHz, CD$_3$OD): "Ring I": $\delta_H$=1.21 (d, 3H, J=6.0 Hz, CH$_3$), 2.71 (dd, 1H, J$_1$=4.2, J$_2$=10.3 Hz, H-2'), 3.21 (t, 1H, J=10.0 Hz, H-4'), 3.48 (t, 1H, J=9.6 Hz, H-3'), 3.81 (dd, 1H, J$_1$=3.4, J$_2$=10.0 Hz, H-5'), 4.09 (m, 1H, H-6'), 5.16 (d, 1H, J=2.5 Hz, H-1'); "Ring II": $\delta_H$=1.10 (m, 1H, H-2$_{ax}$), 2.14 (td, 1H, J$_1$=4.5, J$_2$=12.5 Hz, H-2$_{eq}$), 2.49 (m, 1H, H-1), 2.69 (m, 1H, H-3), 3.20 (m, 2H, H-4 and H-6), 3.44 (t, 1H, J=9.1 Hz, H-5). The additional peaks in the spectrum were identified as follows: $\delta_H$=0.97 (t, 3H, J=7.2 Hz), 1.57 (m, 2H), 2.49 (m, 1H), 2.71 (m, 1H).

$^{13}$CNMR (125 MHz, CD$_3$OD): $\delta_C$=11.9, 16.6, 23.7, 34.6 (C-2), 49.7, 51.4, 57.4, 58.9, 67.8, 73.5, 75.8, 76.5, 76.6, 77.8, 90.8, 103.2 (C-1').

MALDI TOFMS calculated for C$_{16}$H$_{34}$N$_3$O$_7$ ([M+H]$^+$) m/e: 380.2; measured m/e: 380.1.

Synthesis of NB147

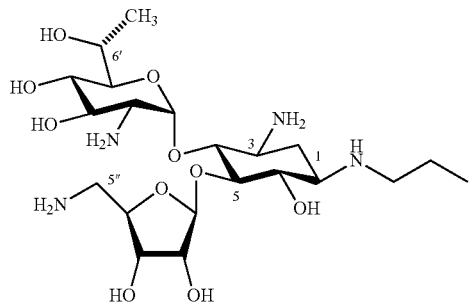

NB147

NB147 was prepared according to Scheme 3 presented hereinbelow (reagents and conditions: a) 5.5 equivalents Ac$_2$O, Py, -20° C., 24 hours; b) BF$_3$OEt$_2$, MS, CH$_2$Cl$_2$, -30° C., 3 hours; c) THF, 0.5M NaOH, 60° C., 24 h; d) PMe3, NaOH, THF, room temperature), starting with Compound 2c (the precursor of the NB146, see Scheme 2 hereinabove).

Scheme 3

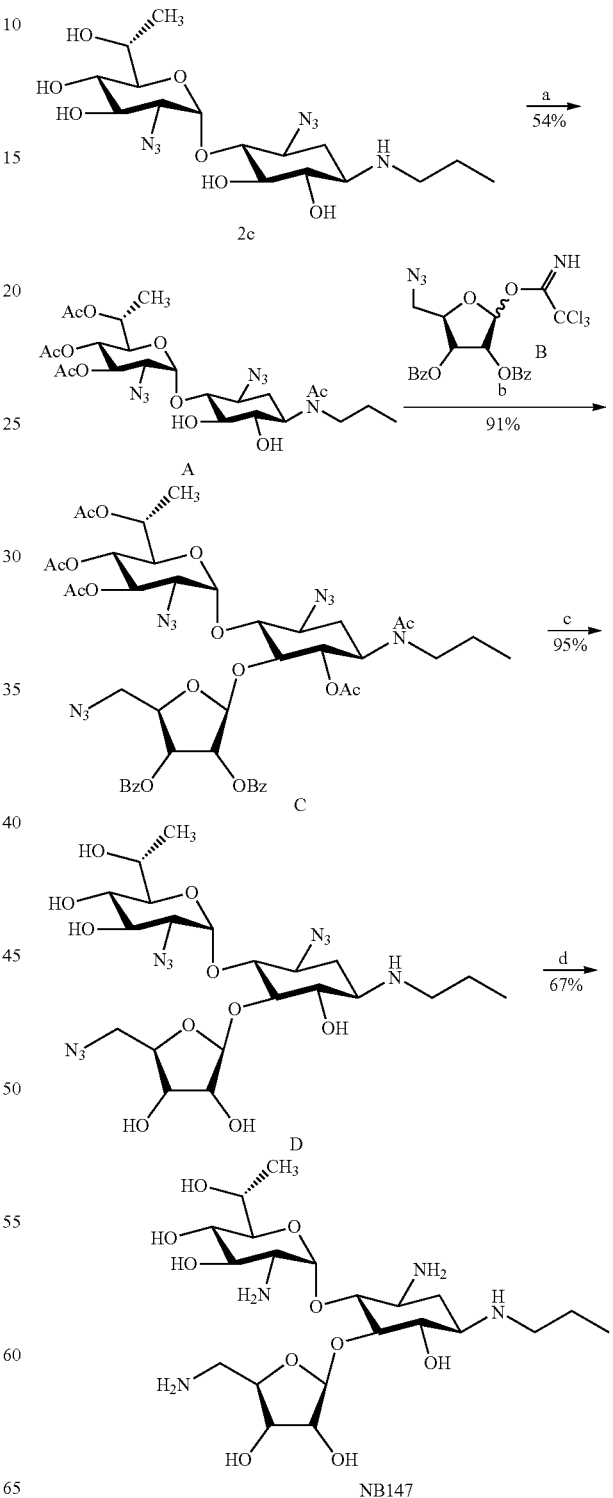

Briefly, Compound 2c was selectively acetylated to afford the required acceptor A which was then glycosylated with trichloroacetimidate donor B as previously described (Nudelman, I. et al., *Bioorg. Med. Chem. Lett.*, 2006, 16, pp. 6310-6315) to give the corresponding trisaccharide C at 91% isolated yield. Two subsequent deprotection steps that included: treatment with strong base (NaOH, 60° C.) to remove all the ester and amide protections and Staudinger reaction to convert azides to the amines obtained the target NB147 at two steps yield of 81%. The final product, along with all the intermediates were characterized by all the standard analytical techniques including $^1$H, $^{13}$C and 2D-NMR, along with 1D-TOXY to assign the structures of the products.

Synthesis of NB147

Compound 2c (750 mg, 1.0 equivalents) was dissolved in anhydrous pyridine (8 mL) and cooled to −20° C. At this temperature, acetic anhydride (2.0 mL, 5.6 equivalents) was added dropwise and allowed the reaction to progress at −20° C. The reaction progress was monitored by TLC, which indicated completion after 17 hours. The reaction mixture was diluted with EtOAc, and extracted with aqueous solution of NaHCO$_3$, HCl (2%), saturated aqueous NaHCO$_3$, and brine. The combined organic layers were dried over anhydrous MgSO$_4$ and concentrated. The crude product was purified by silica gel column chromatography to afford Compound A (600 mg, 54% yield). Anhydrous CH$_2$Cl$_2$ (15 mL) was added to a powdered, flame-dried 4 Å molecular sieves (2.0 grams), followed by the addition acceptor A (500 mg, 1.0 equivalents) and the known donor B (2.5 grams, 4.0 equivalents). The reaction mixture was stirred for 10 min at room temperature and was then cooled to −30° C. At this temperature, catalytic amount of BF$_3$-Et$_2$O (0.15 ml) was added and the mixture was stirred at −30° C. and the reaction progress was monitored by TLC, which indicated the completion after 60 minutes. The reaction mixture was diluted with ethyl acetate and washed with saturated NaHCO$_3$ and brine. The combined organic layer was dried over MgSO$_4$, evaporated and subjected to column chromatography (EtOAc/Hexane) to obtain the titled compound C (715 mg) at 91% yield. Compound C from the above step (715 mg) was dissolved in minimal amount of THF and treated with 0.5M solution of NaOH and refluxed for overnight at 60° C. After which the reaction mixture was cooled to room temperature and evaporated to dryness. The crude product was purified by DOWEX-H$^+$ ion exchange column to obtain the title compound D (400 mg) in 95% yield.

$^1$H NMR (500 MHz, CD$_3$OD): "Ring I": $\delta_H$=1.25 (d, 3H, J=6.0 Hz, CH$_3$), 3.12 (dd, 1H, J$_1$=3.4, J$_2$=10.0 Hz, H-2'), 3.34 (t, 1H, J=9.0 Hz, H-4'), 3.96 (m, 1H, H-3' and H-5'), 4.04 (m, 1H, H-6'), 6.00 (d, 1H, J=3.2 Hz, H-1'); "Ring II": $\delta_H$=1.20 (m, 1H, H-2ax), 2.27 (td, 1H, J$_1$=4.5, J$_2$=12.5 Hz, H-2eq), 2.54 (m, 1H, H-1), 3.24 (t, 1H, J=9.0 Hz, H-6), 3.50 (m, 1H, H-3), 3.64 (t, 1H, J=9.5 Hz, H-5), 3.72 (t, 1H, J=9.0 Hz, H-4); "Ring III": $\delta_H$=3.48-3.59 (m, 2H, H-5" and H-5"), 4.01 (m, 1H, H-4"), 4.05 (m, 1H, H-3") 4.15 (m, 1H, H-2"), 5.36 (s, 1H, H-1"). The additional peaks in the spectrum were identified as follows: $\delta_H$=0.98 (t, 3H, J=7.2 Hz), 1.55 (m, 2H), 2.50 (m, 1H), 2.70 (m, 1H).

$^{13}$C NMR (125 MHz, CD$_3$OD): $\delta_C$=11.9, 17.9, 23.8, 32.7, 49.7, 54.4, 58.0, 62.3, 64.9, 69.3, 72.5, 72.6, 74.4, 75.1, 76.3 (2C), 76.9, 82.4, 86.2, 97.3 (C-1'), 110.7 (C-1").

MALDI TOFMS: calculated for C$_{21}$H$_{37}$N$_{10}$O$_{10}$ ([M+H]$^+$) m/e: 589.2; measured m/e: 589.1.

To a stirred solution of Compound D from the above step (380 mg, 1.0 equivalents) in a mixture of THF (3 mL) and aqueous NaOH (1 mM, 5 mL), PMe$_3$ (1 M solution in THF, 5 mL, 7.8 equivalents) was added. The progress of the reaction was monitored by TLC [CH$_2$Cl$_2$/MeOH/H$_2$O/MeNH$_2$ (33% solution in EtOH), 10:15:6:15], which indicated completion after 3 hours. The reaction mixture was purified by flash chromatography on a short column of silica gel. The column was washed with the following solvents: THF (100 mL), CH$_2$Cl$_2$ (100 mL), EtOH (50 mL), and MeOH (100 mL). The product was then eluted with the mixture of 5% MeNH$_2$ solution (33% solution in EtOH) in 80% MeOH. Fractions containing the product were combined and evaporated under vacuum. The pure product was obtained by passing the above product through a short column of Amberlite CG50 (NH$_4^+$ form). First, the column was washed with water, then the product was eluted with a mixture of 10% NH$_4$OH in water to yield compound NB147 (230 mg, 67% yield). For the storage and biological tests, compound NB147 was converted to its sulfate salt form as follow. The free base form was dissolved in water, the pH was adjusted to 6.7 with H$_2$SO$_4$ (0.1 N) and lyophilized to afford the sulfate salt of NB147.

$^1$HNMR (500 MHz, CD$_3$OD): "Ring I": $\delta_H$=1.22 (d, 3H, J=6.0 Hz, CH$_3$), 2.61 (dd, 1H, J$_1$=3.4, J$_2$=9.0 Hz, H-2'), 3.23 (t, 1H, J=10.0 Hz, H-4'), 3.54 (t, 1H, J=9.6 Hz, H-3'), 3.81 (dd, 1H, J$_j$=3.4, J$_2$=10.0 Hz, H-5'), 4.12 (m, 1H, H-6'), 5.20 (d, 1H, J=3.5 Hz, H-1'); "Ring II": $\delta_H$=1.12 (m, 1H, H-2ax), 2.10 (td, 1H, J$_1$=4.5, J$_2$=12.5 Hz, H-2eq), 2.49 (m, 1H, H-1), 2.75 (m, 1H, H-3), 3.32 (t, 1H, J=9.0 Hz, H-6), 3.38 (t, 1H, J=9.5 Hz, H-4), 3.52 (t, 1H, J=9.0 Hz, H-5); "Ring III" $\delta_H$: 2.80 (dd, 1H, J$_1$=7.0, J$_2$=13.5 Hz, H-5"), 2.94 (dd, 1H, J$_1$=4.3, J$_2$=13.5 Hz, H-5"), 3.86 (m, 1H, H-4"), 3.96 (t, 1H, J=5.4 Hz, H-3"), 4.07 (m, 1H, H-2"), 5.26 (d, 1H, J=2.6 Hz, H-1"). The additional peaks in the spectrum were identified as follows: $\delta_H$=0.97 (t, 3H, J=7.2 Hz), 1.53 (m, 2H), 2.49 (m, 1H), 2.71 (m, 1H).

$^{13}$CNMR (125 MHz, CD$_3$OD): $\delta_C$=11.9, 16.7, 23.7, 34.7 (C-2), 45.2, 49.7, 52.5, 57.9, 58.6, 67.9, 72.5, 73.6, 75.3, 76.3, 76.4, 76.7, 84.9, 85.6, 87.1, 102.0 (C-1'), 110.3 (C-1").

MALDI TOFMS: calculated for C$_{21}$H$_{43}$N$_4$O$_{10}$ ([M+H]$^+$) m/e: 511.2; measured m/e: 511.1.

Synthesis of NB150 (Shown as its TFA Acid Addition Salt)

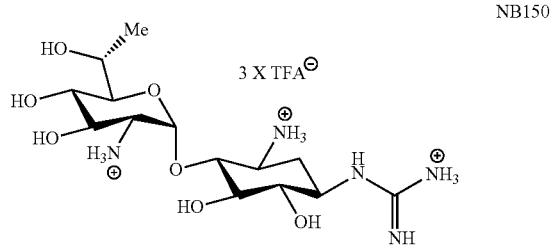

NB150

NB150 was prepared according to Scheme 4 presented hereinbelow, starting with Compound 1. Briefly, the guanidinylation of the free N-1 amine by protected guanidinylation reagent and Et$_3$N as a base afforded the desired Compound 3. Boc deprotection was carried out by TFA to produce Compound 4 with free amines on the guanidinium moiety. Finally, Staudinger reaction was used to remove the azide protection, resulting in the final product NB150

(Scheme 4, reagents and conditions: (a) Et$_3$N, H$_2$O/Dioxane, 81% (b) TFA, CH$_2$Cl$_2$, 0° C.→25° C. (c) PMe$_3$, THF, NaOH 0.1M, (ii) The product was eluted from the ion exchange column with a mixture of 2% TFA in MeOH, at 2 steps yield of 83%).

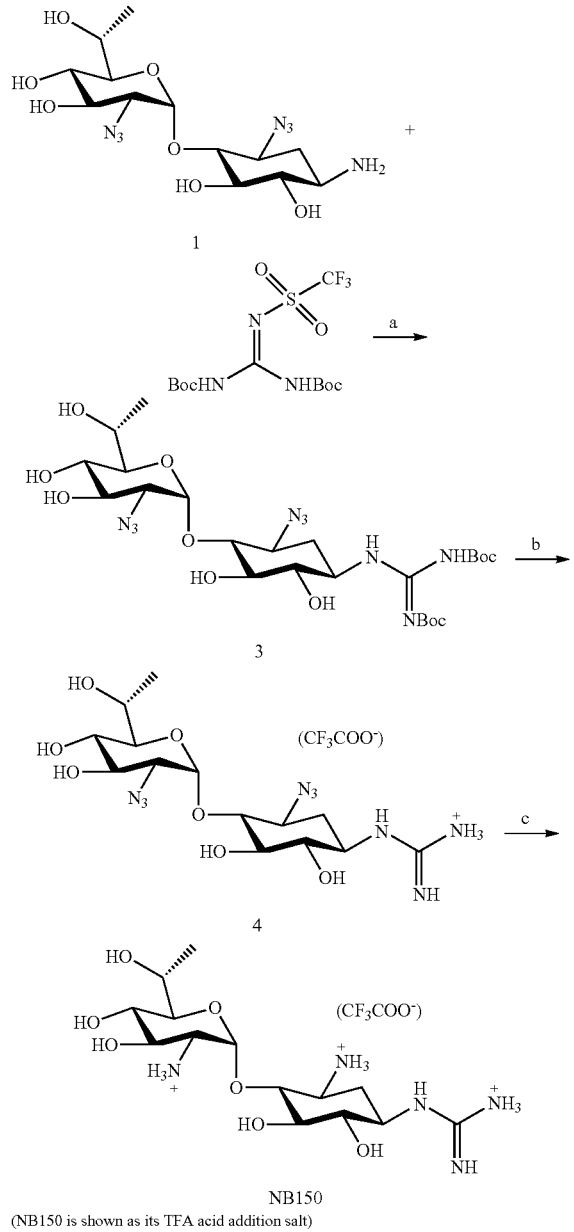

Scheme 4

NB150
(NB150 is shown as its TFA acid addition salt)

To a solution of compound 1 (2.69 grams, 1 equivalents) in H$_2$O (1 mL) was added 1,4-dioxane (5 mL) and N,N'-diBoc-N"-triflylguanidine (4.05 grams, 1.5 equivalents) in alternating portions so the solution remained relatively clear. After 5 min, NEt$_3$ (3 mL, 3 equivalents) was added at room temperature. After 24 hours, the 1,4-dioxane was evaporated, the remaining residue and H$_2$O was extracted with CHCl$_3$ (3×10 mL), washed with H$_2$O and brine, and dried over MgSO$_4$. The guanidinylated product isolated by flash column chromatography on silica gel (CHCl$_3$/MeOH) compound 3 (3.51 grams, 81%).

$^1$H NMR (500 MHz, CDCl$_3$): 'Ring I': $\delta_H$=5.37 (d, 1H, J=3.6 Hz, H-1), 4.03 (t, 1H, J=9.7 Hz, H-3), 4.04-4.00 (m, 1H, H-6), 3.81 (dd, 1H, J=9.7, 5.7 Hz, H-5), 3.58 (t, 1H, J=9.3 Hz, H-4), 3.37 (dd, 1H, J=10.5, 4.2 Hz, H-2), 1.31 (d, 3H, J=5.7 Hz, CH3-6); 'Ring II': $\delta_H$=4.19-4.10 (m, 1H, H-1), 3.67 (t, 1H, J=9.2 Hz, H-5), 3.54-3.47 (m, 1H, H-3), 3.41-3.32 (m, 2H, H-4, H-6), 2.40 (dt, 1H, J=12.5, 4.1 Hz, H-2eq), 1.50 (dd, 1H, J=19.7, 8.8 Hz, H-2ax); Additional peaks in the spectrum were identified as follow: $\delta_H$=11.46 (s, 1H, NH), 8.54 (d, 1H, J=7.0 Hz, NH), 1.49 (s, 9H, Boc), 1.48 (s, 9H, Boc).

$^{13}$C NMR (125 MHz, CDCl$_3$): $\delta_C$=162.7, 157.2, 153.2, 98.7 (C1'), 84.0 (Boc), 82.2, 80.3 (Boc), 77.2 (C5), 76.3, 74.1 (C4'), 73.6 (C5'), 72.3 (C3'), 70.3 (C6'), 63.6, 59.4 (C3), 50.1 (C1), 33.0 (C2), 28.4 (Boc), 28.2 (Boc), 19.3 (CH$_3$-6').

MALDI TOFMS: calculated for C$_{24}$H$_{41}$N$_9$O$_{11}$ ([M+H]$^+$) m/e 632.6; measured m/e 632.6.

To a solution of Compound 3 (498 mg, 1 equivalents) in CH$_2$Cl$_2$ (15 mL) at 10° C., TFA (6 mL) was added dropwise and after the addition the reaction mixture was allowed to attain the room temperature. The reaction progress was monitored by TLC (CH$_2$Cl$_2$/MeOH 8:2) and indicated of the completion of the reaction in 3 hours. The reaction mixture was evaporated to dryness to get the crude product 4 (686 mg). The crude product was subjected to the Staudinger reaction.

To a stirred solution of Compound 4 (686 mg, 1 equivalents) in a mixture of THF (3.0 mL) and aqueous NaOH (1 mM, 5.0 mL), PMe$_3$ (1 M solution in THF, 0.55 mL, 8 equivalents) was added dropwise and the mixture was further stirred overnight. The completion of the reaction was indicated by TLC (TFA/MeOH 1:49). The pure product was obtained by passing the above mixture through a short column of Amberlite CG50 (NH4+ form). The column was washed with the following solvents: Hexane, THF, EtOAc, MeOH and CH$_3$CN. Then the product was eluted with a mixture of TFA/MeOH (1:49) to yield NB150. For the storage and biological tests, NB 150 was dissolved in water and lyophilized to afford the TFA salt of NB 150 (701 mg, 83% for 2 steps).

$^1$H NMR (500 MHz, MeOD): 'Ring I': $\delta_H$=5.41 (d, 1H, J=4.1 Hz, H-1), 4.25 (qd, 1H, J=6.2, 1.8 Hz, H-6), 3.93 (dd, 1H, J=10.2, 2.2 Hz, H, 5), 3.81 (dd, 1H, J=10.6, 8.9 Hz, H-4), 3.39-3.27 (m, 2H), 1.22 (d, 3H, J=6.4 Hz, CH$_3$-6); 'Ring II': $\delta_H$=3.72 (t, 1H, J=9.6 Hz, H-5), 3.62-3.52 (m, 2H, H-1, H-6), 3.48-3.35 (m, 2H, H-3, H-4), 2.30 (dt, 1H, J=12.4, 4.1 Hz, H-2eq), 1.71 (dd, 1H, J=24.9, 12.3 Hz, H-2ax).

$^{13}$C NMR (125 MHz, MeOD): $\delta_C$=159.2, 100.1 (C1'), 85.6 (C5), 77.0 (C5'), 76.5, 76.3 (C4), 72.2, 71.8 (C4'), 66.0 (C6'), 56.4, 52.9, 51.0 (C3), 32.1 (C2), 15.7 (CH$_3$-6').

MALDI TOFMS: calculated for C$_{14}$H$_{29}$N$_5$O$_7$ ([M+H]$^+$) m/e 380.4; measured m/e 380. 8.

NB151 and NB152 were prepared by glycosylation reactions between two different acceptors 6 and 7 with donor 5, which contains guanidinium group, as depicted in Scheme 5 hereinbelow, followed by deprotection steps.

Scheme 5

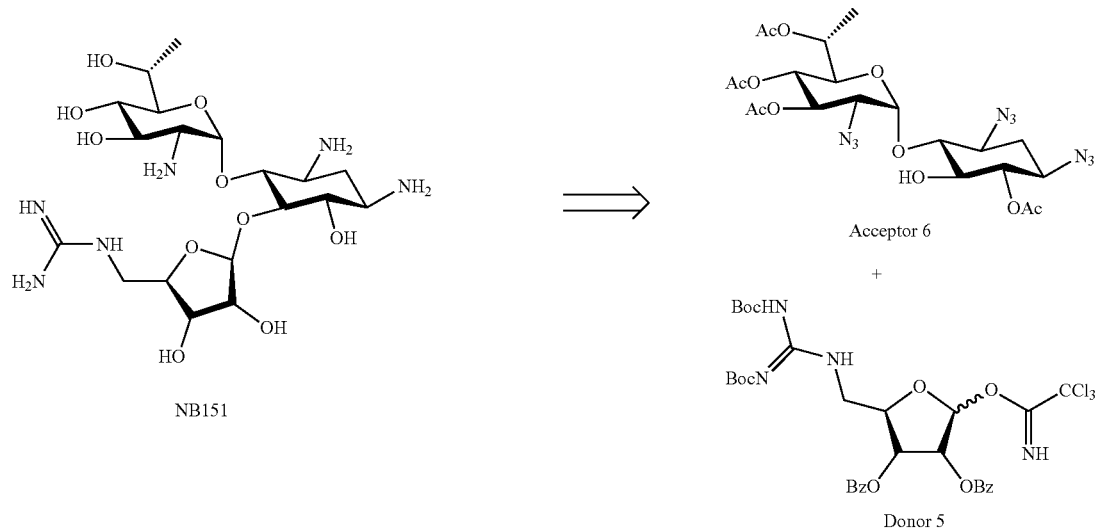

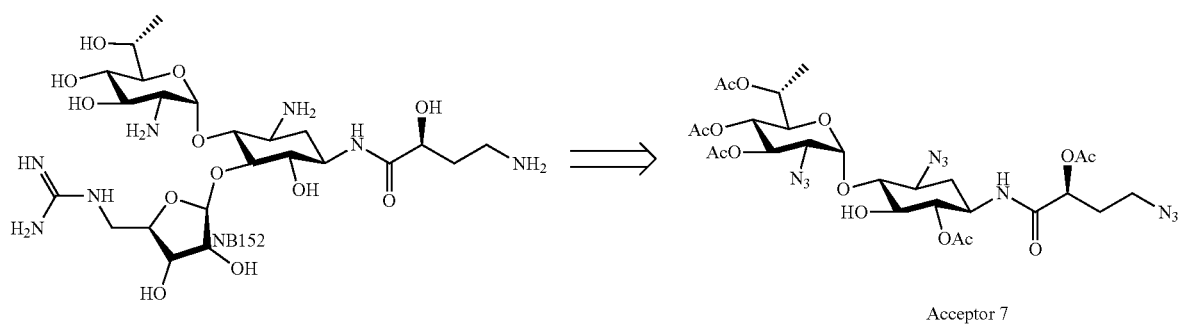

The synthesis of acceptors 6 and 7 in Scheme 5 was performed according to previously published procedures (Nudelman, I. et al., *Bioorg. Med. Chem.*, 2010, 18, pp. 3735-3746). The synthesis of donor 5 was done from the known ribose derivative A (reported previously in Nudelman, I. et al., *Bioorg. Med. Chem. Lett.*, 2006, 16, pp. 6310-6315) as illustrated in the Scheme 6 hereinbelow.

Compound A was converted to Compound B by using two chemical steps in one pot reaction: reduction of azide to amine by $H_2$, Pd/C; the reaction of the resulted amine with guanidinium reagent and $Et_3N$ as a base to receive the desired Compound B. The next two steps were deprotection of STol with N-Bromosuccinimide (NBS) gaining Compound C and substitution of trichloroacetimidate group for gaining the final active donor 5 (Scheme 6, reagents and conditions: (a) $H_2$, Pd/C, DIPEA, 95% (b) NBS, Acetone/ $H_2O$, −25° C., 83% (c) $CCl_3CN$, $K_2CO_3$, 0° C.→25° C., 50% Donor 5).

Scheme 6

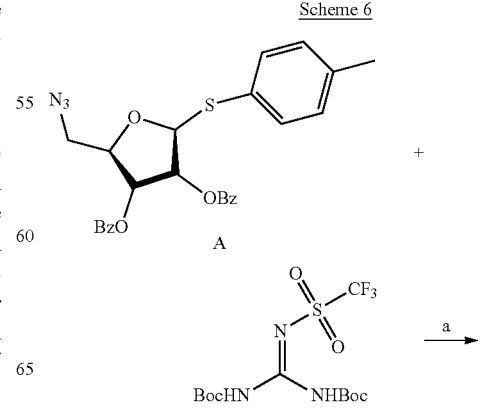

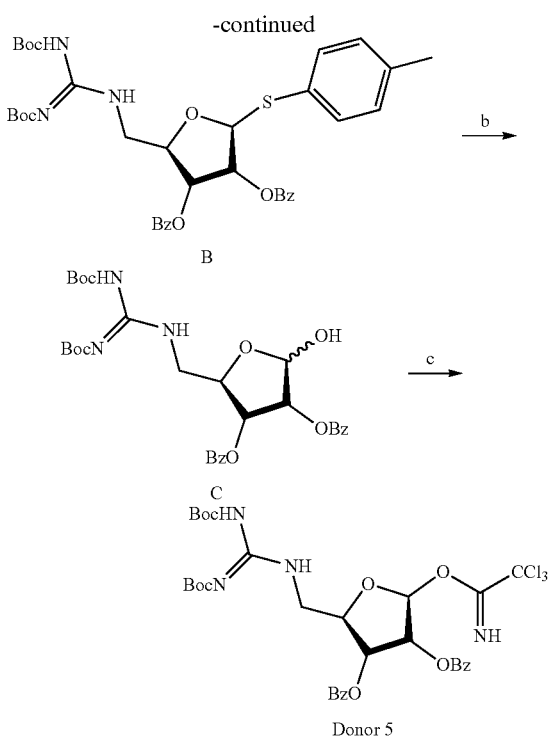

B

C

Donor 5

Donor 5 was prepared by stirring a solution of Compound A (6.87 grams, 1 equivalents) in EtOAc (15 mL) N,N'-diBoc-N"-triflylguanidine (5.48 grams, 1 equivalents; following Santana, A. G. et al., *J. Org. Chem.*, 2010, 75(15), pp. 5371-5374), 20 mole % Pd/C (5% w/w), and diethylisopropylamine (DIPEA) (2.71 grams, 1.5 equivalents) were added. Three vacuum/hydrogen cycles were performed, and the mixture was further stirred under a $H_2$ atmosphere (balloon) overnight. The completion of the reaction was indicated by TLC (EtOAc/Hexane 1:4). The reaction mixture was then filtered over a Celite®pad, which was washed twice with ethyl acetate, and the combined filtrates were evaporated. Column chromatography of the residue (EtOAc/Hexane 15:85) afforded the required guanidinylated Compound B (9.44 grams, 95% yield).

$^1$H NMR (400 MHz, CDCl$_3$): $δ_H$=11.48 (s, 1H, NH), 8.73 (t, 1H, J=4.4 Hz, NH), 7.91 (dd, 4H J=10.0, 8.8 Hz, STol), 7.51 (t, 4H, J=8.6 Hz, Bz), 7.35 (dd, 4H, J=7.9 Hz, Bz), 7.17 (d, 2H, J=7.8 Hz, Bz), 5.65 (t, 1H, J=4.5 Hz, H-2), 5.52 (d, 1H, J=4.0 Hz, H-1), 5.38 (t, 1H, J=5.4 Hz, H-3), 4.48 (dt, 1H, J=7.3, 5.3 Hz, H-4), 3.90 (ddd, 1H, J=13.6, 5.5, 4.5 Hz, H-5), 3.55-3.44 (m, 1H, H-5'), 1.49 (s, 9H, Boc), 1.45 (s, 9H, Boc).

$^{13}$C NMR (125 MHz, CDCl$_3$): $δ_C$=21.3 (STol), 43.1 (C-5), 72.9 (C-3), 75.1 (C-2), 79.4, 80.2 (C-4), 83.3, 88.9 (C-1), 127.7, 128.5 (2C), 129.2 (2C), 129.9, 130.1, 133.5 (2C), 134.7, 139.1, 153.1 (Boc), 156.5 (Boc), 163.5 (Boc), 165.1 (Bz), 165.3 (Bz).

MALDI TOFMS: calculated for $C_{37}H_{43}N_3O_9S$ ([M+H]$^+$) m/e 706.8; measured m/e 706.6.

A stirred solution of Compound B (3 grams, 1 equivalent) in a mixture of Acetone/H$_2$O (50:5 mL) was cooled to −25° C. After stirring for 10 min, NBS (3 grams, 4 equivalents) was added in portions. The progress of the reaction was monitored by TLC (EtOAc/Hexane 1:4) and indicated that the reaction was completed in 1.5 hours. At this stage the reaction mass was diluted with EtOAc (50 mL). The diluted solution was extracted with NaHCO$_3$ (2×30 mL). Then the organic layer was washed with saturate NaCl solution and dried over anhydrous MgSO$_4$. The solvent was evaporated to dryness and subjected column chromatography (EtOAc/Hexane 1:4) to yield Compound C (13.3 grams, 83%).

MALDI TOFMS: calculated for $C_{30}H_{37}N_3O_{10}$ ([M+H]$^+$) m/e 600.6; measured m/e 600.9.

A stirred solution of Compound C (6.66 grams, 1 equivalents) in distilled CH$_2$Cl$_2$ (85 mL) under argon atmosphere was cooled to 0° C. After stirring for 10 minutes, CCl$_3$CN (12.82 grams, 8 equivalents) was added dropwise. Then K$_2$CO$_3$ (4.6 grams, 3 equivalents) and dried MgSO$_4$ (8.5 grams) were added. After stirring for 30 minutes at 0° C., the mixture was allowed to warm to room temperature and stirred overnight. The completion of the reaction was indicated by TLC (EtOAc/Hexane 1:4). The reaction mixture was then filtered over a Celite®pad, which was washed twice with EtOAc, and the combined filtrates were evaporated. Column chromatography of the residue (EtOAc/Hexane 15:85+1 ml Et$_3$N) afforded the required donor 5 (4 grams, 48%).

$^1$H NMR (500 MHz, CDCl$_3$): $δ_H$=11.41 (s, 1H, NH), 8.67 (s, 1H, NH), 8.64 (t, 1H, J=5.4 Hz, NH), 7.96 (dd, 2H, J=8.2, 1.1 Hz, Bz), 7.90 (dd, 2H, J=8.2, 1.0 Hz, Bz), 7.56 (t, 1H, J=7.5 Hz, Bz), 7.51 (t, 1H, J=7.5 Hz, Bz), 7.40 (t, 2H, J=7.9 Hz, Bz), 7.33 (t, 2H, J=7.9 Hz, Bz), 6.54 (s, 1H, H-1), 5.91 (d, 1H, J=4.8 Hz, H-2), 5.68 (dd, 1H, J=7.0, 4.9 Hz, H-3), 4.71 (td, 1H, J=7.2, 4.7 Hz, H-4), 4.03 (ddd, 1H, J=14.0, 6.3, 4.9 Hz, H-5), 3.79 (ddd, 1H, J=13.9, 7.3, 4.9 Hz, H-5'), 1.43 (s, 9H, Boc), 1.41 (s, 9H, Boc).

$^{13}$C NMR (125 MHz, CDCl$_3$): $δ_C$=28.1 (Boc), 28.3 (Boc), 43.5 (C5), 72.6 (C3), 74.9 (C2), 80.9 (C4), 102.7 (C1), 128.5, 128.6, 129.9, 130.0, 133.5, 133.7, 153.0, 156.6, 160.6, 163.5, 165.0, 165.4.

MALDI TOFMS: calculated for $C_{32}H_{37}Cl_3N_4O_{10}$ ([M+H]$^+$) m/e 745.0; measured m/e 745.5.

Synthesis of NB151 (Shown as its TFA Acid Addition Salt)

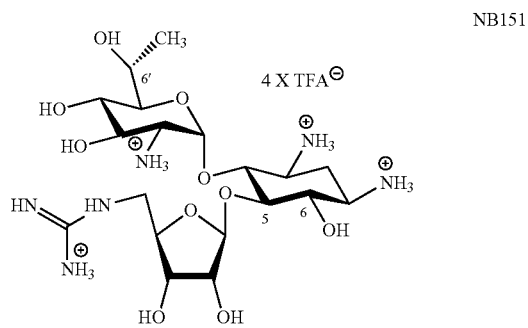

NB151

NB151 was prepared starting with the acceptor 6, and donor 5 as illustrated in Scheme 7 hereinbelow (Reagents and conditions: (a) BF$_3$.Et$_2$O, CH$_2$Cl$_2$, −30° C., 54% (b) MeNH$_2$, 52% (c) TFA, CH$_2$Cl$_2$, 0° C.→25° C. (d) (i) PMe$_3$, THF, NaOH 0.1M, (ii) The product was eluted from the ion exchange column with a mixture of 2% TFA in MeOH, 85% for 2 steps).

Scheme 7

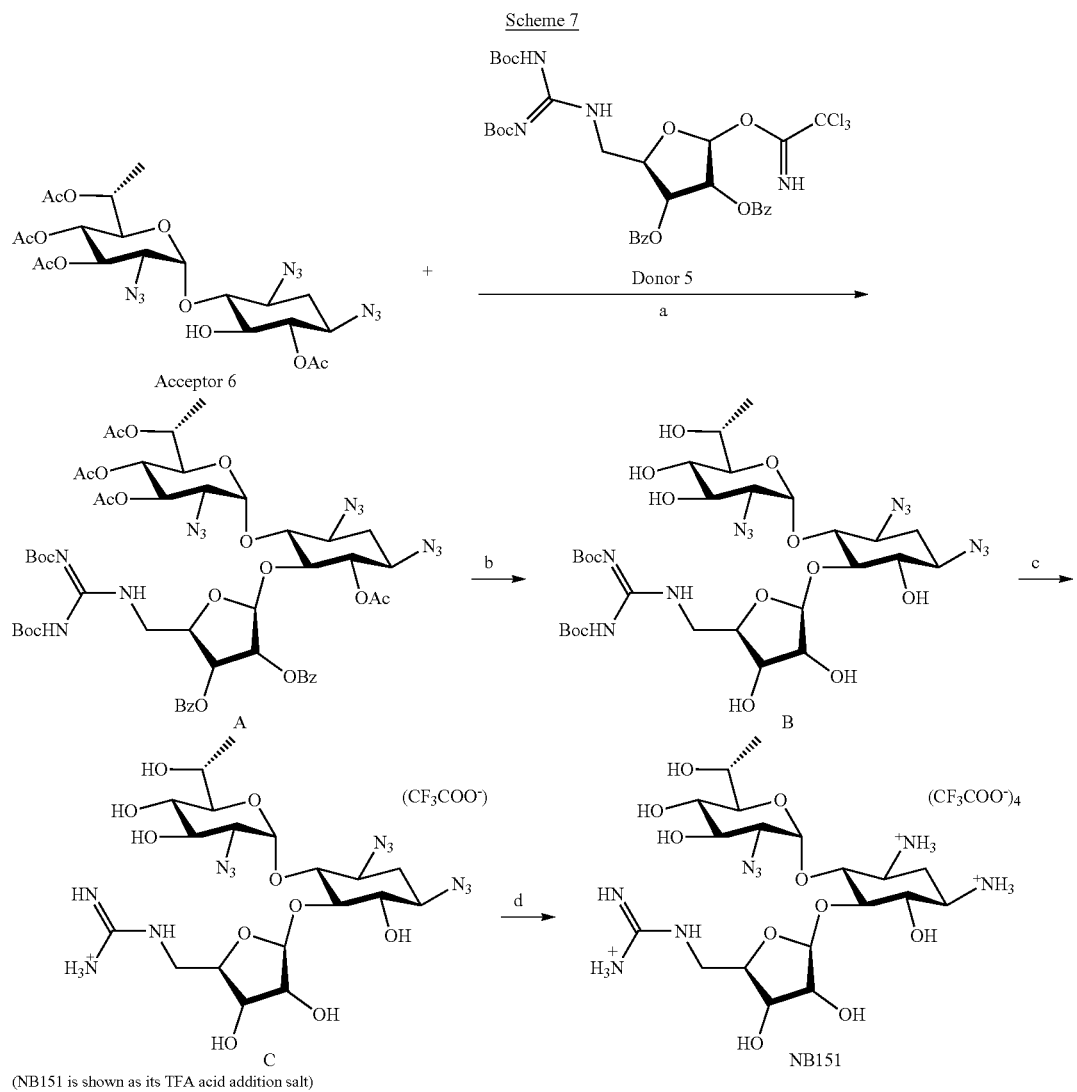

(NB151 is shown as its TFA acid addition salt)

Anhydrous CH$_2$Cl$_2$ (19 mL) was added to a powdered flame dried 4 Å molecular sieves (1.6 grams), followed by the addition of acceptor 6 (142 mg, 1 equivalents) and donor 5 (546 mg, 3 equivalents). The mixture was cooled down to −50° C. and BF$_3$.Et$_2$O was added dropwise. The progress of the reaction was monitored by TLC (EtOAc/Hexane 3:7), and indicated that the reaction was completed in 30 minutes. The reaction was diluted with EtOAc, and filtered through a pad of Celite®. After thorough washing of the Celite® with EtOAc, the washes were combined and evaporated to dryness. The crude was purified by flash chromatography (EtOAc/Hexane 3:7) to yield Compound A (496 mg, 40%).

$^1$H NMR (500 MHz, CDCl$_3$): 'Ring I': $\delta_H$=5.92 (d, 1H, J=4.0 Hz, H-1), 5.38 (dd, 1H, J=10.7, 9.3 Hz, H-3), 4.98 (dd, 1H, J=6.7, 2.0 Hz, H-6), 4.95 (dd, 1H, J=10.5, 9.3 Hz, H-4), 4.45 (dd, 1H, J=10.6, 2.0 Hz, H-5), 3.80 (dd, 1H, J=10.9, 3.9 Hz, H-2), 1.24 (d, 3H, J=6.7 Hz, CH$_3$-6); 'Ring II': $\delta_H$=5.02 (t, 1H, J=9.9 Hz, H-6), 3.83 (t, 1H, J=9.4 Hz, H-5), 3.74 (t, 1H, J=9.7 Hz, H-4), 3.58-3.46 (m, 2H, H-1, H-3), 2.38 (dt, 1H, J=13.2, 4.7 Hz, H-2eq), 1.48 (dd, 1H, J=26.5, 12.9 Hz, H-2ax); 'Ring III': $\delta_H$=5.62 (d, 1H, J=4.3 Hz, H-1), 5.57 (s, 1H, H-3), 5.30 (dd, 1H, J=7.3, 5.2 Hz, H-2), 4.58 (dt, 1H, J=7.4, 2.7 Hz, H-4), 4.06 (ddd, 1H, J=14.5, 6.0, 3.9 Hz, H-5), 3.59 (ddd, 1H, J=13.8, 8.4, 3.8 Hz, H-5); Additional peaks in the spectrum were identified as follow: $\delta_H$=11.53 (s, 1H, NH), 8.72 (dd, 1H, J=6.2, 4.2 Hz, NH), 7.92-7.87 (m, 4H, Bz), 7.57-7.49 (m, 2H, Bz), 7.39-7.32 (m, 4H, Bz), 2.07 (s, 3H, Ac), 2.05 (s, 3H, Ac), 2.04 (s, 3H, Ac), 1.69 (s, 3H, Ac), 1.54 (s, 9H, Boc), 1.46 (s, 9H, Boc).

$^{13}$C NMR (125 MHz, CDCl$_3$): $\delta_C$=170.2 (Ac), 170.2 (Ac), 170.1 (Ac), 169.9 (Ac), 165.6 (Bz), 165.2 (Bz), 163.5, 156.4, 153.4, 133.8 (Bz), 133.6 (Bz), 129.9 (Bz), 129.8 (Bz), 128.6 (Bz), 128.5 (Bz), 108.1 (C3"), 96.5 (C1'), 80.1 (C5), 79.5 (C4"), 77.5 (C4), 74.7 (C1"), 73.7 (C6), 72.2 (C2"), 71.1 (C3'), 70.2 (C5'), 69.2 (C4'), 68.7 (C6'), 61.6 (C2'), 58.9, 58.6, 43.8 (C5"), 32.4 (C2), 28.3 (Boc), 28.3 (Boc), 21.3 (Ac), 21.0 (Ac), 20.9 (Ac), 20.7 (Ac), 13.7 (CH$_3$-6').

MALDI TOFMS: calculated for C$_{51}$H$_{64}$N$_{12}$O$_{20}$ ([M+H]$^+$) m/e 1166.1; measured m/e 1166.1.

Compound A (495 mg) was dissolved in a solution of MeNH$_2$ (33% solution in EtOH, 20 mL) at room temperature overnight. The completion of the reaction was indicated by TLC (MeOH/EtOAc 1:4). Thereafter, the reaction mixture was evaporated to dryness. The crude product was subjected to column chromatography (MeOH/EtOAc 1:4) to yield Compound B (175 mg, 52%).

¹H NMR (500 MHz, MeOD): 'Ring I': $\delta_H$=5.95 (d, 1H, J=3.0 Hz, H-1), 4.03-3.99 (m, 1H, H-5), 3.98-3.90 (m, 2H, H-3, H-6), 3.38 (t, 1H, J=8.9 Hz, H-4), 3.17 (dd, 1H, J=10.6, 5.2 Hz, H-2), 1.24 (d, 3H, J=4.5 Hz, CH$_3$-6); 'Ring II': $\delta_H$=3.69 (t, 1H, J=10.0 Hz, H-4), 3.62 (t, 1H, J=9.6 Hz, H-5), 3.54 (ddd, 1H, J=15.4, 10.9, 4.4 Hz, H-1), 3.48-3.40 (m, 1H, H-3), 3.37 (t, J=9.9 Hz, H-6), 2.21 (dt, 1H, J=11.7, 4.0 Hz, H-2eq), 1.32 (dd, 1H, J=26.2, 13.1 Hz, H-2ax); 'Ring III': $\delta_H$=5.35 (s, 1H, H-1), 4.21 (d, 1H, J=4.3 Hz, H-2), 4.06-3.99 (m, 1H, H-3), 3.85 (dd, 1H, J=14.2, 1.1 Hz, H-4), 3.43 (dd, 1H, J=13.9, 1.3 Hz, H-5); Additional peaks in the spectrum were identified as follow: $\delta_H$=1.55 (s, 9H, Boc), 1.49 (s, 9H, Boc).

¹³C NMR (125 MHz, MeOD): $\delta_C$=164.4, 157.7, 154.0, 111.4 (C1"), 97.6 (C1'), 85.2 (C5), 81.6, 77.6, 77.0 (C4), 76.4 (C2"), 75.0, 74.4, 73.0, 72.4, 69.7, 64.6, 62.1, 61.5, 45.0 (C5"), 33.3 (C2), 28.6 (Boc), 28.4 (Boc), 18.3 (CH$_3$-6').

MALDI TOFMS: calculated for $C_{29}H_{48}N_{12}O_{14}$ ([M+Na]+) m/e 811.7; measured m/e 811.8.

To a solution of Compound B (175 mg, 1 equivalents) in CH$_2$Cl$_2$ (10 mL) at −10° C., TFA (3.2 mL) was added dropwise and after the addition the reaction mixture was allowed to attain the room temperature. The reaction progress was monitored by TLC (CH$_2$Cl$_2$/MeOH 8:2) and indicated of the completion of the reaction in 3 hours. The reaction mixture was evaporated to dryness to get the crude product C (185 mg). The crude product was subjected to the Staudinger reaction.

To a stirred solution of Compound C (185 mg, 1 equivalents) in a mixture of THF (3 mL) and aqueous NaOH (1 mM, 5.0 mL), PMe$_3$ (1 M solution in THF, 3 mL, 7.8 equivalents) was added dropwise and the mixture was further stirred overnight. The completion of the reaction was indicated by TLC (TFA/MeOH 1:49). The pure product was obtained by passing the above mixture through a short column of Amberlite CG50 (NH4⁺ form). The column was washed with the following solvents: Hexane, THF, EtOAc, MeOH and CH3CN. Then the product was eluted with a mixture of TFA/MeOH (1:49) to yield NB151. For the storage and biological tests, NB151 was dissolved in water and lyophilized to afford the TFA salt of NB151 (574 mg, 85% for 2 steps).

¹H NMR (500 MHz, MeOD): 'Ring I': $\delta_H$=5.54 (d, 1H, J=4.0 Hz, H-1), 4.30-4.20 (m, 1H, H-6), 3.90 (dd, 1H, J=9.6, 1.9 Hz, H-5), 3.83 (t, 1H, J=9.6 Hz, H-3), 3.40-3.29 (m, 2H, H-2, H-4), 1.20 (d, 3H, J=7.3 Hz, CH$_3$-6); 'Ring II': $\delta_H$=3.97 (t, 1H, J=9.8 Hz, H-4), 3.82 (t, 1H, J=8.9 Hz, H-5), 3.64 (t, 1H, J=9.7 Hz, H-6), 3.51 (ddd, 1H, J=18.4, 14.2, 8.3 Hz, H-1), 3.31-3.21 (m, 1H, H-3), 2.48 (dt, 1H, J=12.6, 3.9 Hz, H-2eq), 1.85 (dd, 1H, J=25.1, 12.3 Hz, H-2ax); 'Ring III': $\delta_H$=5.31 (d, 1H, J=4.0 Hz, H-1), 4.09 (t, 1H, J=4.9 Hz, H-2), 4.06-3.97 (m, 2H, H-3, H-4), 3.56-3.46 (m, 2H, H-5).

¹³C NMR (125 MHz, MeOD): $\delta_C$=159.1, 110.9 (C1"), 98.5 (C1'), 85.1, 82.5, 82.0 (C4), 77.5 (C5'), 75.6 (C2"), 73.6 (C6), 71.8, 71.7, 71.3, 66.2 (C6'), 55.8, 50.9 (C1), 50.9 (C3), 44.5 (C5"), 29.6 (C2), 15.85 (CH$_3$—C6').

MALDI TOFMS: calculated for $C_{19}H_{38}N_6O_{10}$ ([M+H]⁺) m/e 511.5; measured m/e 511.9.

Synthesis of NB152 (Shown as its TFA Acid Additional Salt)

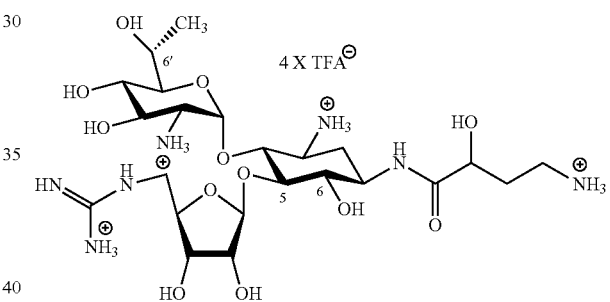

NB152 was prepared starting with the acceptor 7 and Donor 5 as illustrated in Scheme 7 (reagents and conditions: (a) BF$_3$.Et$_2$O, CH$_2$Cl$_2$, −30° C., 40% (b) MeNH$_2$, 78% (c) TFA, CH$_2$Cl$_2$, 0° C.→25° C. (d) (i) PMe$_3$, THF, NaOH 0.1M, (ii) The product was eluted from the ion exchange column with a mixture of 2% TFA in MeOH, 88% for 2 steps).

Scheme 7

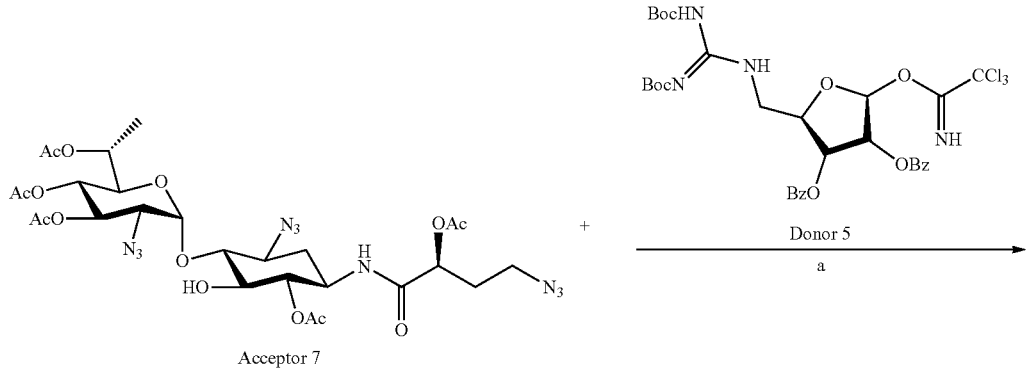

-continued

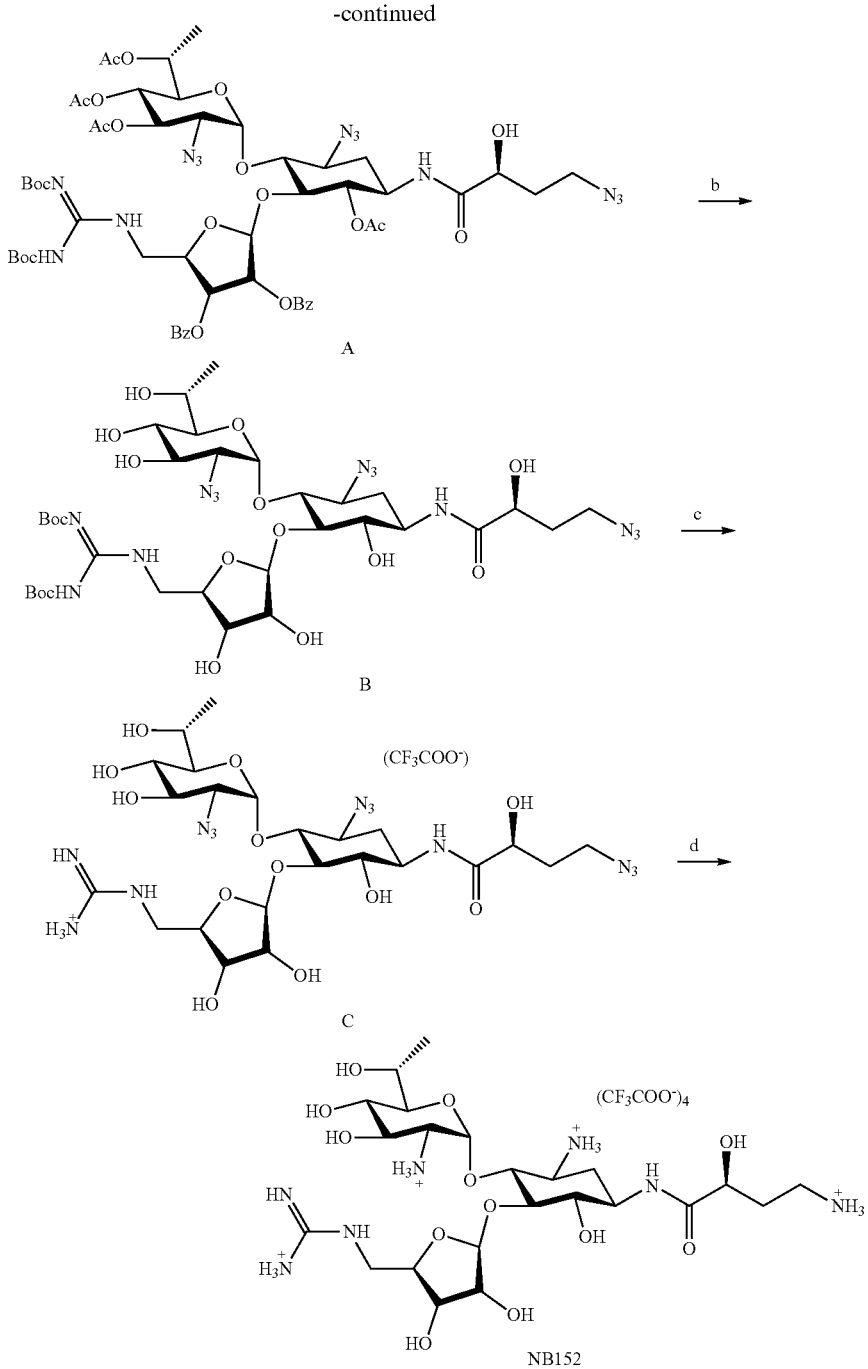

(NB152 is shown as its TFA acid addition salt)

To a powdered, flame dried 4 Å molecular sieves (5.85 grams) was added anhydrous $CH_2Cl_2$ (78 mL), followed by the addition of acceptor 7 (755 mg, 1 equivalents) and donor 5 (2.3 grams, 3 equivalents). The mixture was cooled down to −50° C. and $BF_3$-$Et_2O$ was added dropwise. The progress of the reaction was monitored by TLC (EtOAc/Hexane 3:7), and indicated that the reaction was completed in 10 minutes. The reaction was diluted with EtOAc, and filtered through a pad of Celite®. After thorough washing of the Celite® with EtOAc, the washes were combined and evaporated to dryness. The crude was purified by flash chromatography (EtOAc/Hexane 3:7) to yield Compound A (496 mg, 40%).

$^1$H NMR (500 MHz, $CDCl_3$): 'Ring I': $\delta_H$=5.90 (d, 1H, J=3.9 Hz, H-1), 5.39 (t, J=10.4 Hz, 1H), 4.98 (dd, 1H, J=12.2, 8.0 Hz, H-4), 4.48 (d, 1H, J=10.6 Hz, H-5), 3.79 (dd, 1H, J=10.7, 3.9 Hz, H-2), 1.24 (d, 3H, J=6.7 Hz, $CH_3$-6); 'Ring II': $\delta_H$=4.91 (t, 1H, J=10.1 Hz, H-6), 4.03-3.96 (m, 1H, H-1), 3.93 (t, 1H, J=9.2 Hz, H-5), 3.71 (t, 1H, J=9.4 Hz, H-4), 3.64-3.54 (m, 1H, H-3), 2.54 (dt, 1H, J=12.6, 4.1 Hz, H-2eq), 1.35 (dd, 1H, J=24.8, 12.3 Hz, H-2ax); 'Ring III': $\delta_H$=5.69 (d, 1H, J=4.0 Hz, H-1), 5.61 (s, 1H, H-3), 5.37 (dd, 1H, J=7.0, 5.4 Hz, H-2), 4.57 (dd, 1H, J=8.3, 4.8 Hz, H-4), 4.11-4.01 (m, 1H, H-5), 3.61-3.50 (m, 1H, H-5); Additional peaks in the spectrum were identified as follow: $\delta_H$=11.54 (s, 1H), 8.72 (t, J=4.3 Hz, 1H), 7.99-7.78 (m, 6H, Bz), 7.42-7.30 (m, 4H, Bz), 5.18 (dd, 1H, J=6.7, 5.0 Hz), 3.54-3.45 (m, 2H), 2.14-2.02 (m, 1H), 1.57-1.52 (m, 1H), 2.29 (s, 3H, Ac), 2.21 (s, 3H, Ac), 2.07 (s, 3H, Ac), 2.06 (s, 3H, Ac), 2.05 (s, 3H, Ac), 1.54 (s, 9H, Boc), 1.45 (s, 9H, Boc).

$^{13}$C NMR (125 MHz, CDCl$_3$): $\delta_C$=177.1, 170.2 (Ac), 170.1 (Ac), 170.0 (Ac), 169.9 (Ac), 165.5 (Bz), 165.1 (Bz), 164.1, 157.3, 153.6, 133.7 (Bz), 129.7 (Bz), 128.8 (Bz), 108.1 (C3"), 96.6 (C1'), 80.5 (C5), 78.9 (C4"), 77.7 (C4), 74.8 (C1"), 73.3 (C6), 72.2, 71.5, 70.9, 70.4 (C5'), 68.6 (C4'), 61.6 (C2'), 58.7 (C3), 49.0 (C1), 43.8 (C5"), 32.9 (C2), 28.3 (Boc), 28.1 (Boc), 21.0 (Ac), 20.9 (Ac), 20.5 (Ac), 13.9 (CH$_3$-6').

MALDI TOFMS: calculated for C$_{57}$H$_{73}$N$_{13}$O$_{23}$ ([M+H]$^+$) m/e 1309.3; measured m/e 1309.7.

Compound A (50 mg) was dissolved in a solution of MeNH$_2$ (33% solution in EtOH, 2 mL) at room temperature overnight. The completion of the reaction was indicated by TLC (MeOH/EtOAc 1:4). After the completion of the reaction, the reaction mixture was evaporated to dryness. The crude product was subjected to column chromatography (MeOH/EtOAc 1:49) to yield Compound B (27 mg, 78%).

$^1$H NMR (500 MHz, MeOD): 'Ring I': $\delta_H$=5.98 (d, 1H, J=2.8 Hz, H-1), 4.08-3.91 (m, 2H, H-5, H-6), 3.96 (t, 1H, J=9.5 Hz, H-3), 3.36 (t, 1H, J=9.6 Hz, H-4), 3.18 (dd, 1H, J=10.8, 5.2 Hz, H-2), 1.26 (d, 3H, J=3.9 Hz, CH3-6); 'Ring II': $\delta_H$=3.63-3.72 (m, 2H, H-1, H-4, H-5), 3.54-3.58 (m, 1H, H-1), 3.34-3.38 (m, 2H, H-3, H-6), 2.15 (dt, 1H, J=12.9, 4.0 Hz, H-2eq), 1.48 (dd, 1H, J=25.0, 12.7 Hz, H-2ax); 'Ring III': $\delta_H$=5.37 (s, 1H, H-1), 4.19 (d, 1H, J=4.0 Hz, H-2), 4.01 (s, 1H, H-3), 3.88 (d, 1H, J=15.2 Hz, H-4), 3.38 (d, 2H, J=14.4 Hz, H-5); Additional peaks in the spectrum were identified as follow: $\delta_H$=4.15 (dd, 1H, J=3.9, 8.8 Hz), 3.53-3.44 (m, 2H), 2.13-1.99 (m, 1H), 1.92-1.82 (m, 1H), 1.54 (s, 9H, Boc), 1.47 (s, 9H, Boc).

$^{13}$C NMR (125 MHz, MeOD): $\delta_C$=177.4, 164.5, 157.7 (Boc), 154.0 (Boc), 111.4 (C1"), 97.6 (C1'), 86.1, 81.6, 80.5, 77.1, 76.5 (C2"), 75.7 (C5"), 75.1, 74.5, 73.2, 72.3, 70.2, 69.4, 64.6 (C2'), 61.9 (C1), 50.5, 47.5, 45.3, 34.7, 32.1 (C2), 28.4 (Boc), 26.3 (Boc), 18.1 (CH3-6').

MALDI TOFMS: calculated for C$_{33}$H$_{55}$N$_{13}$O$_{16}$ ([M+Na]+) m/e 912.8; measured m/e 912.7.

To a solution of Compound B (109 mg, 1 equivalents) in CH$_2$Cl$_2$ (3.3 mL) at −10° C., TFA (1.3 mL) was added dropwise and after the addition the reaction mixture was allowed to attain the room temperature. The reaction progress was monitored by TLC (CH$_2$Cl$_2$/MeOH 8:2) and indicated of the completion of the reaction in 2 hours. The reaction mixture was evaporated to dryness to get the crude product C (169 mg). The crude product was subjected to the Staudinger reaction.

To a stirred solution of Compound C (169 mg, 1 equivalents) in a mixture of THF (3 mL) and aqueous NaOH (1 mM, 5.0 mL), PMe$_3$ (1 M solution in THF, 2.74 mL, 7.8 equivalents) was added dropwise and the mixture was further stirred overnight. The completion of the reaction was indicated by TLC (TFA/MeOH 1:49). The pure product was obtained by passing the above mixture through a short column of Amberlite CG50 (NH4$^+$ form). The column was washed with the following solvents: Hexane, THF, EtOAc, MeOH and CH$_3$CN. Then the product was eluted with a mixture of TFA/MeOH (1:49) to yield NB152. For the storage and biological tests, NB152 was dissolved in water and lyophilized to afford the TFA salt of NB152 (350 mg, 88% for 2 steps).

$^1$H NMR (500 MHz, MeOD): 'Ring I': $\delta_H$=5.52 (d, 1H, J=3.9 Hz, H-1), 4.22 (d, 1H, J=5.8 Hz, H-6), 3.88 (d, 1H, J=9.1 Hz, H-5), 3.81 (t, 1H, J=9.6 Hz, H-4), 3.36-3.28 (m, 2H, H-2, H-3), 1.19 (d, 3H, J=6.32 Hz, CH$_3$-6); 'Ring II': $\delta_H$=3.93-3.83 (m, 2H, H-1, H-4), 3.75 (t, 1H, J=9.1 Hz, H-5), 3.60 (t, 1H, J=9.7 Hz, H-6), 3.45-3.37 (m, 1H, H-3), 2.20 (dt, 1H, J=13.1, 3.8 Hz, H-2eq), 1.69 (dd, 1H, J=25.2, 12.4 Hz, H-2ax); 'Ring III': $\delta_H$=5.28 (d, 1H, J=3.5 Hz, H-1), 4.07 (t, 1H, J=4.3 Hz, H-2), 4.04-3.96 (m, 2H, H-3, H-4), 3.49 (t, 2H, J=5.2 Hz, H-5); Additional peaks in the spectrum were identified as follow: $\delta_H$=4.21 (dd, 1H, J=4.5, 8.9 Hz), 3.14-3.01 (m, 2H), 2.15-2.03 (m, 1H), 2.03-1.97 (m, 1H).

$^{13}$C NMR (125 MHz, MeOD): $\delta_C$=176.2, 159.2, 111.2 (C1"), 98.5 (C1'), 86.0 (C5), 82.44, 82.1, 77.4, 75.8 (C2"), 74.7 (C6), 71.8, 71.8, 71.4 (C4'), 71.0 (C6'), 66.2, 55.9, 51.4 (C3), 49.8, 44.5 (C5"), 37.8, 32.7, 31.7 (C2), 15.9 (CH$_3$-6').

MALDI TOFMS: calculated for C$_{23}$H$_{45}$N$_7$O$_{11}$ ([M+H]$^+$) m/e 612.6; measured m/e 612.9.

Example 2

Readthrough Activity in Cell-Based Assay of Compounds of Example 1

Experimental Method

Suppression of nonsense mutations (readthrough activity) by the tested compounds according to embodiments of the present invention was tested in vitro using reporter plasmids harboring a mutation in the chosen gene, as described, for example, in U.S. Pat. No. 8,895,519 and by Vecsler, M. et al. [*PLoS ONE*, 2011, 6(6) p. e20733].

Briefly, HEK-293T cells were transfected by the plasmids, and 24 hours post transfection the cells were lysed and tested for the expression levels of the firefly luciferase and *renilla* luciferase. Wild-type (WT) plasmids expressed both firefly luciferase and *renilla* luciferase while mutant plasmids only expressed the *renilla* luciferase due to the stop codon found in the inserted sequence. In the tested compounds' readthrough activity assays, the compounds were added to the cells' suspension 6 hours post-transfection. In case the compounds exerted suppression of the premature nonsense/stop codon mutation, the firefly luciferase was expressed and a fold-change in its expression was observed.

Results:

To determine whether the tested compounds can induce the functional suppression of disease-causing nonsense mutations in human cells, the synthesis of firefly luciferase and *renilla* luciferase from cDNAs containing naturally occurring premature stop codon mutations that cause Rett syndrome were assayed. In all cases, the mutations introduce an in-frame ochre (UGA) stop codon in place of arginine residue, R168X R270X and R294X mutations, which result in UGAG, UGAA and UGAU tetranucleotide termination signals, respectively.

Readthrough activity of Rett syndrome mutations was tested using the compounds presented in Table 1, and the mutation suppression was calculated based on firefly/*renilla* ratio values, normalized the value with the same ratio obtained without a tested compound (control), and compare the result to the expression levels observed in the WT. In general, since the *renilla* reporter gene is situated upstream with respect to the tested gene, and the firefly reporter gene is situated downstream, readthrough activity can be quantified by calculating the ratio of downstream expression to upstream expression (firefly/*renilla* expression ratio) and noting the proportion (percent) of this ratio with respect to the same measurements using the WT sequence, namely as normalized fractions of the expression level ratio observed for the WT. Alternatively, the firefly/*renilla* expression ratio can be normalized with respect to the firefly/*renilla* expression ratio observed in the control experiment (no readthrough-inducing compound). Since the firefly/*renilla* expression ratio in the WT is essentially insensitive to the presence of the readthrough-inducing compound, and the control experiment is essentially also insensitive to the presence of the readthrough-inducing compound, as none is present, the two normalization methods are expected to show similar trends, as seen in the results presented hereinbelow.

Measuring the same firefly/*renilla* expression ratios using the same compounds and control, but using the WT sequence, will signify the effect of the tested compounds on general expression level, regardless of the readthrough activity, thereby indicating if the tested compound exerts protein synthesis inhibition activity, as typical aminoglycoside antibiotics do. The WT measurements are also indicative of the experimental error.

Hence, if a given readthrough-inducing compound, according to some embodiments of the present invention, exerts some readthrough activity, the measurements will show a large firefly/*renilla* expression ratio compared to the firefly/*renilla* expression ratio observed for the control (no readthrough-inducing compound), and a high proportional value (in the order of hundreds percent). If there is no readthrough activity, the firefly/*renilla* expression ratios for both the inactive compound and the control are expected to be small absolutely and similar proportionally, giving a value of about 100%.

FIGS. 2A-C present comparative bar plot showing readthrough levels of the Rett syndrome causing premature stop codon mutations R168X (FIG. 2A), R270X (FIG. 2B) and R294X (FIG. 2C), as measured and calculated for the compounds presented in Table 1 being contacted with expression cells at a concentration of 0.3 mM and 1 mM, as well as for a control sample (no added compound), based on the firefly/*renilla* expression ratios versus the expression ratios observed in the WT.

Figure 3A:
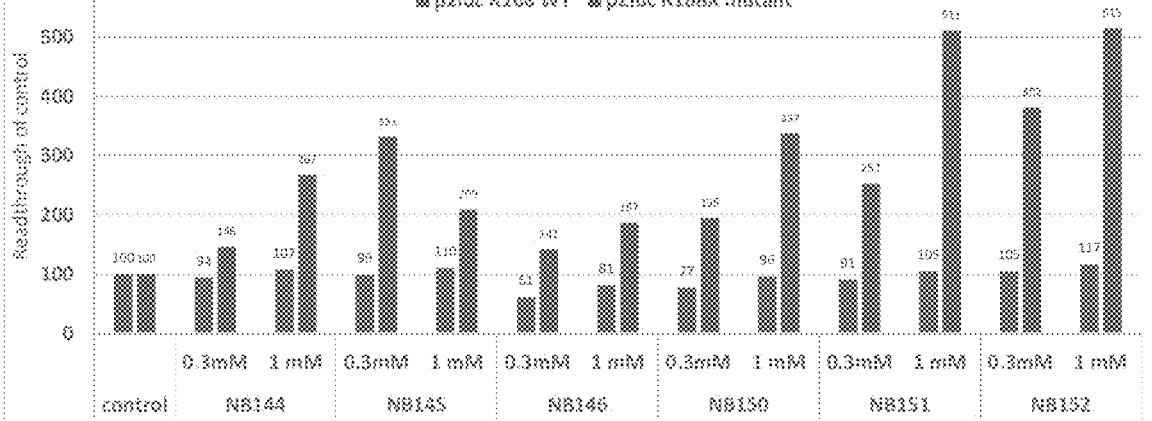
FIGS. 3A-C present comparative bar plot showing read-through levels of the Rett syndrome causing premature stop codon mutations R168X (FIG. 3A), R270X (FIG. 3B) and R294X (FIG. 3C), as measured and calculated for exemplary compounds according to some embodiments of the present invention, being contacted with expression HEK293 cells at a concentration of 0.3 mM and 1 mM, as well as for a control sample (no added compound), and presented as fractions of the firefly/*renilla* expression ratios observed for the control sample (100%) and compared to the expression ratios observed in the WT.
Figure 3B:
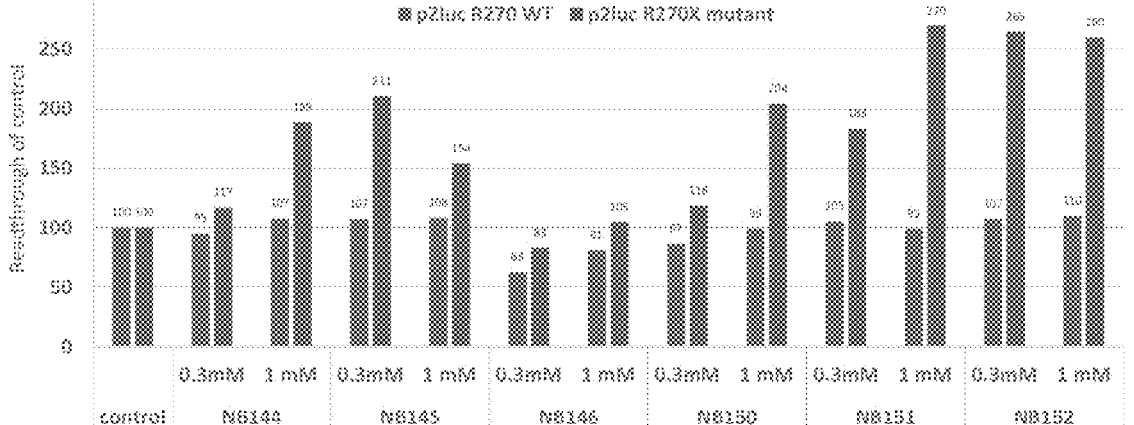
Figure 3C:
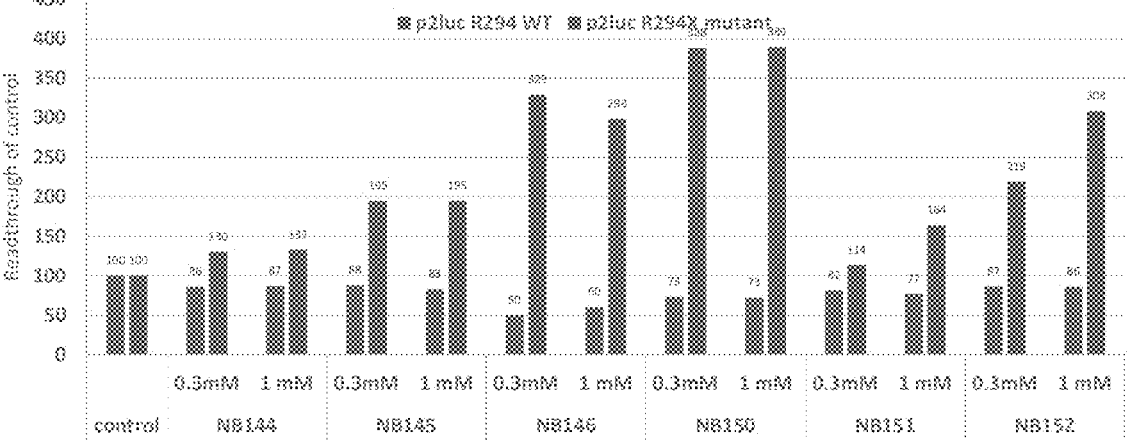

FIGS. 3A-C present comparative bar plot showing readthrough levels of the Rett syndrome causing premature stop codon mutations R168X (FIG. 3A), R270X (FIG. 3B) and R294X (FIG. 3C), as measured and calculated for the compounds presented in Table 1 being contacted with expression cells at a concentration of 0.3 mM and 1 mM, as well as for a control sample (no added compound), and presented as fractions of the firefly/*renilla* expression ratios observed for the control sample (100%) and compared to the expression ratios observed in the WT.

As can be seen in FIGS. 2A-C, the exemplary compounds according to some embodiments of the present invention exhibited a notable and dose-dependent readthrough activity in all three Rett syndrome mutation models. Compounds NB150 and NB151 presented similar readthrough activity to the level shown for the aminoglycoside antibiotic agent G418 (Geneticin) at 0.3 and 1 mM doses. This result may be associated with the significant cytotoxicity of the G418 that in turn was associated with an overall limited readthrough level.

As can be seen in FIGS. 3A-C, the readthrough activity compared with control (non-treated cells) is unaffected in the wild type cells (approx. 100%); however, in all three Rett syndrome mutation models there is a significant and dose-dependent impact of the different treatments on the readthrough activity (>100%). Compounds NB150, NB151 and NB152 presented similar readthrough activity to the level shown for the aminoglycoside antibiotic agent G418 (Geneticin) at 0.3 and 1 mM doses. This result may be associated with the significant cytotoxicity of the G418 that in turn was associated with an overall limited readthrough level.

Example 3

Readthrough Activity in Cell-Free Assay of Compounds of Example 1

Experimental Method

The plasmids were transcribed in vitro and translated using rabbit reticulocytes (TNT mix) and then tested for the expression levels of the firefly and *renilla* luciferases. WT plasmids expressed both firefly and *renilla* luciferases while mutant plasmids expressed only the *renilla* luciferase due to the stop codon found in the inserted sequence. The readthrough assays were conducted for the tested compounds and the controls by adding the compounds to the in vitro transcription/translation reaction mixture. In case the compounds exerted suppression of the premature nonsense/stop codon mutation, the firefly luciferase was expressed and a fold-change in its expression was observed.

Results:

Readthrough activity of Cystic Fibrosis (CF) mutation G542X was tested using the compounds presented in Table 1, and the mutation suppression was calculated based on firefly/*renilla* expression ratio values, and normalized with respect to the expression level of the WT and the control sample (no tested compound).

Figure 4A:
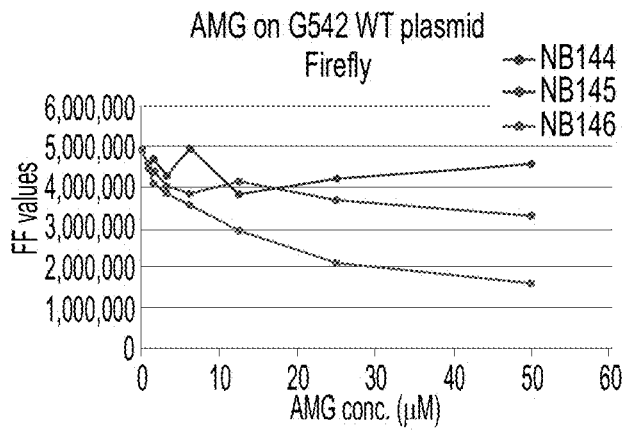
Figure 4B:
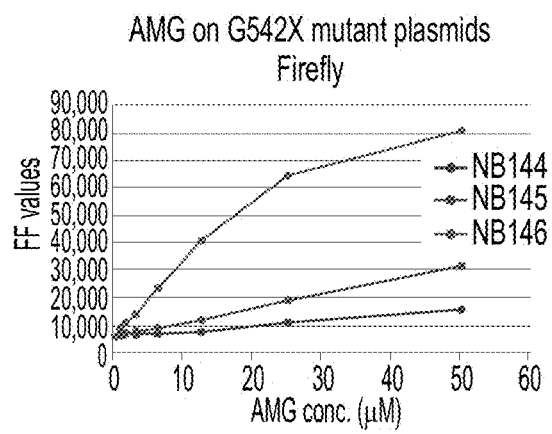
Figure 4C:
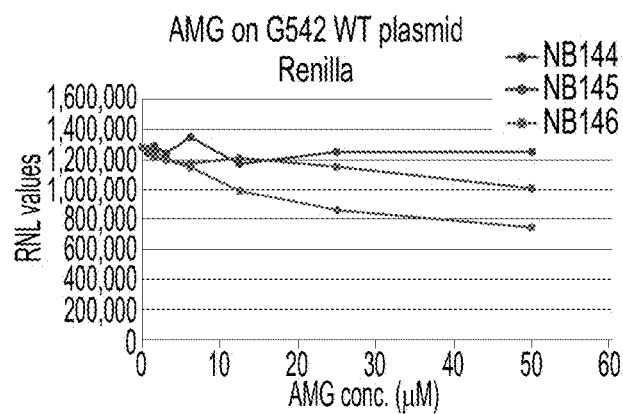
Figure 4D:
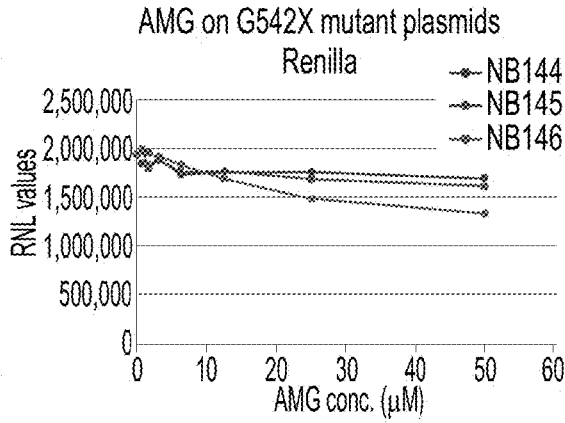
Figure 4E:
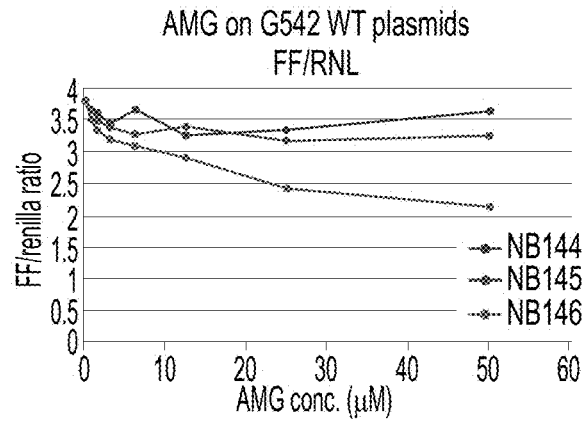
Figure 4F:
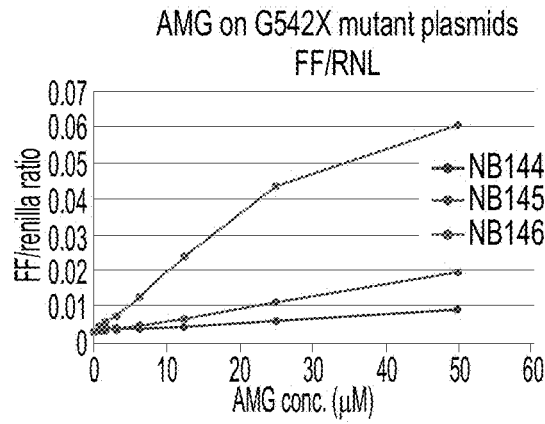

FIGS. 4A-F present the results of cystic fibrosis G542X nonsense mutation suppression dose-response cell-free assays conducted for three exemplary compounds according to embodiments of the present invention, NB144, NB145 and NB146, at a concentration rage of 0-50 µM, wherein FIG. 4A shows the expression level of the firefly luciferase which is found downstream of the WT sequence, FIG. 4B shows the expression level of the firefly luciferase which is found downstream of the G542X mutant sequence, FIG. 4C shows the expression level of the *renilla* luciferase which is found upstream of the WT sequence, FIG. 4D shows the expression level of the *renilla* luciferase which is found upstream of the G542X mutant sequence, FIG. 4E shows the firefly/*renilla* expression ratio measured in the WT sequence, and FIG. 4F shows the firefly/*renilla* expression ratio measured in the G542X mutant sequence.

As can be seen in FIGS. 4A-F, the expression levels up or downstream of the WT sequence are grossly insensitive to the concentration of the tested compounds, with a relatively small decrease the expression levels at high concentrations of the tested compound, presumably due to the residual protein synthesis inhibitory effect thereof (see, FIGS. 4A, 4C and 4E). In sharp contrast, the expression levels downstream of the mutant sequence showed an intense dose-dependent response, which is not seen upstream of the mutant sequence (see, FIGS. 4B and 4D), therefore the downstream to upstream expression level ratio (firefly/*renilla* expression ratio) also exhibits an intense dose-dependent response, indicative of the mutation suppression activity of the tested compounds (FIG. 4F).

Figure 5A:
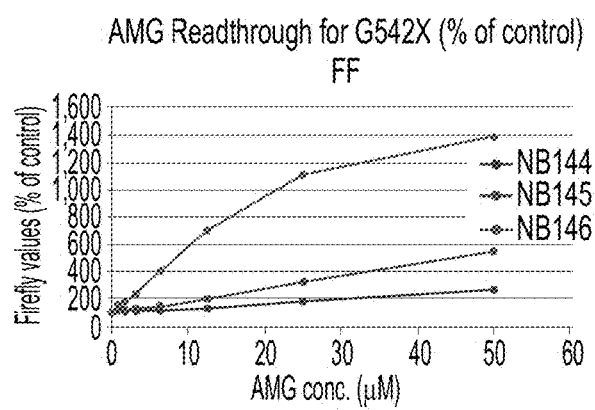
Figure 5B:
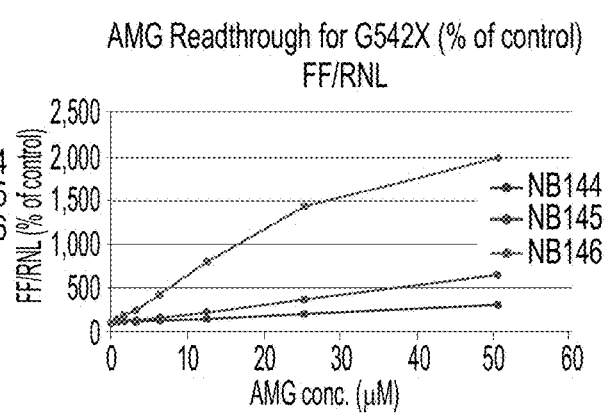

FIGS. 5A-B present the results of cystic fibrosis G542X nonsense mutation suppression dose-response cell-free assays conducted for three exemplary compounds according to embodiments of the present invention, NB144, NB145 and NB146, at a concentration rage of 0-50 μM, wherein FIG. 5A shows the expression level of the firefly luciferase, which is found downstream of the mutant sequence, as a fraction of the expression level exhibited in the control experiment (no added compound), and FIG. 5B shows the firefly/*renilla* expression ratio, down and upstream of the mutant sequence, as a fraction of the expression level in the control experiment.

As can be seen in FIGS. 5A-B, the mutation suppression activity of the three exemplary compounds, according to embodiments of the present invention, is clearly dose-dependent for all three compounds, and particularly for NB146, which also shown more protein synthesis inhibitory effect (see, FIGS. 4A, 4C and 4E), particularly for the firefly luciferase gene.

Figure 6A:
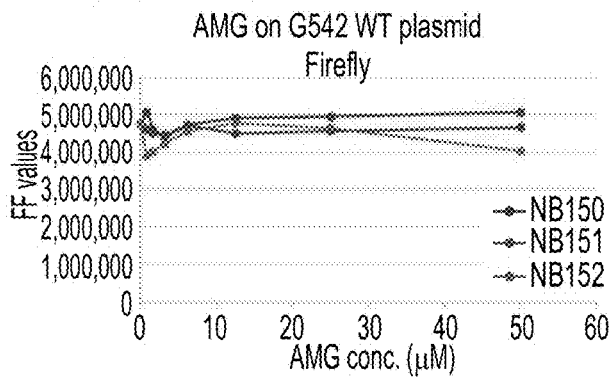
Figure 6B:
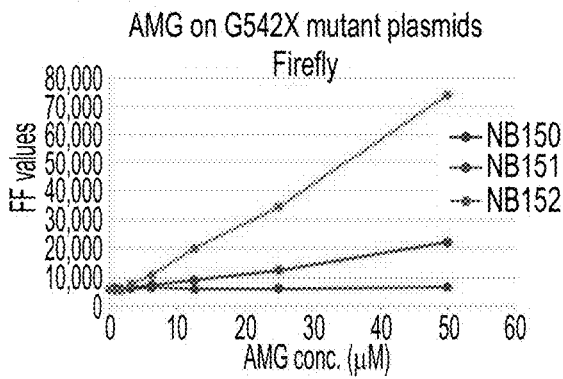
Figure 6C:
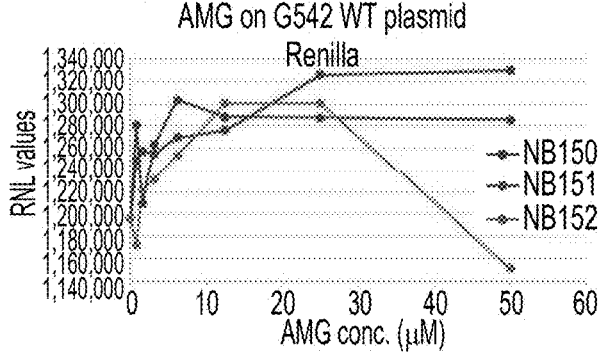
Figure 6D:
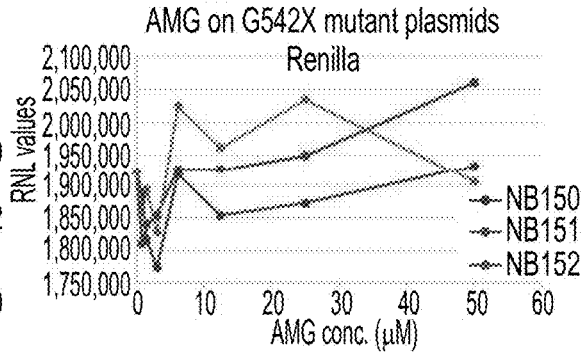
Figure 6E:
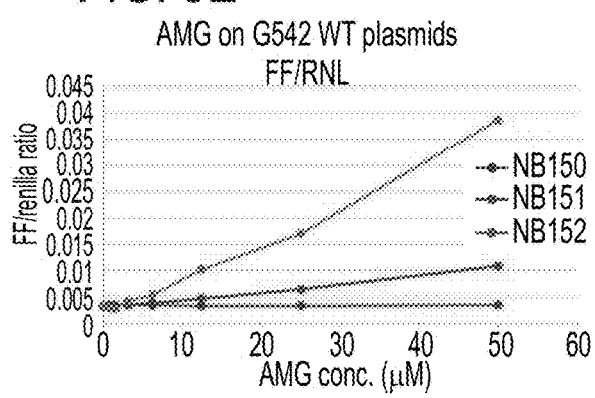
Figure 6F:
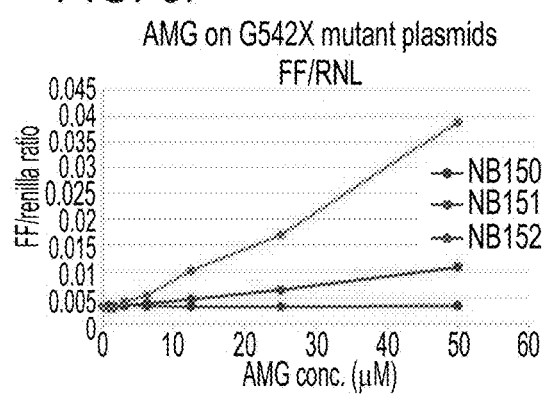

FIGS. 6A-F present the results of cystic fibrosis G542X nonsense mutation suppression dose-response cell-free assays conducted for three exemplary compounds according to embodiments of the present invention, NB150, NB151 and NB152, at a concentration rage of 0-50 μM, wherein FIG. 6A shows the expression level of the firefly luciferase which is found downstream of the WT sequence, FIG. 6B shows the expression level of the firefly luciferase which is found downstream of the G542X mutant sequence, FIG. 6C shows the expression level of the *renilla* luciferase which is found upstream of the WT sequence, FIG. 6D shows the expression level of the *renilla* luciferase which is found upstream of the G542X mutant sequence, FIG. 6E shows the firefly/*renilla* expression ratio measured in the WT sequence, and FIG. 6F shows the firefly/*renilla* expression ratio measured in the G542X mutant sequence.

Figure 7A:
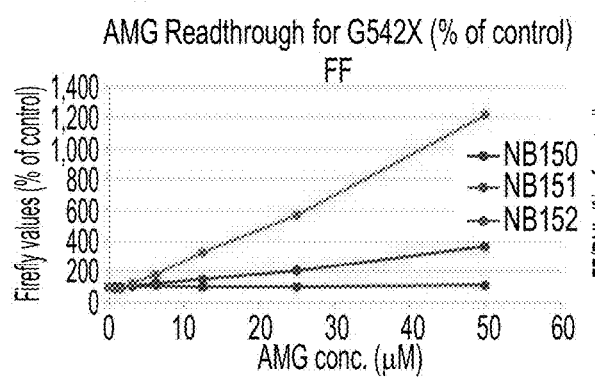
Figure 7B:
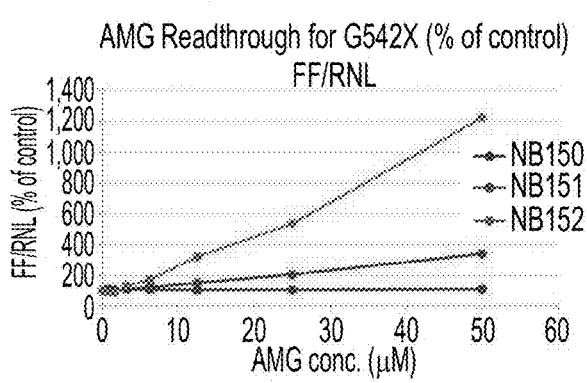

FIGS. 7A-B present the results of cystic fibrosis G542X nonsense mutation suppression dose-response cell-free assays conducted for three exemplary compounds according to embodiments of the present invention, NB150, NB151 and NB152, at a concentration rage of 0-50 μM, wherein FIG. 7A shows the expression level of the firefly luciferase, which is found downstream of the mutant sequence, as a fraction of the expression level exhibited in the control experiment (no added compound), and FIG. 7B shows the firefly/*renilla* expression ratio, down and upstream of the mutant sequence, as a fraction of the expression level in the control experiment.

As can be seen in FIGS. 6A-F and FIGS. 7A-B, also compounds NB150, NB151 and NB152 exhibit essentially the same mutation suppression activity as observed for the exemplary compounds NB144, NB145 and NB146 in FIGS. 4A-F and FIGS. 5A-B, namely a notable dose-dependent readthrough activity, which is correlated to some extent to protein synthesis inhibition, as seen for NB152, particularly for the *renilla* luciferase gene.

Figure 8A:
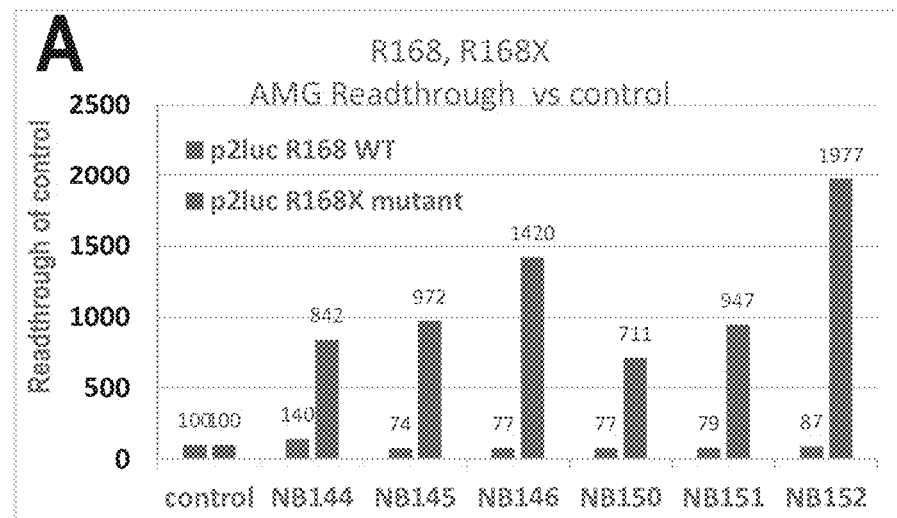
FIGS. 8A-C present the results of Rett syndrome R168X (FIG. 8A), R270X (FIG. 8B) and R294X (FIG. 8C) nonsense mutations suppression cell-free assays conducted for exemplary compounds according to some embodiments of the present invention, NB144, NB145, NB146, NB150, NB151 and NB152, at a concentration of 5 µM, showing the firefly/*renilla* expression ratio as a fraction of the firefly/*renilla* expression ratio measured for the control sample (no compound added; 100%)
Figure 8B:
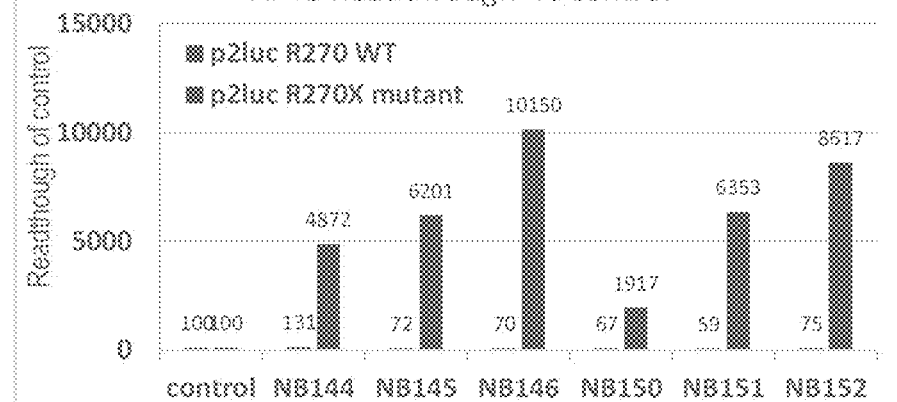
Figure 8C:
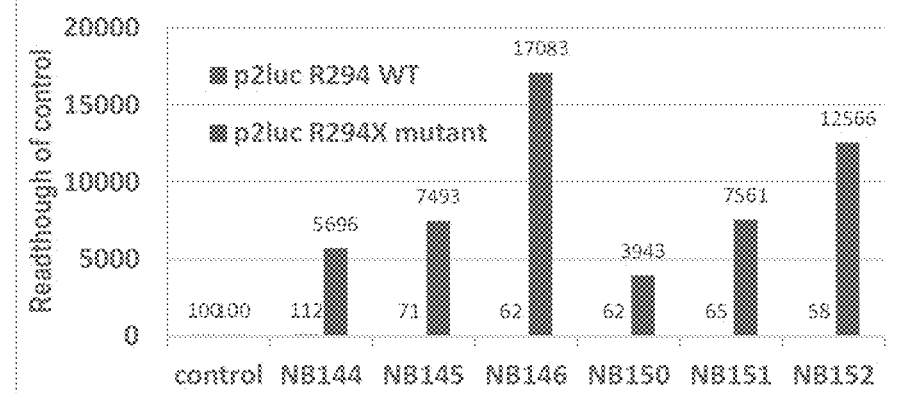

FIGS. 8A-C present the results of Rett syndrome R168X (FIG. 8A), R270X (FIG. 8B) and R294X (FIG. 8C) nonsense mutations suppression cell-free assays conducted for six exemplary compounds according to embodiments of the present invention, NB144, NB145, NB146, NB150, NB151 and NB152, at a concentration of 5 μM. As shown therein, when compared with the control (non-treated cell extracts), the wild type cell extracts are unaffected (approx. 100%); however, in all three Rett syndrome mutation models there is a significant impact of the different treatments on the readthrough activity (>>>100%).

As can be seen in FIGS. 8A-C, the readthrough activity of the tested compounds is notably more substantial than the protein synthesis inhibitory effect, demonstrating the effectiveness of the tested exemplary compounds in suppressing the nonsense mutations while exhibiting a relatively low degree of the inhibitory side effect. Among the N1-substituted derivatives, NB146 exhibited a better activity compared to NB144 and NB145; and among the guanidine derivatives the pseudo-trisaccharide NB152 showed a higher activity compared to NB150 and NB151. These data suggest that inclusion of a hydrophobic moiety at the N1 position has a pronounced effect on the biological effect of aminoglycosides.

Example 4

Chemical Syntheses of Exemplary Diol-Containing Aminoglycosides According to Some Embodiments of the Present Invention General Techniques:

NMR spectra (including 1H, 13C, DEPT, 2D-COSY, 1D TOCSY, HMQC, HMBC) were routinely recorded on a Bruker Avance™ 500 spectrometer, and chemical shifts reported (in ppm) are relative to internal Me$_4$Si ($\delta$=0.0) with CDCl$_3$ as the solvent, and to MeOD ($\delta$=3.35) as the solvent. $^{13}$C NMR spectra were recorded on a Bruker Avance™ 500 spectrometer at 125.8 MHz, and the chemical shifts reported (in ppm) relative to the solvent signal for CDCl$_3$ ($\delta$=77.00), or to the solvent signal for MeOD ($\delta$=49.0).

Mass spectra analyses were obtained either on a Bruker Daltonix Apex 3 mass spectrometer under electron spray ionization (ESI) or by a TSQ-70B mass spectrometer (Finnigan Mat).

Reactions were monitored by TLC on Silica Gel 60 F254 (0.25 mm, Merck), and spots were visualized by charring with a yellow solution containing (NH$_4$)Mo$_7$O$_{24}$.4H$_2$O (120 grams) and (NH$_4$)$_2$Ce(NO$_3$)$_6$ (5 grams) in 10% H$_2$SO$_4$ (800 mL).

Flash column chromatography was performed on Silica Gel 60 (70-230 mesh).

All reactions were carried out under an argon atmosphere with anhydrous solvents, unless otherwise indicated.

G418 (geneticin) and gentamicin were purchased from Sigma. All other chemicals and biochemicals, unless otherwise indicated, were obtained from commercial sources.

Compounds NB153, NB 155, NB156 and NB157, presented in Table 3 below, are prepared essentially as described hereinabove and in further detail hereinbelow.

All the structures were confirmed by a combination of various 1D and 2D NMR techniques, including 1D TOCSY, 2D COSY, 2D $^1$H-$^{13}$C HMQC and HMBC, along with mass spectrometry.

TABLE 3

| Compound | Structure |
|---|---|
| NB153 | 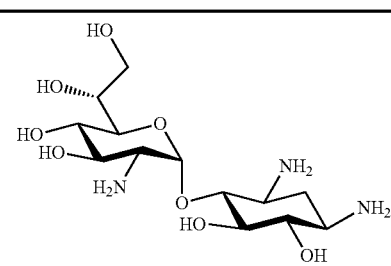 |

TABLE 3-continued
| Compound | Structure |
|---|---|
| NB155 | 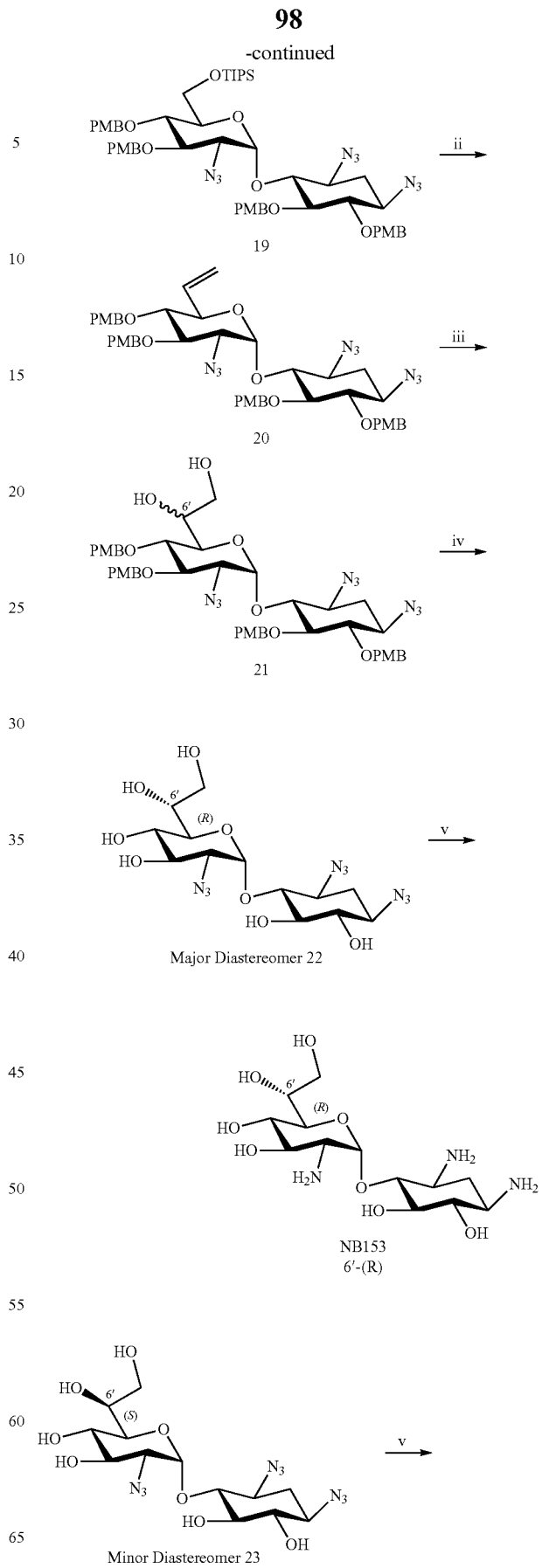 |
| NB156 | 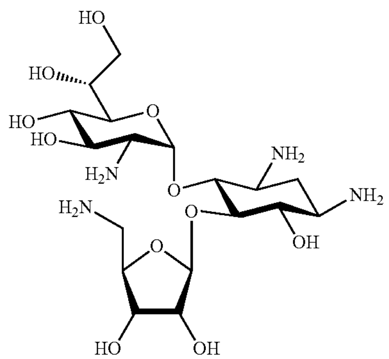 |
| NB157 | 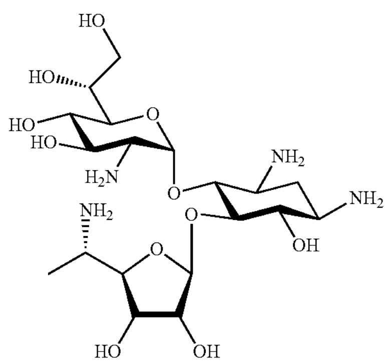 |
Syntheses of Pseudo-Disaccharides NB153 and NB155
NB153 and NB155 pseudo-disaccharides are two diastereomers at C6' position of the 6',7'-diol, exhibiting 6'-(R) configuration and 6'-(S) configuration, respectively.
The syntheses of compounds NB153 and NB155 are illustrated in Scheme 8 below.
Scheme 8
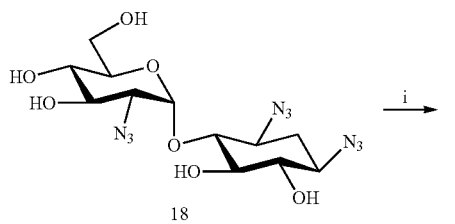

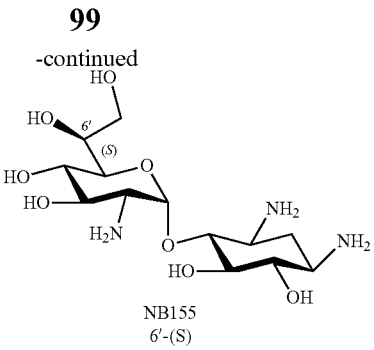

NB155
6'-(S)

Reagents and conditions:
(i) (a) TIPSCI, DMF, 4-DMAP, 0-25° C., 83%;
(b) PMBCl, NaH, DMF, 0-25° C., 84%;
(ii) (a) TBAF, THF, 0-25° C., 88%;
(b) IBX, EtOAc, 80° C., 85%;
(c) CH$_3$P(Ph)$_3$I, n-BuLi, THF, 0-25° C., 56%;
(iii) K$_2$OsO$_4$·2H$_2$O, NMO, acetone/H$_2$O/t-BuOH, 93% (3:1 ratio);
(iv) (a) DDQ, CH$_2$Cl$_2$/H$_2$O;
(b) Ac$_2$O, Py, 0-25° C., 91% for 2 steps;
(c) NaOMe, MeOH, 60%;
(v) PMe$_3$, THF, NaOH (0.1M), 73% [NB153]; 78% [NB155].

Briefly, the perazido derivative 18 was selectively protected by TIPSCI, and the remaining hydroxyls were protected by pmethoxybenzyl (PMB) groups to afford 19. Selective deprotection of silyl group with TBAF was followed by oxidation with 2-iodoxy benzoic acid (IBX) and Wittig reaction to afford the terminal alkene 20. The alkene 20 was dihydroxylated to provide the diol 21 as an inseparable mixture of 6-diastereomers. Treatment of 21 with DDQ was followed by acetylation (Ac$_2$O) and deacetylation (NaOMe) steps to afford the mixture of 6'-diastereomers (about 3:1 ratio), which was successfully separated by column chromatography to give the major diastereomer 22 and the minor diastereomer 23. The absolute configuration at 6'-position was assigned by using $^1$H-NMR magnetic anisotropy, as detailed hereinbelow, which established 6-(R)- and 6-(S)-configuration for the major and minor diastereomers, respectively. The two diastereomers 22 and 23 were separately subjected to Staudinger reaction to produce the pseudodisaccharides NB153 and NB155, respectively.

Synthesis of (2R, 3S, 4R, 5R, 6S)-5-azido-6-(((1R, 2R, 3S, 4R, 6)-4,6-diazido-2,3-dihydroxycyclohexyl)oxy)-2-(hydroxymethyl)tetrahydro-2H-pyran-3,4-diol (Compound 18): Compound 18 was prepared according to previously published procedure [Nyffeler et al. J. Am. Chem. Soc. 2002, 124, 10773-10778]. Briefly, the paromamine (1.0 gram, 3.0 mmol), NaHCO$_3$ (3.1 grams, 36.9 mmol) and copper (II) sulfate (6 mg, 0.24 mmol) were dissolved in water (5.0 mL). Triflic azide stock solution prepared from Tf$_2$O (4.6 mL, 27.6 mmol) and NaN$_3$ (3.6 grams, 55.7 mmol) was added followed by the addition of methanol (40 mL) to reach the homogeneous solution. The reaction mixture (blue color) was stirred vigorously at room temperature and the completion of the reaction was monitored by the change of blue color to green. After stirring for 48 hours, TLC (EtOAc/MeOH 95:5) analysis indicated the completion of the reaction. The solvents were evaporated to dryness and the residue was subjected to column chromatography (EtOAc 100%) to thereby obtain compound 18 (650 mg, 52% yield).

$^1$H NMR (500 MHz, MeOD): 'Ring I': δ=H 5.69 (d, 1H, J=3.7 Hz, H-1), 3.99 (ddd, 1H, J=9.9, 4.1, 2.6 Hz, H-5), 3.94 (dd, 1H, J=10.2, 9.1 Hz, H-3), 3.84 (dd, 1H, J=11.9, 2.3 Hz, H-6), 3.78 (dd, 1H, J=11.8, 4.4 Hz, H-6), 3.46 (dd, 1H, J=9.7, 9.3 Hz, H-4), 3.13 (dd, 1H, J=10.5, 3.7 Hz, H-2); 'Ring II': 6H 3.80 (t, 1H, J=8.8 Hz, H-5), 3.77-3.67 (m, 3H, H-1, H-3, H-4), 3.56 (t, 1H, J=9.6 Hz, H-6), 2.59-2.48 (m, 1H), 1.68 (dd, 1H, J=26.3, 12.7 Hz, H-2).

$^{13}$C NMR (125 MHz, MeOD): δ=C 99.3 (C1'), 80.7, 77.8 (C5), 77.7 (C6), 73.9 (C5'), 72.4 (C3'), 71.6, 64.8 (C2'), 62.1 (C6'), 61.6, 60.9, 33.1 (C2).

MALDI TOFMS: calculated for C$_{12}$H$_{19}$N$_9$O$_7$ ([M+K]+) m/e 440.3; measured m/e 440.2.

Synthesis of (((2R, 3S, 4R, 5R, 6S)-5-azido-6-(((1R, 2R, 3S, 4R, 6S)-4,6-diazido-2,3-bis((4-methoxybenzyl)oxy)cyclohexyl)oxy)-3,4-bis((4-methoxybenzyl) oxy)tetrahydro-2H-pyran-2-yl)methoxy)triisopropylsilane (Compound 19): Compound 18 (11.6 grams, 28.9 mmol) was dissolved in anhydrous DMF (80 mL) and cooled to 0° C. Triisopropylsilyl chloride (TIPSCl, 8 mL, 37.3 mmol) was added dropwise, followed by addition of 4-DMAP (10.6 grams, 86.7 mmol). The reaction mixture was allowed to attain the room temperature under stirring, and the reaction progress was monitored by TLC (EtOAc/Hexane 7:3), which indicated the completion after 5 hours. The reaction mixture was diluted with ethyl acetate (50 mL) and H$_2$O (20 mL), and the two layers were separated. The aqueous layer was thoroughly washed with ethyl acetate (4×30 mL). The combined organic layers were washed with sat. NaCl solution and dried over anhydrous MgSO$_4$. The solvent was evaporated to dryness and the residue was subjected to column chromatography (EtOAc/Hexane 25:75) to yield the corresponding silyl ether (18a) (13.3 grams, 83%).

$^1$H NMR (500 MHz, CDCl$_3$): 'Ring I': δ=H 5.14 (d, 1H, J=4.0 Hz, H-1), 4.09-4.02 (m, 2H, H-3, H-6), 3.98 (td, 1H, J1=8.0, J2=4.5 Hz, H-5), 3.82 (dd, 1H, J1=9.5, J2=8.0 Hz, H-6), 3.66 (t, 1H, J=9.0 Hz, H-4), 3.48 (dd, 1H, J1=10.5, J2=4.0 Hz, H-2); 'Ring II': δ=H 3.52 (t, 1H, J=8.0 Hz, H-5), 3.47-3.37 (m, 2H, H-1, H-6), 3.34-3.22 (m, 2H, H-3, H-4), 2.29 (dt, 1H, J1=12.0, J2=4.0 Hz, H-2eq), 1.47 (ddd, 1H, J1=J2=J3=12.0 Hz, H-2ax); The additional peaks in the spectrum were identified as follow: δ=H 1.16-1.09 (m, 3H, TIPS), 1.07 (s, 12H, TIPS), 1.06 (s, 6H, TIPS).

$^{13}$C NMR (125 MHz, CDCl$_3$): δ=C 99.3 (C1'), 83.4 (C4), 76.1 (C5), 75.5 (C6), 75.1 (C4'), 72.6 (C3'), 69.6 (C5'), 66.0 (C6'), 63.5 (C2'), 59.8 (C1), 58.9 (C3), 32.1 (C2), 17.9 (2C, TIPS), 11.8 (TIPS).

MALDI TOFMS: calculated for C$_{21}$H$_{39}$N$_9$O$_7$Si ([M+Na]+) m/e 580.6; measured m/e 580.3.

To a stirred solution of the silyl ether from above (9.82 grams, 17.6 mmol) and sodium hydride (3.38 grams, 140 mmol) in DMF (200 mL), was added p-Methoxybenzyl chloride (14.3 mL, 105.3 mmol) at 0° C. The reaction progress was monitored by TLC (EtOAc/Hexane 3:7). After 8 hours the reaction was completed and ice was added in small portions to quench the reaction. The mixture was diluted with ethyl acetate (100 mL) and washed with water (2×50 mL). The combined aqueous layers were extracted with diethyl ether (2×50 mL); the combined organic layers were dried over anhydrous MgSO$_4$, and evaporated to dryness. The residue was purified by column chromatography (EtOAc/Hexane 8:92) to thereby obtain compound 19 (15.28 grams, 84%).

$^1$H NMR (500 MHz, CDCl$_3$): 'Ring I': δ=H 5.45 (d, 1H, J=3.5 Hz, H-1), 3.94 (m, 2H, H-3, H-5), 3.88-3.78 (m, 2H, H-6), 3.59 (t, 1H, J=9.5 Hz, H-4), 3.17 (dd, 1H, J1=10.5, J2=3.5 Hz, H-2); 'Ring II': δ=H 3.56-3.42 (m, 2H, H-4, H-5), 3.41-3.32 (m, 1H, H-1), 3.32-3.20 (m, 2H, H-3, H-6), 2.17 (dt, 1H, J1=12.5, J2=4.0 Hz, H-2eq), 1.34 (ddd, 1H, J1=J2=J3=12.5 Hz, H-2ax); The additional peaks in the spectrum were identified as follow: δ=H 7.21 (d, 2H, J=8.0 Hz, PMB), 7.17 (d, 6H, J=8.0 Hz, PMB), 6.85-6.72 (m, 8H, PMB), 4.86 (d, 1H, J=10.0 Hz, PMB), 4.80-4.65 (m, 6H, PMB), 4.61 (d, 1H, J=10.0 Hz, PMB), 3.74-3.68 (m, 12H, PMB), 1.04-0.94 (m, 21H, TIPS).

$^{13}$C NMR (125 MHz, CDCl$_3$): δ=C 159.5 (PMB), 159.4 (PMB), 159.3 (PMB), 159.2 (PMB), 130.7 (PMB), 130.3 (PMB), 130.2 (PMB), 129.9 (PMB), 129.8 (PMB), 129.7 (PMB), 129.3 (PMB), 128.7 (PMB), 113.9 (2C, PMB), 97.5 (C1'), 84.5, 84.4, 79.8, 77.9 (C4'), 76.9, 75.6 (PMB), 75.2 (PMB), 74.9 (PMB), 74.5 (PMB), 72.9, 63.5 (C2'), 62.3 (C6'), 60.3 (C1), 59.5, 55.3 (4C, PMB), 32.4 (C2), 18.1 (2C, TIPS), 12.1 (TIPS).

MALDI TOFMS: calculated for C$_{53}$H$_{71}$N$_9$O$_{11}$Si ([M+Na]+) m/e 1061.2; measured m/e 1061.6.

Synthesis of (2R, 3R, 4R, 5R, 6R)-3-azido-24(1R,2R,3S,4R,6S)-4,6-diazido-2,3-bis((4-methoxybenzyl)oxy)cyclohexyl)oxy)-4,5-bis((4-methoxybenzyl) oxy)-6-vinyltetrahydro-2H-pyran (Compound 20): To a stirred solution of compound 19 (19.82 grams, 19 mmol) in THF (230 mL) at 0° C., TBAF (11.05 mL, 38.1 mmol) was added and the reaction progress was monitored by TLC (EtOAc/Hexane 2:3). After 19 hours, the solvent was evaporated to dryness and the obtained residue was subjected to column chromatography (EtOAc/Hexane 3:7) to thereby obtain the corresponding 6'-alcohol (14.74 grams, 88%).

$^1$H NMR (500 MHz, CDCl$_3$): 'Ring I': δ=H 5.51 (d, 1H, J=4.0 Hz, H-1), 3.98 (dt, 1H, J1=8.0, J2=2.0 Hz, H-5), 3.92 (t, 1H, J=10.0 Hz, H-3), 3.70 (dd, 1H, J1=12.0, J2=2.0 Hz, H-6), 3.64 (dd, 1H, J1=12.0, J2=2.0 Hz, H-6), 3.49 (dd, 1H, J1=10.0, J2=8.0 Hz, H-4), 3.17 (dd, 1H, J1=10.0, J2=4.0 Hz, H-2); 'Ring II': δ=H 3.53-3.44 (m, 2H, H-4, H-5), 3.38 (ddd, 1H, J1=12.5, J2=10.0, J3=4.5 Hz, H-1), 3.34-3.24 (m, 2H, H-3, H-6), 2.20 (dt, 1H, J1=12.5, J2=4.5 Hz, H-2eq), 1.36 (ddd, 1H, J1=J2=J3=12.5 Hz, H-2ax); The additional peaks in the spectrum were identified as follow: δ=H 7.23 (d, 2H, J=8.0 Hz, PMB), 7.20-7.14 (m, 6H, PMB), 6.83-6.75 (m, 8H, PMB), 4.89 (d, 1H, J=10.0 Hz, PMB), 4.80-4.68 (m, 6H, PMB), 4.55 (d, 1H, J=10.0 Hz, PMB), 3.73-3.7 (m, 12H, PMB).

$^{13}$C NMR (125 MHz, CDCl$_3$): δ=C 159.5 (PMB), 159.4 (2C, PMB), 159.2 (PMB), 130.2 (PMB), 130.1 (2C, PMB), 129.9 (PMB), 129.8 (PMB), 129.6 (2C, PMB), 128.8 (PMB), 114.0 (2C, PMB), 113.9 (2C, PMB), 97.6 (C1'), 84.4, 84.3, 79.8 (C3'), 77.4, 75.6 (PMB), 75.2 (PMB), 75.1 (PMB), 74.6 (PMB), 72.0 (C5'), 63.3 (C2'), 61.4 (C6'), 60.3 (C1), 59.5, 55.3 (3C, PMB), 32.4 (C2).

MALDI TOFMS: calculated for C44H51N9O11 ([M+Na]+) m/e 903.3; measured m/e 903.9.

To a solution of the 6'-alcohol from the above reaction (100 mg, 0.11 mmol) in ethyl acetate (5 mL), IBX (95 mg, 0.33 mmol) was added in one portion. The resulting suspension was heated at 80° C. and stirred vigorously. After the reaction was completed (3.5 hours) as indicated by TLC (EtOAc/Hexane 2:3), the reaction was cooled to room temperature and filtered through Celite®. The Celite® was thoroughly washed with ethyl acetate (2×50 mL) and the combined organic layers were evaporated under reduced pressure. The crude product was subjected to flash column chromatography (EtOAc/Hexane 35:65) to thereby obtain the 6'-aldehyde (85 mg, 85%).

$^1$H NMR (500 MHz, CDCl$_3$): 'Ring I': δ=H 9.53 (s, 1H, H-6), 5.56 (d, 1H, J=4.0 Hz, H-1), 4.60 (d, 1H, J=10.0 Hz, H-4), 3.98 (dd, 1H, J1=J2=10.0 Hz, H-3), 3.52-3.45 (m, 1H, H-5), 3.17 (dd, 1H, J1=10.0, J2=4.0 Hz, H-2); 'Ring II': δ=H 3.53-3.43 (m, 2H, H-4, H-5), 3.37 (ddd, 1H, J1=12.0, J2=10.0, J3=4.0 Hz, H-1), 3.33-3.24 (m, 2H, H-3, H-6), 2.20 (dt, 1H, J1=12.5, J2=4.0 Hz, H-2eq), 1.35 (ddd, 1H, J1=J2=J3=12.5 Hz, H-2ax); The additional peaks in the spectrum were identified as follow: δ=H 7.23 (d, 2H, J=8.0 Hz, PMB), 7.19-7.10 (m, 6H, PMB), 6.83-6.72 (m, 8H, PMB), 4.89 (d, 1H, J=10.0 Hz, PMB), 4.80-4.64 (m, 6H, PMB), 4.51 (d, 1H, J=10.0 Hz, PMB), 3.73 (s, 3H, PMB), 3.71 (s, 6H, PMB), 3.70 (s, 3H, PMB).

$^{13}$C NMR (125 MHz, CDCl$_3$): δ=C 197.3 (CHO), 159.7 (PMB), 159.6 (2C, PMB), 159.2 (PMB), 130.2 (PMB), 130.0 (PMB), 129.9 (2C, PMB), 129.7 (PMB), 129.6 (PMB), 129.3 (PMB), 128.6 (PMB), 114.1 (PMB), 114.0 (3C, PMB), 97.5 (C1'), 84.3, 84.2, 79.8 (C3'), 78.0, 77.6, 75.6 (PMB), 75.5 (PMB), 75.2 (C4'), 75.1 (PMB), 74.8 (PMB), 62.8 (C2'), 60.2 (C1), 59.1, 55.4 (PMB), 55.3 (PMB), 32.21 (C2).

MALDI TOFMS: calculated for C44H49N9O11 ([M+Na]+) m/e 902.3; measured m/e 902.3.

To a cooled suspension of Methyltriphenylphosphonium Iodide (70 mg, 0.19 mmol) in anhydrous THF at 0° C., n-BuLi (1.6 M in hexane, 136 µL) was added drop wise and the resulting yellow solution was stirred for additional 30 minutes at 0° C. The 6'-aldehyde from the previous step (61 mg, 0.069 mmol) in anhydrous THF (0.3 mL) was thereafter added at 0° C., and the reaction was allowed to stir for additional 1.5 hours at room temperature. After completion of the reaction, as indicated by TLC (EtOAc/Hexane 2:3), the reaction was quenched with saturated NH$_4$Cl solution. The layers were separated and the aqueous layer was extracted with ether (2×10 mL). The combined organic layers were washed with brine, dried over anhydrous MgSO$_4$ and evaporated to dryness. The crude product was purified by flash chromatography (EtOAc/Hexane 2.5:7.5) to thereby obtain Compound 20 (27 mg, 56%).

$^1$H NMR (500 MHz, CDCl$_3$): 'Ring I': δ=H 5.83-5.74 (m, 1H, H-6), 5.47 (d, 1H, J=4.0 Hz, H-1), 5.37 (d, 1H, J=16.5 Hz, H-7trans), 5.21 (d, 1H, J=9.5 Hz, H-7cis), 4.49 (dd, 1H, J1=9.5, J2=7.5 Hz, H-5), 3.90 (t, 1H, J=9.5 Hz, H-3), 3.25-3.14 (m, 2H, H-2, H-4); 'Ring II': δ=H 3.54-3.44 (m, 2H, H-4, H-5), 3.38 (ddd, 1H, J1=12.0, J2=9.5, J3=4.0 Hz, H-1), 3.34-3.25 (m, 2H, H-3, H-6), 2.21 (dt, 1H, J1=12.5, J2=4.0 Hz, H-2eq), 1.38 (ddd, 1H, J1=J2=J3=12.5 Hz, H-2ax); The additional peaks in the spectrum were identified as follow: δ=H 7.25-7.09 (m, 8H, PMB), 6.84-6.73 (m, 8H, PMB), 4.88 (d, 1H, J=10.0 Hz, PMB), 4.77 (dd, 2H, J=10.0, 2.5 Hz, PMB), 4.74-4.66 (m, 3H, PMB), 4.59 (d, 1H, J=10.5 Hz, PMB), 4.52 (d, 1H, J=10.5 Hz, PMB), 3.73 (s, 3H, PMB), 3.72 (s, 6H, PMB), 3.71 (s, 3H, PMB).

$^{13}$C NMR (125 MHz, CDCl3): δ=C 159.5 (PMB), 159.4 (2C, PMB), 159.2 (PMB), 134.9 (C6'), 130.3 (PMB), 130.2 (2C, PMB), 129.9 (2C, PMB), 129.6 (2C, PMB), 128.7 (PMB), 118.8 (C7'), 114.0 (PMB), 113.9 (2C, PMB), 97.6 (C1'), 84.4, 84.3, 82.4 (C4'), 79.4 (C3'), 77.6, 75.6 (PMB), 75.3 (PMB), 75.0 (PMB), 74.6 (PMB), 72.7 (C5'), 63.4 (C2'), 60.3 (C1), 59.3, 55.4 (PMB), 55.3 (PMB), 32.3 (C2).

MALDI TOFMS: calculated for C45H51N9O10 ([M+Na]+) m/e 900.9; measured m/e 900.5.

Synthesis of 1-((2R, 3S, 4R, 5R, 6S)-5-azido-6-(((1R, 2R, 3S, 4R, 6S)-4,6-diazido-2,3-bis((4-methoxybenzyl)oxy)cyclohexyl)oxy)-3,4-bis((4-methoxybenzyl) oxy)tetrahydro-2H-pyran-2-yl)ethane-1,2-diol (Compound 21): To a stirred solution of Compound 20 (383 mg, 0.436 mmol) in acetone (5 mL), water (1.5 mL) and t-BuOH (5 mL), K$_2$OsO$_4$.2H2O (16 mg, 0.043 mmol) and NMO (181 µL) were added sequentially. The progress of the reaction was monitored by TLC (EtOAc/Hexane 2:3), which indicated the completion after 24 hours. The solvent was then evaporated to dryness; the residue was dissolved in EtOAc to which an aqueous solution of Na$_2$S$_2$O$_3$ was added. The layers were separated and the organic phase was washed with brine, dried over MgSO$_4$ and evaporated. The crude product was subjected to column chromatography (EtOAc/Hexane 1:1) to thereby obtain compound 21 (370 mg, 93%) as a 6'-diasteromeric mixture.

Synthesis of (2R, 3S, 4R, 5R, 6S)-5-azido-6-(((1R, 2R, 3S, 4R, 6S)-4,6-diazido-2,3-dihydroxycyclohexyl)oxy)-2-((R)-1,2-dihydroxyethyl)tetrahydro-2H-pyran-3,4-diol (Compound 22) and (2R, 3S,4R, 5R, 6S)-5-azido-6-(((1R, 2R, 3S, 4R,6S)-4,6-diazido-2,3-dihydroxycyclohexyl)oxy)-2-((S)-1,2-dihydroxyethyl) tetrahydro-2H-pyran-3,4-diol (Compound 23): Compound 21 (220 mg, 1.0 equiv.) from above was stirred with 2,3-dichloro-5,6-dicyano-1,4-benzoquinone (DDQ) (383 mg, 6 equiv.) in methylene chloride and water (20:1 v/v, 15 mL) at room temperature. After the addition of DDQ, a dark green color charge transfer complex formed immediately and slowly faded to orange color as the reaction progressed. TLC (EtOAc/MeOH 98:2) showed that the reaction completed after 15 hours. The solvents were then evaporated and the residue was loaded onto the silica gel column without prior work up. Due to high polarity of the titled compound, this column chromatography allowed the removal of only parts of the DDQ reaction byproducts. Therefore, in order to obtain the analytically pure product, the fractions containing the product were combined, evaporated and the residue was then subjected to peracetylation and deacetylation steps, as follows. The crude material from above was dissolved in anhydrous pyridine (5 mL) and cooled to 0° C. Acetic anhydride (0.73 mL, 9 equiv.) was added dropwise, followed by the addition of 4-DMAP (0.621 gram, 6 equiv.). After completion of the reaction (2 hours), as indicated by TLC (EtOAc/Hexane 2:3), the reaction was diluted with EtOAc (20 mL) and washed with 5% HCl solution, Sat. NaHCO$_3$, and brine, and dried over anhydrous MgSO$_4$. The solvent was evaporated to dryness and the residue was subjected to a column chromatography (EtOAc/Hexane 3:7) to thereby obtain the corresponding peracetate as an inseparable mixture of 6'-diastereomers (150 mg, 91% for 2 steps).

The peracetate (215 mg, 0.314 mmol) from above was dissolved in anhydrous MeOH (5 mL) and NaOMe (152 mg, 2.81 mmol) was added in one portion to the stirred solution at room temperature. The reaction progress was monitored by TLC (EtOAc/MeOH 95:5), which indicated completion after 4 hours. The reaction mixture was passed through a short silica gel column and the product was eluted with MeOH. The fractions with the compound were combined, evaporated and the crude product was subjected to an additional column chromatography (EtOAc/MeOH 99:1), which allowed complete separation of the two diastereomers, the major (Rf=0.36) and minor (Rf=0.2). The major diastereomer was later assigned, as detailed hereinunder, as the 6'-(R)-diastereomer (Compound 22) and the minor one as the 6'-(S)-diastereomer (Compound 23).

Major Diastereomer (22): $^1$H NMR (500 MHz, MeOD): 'Ring I': δ=H 5.68 (d, 1H, J=4.0 Hz, H-1), 4.04 (dd, 1H, J1=9.5, J2=4.0 Hz, H-4), 3.97-3.92 (m, 1H, H-6), 3.93 (t, 1H, J=10.0 Hz, H-3), 3.79 (dd, 1H, J=11.5, 3.5 Hz, H-7), 3.70 (dd, 1H, J1=11.5, J2=7.0 Hz, H-7), 3.58 (t, 1H, J=9.5 Hz, H-5), 3.13 (dd, 1H, J1=10.0, J2=4.0 Hz, H-2); 'Ring II': δ=H 3.57-3.47 (m, 3H, H-3, H-4, H-5), 3.44 (ddd, 1H, J1=16.5, J2=8.5, J3=4.0 Hz, H-1), 3.29 (t, 1H, J=9.5 Hz, H-6), 2.26 (dt, 1H, J1=12.5, J2=4.0 Hz, H-2eq), 1.43 (ddd, 1H, J1=J2=J3=12.5 Hz, H-2ax).

$^{13}$C NMR (125 MHz, MeOD): δ=C 99.1 (C1'), 80.5, 77.9 (C6), 77.9, 74.8 (C6'), 73.7 (C4'), 72.9 (C5'), 72.3 (C3'), 64.5 (C2'), 64.3 (C7'), 61.7 (C1), 61.0, 33.3 (C2).

MALDI TOFMS: calculated for C$_3$H$_{27}$N$_3$O$_8$ ([M+H]+) m/e 432.3; measured m/e 432.8.

Minor Diastereomer (23): $^1$H NMR (500 MHz, MeOD): Ring I': δ=H 5.72 (d, 1H, J=3.6 Hz, H-1), 4.00 (ddd, 1H, J1=6.8, J2=6.0, J3=1.1 Hz, H-6), 3.97-3.91 (m, 2H, H-5, H-3), 3.74-3.67 (m, 2H, H-7, H-7), 3.64-3.59 (m, 1H, H-4), 3.10 (dd, 1H, J1=10.5, J2=3.7 Hz, H-1); 'Ring II': δ=H 3.57-3.50 (m, 2H, H-1, H-6), 3.45-3.37 (m, 2H, H-3, H-4), 3.26 (t, 1H, J=9.5 Hz, H-5), 2.24 (dt, 1H, J1=12.8, J2=4.4 Hz, H-2eq), 1.40 (ddd, 1H, J1=J2=J3=12.5 Hz, H-2ax).

$^{13}$C NMR (125 MHz, MeOD): δ=C 99.1 (C-1'), 80.1 (C-4), 78.0 (C-6), 77.5 (C-5), 73.1 (C-5'), 72.3 (C-3'), 71.3 (C-4'), 70.8 (C-6'), 65.3 (C-7'), 64.4 (C-2'), 61.7 (C-3), 61.1 (C-1), 33.3 (C-2).

MALDI TOFMS: calculated for C$_{13}$H$_{27}$N$_3$O$_8$ ([M+H]+) m/e 432.3; measured m/e 432.8.

Synthesis of (2R, 3S, 4R, 5R, 6S)-5-amino-6-(((1R, 2R, 3S, 4R, 6S)-4,6-diamino-2,3-dihydroxycyclohexyl)oxy)-2-((R)-1,2-dihydroxyethyl)tetrahydro-2H-pyran-3,4-diol [NB153 ((R)-diasteromer)]: To a stirred solution of compound 22 (82 mg, 0.19 mmol) in a mixture of THF (3 mL) and aqueous NaOH (1 mM, 5 mL), PMe$_3$ (1 M solution in THF, 0.15 mL, 2.5 mmol) was added. The progress of the reaction was monitored by TLC [CH$_2$Cl$_2$/MeOH/H$_2$O/MeNH$_2$ (33% solution in EtOH), 10:15:6:15], which indicated completion after 1 hour. The reaction mixture was thereafter purified by flash chromatography on a short column of silica gel. The column was washed with the following solvents: THF (100 mL), CH$_2$Cl$_2$ (100 mL), EtOH (50 mL), and MeOH (100 mL). The product was then eluted with a mixture of 5% MeNH$_2$ solution (33% solution in EtOH) in 80% MeOH. Fractions containing the product were combined and evaporated under vacuum. The pure product was obtained by passing the above product through a short column of Amberlite CG50 (NH4$^+$ form). First, the column was washed with water, then the product was eluted with a mixture of 10% NH$_4$OH in water, to thereby obtain NB153 (49.0 mg, 73%). For storage and biological tests, NB153 was converted to its sulfate salt form as follow: The free base form was dissolved in water, the pH was adjusted to 6.7 with H$_2$SO$_4$ (0.1 N) and lyophilized to afford the sulfate salt of NB153 as white foamy solid.

$^1$H-NMR (500 MHz, MeOD, —NH2 form): 'Ring I': δ=H 5.18 (d, 1H, J=4.0 Hz, H-1), 3.98-3.93 (m, 1H, H-6), 3.90 (dd, 1H, J1=10.0, J2=4.0 Hz, H-4), 3.76 (dd, 1H, J1=11.5, J2=4.0 Hz, H-7), 3.70 (dd, 1H, J1=11.5, J2=6.0 Hz, H-7), 3.51 (t, 1H, J=10.0 Hz, H-3), 3.44 (m, 1H, H-5), 2.74 (dd, 1H, J1=10.0, J2=4.0 Hz, H-2); 'Ring II': δ=H 3.43 (t, 1H, J=9.0 Hz, H-5), 3.20 (t, 1H, J=9.0 Hz, H-4), 3.10 (t, 1H, J=9.5 Hz, H-6), 2.77 (ddd, 1H, J1=10.5, J2=9.0, J3=5.0 Hz, H-3), 2.66 (ddd, 1H, J1=10.5, J2=9.5, J3=5.0 Hz, H-1), 2.02 (dt, 1H, J1=12.5, J2=4.0 Hz, H-2eq), 1.22 (ddd, 1H, J1=J2=J3=12.5 Hz, H-2ax).

$^{13}$C NMR (125 MHz, MeOD): δC 102.9 (C-1'), 90.0 (C-4), 78.2 (C-6), 77.5, 75.6 (C-3'), 74.3 (C-4'), 73.6 (C-6'), 73.3, 63.3 (C-7'), 57.1 (C-2'), 52.4 (C-3), 51.3 (C-1), 36.7 (C2).

MALDI TOFMS: calculated for C$_{13}$H$_{27}$N$_3$O$_8$ ([M+H]+) m/e 354.3; measured m/e 354.8.

Synthesis of (2R, 3S, 4R, 5R, 6S)-5-amino-6-(((1R, 2R, 3S, 4R, 6S)-4,6-diamino-2,3-dihydroxycyclohexyl)oxy)-2-((S)-1,2-dihydroxyethyl)tetrahydro-2H-pyran-3,4-diol [NB155 ((S)-diastereomer)]: To a stirred solution of Compound 23 (52 mg, 0.12 mmol) in a mixture of THF (3 mL) and aqueous NaOH (1 mM, 5 mL), PMe$_3$ (1 M solution in THF, 0.15 mL, 2.5 mmol) was added. The progress of the reaction was monitored by TLC [CH$_2$Cl$_2$/MeOH/H$_2$O/

MeNH$_2$ (33% solution in EtOH), 10:15:6:15], which indicated completion after 1 hour. The reaction mixture was purified by flash chromatography on a short column of silica gel. The column was washed with the following solvents: THF (100 mL), CH$_2$Cl$_2$ (100 mL), EtOH (50 mL), and MeOH (100 mL). The product was then eluted with the mixture of 5% MeNH$_2$ solution (33% solution in EtOH) in 80% MeOH. Fractions containing the product were combined and evaporated under vacuum. The pure product was obtained by passing the above product through a short column of Amberlite CG50 (NH4$^+$ form). First, the column was washed with water, then the product was eluted with a mixture of 10% NH$_4$OH in water to thereby obtain NB155 (36.0 mg, 78%). For storage and biological tests, NB155 was converted to its sulfate salt form as follow: The free base form was dissolved in water, the pH was adjusted to 6.7 with H$_2$SO$_4$ (0.1 N) and lyophilized to afford the sulfate salt of NB155 as white foamy solid.

$^1$H NMR (500 MHz, MeOD, —NH2 form): 'Ring I': δ=H 5.28 (d, 1H, J=3.8 Hz, H-1'), 3.97 (td, 1H, J1=7.1, J2=1.0 Hz, H-6'), 3.89-3.82 (m, 1H, H-4'), 3.63 (d, 2H, J=7.2 Hz, H-7', H-7'), 3.59-3.51 (m, 2H, H-5', H-3'), 2.72 (m, 1H, H-2'); 'Ring II': δ=H 3.41 (t, 1H, J=9.1 Hz, H-5), 3.20 (t, 1H, J=9.2 Hz, H-4), 3.08 (t, 1H, J=9.4 Hz, H-6), 2.74 (m, 1H, H-3), 2.64 (ddd, 1H, J1=12.2, J2=9.7, J3=4.1 Hz, H-1), 2.00 (dt, 1H, J1=12.9, J2=4.1 Hz, H-2eq), 1.21 (ddd, 1H, J1=J2=J3=12.3 Hz, H-2ax).

$^{13}$C NMR (125 MHz, MeOD): δ=C 102.9 (C-1'), 89.6 (C-4), 79.0 (C-6), 77.9 (C-5), 75.8 (C-3'), 72.3 (C-4'), 71.1 (C-5'), 70.2 (C-6'), 63.2 (C-7'), 57.1 (C-2'), 52.4 (C-1), 51.4 (C-3), 37.7 (C-2).

MALDI TOFMS: calculated for C$_{13}$H$_{27}$N$_3$O$_8$ ([M+H]+) m/e 354.3; measured m/e 354.8.

Syntheses of Pseudo-Trisaccharides NB156 and NB157:

The syntheses of compounds NB156 and NB157 are illustrated in Scheme 9 below, and were accomplished from the intermediate Compound 22 by using essentially the same chemical transformations as for NB153 and NB155.

Scheme 9

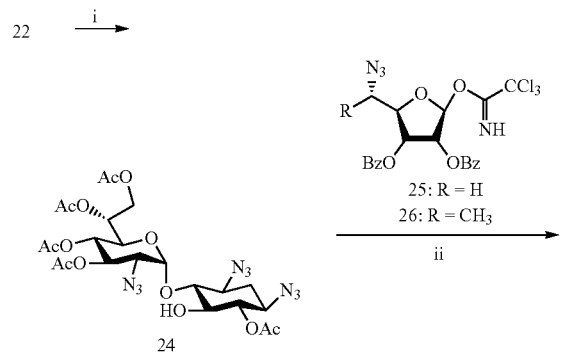

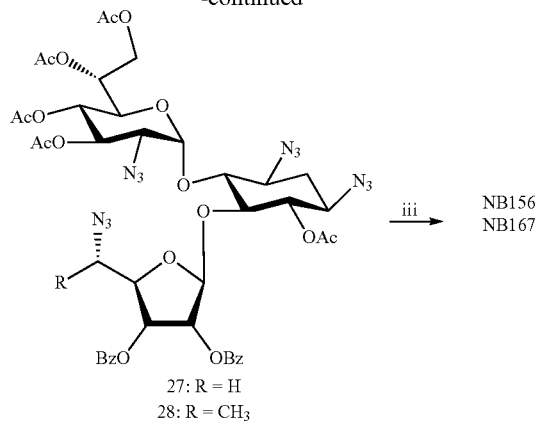

27: R = H
28: R = CH$_3$

Reagents and conditions:
(i) Ac$_2$O, Py., -20° C., 53%;
(ii) BF$_3$-OEt$_2$, CH$_2$Cl$_2$, -30° C., 85% of 27, 93% of 28;
(iii) (a) MeNH$_2$, r.t., 80% (R = H), 98% (R = CH$_3$);
(b) PMe$_3$, THF, NaOH (0.1M), 60% of NB156, 64% of NB157.

Briefly, regioselective acetylation of Compound 22 with Ac$_2$O at low temperature gave the corresponding C5 acceptor Compound 24. For the glycosylation of 24 the trichloroacemidate donors 25 and 26 which furnished the corresponding pseudo-trisaccharides 27 and 28 in 85% and 93% isolated yields, respectively, exclusively as β-anomers. Treatment with methylamine was followed by Staudinger reaction to afford NB156 and NB157.

Synthesis of NB156:
Synthesis of (2R, 3S, 4R, 5R, 6S)-6-(((1R, 2S, 3S, 4R, 6S)-3-acetoxy-4, 6-diazido-2-hydroxycyclohexyl)oxy)-5-azido-2-((R)-1,2-diacetoxyethyl)tetrahydro-2H-pyran-3,4-diyl diacetate (24): Compound 22 (370 mg, 0.857 mmol) was dissolved in anhydrous pyridine (8 mL) and cooled to -20° C. Acetic anhydride (0.45 mL, 4.8 mmol) was added dropwise and the reaction was allowed to progress at -20° C. The reaction progress was monitored by TLC, which indicated completion after 17 hours. The reaction mixture was diluted with EtOAc, and extracted with aqueous solution of HCl (2%), saturated aqueous NaHCO$_3$, and brine. The combined organic layers were dried over anhydrous MgSO$_4$ and concentrated. The crude product was purified by silica gel column chromatography (EtOAc/Hexane 3:7) to afford Compound 24 (292 mg, 53% yield).

$^1$H NMR (500 MHz, CDCl$_3$): 'Ring I': δ=H 5.45 (dd, 1H, J1=10.5, J2=9.3 Hz, H-3'), 5.37 (d, 1H, J=3.5 Hz, H-1'), 5.19 (ddd, 1H, J1=7.6, J2=4.0, J3=2.0 Hz, H-6'), 5.07 (dd, 1H, J1=10.4, J2=9.2 Hz, H-4'), 4.40 (dd, 1H, J1=10.5, J2=1.8 Hz, H-5'), 4.31 (dd, 1H, J1=12.0, J2=4.1 Hz, H-7'), 4.19-4.08 (m, 1H, H-7'), 3.63-3.56 (m, 1H, H-2'); 'Ring II': δ=H 4.91 (dd, 1H, J1=12.8, J2=7.1 Hz, H-6) 3.66 (td, 1H, J1=9.6, J2=3.5 Hz, H-5), 3.53 (ddd, 1H, J1=12.4, J2=10.1, J3=4.5 Hz, H-1), 3.45 (dd, 1H, J1=19.1, J2=9.2 Hz, H-4), 3.38-3.31 (m, 1H, H-3), 2.38 (dt, 1H, J1=13.2, J2=4.4 Hz, H-2eq), 1.58 (ddd, 1H, J1=J2=J3=12.6 Hz, H-2ax). The additional peaks in the spectrum were identified as follow: δ=H 2.17 (s, 3H, CH$_3$CO), 2.08 (d, 9H, J=1.5 Hz, CH$_3$CO), 2.04 (s, 3H, CH$_3$CO).

$^{13}$C NMR (125 MHz, CDCl$_3$): δ=C 170.7 (C=O), 170.6 (C=O), 170.2 (C=O), 170.0 (C=O), 169.9 (C=O), 98.5 (C-1'), 82.9 (C-4), 75.1 (C-6), 74.6 (C-5), 71.4 (C-3'), 70.0 (C-6'), 69.9 (C-5'), 68.9 (C-4'), 61.8 (C-7'), 61.5 (C-2'), 58.2 (C-3), 58.0 (C-1), 32.0 (C-2), 20.96 (CH$_3$), 20.92 (CH$_3$), 20.89 (CH$_3$), 20.86 (CH$_3$), 20.8 (CH$_3$), 20.7 (CH$_3$).

MALDI TOFMS: calculated for $C_{23}H_{31}N_9O_{13}$ ([M+Na]+) m/e 664.20; measured m/e 664.20.

Synthesis of (2S, 3S, 4S, 5R)-2-(((1S, 2S, 3R, 5S, 6R)-2-acetoxy-3,5-diazido-6-(((2S, 3R, 4R, 5S, 6R)-4,5-diacetoxy-3-azido-6-((R)-1,2-diacetoxyethyl)tetrahydro-2H-pyran-2-yl)oxy)cyclohexyl)oxy)-5-(azidomethyl)tetrahydrofuran-3,4-diyl dibenzoate (27): Anhydrous $CH_2Cl_2$ (15 mL) was added to a powdered, flame-dried 4 Å molecular sieves (2.0 grams), followed by the addition of acceptor Compound 24 (292 mg, 0.455 mmol) and donor Compound 25 (1.0 gram, 1.9 mmol). The reaction mixture was stirred for 10 minutes at room temperature and was then cooled to −30° C. Catalytic amount of $BF_3$-$Et_2O$ (50 μL) was added and the mixture was stirred at −30° C.; the reaction progress was monitored by TLC, which indicated the completion after 60 minutes. The reaction mixture was diluted with ethyl acetate and washed with saturated $NaHCO_3$ and brine. The combined organic layer was dried over $MgSO_4$, evaporated and subjected to column chromatography (EtOAc/Hexane) to obtain the Compound 27 (393 mg, 85% yield).

$^1$H NMR (500 MHz, $CDCl_3$): 'Ring I': δ=H 5.87 (d, 1H, J=3.8 Hz, H-1), 5.42-5.34 (m, 1H, H-3), 5.24-5.13 (m, 1H, H-6), 5.10-5.03 (m, 1H, H-4), 4.54 (dd, 1H, J1=10.5, J2=2.2 Hz, H-5), 4.33 (dd, 1H, J1=12.0, J2=4.1 Hz, H-7), 4.20 (dd, 1H, J1=11.9, J2=7.8 Hz, H-7), 3.50 (dd, 1H, J1=10.9, J2=3.8 Hz, H-2); 'Ring II': δ=H 5.01 (t, 1H, J=10.0 Hz, H-6), 3.87 (t, 1H, J=9.3 Hz, H-5), 3.71 (t, 1H, J=9.5 Hz, H-4), 3.57-3.48 (m, 2H, H-1, H-3), 2.38 (dt, 1H, J1=12.9, J2=4.3 Hz, H-2eq), 1.52 (ddd, 1H, J1=J2=J3=12.7 Hz, H-2ax); 'Ring III': δ=H 5.61 (s, 1H, H-1), 5.57 (d, 1H, J=4.7 Hz, H-2), 5.42-5.35 (m, 1H, H-3), 4.59-4.47 (m, 1H, H-4), 3.63-3.55 (m, 2H, H-5, H-5). The additional peaks in the spectrum were identified as follow: δ=H 7.93 (d, 2H, J=7.1 Hz, Ar), 7.87 (d, 2H, J=7.1 Hz, Ar), 7.54 (dt, 2H, J1=19.0, J2=7.4 Hz, Ar), 7.39 (t, 2H, J=7.8 Hz, Ar), 7.34 (t, 2H, J=7.8 Hz, Ar), 2.29 (s, 3H, $CH_3$), 2.08-2.04 (m, 12H, 4×$CH_3$).

$^{13}$C NMR (125 MHz, $CDCl_3$): δ=C 170.7 (C=O), 170.1 (C=O), 170.08 (C=O), 170.06 (C=O), 169.9 (C=O), 165.5 (Ar), 165.2 (Ar), 133.8 (Ar), 133.7 (Ar), 129.8 (Ar), 129.7 (Ar), 128.8 (Ar), 128.68 (Ar), 128.63 (Ar), 128.5 (Ar), 107.7 (C-1"), 96.1 (C-1'), 80.9 (C-4"), 79.8 (C-5), 77.2 (C-4), 74.5 (C-2"), 73.9 (C-6), 72.0 (C-3'), 70.7 (C-3"), 69.9 (C-6'), 69.2 (C-5'), 68.8 (C-4'), 61.5 (C-7'), 61.4 (C-2'), 58.9 (C-3), 58.3 (C-1), 53.1 (C-5"), 32.1 (C-2), 21.04 ($CH_3$), 21.03 ($CH_3$), 20.8 ($CH_3$), 20.7 ($CH_3$), 20.6 ($CH_3$).

MALDI TOFMS: calculated for $C_{42}H_{46}N_{12}O_{18}$ ([M+Na]+) m/e 1029.31; measured m/e 1029.29.

Synthesis of (2R, 3S, 4R, 5R, 6S)-5-amino-6-(((1R, 2R, 3S, 4R, 6S)-4,6-diamino-2-(((2S, 3S, 4R, 5R)-5-(aminomethyl)-3,4-dihydroxytetrahydrofuran-2-yl)oxy)-3-hydroxycyclohexyl)oxy)-2-((R)-1,2-dihydroxy ethyl)tetrahydro-2H-pyran-3,4-diol (NB156): The glycosylation product 27 (393 mg, 0.390 mmol) was treated with a solution of $MeNH_2$ (33% solution in EtOH, 15 mL) and the reaction progress was monitored by TLC (EtOAc/MeOH 85:15), which indicated completion after 12 hours. The reaction mixture was evaporated to dryness and was subjected to column chromatography (MeOH/EtOAc 2:8) to thereby obtain the corresponding completely de-esterified perazido derivative (183 mg) in 80% yield.

$^1$H NMR (500 MHz, MeOD): 'Ring I': δ=H 5.89 (d, 1H, J=3.8 Hz, H-1), 3.97 (dd, 1H, J1=9.7, J2=4.6 Hz, H-5), 3.84 (dd, 2H, J1=7.1 Hz, H-6, H-3), 3.69 (d, 1H, J=8.5 Hz, H-7), 3.60 (dd, 1H, J1=11.6, J2=6.4 Hz, H-7), 3.45 (dd, 1H, J1=10.0, J2=8.7 Hz, H-4), 3.06 (dd, 1H, J1=10.6, J2=4.4 Hz, H-2); 'Ring II': δ=H 3.62-3.54 (m, 2H, H-4, H-5), 3.50-3.43 (m, 1H, H-3), 3.40-3.33 (m, 1H, H-1), 3.33-3.26 (m, 1H, H-6), 2.12 (dt, 1H, J1=13.3, J2=4.4 Hz, H-2 eq), 1.29 (ddd, 1H, J1=J2=J3=12.4 Hz, H-2 ax); 'Ring III': δ=H 5.28 (d, 1H, J=0.8 Hz, H-1), 4.11 (dd, 1H, J1=4.4, J2=0.8 Hz, H-2), 3.98 (dd, 1H, J1=7.4, J2=4.2 Hz, H-3), 3.94 (dd, 1H, J1=7.0, J2=3.4 Hz, H-4), 3.49 (dd, 1H, J1=13.3, J2=2.8 Hz, H-5), 3.41 (dd, 1H, J1=13.1, J2=6.3 Hz, H-5).

$^{13}$C NMR (125 MHz, MeOD): δ=C 111.2 (C-1"), 97.4 (C-1'), 85.2 (C-4), 82.3 (C-5'), 77.6 (C-6), 76.8 (C-5), 76.3 (C-2"), 74.6 (C-6'), 73.3 (C-3"), 73.2 (C-4'), 72.7 (C-4"), 72.5 (C-3'), 64.7 (C-2'), 64.1 (C-7'), 61.9 (C-3), 61.4 (C-1), 54.5 (C-5"), 33.1 (C-2).

MALDI TOFMS: calculated for $C_{18}H_{28}N_{12}O_{11}$ ([M+Na]+) m/e 611.20; measured m/e 611.19.

To a stirred solution of a perazido derivative from the above reaction (183 mg, 0.311 mmol) in a mixture of THF (3 mL) and aqueous NaOH (1 mM, 5 mL), $PMe_3$ (1 M solution in THF, 0.22 mL, 3.0 mmol) was added. The progress of the reaction was monitored by TLC [$CH_2Cl_2$/MeOH/$H_2O$/$MeNH_2$ (33% solution in EtOH), 10:15:6:15], which indicated completion after 1 hour. The reaction mixture was purified by flash chromatography on a short column of silica gel. The column was washed with the following solvents: THF (100 mL), $CH_2Cl_2$ (100 mL), EtOH (50 mL), and MeOH (100 mL). The product was then eluted with the mixture of 5% $MeNH_2$ solution (33% solution in EtOH) in 80% MeOH. Fractions containing the product were combined and evaporated under vacuum. The pure product was obtained by passing the above product through a short column of Amberlite CG50 ($NH_4^+$ form). First, the column was washed with water, and then the product was eluted with a mixture of 10% $NH_4OH$ in water to yield Compound NB156 as a free base form (90.0 mg, 60%).

For storage and biological tests, NB156 was converted to its sulfate salt form as follow: The free base form was dissolved in water, the pH was adjusted to 6.7 with $H_2SO_4$ (0.1 N) and lyophilized to afford the sulfate salt of NB156 as white foamy solid.

$^1$H NMR (500 MHz, MeOD): 'Ring I': δ=H 5.18 (d, 1H, J=3.6 Hz, H-1), 3.91 (dt, 1H, J1=6.3, J2=3.9 Hz, H-6), 3.85 (dd, 1H, J1=10.2, J2=2.8 Hz, H-5), 3.70 (dd, 1H, J1=11.5, J2=3.7 Hz, H-7), 3.64 (dd, 1H, J1=11.5, J2=6.4 Hz, H7), 3.50 (dd, 1H, J1=10.0, J2=9.0 Hz, H-3), 3.40 (t, 1H, J=9.5 Hz, H-4), 2.60 (dd, 1H, J1=10.2, 3.3 Hz, H-2); 'Ring II': δ=H 3.44 (t, 1H, J=9.2 Hz, H-5), 3.33 (dd, 1H, J1=11.0, J2=7.6 Hz, H-4), 3.13 (t, 1H, J=9.5 Hz, H-6), 2.79-2.70 (m, 1H, H-3), 2.60 (td, 1H, J1=9.4, J2=4.4 Hz, H-1), 1.93 (dt, 1H, J1=13.0, J2=4.0 Hz, H-2eq), 1.16 (ddd, 1H, J1=J2=J3=12.4 Hz, H-2ax); 'Ring III': δ=H 5.20 (d, 1H, J=2.7 Hz, H-1), 4.04 (dd, 1H, J1=5.1, J2=2.8 Hz, H-2), 3.95-3.90 (m, 1H, H-3), 3.83 (dt, 1H, J1=5.3, J2=3.4 Hz, H-4), 2.89 (dd, 1H, J1=13.2, J2=4.0 Hz, H-5), 2.75 (dd, 1H, J1=13.2, J2=7.3 Hz, H-5).

$^{13}$C NMR (125 MHz, MeOD): δ=C 110.6 (C-1"), 101.7 (C-1'), 86.8 (C-4), 85.5 (C-5), 84.7 (C-4"), 78.8 (C-6), 76.2 (C-2"), 75.3 (C-3'), 74.7 (C-5'), 73.8 (C-6'), 73.0 (C-4'), 72.5 (C-3"), 63.4 (C-7'), 57.5 (C-2'), 52.5 (C-3), 52.3 (C-1), 45.2 (C-5"), 37.5 (C-2).

MALDI TOFMS: calculated for $C_{18}H_{36}N_4O_{11}$ ([M+H]+) m/e 485.24; measured m/e 485.19.

Synthesis of NB157:

Synthesis of (2S, 3S, 4S, 5R)-2-(((1S, 2S 3R, 5S, 6R)-2-acetoxy-3,5-diazido-6-(((2S, 3R, 4R, 5S, 6R)-4,5-diacetoxy-3-azido-6-((R)-1,2-diacetoxyethyl)tetrahydro-2H-pyran-2-yl)oxy)cyclohexyl)oxy)-5-((S)-1-azidoethyl)tetrahydrofuran-3,4-diyl dibenzoate (Compound 28): Anhydrous $CH_2C_{12}$ (15 mL) was added to a powdered, flame-dried 4 Å molecular sieves (2.0 grams), followed by the addition of acceptor Compound 24 (265 mg, 0.413 mmol) and donor Compound 26 (0.895 gram, 1.65 mmol). The reaction mixture was stirred for 10 minutes at room temperature and was then cooled to −30° C. At this temperature, catalytic amount of $BF_3$-$Et_2O$ (50 µL) was added and the mixture was stirred at −30° C. The reaction progress was monitored by TLC, which indicated the completion after 60 minutes. The reaction mixture was diluted with ethyl acetate and washed with saturated $NaHCO_3$ and brine. The combined organic layer was dried over $MgSO_4$, evaporated and subjected to column chromatography (EtOAc/Hexane) to obtain Compound 28 (393 mg) in 93% yield.

$^1$H NMR (600 MHz, $CDCl_3$): 'Ring I': δ=H 5.88 (d, 1H, J=4.0 Hz, H-1), 3.58 (dd, 1H, J1=10.7, J2=4.0 Hz, H-2), 5.36 (dd, 1H, J1=10.6, J2=9.3 Hz, H-3), 5.07 (dd, 1H, J1=10.5, J2=9.3 Hz, H-4), 4.53 (dd, 1H, J1=10.6, J2=2.2 Hz, H-5), 5.18 (ddd, 1H, J1=7.5, J2=4.1, J3=2.2 Hz, H-6), 4.33 (dd, 1H, J1=12.0, J2=3.9 Hz, H-7), 4.19 (dd, 1H, J1=12.1, J2=7.6 Hz, H-7); 'Ring II': δ=H 5.01 (t, 1H, J=9.9 Hz, H-6), 3.84 (t, 1H, J=9.4 Hz, H-5), 3.71 (t, 1H, J=9.5 Hz, H-4), 3.52 (ddd, 2H, J1=12.5, J2=10.0, J3=4.6 Hz, H-1, H-3), 2.39 (dt, 1H, J1=5.2, J2=4.5 Hz, H-2eq), 1.52 (ddd, 1H, J1=J2=J3=12.7 Hz, H-2ax); 'Ring III': δ=H 5.60 (t, 2H, J=2.3 Hz, H-1, H-2), 5.41 (dd, 1H, J1=7.6, J2=4.9 Hz, H-3), 4.33 (t, 1H, J=7.3 Hz, H-4), 3.77-3.64 (m, 1H, H-5), 1.24 (d, 3H, J=6.8 Hz, 6-CH3). The additional peaks in the spectrum were identified as follow: δ=H 7.92-7.89 (m, 2H, Ar), 7.89-7.85 (m, 2H, Ar), 7.60-7.50 (m, 2H, Ar), 7.39 (t, 2H, J=7.8 Hz, Ar), 7.34 (t, 2H, J=7.9 Hz, Ar), 2.41-2.35 (m, 3H, $CH_3$), 2.08 (s, 3H, $CH_3$), 2.07 (s, 3H, $CH_3$), 2.07 (s, 3H, $CH_3$), 2.05 (s, 3H, $CH_3$).

$^{13}$C NMR (151 MHz, $CDCl_3$): δ=C 170.7 (C=O), 170.3 (C=O), 170.07 (C=O), 170.03 (C=O), 169.9 (C=O), 165.5 (Ar), 165.0 (Ar), 133.8 (Ar), 133.7 (Ar), 129.8 (Ar), 129.7 (Ar), 128.8 (Ar), 128.6 (Ar), 128.58 (Ar), 128.56 (Ar), 107.8 (C-1"), 96.1 (C-1'), 84.6 (C-4"), 79.7 (C-5), 77.6 (C-4), 74.7 (C-2"), 73.7 (C-6), 72.0 (C-3"), 71.0 (C-3), 70.0 (C-6'), 69.2 (C-4'), 68.9 (C-5'), 61.7 (C-2'), 61.5 (C-7'), 59.6 (C-5"), 58.9 (C-1), 58.5 (C-3), 32.2 (C-2), 21.1 ($CH_3$), 21.0 ($CH_3$), 20.8 ($CH_3$), 20.79 ($CH_3$), 20.78 ($CH_3$), 15.8 (C-6", $CH_3$).

MALDI TOFMS: calculated for $C_{43}H_{48}N_{12}O_{18}$ ([M+Na]+) m/e 1043.32; measured m/e 1043.30.

Synthesis of (2R, 3S, 4R, 5R, 6S)-5-amino-6-(((1R, 2R, 3S, 4R, 6S)-4,6-diamino-2-(((2S, 3S, 4R, 5R)-5-((S)-1-aminoethyl)-3,4-dihydroxytetrahydrofuran-2-yl)oxy)-3-hydroxycyclohexyl)oxy)-2-((R)-1,2-dihydroxyethyl)tetrahydro-2H-pyran-3,4-diol (NB157): The glycosylation product Compound 28 (0.393 gram, 0.384 mmol) was treated with a solution of $MeNH_2$ (33% solution in EtOH, 15 mL) and the reaction progress was monitored by TLC (EtOAc/MeOH 85:15), which indicated completion after 12 hours. The reaction mixture was evaporated to dryness and was subjected to column chromatography (MeOH/EtOAc 2:8) to obtain the corresponding completely de-esterified perazido derivative (230 mg) in 98% yield.

$^1$H NMR (600 MHz, MeOD): 'Ring I': δ=H 5.98 (d, 1H, J=3.8 Hz, H-1), 3.11 (dd, 1H, J1=10.5, J2=3.8 Hz, H-2), 4.03 (dd, 1H, J1=9.7, J2=4.5 Hz, H-4), 3.96-3.88 (m, 2H, H-3, H-6), 3.50 (dd, 1H, J1=10.0, J2=8.8 Hz, H-5), 3.75 (dd, 1H, J1=11.2, J2=2.5 Hz, H-7), 3.66 (dd, 1H, J1=11.6, J2=6.5 Hz, H-7); 'Ring II': δ=H 3.69-3.64 (m, 1H, H-4), 3.60 (t, 1H, J=8.9 Hz, H-5), 3.52 (ddd, 1H, J1=12.3, J2=9.7, J3=4.4 Hz, H-3), 3.42 (ddd, 1H, J1=11.9, J2=9.7, J3=4.4 Hz, H-1), 3.38-3.33 (m, 1H, H-6), 2.18 (dt, 1H, J1=12.6, J2=4.4 Hz, H-2eq), 1.52-1.17 (m, 1H, H-2ax); 'Ring III': δ=H 5.31 (d, 1H, J=0.5 Hz, H-1), 4.17 (dd, 1H, J1=4.8, J2=0.6 Hz, H-2), 4.10 (dd, 1H, J1=7.2, J2=4.7 Hz, H-3), 3.78-3.70 (m, 1H, H-4), 3.69-3.57 (m, 1H, H-5), 1.33 (d, 3H, J=6.7 Hz, 6-$CH_3$).

$^{13}$C NMR (151 MHz, MeOD): δ=C 110.79 (C-1"), 97.41 (C-1'), 86.03 (C-4"), 85.24 (C-5), 77.47 (C-6), 76.76 (C-4), 76.47 (C-2"), 74.60 (C-6'), 73.42 (C-3), 73.31 (C-4'), 72.77 (C-3"), 72.60 (C-3'), 64.66 (C-2'), 64.13 (C-7'), 61.96 (C-1), 61.51 (C-5'), 60.86 (C-5"), 33.17 (C-2), 16.06 (C-6", $CH_3$).

MALDI TOFMS: calculated for $C_{19}H_{30}N_{12}O_{11}$ ([M+Na]+) m/e 625.22; measured m/e 625.20.

To a stirred solution of the perazido derivative from the above reaction (230 mg, 0.381 mmol) in a mixture of THF (3 mL) and aqueous NaOH (1 mM, 5 mL), $PMe_3$ (1 M solution in THF, 0.22 mL, 3.0 mmol) was added. The progress of the reaction was monitored by TLC [$CH_2Cl_2$/MeOH/$H_2O$/$MeNH_2$ (33% solution in EtOH), 10:15:6:15], which indicated completion after 1 hour. The reaction mixture was purified by flash chromatography on a short column of silica gel. The column was washed with the following solvents: THF (100 mL), $CH_2Cl_2$ (100 mL), EtOH (50 mL), and MeOH (100 mL). The product was then eluted with the mixture of 5% $MeNH_2$ solution (33% solution in EtOH) in 80% MeOH. Fractions containing the product were combined and evaporated under vacuum. The pure product was obtained by passing the above product through a short column of Amberlite CG50 ($NH_4^+$ form). First, the column was washed with water, then the product was eluted with a mixture of 10% $NH_4OH$ in water to yield NB157 (123 mg, 64%) in its free base form.

For storage and biological tests, NB157 was converted to its sulfate salt form as follow: The free base form was dissolved in water, the pH was adjusted to 6.7 with $H_2SO_4$ (0.1 N) and lyophilized to afford the sulfate salt of NB157 as a white foamy solid.

$^1$H NMR (600 MHz, MeOD): 'Ring I': δ=H 5.25 (d, 1H, J=3.6 Hz, H-1), 4.00-3.94 (m, 1H, H-6), 3.90 (dd, 1H, J1=9.9, J2=3.5 Hz, H-5), 3.56-3.50 (m, 1H, H-3), 3.47 (dd, 1H, J1=18.3, J2=8.8 Hz, H-4), 2.66 (dd, 1H, J1=10.3, J2=3.5 Hz, H-2), 3.76 (dd, 1H, J1=11.5, J2=3.7 Hz, H-7), 3.70 (dd, 1H, J1=11.5, J2=6.4 Hz, H-7); 'Ring II': δ=H 3.48 (dd, 1H, J1=15.9, J2=6.7 Hz, H-5), 3.37 (dd, 1H, J1=16.5, J2=7.2 Hz, H-4), 3.18 (dd, 1H, J1=13.1, J2=5.6 Hz, H-6), 2.78 (dd, 1H, J1=9.9, J2=8.2 Hz, H-3), 2.64 (dd, 1H, J1=22.9, J2=10.3 Hz, H-1), 1.96 (dt, 1H, J1=7.8, J2=3.7 Hz, H-2eq), 1.23 (ddd, 1H, J1=J2=J3=12.5 Hz, H-2ax); 'Ring III': δ=H 5.26 (d, 1H, J=2.7 Hz, H-1), 4.05 (d, 1H, J=1.8 Hz, H-2), 4.01 (t, 1H, J=5.7 Hz, H-3), 3.56 (t, 1H, J=6.3 Hz, H-4), 3.01-2.86 (m, 1H, H-5), 1.16 (d, 3H, J=6.4 Hz, 6-$CH_3$).

$^{13}$C NMR (151 MHz, MeOD): δ=C 109.78 (C-1"), 101.67 (C-1'), 88.61 (C-4"), 86.80 (C-4), 84.86 (C-5), 78.70 (C-6), 76.28 (C-2"), 75.46 (C-3'), 74.72 (C-5'), 73.79 (C-6'), 73.07 (C-4'), 72.30 (C-3"), 63.43 (C-7'), 57.55 (C-2'), 52.53 (C-3), 52.35 (C-1), 50.68 (C-5"), 49.85 (C-4), 37.64 (C-2), 19.37 (C-6", $CH_3$).

MALDI TOFMS: calculated for $C_{19}H_{38}N_4O_{11}$ ([M+H]+) m/e 498.25; measured m/e 499.26.

Determination of Absolute Configuration at 6'-Position of NB153 and NB155:

In order to determine the absolute stereochemistry at the side-chain C6'-alcohols in NB153 and NB155, the major C6'-diasteromer alcohol 31 was synthesized, as illustrated in Scheme 10.

Scheme 10

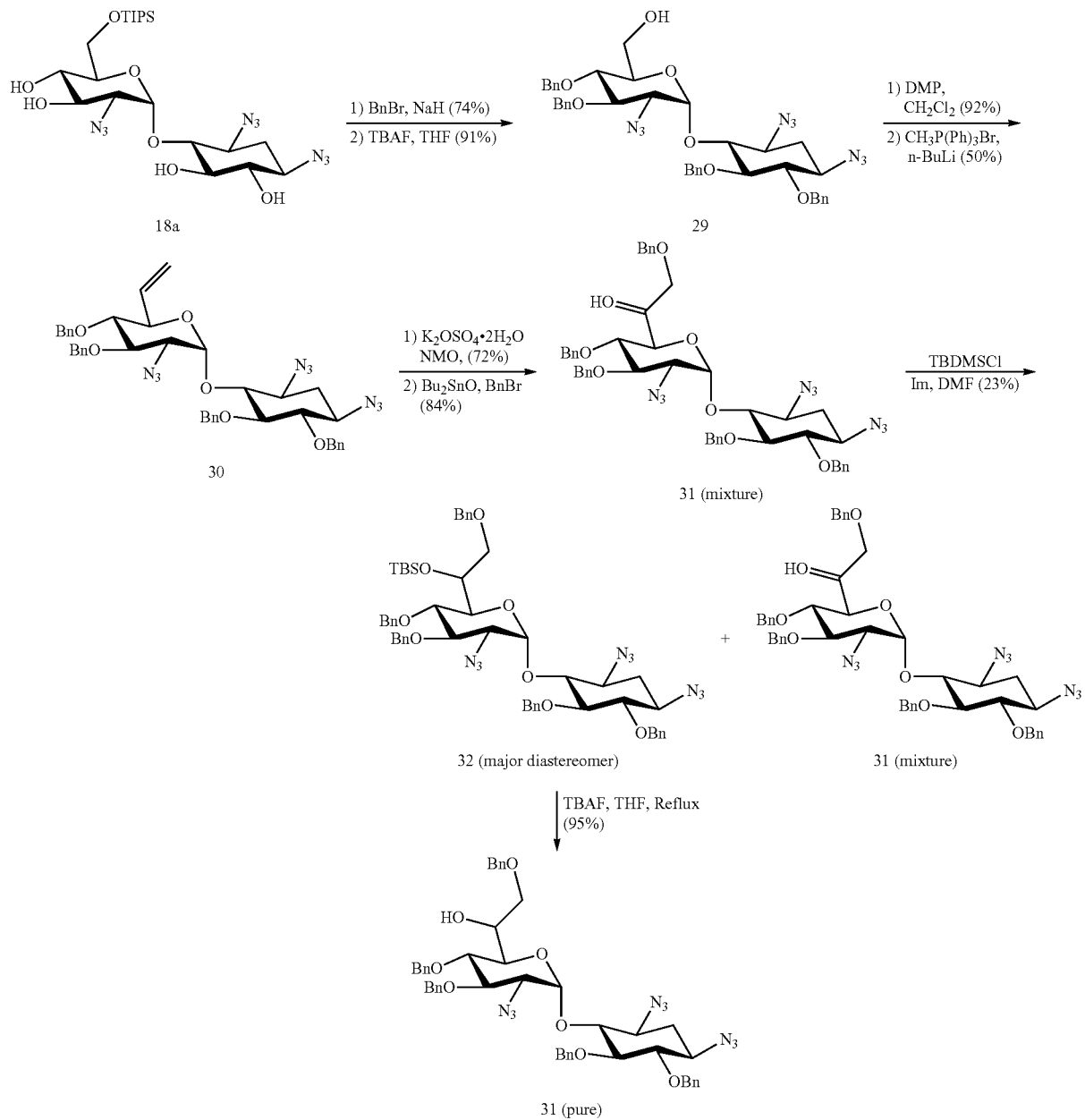

It was assumed that the change of protecting group on the secondary alcohols would improve the yields and isolation of the intermediate products at various synthetic steps experienced in the pathway in Scheme 8. The PMB protection in Scheme 8 was replaced with the benzyl protection shown in Scheme 10. Thus, the benzylation of TIPS protected Compound 18a was followed by silyl deprotection with TBAF to provide the 6'-alcohol 29 in good overall yields. Dess-Martin Periodinane (DMP) oxidation provided the corresponding aldehyde, which was treated with Wittig reagent to provide the terminal alkene 30. Dihydroxylation step was followed by selective benzylation of the primary alcohol to afford the desired 6'-alcohol 31 as a mixture of two 6'-diastereomers. Attempts to separate this mixture by using column chromatography with several different solvent systems proved unsuccessful, and it was found that the silylation of the mixture 31 with t-butyldimethylsilyl chloride (TBDMSCl) in the presence of imidazole proceeded very slow and with high selectivity of the major 6'-diastereomer. Using this advantage the silylated product of the major diastereomer 32 could be isolated in its pure form. Treatment of 32 with TBAF produced the desired product 31, which was used for configuration assignment.

To assign the absolute stereochemistry at 6' position in compound 31, the major diastereomer 31 was separately coupled with (R)-2-methoxy-2(1-naphthyl)propanoic acid [(R)-MαNP] 33 and [(S)-MαNP] 34 of known absolute stereochemistry in presence of DCC, 4-DMAP and CSA6 to afford the respective esters (R,X)-MαNP 35 and (S,X)-MαNP 36, as shown in Scheme 11.

Scheme 11

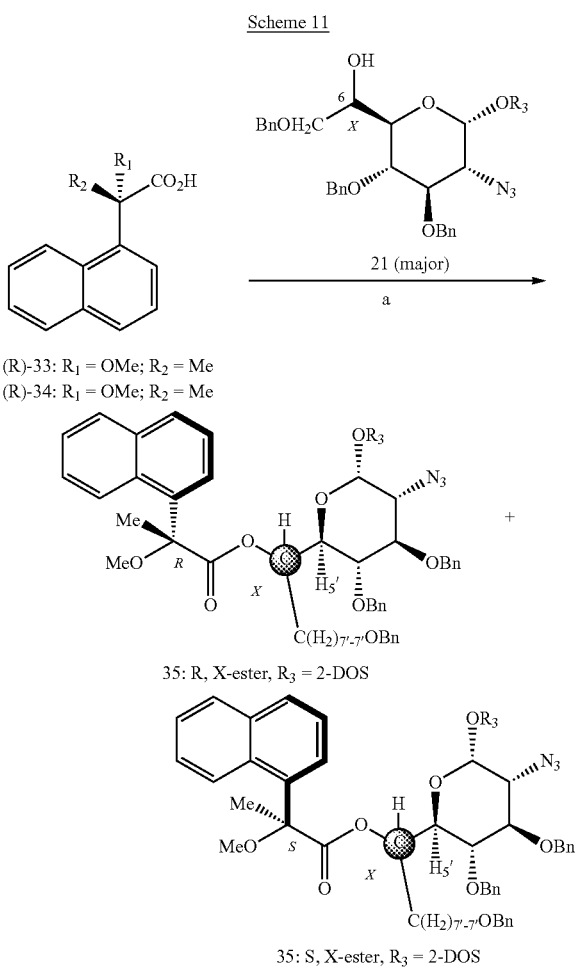

Synthesis of ((2R, 3S, 4R, 5R, 6S)-5-azido-3, 4-bis(benzyloxy)-6-(((1R, 2R, 3S, 4R, 6S)-4,6-diazido-2,3-bis(benzyloxy)cyclohexyl)oxy)tetrahydro-2H-pyran-2-yl)methanol (29): To a stirred solution of the silyl ether Compound 18a (0.2 gram, 0.358 mmol) and sodium hydride (0.114 gram, 4.75 mmol) in DMF (5 mL), was added benzyl bromide (0.255 mL, 2.14 mmol) at 0° C. The reaction progress was monitored by TLC (EtOAc/Hexane 3:7). After 8 hours the reaction was completed and ice was added in small portions to quench the reaction. The mixture was diluted with ethyl acetate (30 mL) and washed with water (2×50 mL). The combined aqueous layers were extracted with diethyl ether (2×50 mL); the combined organic layers were dried over anhydrous $MgSO_4$, and evaporated to dryness. The residue was purified by column chromatography (EtOAc/Hexane 8:92) to yield perbenzylated silyl ether (0.243 gram, 74%).

$^1$H NMR (500 MHz, $CDCl_3$): 'Ring I': δ=H 5.46 (d, 1H, J=3.3 Hz, H-1), 3.97 (dd, 1H, J1=17.7, J2=8.2 Hz, H-3, H-5), 3.90 (d, 1H, J=11.6 Hz, H-6), 3.84 (d, 1H, J=11.0, H-6), 3.72-3.53 (m, 1H, H-4), 3.19 (dd, 1H, J1=10.6, J2=4.4 Hz, H-2); 'Ring II': δ=H 3.53 (m, 2H, H-4, H-5), 3.40 (td, 1H, J1=9.9, J2=5.3 Hz, H-1), 3.30 (ddd, 2H, J1=17.6, J2=15.1, J3=9.2 Hz, H-3, H-6), 2.21 (dd, 1H, J1=8.2, J2=4.2 Hz, H-2eq), 1.34 (dt, 1H, J1=J2=12.9 Hz, H-2ax); The additional peaks in the spectrum were identified as follow: δ=H 7.28 (m, 20H, Bn), 4.94 (m, 2H, O(CH2)Bn), 4.80 (m, 6H, O(CH2)Bn), 1.14-0.95 (m, 21H, TIPS).

$^{13}$C NMR (125 MHz, $CDCl_3$): δC 138.54 (Bn), 138.17 (Bn), 138.03 (Bn), 137.49 (Bn), 128.61 (Bn), 128.58 (Bn), 128.55 (Bn), 128.31 (Bn), 128.28 (Bn), 128.14 (Bn), 127.99 (Bn), 127.78 (Bn), 127.72 (Bn), 127.10 (Bn), 97.7 (C1'), 84.8, 84.62, 80.2, 77.3 76.0, 75.7, 75.2, 74.9, 72.9, 63.5 (C2'), 62.3 (C6), 60.4 (C1), 59.5, 32.5 (C2), 18.2 (TIPS), 18.1(TIP S), 12. 1(TIP S).

To a stirred solution of perbenzylated silyl ether compound from the above step (9.24 grams, 10.0 mmol) in THF (100 mL) at 0° C., TBAF (9.0 mL, 31.0 mmol) was added and the reaction progress was monitored by TLC (EtOAc/Hexane 2:3). After 15 hours, the solvent was evaporated to dryness and the obtained residue was subjected to column chromatography (EtOAc/Hexane 3:7) to yield the corresponding perbenzylated 6'-alcohol 29 (7.0 grams, 91%).

$^1$H NMR (500 MHz, $CDCl_3$): 'Ring I': δ=H 5.60 (d, 1H, J=3.8 Hz, H-1), 4.11 (d, 1H, J=10.0 Hz, H-5), 4.05 (t, 1H, J=9.7 Hz, H-3), 3.83 (dd, 1H, J1=12.0, J2=2.0 Hz, H-6), 3.76 (dd, 1H, J1=12.1, J2=2.9 Hz, H-6), 3.69-3.57 (m, 1H, H-4), 3.28 (dd, 1H, J1=10.6, J2=4.6 Hz, H-2); 'Ring II': δ=H 3.60-3.57 (m, 2H, H-4, H-5), 3.55-3.46 (m, 1H, H-1), 3.46-3.37 (m, 2H, H-3, H-6), 2.31 (dt, 1H, J1=13.2, J2=4.5 Hz, H-2eq), 1.47 (ddd, 1H, J1=J2=J3=10.6 Hz, H-2ax); The additional peaks in the spectrum were identified as follow: δ=H 7.52-7.28 (m, 20H, Bn), 5.04 (d, 1H, J=10.8 Hz, O(CH$_2$)Bn), 4.93 (dd, 2H, J1=10.7, J2=6.0 Hz, O(CH$_2$)Bn), 4.90-4.86 (m, 3H, O(CH$_2$)Bn), 4.84 (d, 1H, J=10.5 Hz, O(CH$_2$)Bn), 4.71 (d, 1H, J=11.2 Hz, O(CH$_2$)Bn).

$^{13}$C NMR (125 MHz, $CDCl_3$): δ=C 138.0 (Bn), 138.0 (Bn), 137.8 (Bn), 137.3 (Bn), 128.6 (Bn), 128.6 (Bn), 128.5 (Bn), 128.2 (Bn), 128.1 (Bn), 128.1 (Bn), 128.0 (Bn), 128.0 (Bn), 127.7 (Bn), 127.1 (Bn), 97.7 (C1'), 84.7, 84.5, 80.1 (C3'), 77.6, 77.5, 76.0, 75.6, 75.3, 75.0, 72.0 (C5'), 63.4 (C2'), 61.4 (C6'), 60.3, 59.4, 32.4 (C2).

Synthesis of (2R, 3R, 4R, 5R, 6R)-3-azido-4, 5-bis(benzyloxy)-24(1R, 2R, 3S, 4R, 6S)-4,6-diazido-2,3-bis(benzyloxy)cyclohexyl)oxy)-6-vinyltetrahydro-2H-pyran (30): To a solution of the 6'-alcohol 29 (1.0 gram, 1.31 mmol) in ethyl acetate (40 mL), IBX (1.1 gram, 3.92 mmol) was added in one portion. The resulting suspension was heated at 80° C. and stirred vigorously. After the reaction was completed (3.5 hours) as indicated by TLC (EtOAc/Hexane 2:3), the reaction was cooled to room temperature and filtered through Celite®. The Celite® was thoroughly washed with ethyl acetate (2×50 mL) and the combined organic layers were evaporated under reduced pressure. The crude product was subjected to flash column chromatography (EtOAc/Hexane 35:65) to yield the 6'-aldehyde (0.925 gram, 92%).

$^1$H NMR (500 MHz, $CDCl_3$): 'Ring I': δ=H 9.62 (s, 1H, H-6(CHO)), 5.62 (s, 1H, H-1), 4.69 (d, 1H, J=9.9 Hz, H-4), 4.01 (t, 1H, J=9.3 Hz, H-3), 3.56 (dd, 1H, J1=18.0, J2=9.1 Hz, H-5), 3.19 (d, 1H, J=14.0, H-2); 'Ring II': δ=H 3.56 (dd, 2H, J1=18.0, J2=9.1 Hz, H-4, H-5), 3.44 (d, 1H, J=11.7 Hz, H-1), 3.37 (t, 2H, J=8.2 Hz, H-3, H-6), 2.28 (d, 1H, J1=10.2 Hz, H-2eq), 1.44 (ddd, 1H, J1=J2=J3=14.0 Hz, H-2ax); The additional peaks in the spectrum were identified as follow: δ=H 7.27 (m, 20H, Bn), 5.00 (d, 1H, J=10.9 Hz, O(CH$_2$)Bn), 4.92-4.75 (m, 6H, O(CH$_2$)Bn), 4.63 (d, 1H, J=10.7 Hz, O(CH$_2$)Bn).

$^{13}$C NMR (125 MHz, $CDCl_3$): δ=C 197.2 (CHO), 138.0 (Bn), 137.5 (Bn), 137.3 (Bn), 137.1 (Bn), 128.7 (Bn), 128.6 (Bn), 128.6 (Bn), 128.6 (Bn), 128.3 (Bn), 128.3 (Bn), 128.2 (Bn), 128.1 (Bn), 97.6 (C1'), 84.6, 84.3, 80.1 (C3'), 78.4, 77.7, 76.1, 75.8, 75.3, 75.2, 62.8 (C2'), 60.3, 59.1 (C1), 32.2 (C2).

To a cooled suspension of Methyltriphenylphosphonium Iodide (0.966 gram, 2.7 mmol) in anhydrous THF at 0° C., n-BuLi (1.6 M in hexane, 0.32 mL) was added dropwise and the resulted yellow solution was stirred for an additional 30 minutes at 0° C. The 6'-aldehyde from the above step (0.822 gram, 1.08 mmol) in anhydrous THF (0.3 mL) was added at 0° C., and the reaction was allowed to stir for an additional 1.5 hour at room temperature. After completion of the reaction as indicated by TLC (EtOAc/Hexane 2:3), the reaction was quenched with saturated NH$_4$Cl solution. The layers were separated and the aqueous layer was extracted with ether (2×10 mL). The combined organic layers were washed with brine, dried over anhydrous MgSO$_4$ and evaporated to dryness. The crude product was purified by flash chromatography (EtOAc/Hexane 2.5:7.5) to yield Compound 30 (0.4 gram, 50%).

$^1$H NMR (400 MHz, CDCl$_3$): 'Ring I': δ=H 5.89 (ddd, 1H, J1=17.2, J2=10.4, J3=6.8 Hz, H-6), 5.56 (d, 1H, J=3.9 Hz, H-1), 5.47 (d, 1H, J=17.2 Hz, H-7trans), 5.33-5.27 (m, 1H, H-7cis), 4.64-4.56 (m, 1H, H-5), 4.09 (m, H-3), 3.32-3.27 (m, 2H, H-2, H-4); 'Ring II': δ=H 3.69-3.56 (m, 2H, H-4, H-5), 3.54-3.45 (m, 1H, H-1), 3.45-3.35 (m, 2H, H-3, H-6), 2.31 (dt, 1H, J1=13.2, J2=4.5 Hz, H-2eq), 1.49 (ddd, 1H, J1=J2=J3=12.6 Hz, H-2ax); The additional peaks in the spectrum were identified as follow: δ=H 7.32-7.29 (m, 20H, Bn), 5.02 (d, 1H, J=10.9 Hz, O(CH$_2$)Bn), 4.94 (dd, 1H, J1=9.9, J2=5.4 Hz, O(CH$_2$)Bn), 4.89 (d, 1H, J=6.6 Hz, O(CH$_2$)Bn), 4.83 (dd, 2H, J=10.7, 8.5 Hz, O(CH$_2$)Bn), 4.73 (d, 1H, J=10.9 Hz, O(CH$_2$)Bn), 4.67 (d, 1H, J=10.9 Hz, O(CH$_2$)Bn), 4.64-4.56 (m, 1H, O(CH$_2$)Bn).

$^{13}$C NMR (100 MHz, CDCl$_3$): δ=C 138.2 (Bn), 138.0 (Bn), 138.0 (Bn), 137.4 (Bn), 134.9 (Bn), 128.6 (Bn), 128.5 (Bn), 128.5 (Bn), 128.5 (Bn), 128.3 (Bn), 128.2 (Bn), 128.1 (Bn), 127.9 (Bn), 127.9 (Bn), 127.7 (Bn), 127.0 (Bn), 118.9 (C7'), 97.7 (C1'), 84.7, 84.5, 82.7 (C4'), 79.7 (C3'), 77.7, 76.05, 75.6, 75.3, 75.0, 72.7 (C5'), 63.4 (C2'), 60.3 (C1), 59.3, 32.4 (C2).

Synthesis of 1-((2R, 3S, 4R, 5R, 6S)-5-azido-3,4-bis(benzyloxy)-6-(((1R, 2R, 3S, 4R, 6S)-4,6-diazido-2,3-bis(benzyloxy)cyclohexyl)oxy)tetrahydro-2H-pyran-2-yl)-2-(benzyloxy)ethanol (31): To a stirred solution of Compound 30 (402 mg, 0.53 mmol) in acetone (10 mL), water (3 mL) and t-BuOH (10 mL), K2OsO$_4$.2H$_2$O (16 mg, 0.051 mmol) and NMO (0.22 mL) were added sequentially. The progress of the reaction was monitored by TLC (EtOAc/Hexane 2:3), which indicated the completion after 24 hours. The solvent was thereafter evaporated to dryness; the residue was dissolved in EtOAc to which an aqueous solution of Na$_2$S$_2$O$_3$ was added. The layers were separated and the organic phase was washed with brine, dried over MgSO$_4$ and evaporated. The crude product was subjected to column chromatography (EtOAc/Hexane 1:1) to yield dihydroxylated product (300 mg, 72%) as a 6'-diasteromeric mixture.

A mixture of dihydroxylated compound (0.3 gram, 0.378 mmol) from the above step and Bu$_2$SnO (0.103 gram, 0.413 mmol) in toluene/MeOH (10:1, 7 mL) was refluxed for 3 hours and concentrated under reduced pressure. To a solution of this residue in toluene (3 mL) was added tetrabutylammonium bromide (0.122 gram, 0.378 mmol) and BnBr (0.09 mL, 0.756 mmol). The mixture was stirred at 85° C. overnight and quenched with addition CH$_2$Cl$_2$ (10 mL) and saturated NaHCO$_3$ (2 mL). After filteration through a pad of Celite®, the organic phase was washed with H$_2$O (3 mL), brine (5 mL), dried over MgSO$_4$ and concentrated under reduced pressure. The crude product was purified by column chromatography (EtOAc/Hexane 2:3) to give the Compound 31 (0.280 gram, 84%) as a 6'-diasteromeric mixture.

Synthesis of (1-((2S, 3S, 4R, 5R, 6S)-5-azido-3,4-bis(benzyloxy)-6-(((1R, 2R, 3S, 4R, 6S)-4,6-diazido-2,3-bis(benzyloxy)cyclohexyl)oxy)tetrahydro-2H-pyran-2-yl)-2-benzyloxy)ethoxy)(tert-butyl)dimethylsilane (32): Compound 31 (205 mg, 0.232 mmol) was dissolved in anhydrous DMF (5 mL) and cooled to 0° C. t-butyldimethylsilyl chloride (TBSCl, 45 mg, 0.298 mmol) was added, followed by addition of Imidazole (39 mg, 0.572 mmol). The reaction mixture was allowed to attain the room temperature under stirring, and the reaction progress was monitored by TLC (EtOAc/Hexane 3:7). From TLC, reaction did not complete even after prolonged reaction times (24 hours) and at this stage the reaction was stopped by adding mixture of ethyl acetate (10 mL) and H$_2$O (10 mL), and the two layers were separated. The aqueous layer was thoroughly washed with ethyl acetate (4×30 mL). The combined organic layers were washed with sat. NaCl solution and dried over anhydrous MgSO$_4$. The solvent was evaporated to dryness and the residue was subjected to column chromatography (EtOAc/Hexane 25:75) to yield corresponding silyl ether (32) (85 mg, 23%) as a pure major diastereomer.

Synthesis of 1-((2R,3S,4R,5R,6S)-5-azido-3,4-bis(benzyloxy)-6-(((1R, 2R,3S,4R,6S)-4,6-diazido-2, 3-bis(benzyloxy)cyclohexyl)oxy)tetrahydro-2H-pyran-2-yl)-2-(benzyloxy)ethanol (31 as pure major diastereomer): To a stirred solution of Compound 32 (60 mg, 0.06 mmol) in THF (3 mL) at room temperature, TBAF (0.052 mL, 0.179 mmol) was added and the reaction was refluxed at 50° C. overnight. After completion of the reaction as indicated by TLC (EtOAc/Hexane 2:3), the solvent was evaporated to dryness and the obtained residue was subjected to column chromatography (EtOAc/Hexane 3:7) to yield single diastereromer 31 (52 mg, 95%).

$^1$H NMR (500 MHz, CDCl$_3$): 'Ring I': δ=H 5.53 (d, 1H, J=3.9 Hz, H-1), 4.17 (dd, 1H, J1=10.0, J2=2.4 Hz, H-5), 4.12 (m, 1H, H-6), 3.96 (dd, 1H, J1=10.3, J2=8.9 Hz, H-3), 3.69-3.61 (m, 1H, H-4), 3.50-3.45 (m, 2H, H-7, H-7), 3.22 (dd, 1H, J1=10.3, J2=3.9 Hz, H-2), 3.59 (BrS, 1H, 6'-OH); 'Ring II': δ=H 3.58-3.49 (m, 2H, H-4, H-5), 3.44-3.11 (m, 3H, H-1, H-3, H-6), 2.23 (dt, 1H, J1=13.2, J2=4.5 Hz, H-2eq), 1.38 (ddd, 1H, J1=J2=J3=12.6 Hz, H-2ax); The additional peaks in the spectrum were identified as follow: δ=H 7.29-7.23 (m, 25H, Bn), 4.98 (d, 1H, J=10.8 Hz, O(CH$_2$)Bn), 4.92-4.74 (m, 6H, O(CH$_2$)Bn), 4.65 (d, 1H, J=11.1 Hz, O(CH$_2$)Bn), 4.42 (q, 2H, J=11.9 Hz, O(CH$_2$)Bn).

$^{13}$C NMR (125 MHz, CDCl$_3$): δ=C 138.0 (Bn), 138.0 (Bn), 137.9 (Bn), 137.7 (Bn), 137.3 (Bn), 128.6 (Bn), 128.6 (Bn), 128.5 (Bn), 128.5 (Bn), 128.5 (Bn), 128.3 (Bn), 128.1 (Bn), 128.1 (Bn), 128.0 (Bn), 127.9 (Bn), 127.8 (Bn), 127.7 (Bn), 127.6 (Bn), 127.0 (Bn), 97.4 (C1'), 84.6, 84.4, 80.8, 78.4 (C4'), 77.5, 76.0 (Bn), 75.6 (Bn), 75.3 (Bn), 74.6 (Bn), 73.4 (Bn), 71.8, 71.6, 71.2 (C7'), 63.3 (C2'), 60.2 (C1), 59.5 (C3), 32.4 (C2).

Synthesis of (R,X)-Ester: A mixture of (R)-2-methoxy-2 (1-naphthyl)propanoic acid [(R)-MαNP] (0.01 gram, 0.04 mmol), 4-dimethylaminopyridine (DMAP, 0.006 gram, 0.049 mmol), 10-camphorsulfonic acid (CSA, 0.002 gram, 0.008 mmol), and 1,3-dicyclohexylcarbodiimide (DCC, 0.047 gram, 0.22 mmol) was stirred in CH$_2$Cl$_2$ (3 mL) at 0° C. The major alcohol 31 from the above (0.038 gram, 0.043 mmol) was dissolved in CH$_2$Cl$_2$ (2 ml), slowly added to the above stirred mixture, and the reaction was left at room temperature for 72 hours. The mixture was diluted with EtOAc and washed with 1% HCl solution, saturated NaHCO$_3$ and brine. The combined organic layer was dried over MgSO$_4$, evaporated and subjected to a column chromatography (EtOAc/Hexane) to yield the desired ester (R,X)-35 (0.008 gram, 17%).

¹H NMR (600 MHz, CDCl₃): 'Ring I': δ=H 5.55 (dd, 1H, J=9.9, 3.7 Hz, H-6), 4.87 (d, 1H, J=3.4 Hz, H-1), 3.86 (d, 1H, J=10.0 Hz, H-4), 3.50-3.46 (m, 1H, H-7), 3.38 (d, 1H, J=10.2 Hz, H-3), 3.36-3.32 (m, 1H, H-7), 1.55-1.50 (m, 1H, H-5), 1.28 (dd, 1H, J1=10.4, J2=3.9 Hz, H-2), 'Ring II': δ=H 3.51 (d, 1H, J1=9.7 Hz, H-6), 3.43 (dt, 3H, J1=12.1, J2=7.8 Hz, H-4, H-5, H-3), 3.25 (ddd, 1H, J1=12.6, J2=10.0, J3=4.6 Hz, H-1), 2.23 (dd, 1H, J1=10.9, J2=6.5 Hz, H-2eq), 1.46-1.39 (m, 1H, H-2ax); The additional peaks in the spectrum were identified as follow: δ=8.39 (d, 1H, J=8.7 Hz, Ar), 7.80-7.75 (m, 2H, Ar), 7.63 (d, 1H, J=6.4 Hz, Ar), 7.54 (t, 2H, J=7.6 Hz, Ar), 7.47-7.40 (m, 2H, Ar), 7.38 (d, 2H, J=7.1 Hz, Ar), 7.37-7.33 (m, 2H, Ar), 7.32-7.27 (m, 9H, Ar), 7.23 (ddd, 4H, J1=6.5, J2=4.7, J3=2.2 Hz, Ar), 7.20 (d, 3H, J=8.0 Hz, Ar), 7.09 (ddd, 1H, J1=8.5, J2=6.8, J3=1.5 Hz, Ar), 7.06-7.02 (m, 1H, Ar), 6.96-6.92 (m, 2H, Ar), 5.01 (d, 1H, J=11.2 Hz, O(CH₂)Bn), 4.88 (d, 2H, J=4.1 Hz, O(CH₂)Bn), 4.84 (d, 1H, J=10.8 Hz, O(CH₂)Bn), 4.59 (d, 1H, J=11.4 Hz, O(CH₂)Bn), 4.50 (d, 1H, J=11.3 Hz, O(CH₂)Bn), 4.44 (d, 1H, J=11.8 Hz, O(CH₂)Bn), 4.25 (d, 1H, J=11.9 Hz, O(CH₂)Bn), 3.99 (d, 1H, J=11.3 Hz, O(CH₂)Bn), 3.71 (d, 1H, J=11.3 Hz, O(CH₂)Bn), 3.07 (s, 1H, OCH₃), 2.02 (s, 3H, CH₃).

¹³C NMR (125 MHz, CDCl₃): δ=C 173.3 (Ar), 138.5 (Ar), 138.4 (Ar), 137.9 (Ar), 137.7 (Ar), 137.3 (Ar) 135.3 (Ar), 134.2 (Ar), 131.8 (Ar), 130.1 (Ar), 128.9 (Ar), 128.65 (Ar), 128.62 (Ar), 128.5 (Ar), 128.46 (Ar), 128.44 (Ar), 128.22 (Ar), 128.22 (Ar), 127.76 (Ar), 127.71 (Ar), 127.5 (Ar), 127.4 (Ar), 127.2 (Ar), 126.7 (Ar), 126.4 (Ar), 126.3 (Ar), 126.2 (Ar), 124.8 (Ar), 99.7 (C1'), 84.5, 84.43 (s), 81.1, 79.8, 77.0, 76.7, 76.1, 75.1, 74.2, 74.2, 73.7, 72.7, 70.2, 69.8, 61.8, 60.2, 59.1, 50.7, 32.3, 31.1, 29.8, 21.5 (CH₃).

Synthesis of (S,X)-Ester (36): A mixture of (S)-2-methoxy-2(1-naphthyl)propanoic acid [(S)-MαNP] (0.007 gram, 0.03 mmol), 4-dimethylaminopyridine (DMAP, 0.005 gram, 0.04 mmol), 10-camphorsulfonic acid (CSA, 0.001 gram, 0.004 mmol), and 1,3-dicyclohexylcarbodiimide (DCC, 0.034 gram, 0.16 mmol) was stirred in CH₂Cl₂ (3 mL) at 0° C. The major alcohol 31 from the above (0.028 gram, 0.031 mmol), was dissolved in CH₂Cl₂ (2 ml), slowly added to the above stirred mixture, and the reaction was left at room temperature for 72 hours. The mixture was diluted with EtOAc and washed with 1% HCl solution, saturated NaHCO₃ and brine. The combined organic layer was dried over MgSO₄, evaporated and subjected to a column chromatography (EtOAc/Hexane) to yield the desired ester (S,X)-36 (0.007 gram, 20%).

¹H NMR (600 MHz, CDCl₃): 'Ring I': δ=H 5.49 (dd, 1H, J=8.5, 4.4 Hz, H-6), 5.17 (d, 1H, J=3.8 Hz, H-1), 4.04 (d, 1H, J=10.0 Hz, H-4), 3.58 (t, 1H, J=9.8 Hz, H-3), 3.25 (d, 1H, J=8.5 Hz, H-7), 3.22 (dd, 1H, J1=10.7, J2=4.6 Hz, H-7), 2.34 (dd, 1H, J1=17.0, J2=6.3 Hz, H-5), 2.12-2.02 (m, 1H, H-2) 'Ring II': δ=H 3.51 (dt, 2H, J1=17.8, J2=9.3 Hz, H-4, H-5), 3.46-3.37 (m, 2H, H-1, H-6), 3.33-3.27 (m, 1H, H-3), 2.25 (dt, 1H, J1=13.2, J2=4.5 Hz, H-2eq), 1.43 (ddd, 1H, J1=J2=J3=12.6 Hz, H-2ax); The additional peaks in the spectrum were identified as follow: δ=H 8.08 (d, 1H, J=8.8 Hz, Ar), 7.89 (d, 1H, J=7.3 Hz), 7.76 (dd, 2H, J1=15.9, J2=8.1 Hz, Ar), 7.46 (t, 2H, J=7.5 Hz), 7.44-7.41 (m, 1H, Ar), 7.39 (d, 1H, J=7.5 Hz, Ar), 7.36 (t, 2H, J=7.3 Hz, Ar), 7.34-7.27 (m, 8H, Ar), 7.25-7.23 (m, 2H, Ar), 7.23-7.19 (m, 6H, Ar), 7.16 (t, 1H, J=7.1 Hz, Ar), 7.14-7.09 (m, 3H, Ar), 6.91-6.87 (m, 2H, Ar), 5.01 (d, 1H, J=11.1 Hz, O(CH₂)Bn), 4.90-4.79 (m, 3H, O(CH₂)Bn), 4.63 (q, 2H, J=11.1 Hz, O(CH₂)Bn), 4.22-4.15 (m, 2H, O(CH₂)Bn), 4.12 (d, 1H, J=11.0 Hz, O(CH₂)Bn), 3.66 (d, 1H, J=11.0 Hz, O(CH₂)Bn), 3.29 (S, 3H, OCH₃), 1.97 (s, 3H, CH₃).

¹³C NMR (125 MHz, CDCl₃): δ=C 172.7 (Ar), 138.3 (Ar), 138.0 (Ar), 137.9 (Ar), 137.7 (Ar), 137.3 (Ar) 134.1 (Ar), 130.5 (Ar), 129.3 (Ar), 129.1 (Ar), 128.6 (Ar), 128.6 (Ar), 128.4 (Ar), 128.4 (Ar), 128.3 (Ar), 128.3 (Ar), 128.2 (Ar), 127.9 (Ar), 127.7 (Ar), 127.7 (Ar), 127.6 (Ar), 127.6 (Ar), 127.5 (Ar), 126.9 (Ar), 126.1 (Ar), 125.6 (Ar), 125.1 (Ar), 125.1 (Ar), 124.6 (Ar), 97.1 (C1'), 84.5 (C5), 84.5 (C4), 81.2, 80.1 (C3'), 77.9 (C5'), 77.3, 77.0 (C4), 76.1, 75.2, 74.8, 74.4, 74.3 (C6'), 72.8, 70.4 (C4'), 69.4 (C7'), 62.5 (C2'), 60.2 (C3), 59.1 (C1), 51.4 (OCH₃), 32.3 (C2), 29.85, 21.9 (CH₃).

Figure 9A:
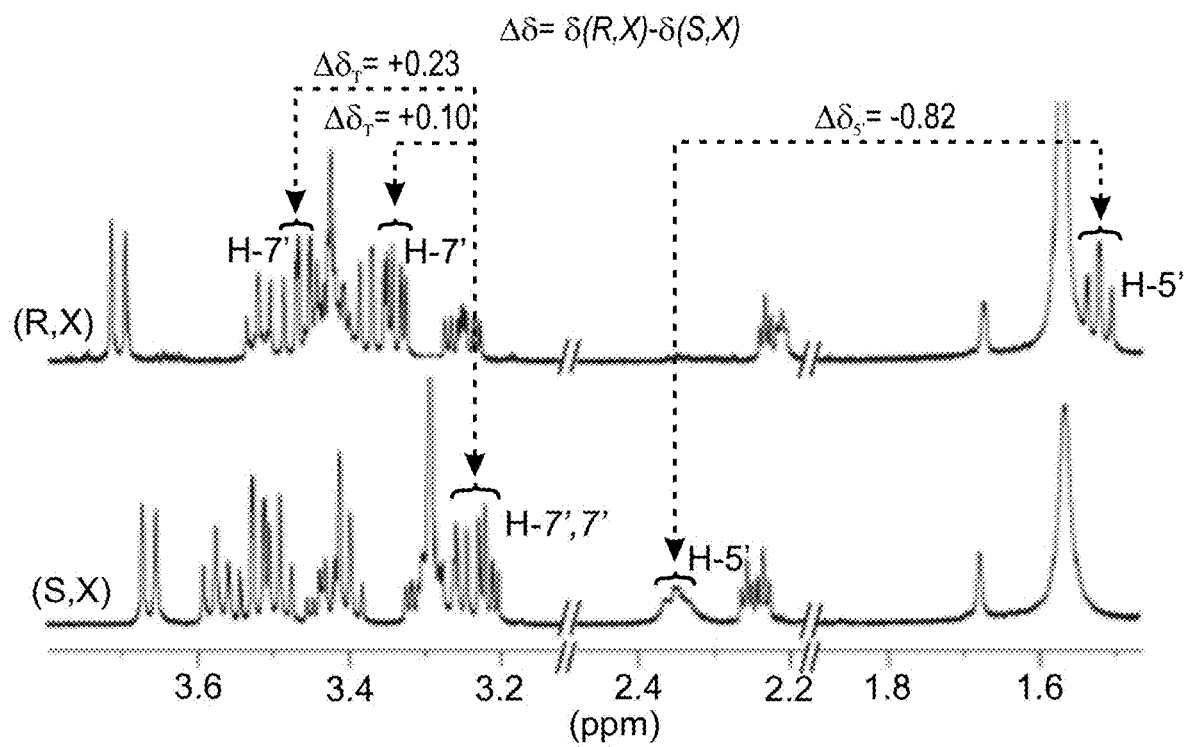
FIGS. 9A-B present $^1$H NMR magnetic anisotropy spectra of Compound 35 (upper spectrum) and Compound 36 (lower spectrum), showing the difference in chemical shift values for the assigned protons in the NMR spectra (FIG. 9A), and the corresponding MαNP Sector Rule (FIG. 9B).
Figure 9B:
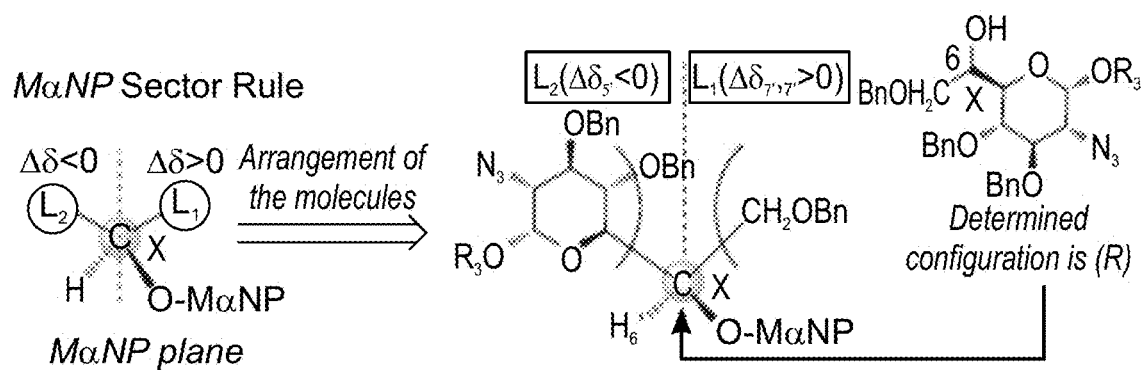

The absolute stereochemistry at the 6' position (denoted by X) was then determined by ¹H NMR magnetic anisotropy, which is based on Sector rule 7 and relays on the difference in chemical shift values for the assigned protons in the NMR spectra (see, FIGS. 9A-B). As shown in FIG. 9A, the difference in chemical shift [Δδ=δ(R, X)−δ(S, X)] for H-5'(−0.82) was negative, while that for H-7', 7' (+0.23, +0.10) was positive. According to the Sector rule shown in FIG. 9B, the structures (R, X)-MαNP 35 and (S, X)-MαNP 36 are arranged such that OMαNP is positioned on the front and H-6' on the back, while the Δδ positive and Δδ negative parts are positioned on the right and left sides, respectively. These data confirms the R configuration (X=R) at the 6' carbon atom in compound 31.

This study establishes that the major and minor diastereomers, compounds NB 153 and NB 155, exhibit (R)- and (S)-configuration at 6' position: 6'-(R)-NB 153 and 6'-(S)-NB 155.

Example 5

Activity Assays of Exemplary Compounds of Example 4

The experimental assay procedure and result analysis was carried out essentially as described hereinabove and in further detail hereinunder.

Materials and Methods:

In all biological tests, all the tested aminoglycosides were in their sulfate salt forms [Mw (gr/mol) of the sulfate salts were as follow: Compound 1-437.1, NB74-564.3, NB124-605.9, NB153-526.8, NB155-512.2, NB156-705.9, NB157-746. 6, G418-692.7, gentamicin-653.2].

Dual Luciferase Readthrough Assays:

DNA fragments derived from PCDH15, CFTR, and IDUA cDNAs, including the tested nonsense mutation or the corresponding wild type (wt) codon, and four to six upstream and downstream flanking codons were created by annealing the following pairs of complementary oligonucleotides:

```
Usher Syndrome:
p.R3Xmut/wt:
                                          (SEQ ID NO: 1)
5'-GATCCCAGAAGATGTTTT/CGACAGTTTTATCTCTGGACAGAGCT-
3'
and
                                          (SEQ ID NO: 2)
5'-CTGTCAGAGATAAAACTGTCA/GAAACATCTTCTG-3';
```

-continued p.R245Xmut/wt:

(SEQ ID NO: 3)
5'GATCCAAAATCTGAATGAGAGGT/CGAACCACCACCACCACCCTCGA
GCT-3'
and (SEQ ID NO: 4)
5'-CGAGGGTGGTGGTGGTTGTTCG/ACCTCTCATTCAGATTTTG-3';

Cystic Fibrosis:
p.G542Xmut/wt:

(SEQ ID NO: 5)
5'-TCGACCAATATAGTTCTTT/GGAGAAGGTGGAATCGAGCT-3'
and
and (SEQ ID NO: 6)
5'-CGATTCCACCTTCTCA/GAAGAACTATATTGG-3';

Hurler Syndrome:
p.Q70Xmut/wt:

(SEQ ID NO: 7)
5'-TCGACCCTCAGCTGGGACT/CAGCAGCTCAACCTCGAGCT-3'
and (SEQ ID NO: 8)
5'-CGAGGTTGAGCTGCTA/GGTCCCAGCTGAGG-3'.

Fragments were inserted in frame into the polylinker of the p2Luc plasmid between either BamHI and Sac' (p.R3X and p.R245X) or SalI and SacI (all the rest) restriction sites. For the in vitro readthrough assays, the obtained plasmids, with addition of the tested aminoglycosides were transcribed and translated using the TNT Reticulocyte Lysate Quick Coupled Transcription/Translation System. Luciferase activity was determined after 90 minutes of incubation at 30° C., using the Dual Luciferase Reporter Assay System (Promega™). Stop codon readthrough was calculated as previously described [Grentzmann et al. RNA 1998, 4, 479-486].

Protein translation inhibition tests:

Prokaryotic in vitro translation inhibition by the different aminoglycosides was quantified in coupled transcription/translation assays by using *E. coli* S30 extract for circular DNA with the pBESTluc plasmid (Promega), according to the manufacturer's protocol. Translation reactions (25 µL) that contained variable concentrations of the tested aminoglycoside were incubated at 37° C. for 60 minutes, cooled on ice for 5 minutes, and diluted with a dilution reagent (tris-phosphate buffer (25 mM, pH 7.8), DTT (2 mM), 1,2-diaminocyclohexanetetraacetate (2 mM), glycerol (10%), Triton X-100 (1%) and BSA (1 mg mL-1)) into 96-well plates. Eukaryotic in vitro translation inhibition was quantified by use of TNT® T7 Quick Coupled Transcription/Translation System with a luciferase T7 control DNA plasmid (Promega), according to the manufacturer protocol. Translation reactions (25 µL) containing variable concentrations of the tested aminoglycoside were incubated at 30° C. for 60 minutes, cooled on ice for 5 minutes, diluted with the dilution reagent and transferred into 96-well plates. In both prokaryotic and eukaryotic systems the luminescence was measured immediately after the addition of the Luciferase Assay Reagent (50 µL; Promega), and the light emission was recorded with a FLx800 Fluorescence Microplate Reader (Biotek). The half-maximal inhibition concentration (IC50) values were obtained from fitting concentration-response curves to the data of at least two independent experiments by using Grafit 5 software.

Antibacterial Activity Tests:

Comparative antibacterial activities were determined in two representative strains of Gram-negative (*E. coli* R477-100) and Gram-positive (*B. subtilis* ATCC-6633) bacteria, by measuring the MIC values using the double-microdilution method according to the National Committee for Clinical Laboratory Standards (NCCLS) (NCCLS. *National Committee for Clinical Laboratory Standards, Performance standards for antimicrobial susceptibility testing. Fifth information supplement: Approved Standard M*100-S5; Villanova, Pa.: NCCLS, 1994). All the experiments were performed in triplicates and analogous results were obtained in three different experiments.

Figure 10:
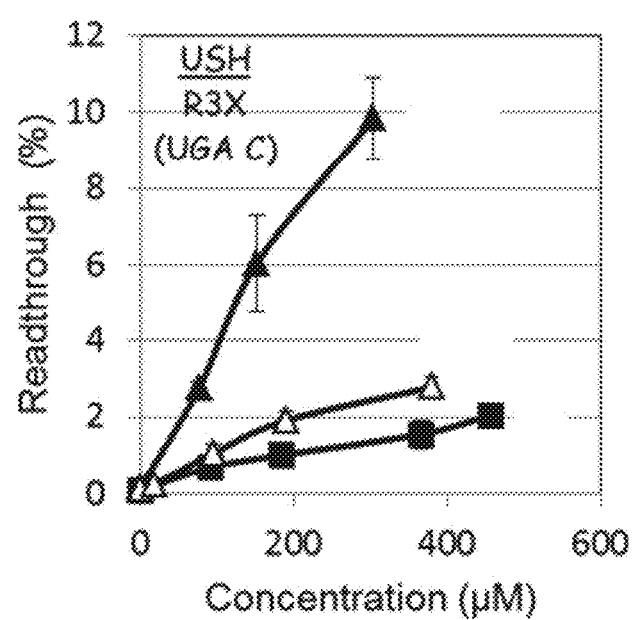
FIG. 10 presents comparative plots showing in vitro stop codon suppression levels induced by Compound 1 (-■-), NB153 (-▲-), and NB155 (-Δ-) in R3X nonsense mutation construct representing USH1 genetic disease.

Results: FIG. 10 presents comparative plots showing in vitro stop codon suppression levels induced by Compound 1 (-■-), NB153 (-▲-), and NB155 (-Δ-) in R3X nonsense mutation construct representing USH1 genetic disease.

These comparative PTC suppression activity tests show that installation of C7'-hydroxyl group (NB153) on Compound 1 dramatically increases its in vitro readthrough activity, and is more pronounced than the effect of NB155. These data show an improved activity attributed to the additional hydroxyl group, and further emphasize the role of stereochemistry at 6' position in RNA target recognition. The observed somewhat higher activity of NB155 to that of Compound 1 suggests that the additional 7'-hydroxyl in NB155 can overcome the configurational penalty at 6' position.

The impact of the additional 7'-hydroxyl in Compounds NB156 and NB157 was evaluated against previously published compounds NB74 and NB124, which differ from NB156 and NB157 by the absence of the 7'-hydroxyl, as shown below.

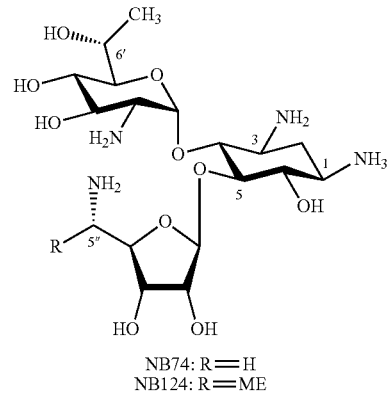

NB74: R═H
NB124: R═ME

Activity was tested using a collection of dual-luciferase reporter plasmids, containing different sequence contests around premature stop codons derived from the PCDH15, CFTR, and IDUA genes that underline USH1, CF, and MPS I-H, respectively. The exemplified nonsense reporters were R3X and R245X for USH1, G542X for CF, and Q70X for MPS I-H.

Figure 11A:
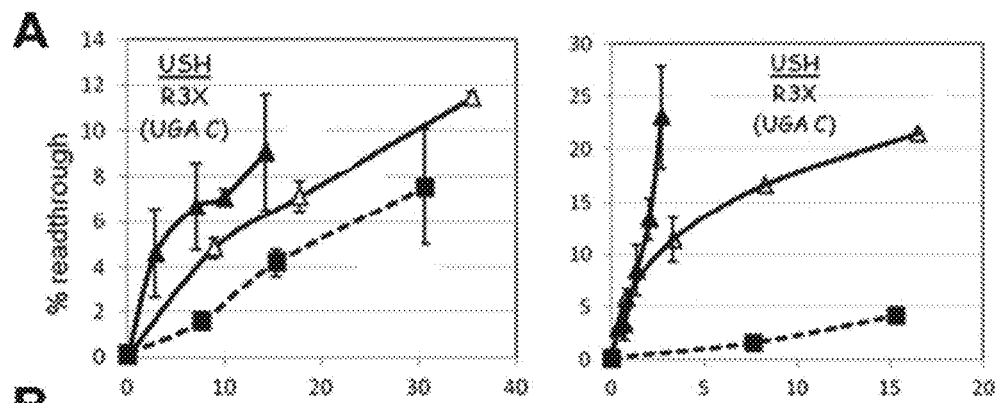
FIGS. 11A-D presents comparative plots showing in vitro stop codon suppression levels induced by NB74 (-Δ-), NB156 (-▲-), and gentamicin (--■--) (left) and by NB124 (-Δ-), NB157 (-▲-), and gentamicin (--■--) (right), in nonsense constructs representing R3X (USH1) (FIG. 11A), R245X (USH1) (FIG. 11B), Q70X (HS) (FIG. 11C), and G542X (CF) (FIG. 11D). FIG.
Figure 11B:
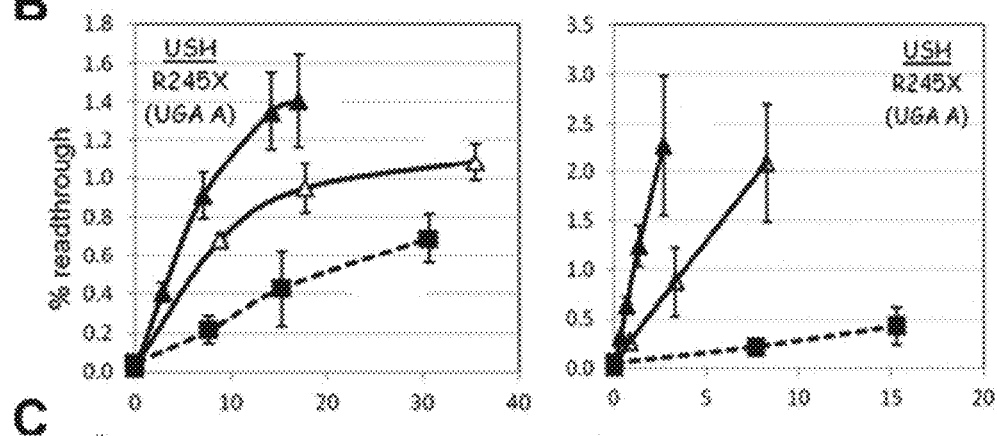
Figure 11C:
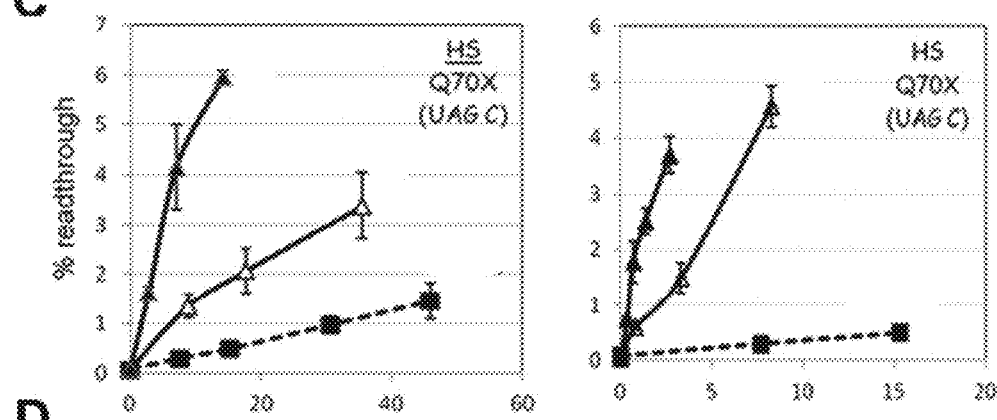
Figure 11D:
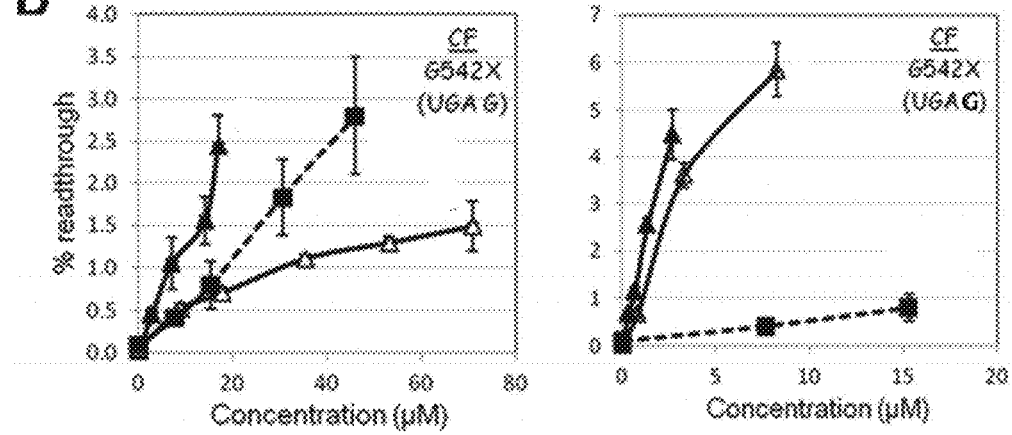

The obtained data is presented in FIGS. 11A-D, showing comparative plots showing in vitro stop codon suppression levels induced by NB74 (-Δ-), NB156 (-▲-), and gentamicin (--■--) (left) and by NB124 (-Δ-), NB157 (-▲-), and gentamicin (--■--) (right), in nonsense constructs representing R3X (USH1) (FIG. 11A), R245X (USH1) (FIG. 11B), Q70X (HS) (FIG. 11C), and G542X (CF) (FIG. 11D). The results are averages of at least three independent experiments.

As clearly shown in FIGS. 11A-D, the positive impact of the C7'-hydroxyl group shown for NB153 is retained also in the pseudo-trisaccharides. In all mutations tested, the readthrough activity of NB156 is substantially better than that of the structurally related NB74, and the activity of NB157 is better than its structurally related NB124. In addition, in all mutations tested, the activities of both NB156 and NB157 were significantly better than that of the clinical drug gentamicin.

In order to evaluate the specificity toward eukaryotic cytoplasmic ribosome, comparative protein translation inhibition of Compounds NB74, NB124, NB156 and NB157 in eukaryotic system was determined, using coupled transcription/translation assays.

In all biological tests, all AGs were in their sulfate salt forms, and the concentrations refer to the free amine form of each AG. The eukaryotic and prokaryotic half-maximal-inhibition values ($IC_{50}^{Euk}$ and $IC_{50}^{Pro}$) were quantified in coupled transcription/translation assays by using active luciferase detection as previously described. Minimal inhibitory concentration (MIC) values were determined by using the double-microdilution method.

The obtained data in presented in Table 4 below.

TABLE 4

| | Translation Inhibition | | Antibacterial Activity MIC (μM) | |
|---|---|---|---|---|
| Compound | $IC_{50}^{Euk}$(μM) | $IC_{50}^{Pro}$ (μM) | E. Coli R 477/100 | B. Subtilis ATCC6633 |
| Gentamicin | 62 ± 9 | 0.03 ± 0.00 | 6 | <0.75 |
| G418 | 2.0 ± 3 | 0.01 ± 0.00 | 9 | <1.25 |
| Compound 1 | 347.1 ± 34.3 | 6.0 ± 1.0 | | |
| NB153 | 120.5 ± 14.5 | 11.0 ± 1.2 | >311 | 311 |
| NB155 | 515.8 ± 15 | 91.9 ± 8.4 | >375 | >375 |
| NB74 | 13.9 ± 1.2 | 1.0 ± 0.1 | 680 | 42 |
| NB156 | 7.5 ± 0.5 | 0.7 ± 0.1 | >273 | 34 |
| NB124 | 1.5 ± 0.1 | 1.1 ± 0.2 | 1267 | 156 |
| NB157 | 1.2 ± 0.1 | 1.2 ± 0.1 | >257 | 64 |

The obtained data indicates that the efficacy with which NB157 (half-maximal inhibitory concentration value $IC_{50}^{Euk}$=1.2 μM) inhibits eukaryotic translation is greater than that of NB156 ($IC_{50}^{Euk}$=13.9 μM) and gentamicin ($IC_{50}^{Euk}$=62 μM), similarly to the PTC suppression activity shown in FIGS. 11A-D. In addition, NB156 and NB157 are 1.85-fold and 1.25-fold more specific to the eukaryotic ribosome than their structurally related Compounds NB74 and NB124, respectively. These data indicate that the elevated PTC suppression activities of NB156 and NB157 are associated with their increased specificity to the eukaryotic ribosome.

The measured $IC_{50}^{Pro}$ and MIC values in Table 4 show that the efficacy with which NB156 and NB157 inhibit the prokaryotic ribosome and their subsequent antibacterial activity are very similar to those of their structurally related Compounds NB74 and NB124, respectively. The observed similar impact on bacterial ribosome by these compounds suggest that NB156 and NB157 are less ototoxic than gentamicin and G418.

Thus, a new pharmacophoric point, 7'-hydroxyl group, is shown herein as a valuable structural element of the glucosamine ring (Ring I) that significantly affects eukaryotic versus prokaryotic selectivity and the subsequent PTC suppression activity.

Further assays were conducted essentially as described hereinabove, and some of the obtained data is presented in FIGS. 12A-13B.

In these assays, the readthrough of a broad arsenal of stop codon mutations in the presence of NB156 and NB157 was tested. Briefly, NB156 and NB157 were tested at escalating doses for their read-through properties towards the nonsense mutation using the wild-type (WT) sequence of each specific complementary DNA (cDNA) as a control, and plasmids bearing the stop codon mutations in a dual-luciferase assay. DNA fragments derived from different cDNAs were prepared using either the WT or nonsense mutation, in which the sequences from the mutant or wild-type codon were surrounded by four to six upstream and downstream flanking codons. The cDNA sequence was inserted into the polylinker of the p2luc plasmid for each sequence.

The tested mutations and the genetic diseases associated therewith are shown in Table 5 below.

TABLE 5

| Mutation | Disease |
|---|---|
| G542X | Cystic fibrosis |
| R553X | Cystic fibrosis |
| W1282X | Cystic fibrosis |
| R3381X | Duchenne muscular dystrophy |
| Q2522X | Duchenne muscular dystrophy |
| mdx | Duchenne muscular dystrophy (mouse) |
| W392X | Hurler Syndrome |
| Q70X | Hurler Syndrome |
| R168X | Rett Syndrome |
| R270X | Rett Syndrome |
| R294X | Rett Syndrome |
| R578X | Severe epidermolysis bullosa |
| Q251X | Severe epidermolysis bullosa |
| R3X | Usher Syndrome |
| R245X | Usher Syndrome |
| R31X | Usher Syndrome |

Figure 12A:
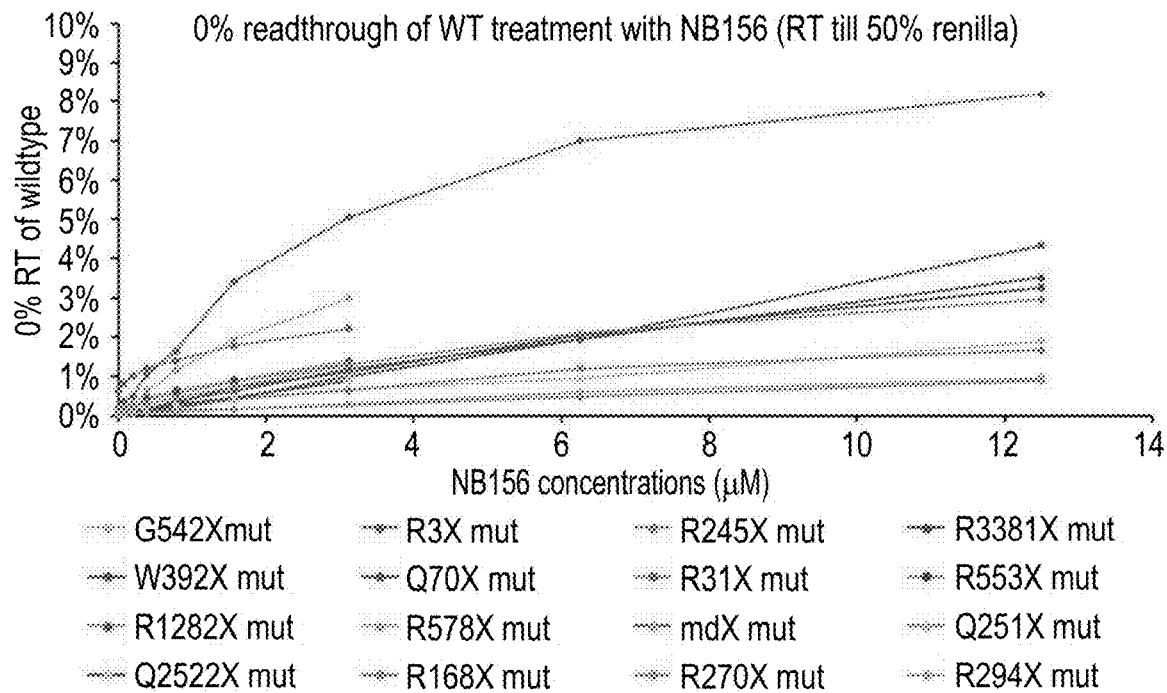
FIG. 12A presents comparative stop-codon mutation readthrough plots, showing percent readthrough as a function of concentration of WT with NB156 (readthrough to 50% *renilla*), comparing the readthrough of several different mutations.

FIG. 12A presents comparative stop-codon mutation readthrough plots, showing percent readthrough as a function of concentration of WT with NB 156 (readthrough to 50% renilla), comparing the readthrough of the mutations G542X W392X, R1282X, Q2522X, R3X, Q70X, R578X, R168X, R245X, R31X, mdX, R270X, R3381X, R553X, Q251X and R294X.

Figure 12B:
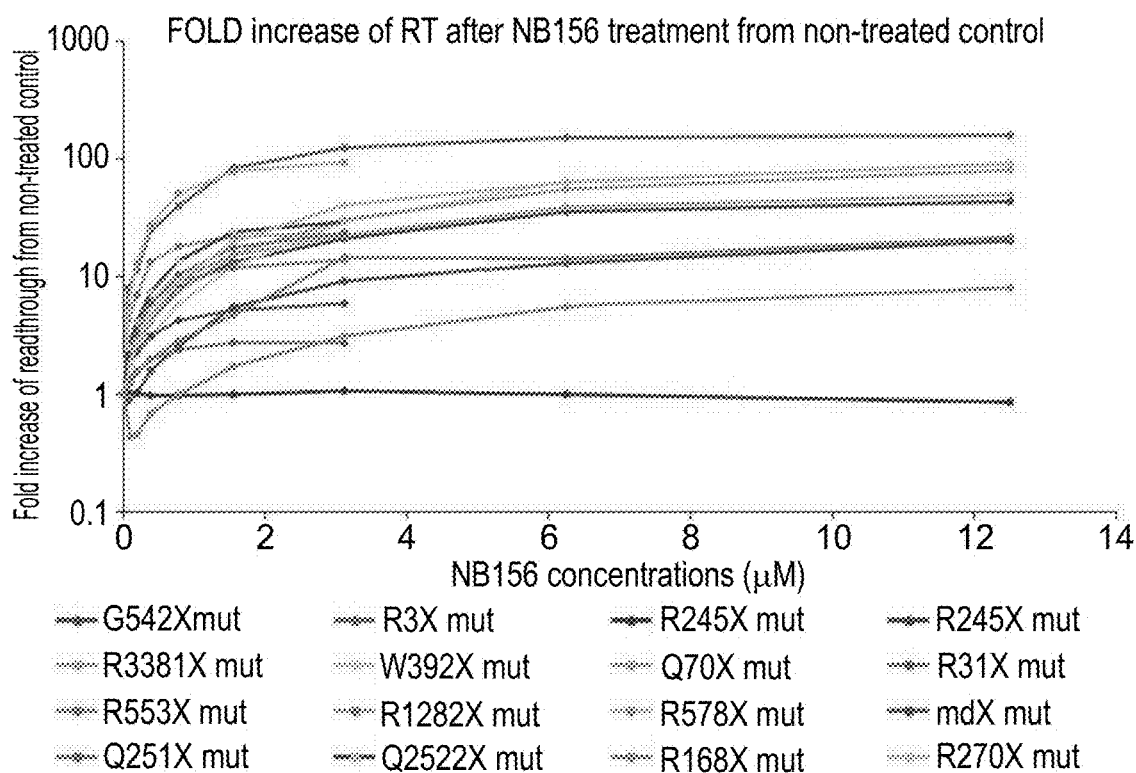
FIG. 12B presents comparative stop-codon mutation readthrough plots, showing fold increase of readthrough after exposure to NB156 from non-treated control as a function of NB156 concentration, comparing the readthrough of several different mutations.

FIG. 12B presents comparative stop-codon mutation readthrough plots, showing fold increase of readthrough after exposure to NB 156 from non-treated control as a function of NB156 concentration, comparing the readthrough of the mutations G542X, W392X R1282X Q2522X R3X, Q70X, R578X, R168X, R245X R31X, mdx, R270X, R3381X R553X Q251X and R294X.

Figure 13A:
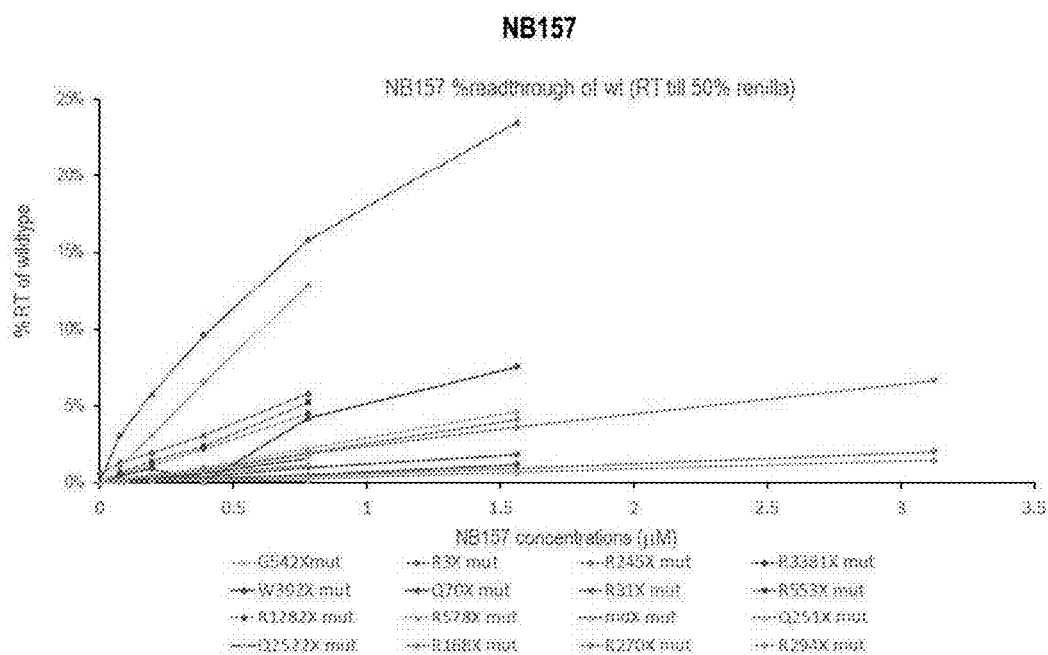
FIG. 13A presents comparative stop-codon mutation readthrough plots, showing percent readthrough as a function of concentration of WT with NB157 (readthrough to 50% *renilla*), comparing the readthrough of several different mutations.

FIG. 13A presents comparative stop-codon mutation readthrough plots, showing percent readthrough as a function of concentration of WT with NB157 (readthrough to 50% renilla), comparing the readthrough of the mutations G542X W392X, R1282X, Q2522X, R3X, Q70X, R578X, R168X, R245X, R31X, mdX, R270X, R3381X, R553X, Q251X and R294X (see, Table 5 above).

Figure 13B:
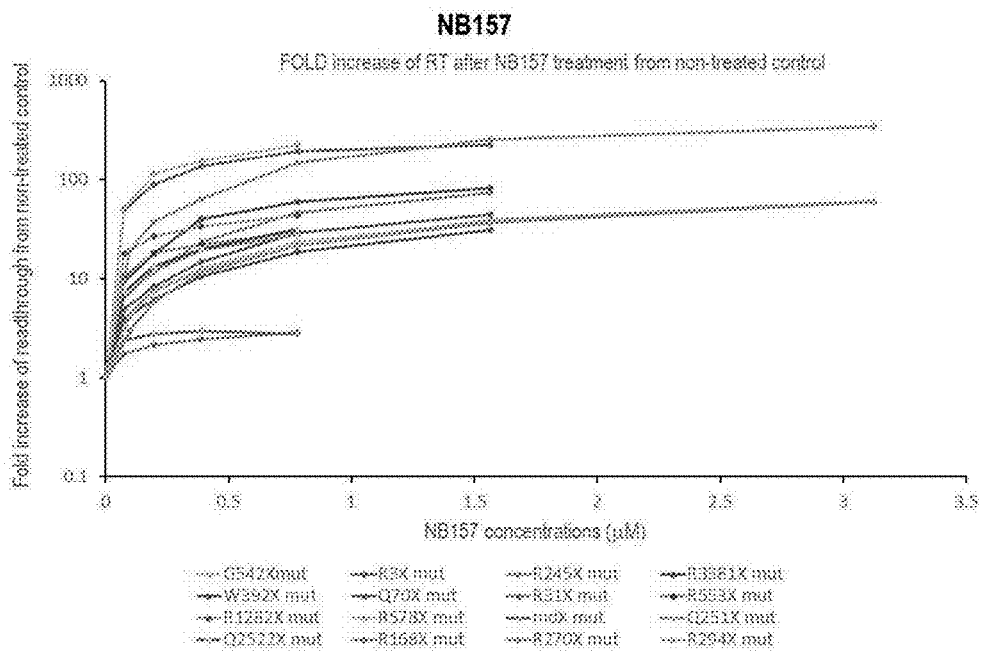
FIG. 13B presents comparative stop-codon mutation readthrough plots, showing fold increase of readthrough after exposure to NB157 from non-treated control as a function of NB157 concentration, comparing the readthrough of several different mutations.

FIG. 13B presents comparative stop-codon mutation readthrough plots, showing fold increase of readthrough after exposure to NB157 from non-treated control as a function of NB157 concentration, comparing the readthrough of the mutations G542X, W392X, R1282X, Q2522X, R3X, Q70X, R578X, R168X, R245X, R31X, mdX, R270X R3381X R553X, Q251X and R294X (see, Table 5 above).

In additional comparative assays, the stop-codon mutation readthrough activity of NB156 was compared to that of NB74. In all tested mutations, NB156 was shown to be more active than NB74.

These data further demonstrate the readthrough activity exhibited by NB156 and NB157 on various stop codon mutations.

Example 6

Unsaturated Glucosamine (Ring I)-Containing Exemplary Compounds According to Some Embodiments of the Present Invention Exemplary new modifications of aminoglycoside structures were performed by inserting unsaturation at ring I (glucosamine ring). It has been assumed that by the deletion of C4'-OH or C3', C4'-hydroxyls with a simultaneous introduction of unsaturation on Ring I makes the ring relatively "free" to move within the binding pocket for better pseudo-pair interaction with G1408 and improved π-π stacking with A1491.

Chemical Syntheses

The following exemplary aminosugars Compounds NB154, NB158 and NB159 were synthesized:

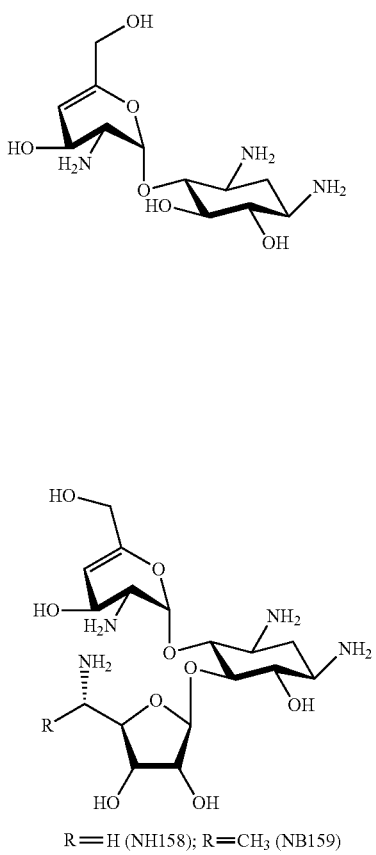

All the structures were confirmed and characterized by a combination of various 1D and 2D NMR techniques, including 1D TOCSY, 2D COSY, 2D $^1$H-$^{13}$C HMQC and HMBC along with mass spectrometry.

Synthesis of NB1.5.4:

The synthesis of NB 154 is depicted in Scheme 12 below.

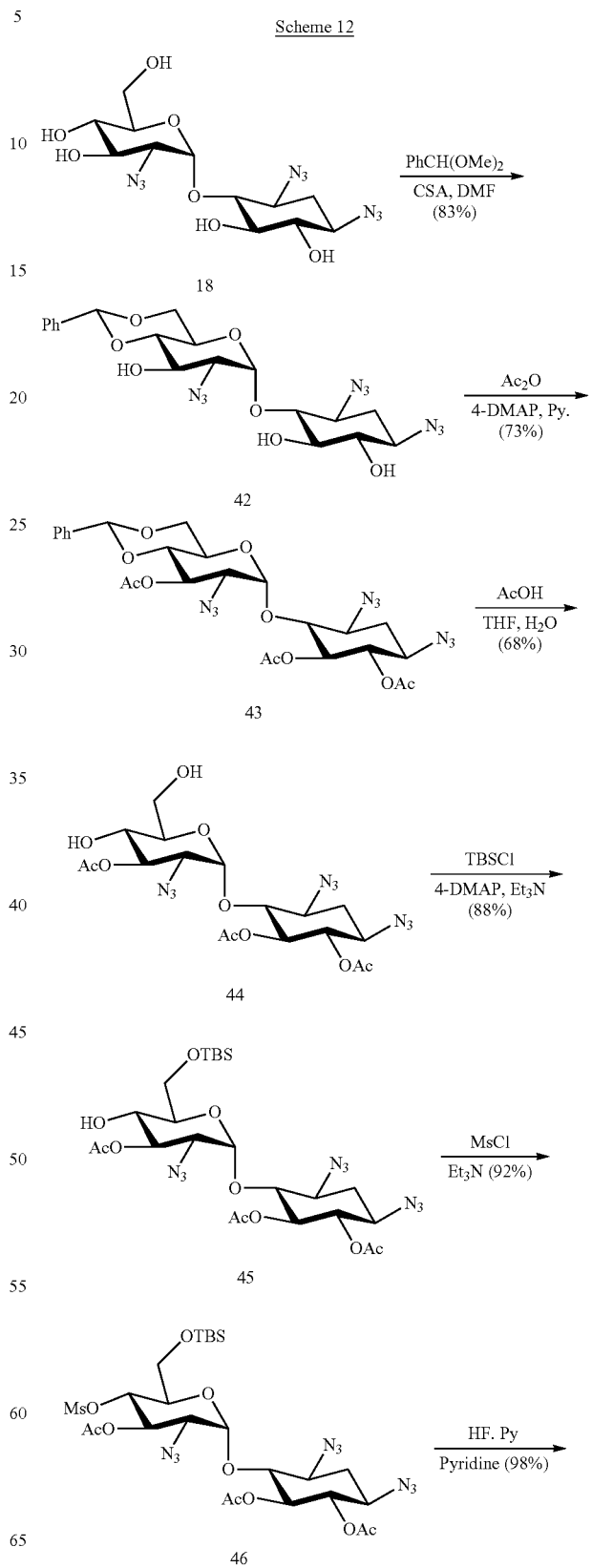

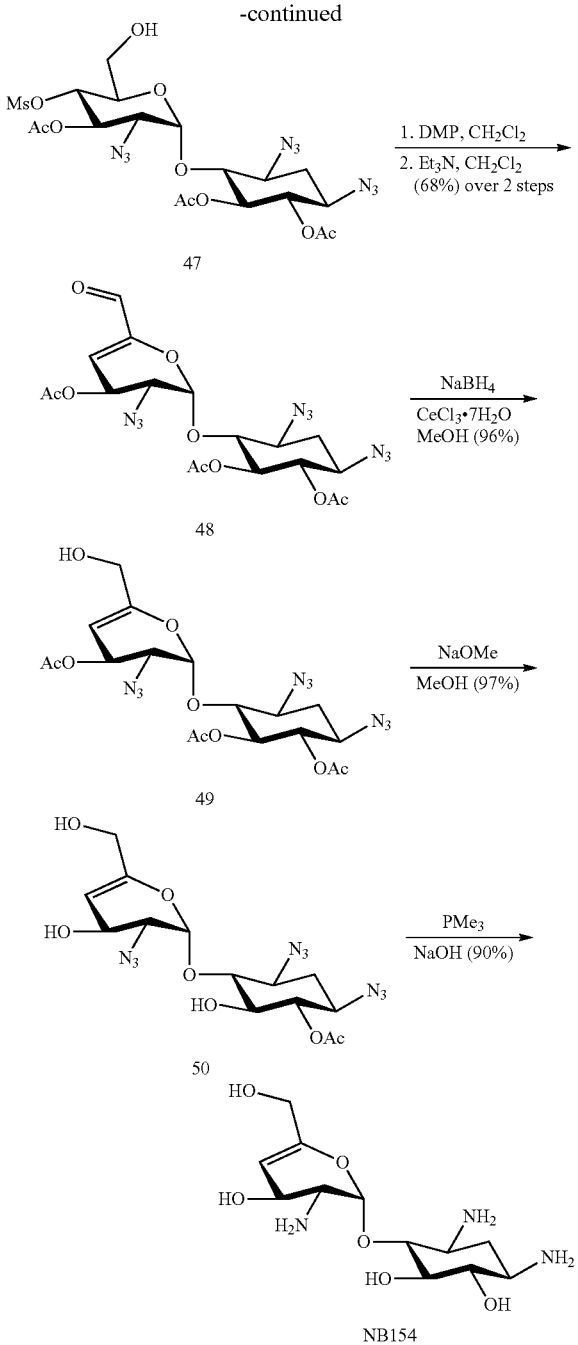

Briefly, the synthesis started from paromamine, which is obtained from commercially available paromomicin sulfate under acidic (HCl/MeOH) hydrolysis, as previously described. Initially, paromamine was converted into the triazide by the action insitu generated triflic azide from triflic anhydride and NaN₃ in the presence of CuSO₄ to yield paromamine perazide (18), as described in further detail hereinabove. Upon obtaining the paromamine perazide, the 4',6'-OH groups were converted into corresponding bebzylidene acetal (42) using benzaldehyde dimethyl acetal under acidic conditions. The other hydroxy groups were converted to acetate esters in presence of acetic anhydride under basic conditions (43). Deprotection of the arylidene group in Compound 43 under mild acidic environment led to the formation of diol 44 which was subjected to further post functional transformations to yield the desired compound. In order to differentiate the 4'-OH and 6'-OH groups so as to perform selective oxidation, the 6'-OH group in compound 43 was protected as its silyl ether 45 by selective protection with tert-butyldiphenylsilyl chloride (TBDPSCl), while the other hydroxyl group was masked as mesylate ester using mesyl chloride (MSCl) under base condition (Et₃N) to thereby obtain Compound 46 in excellent yields.

In order to avoid the hydrolysis of 4'-OMs ester functionality during the silyl deprotection using TBAF, the TBAF reaction mixture was buffered with AcOH and obtained the 6'-OH functional molecule 47 leaving 4'-OMs ester intact with the molecule. DMP oxidation of the C-6' hydroxyl group, followed by concomitant elimination of 4'-OMs ester under basic conditions in one-pot reaction lead to the formation of corresponding α, β-unsaturated aldehyde 48 in good yield. Compound 48, upon Luche reduction conditions gave allylic alcohol 49, which on treatment with NaOMe followed by Staudinger reaction yielded the pseudo-disaccharide NB154.

Synthesis of 1,3,2'-perazido-paromamine (18): Paromomicin sulfate was hydrolyzed under acidic conditions (HCl/MeOH) to paromamine. Paromamine was converted into the triazide by the in situ generated triflic azide from triflic anhydride and NaN₃ in the presence of CuSO₄.

Generation of Triflic azide: To a vigorously stirred solution of NaN₃ (3.6 grams, 18 equiv.) in water (9.0 mL) and Toluene (9.0 mL) at 0° C., triflic anhydride (4.6 mL, 9.0 equiv.) was added drop wise and the reaction mixture was stirred for 30 minutes at 0° C. The temperature was thereafter raised to 10° C. and the biphasic system was stirred for 2 hours. Saturated aqueous NaHCO₃ was then added dropwise until the gas evaluation ceased. The phases were separated and the aqueous phase was extracted with toluene (2×9 mL). The combined organic layers were used in the diazo transfer reaction.

Diazo transfer reaction: Paromamine (1.0 gram, 1.0 equiv.), NaHCO₃ (3.1 grams, 12.0 equiv.) and copper (II) sulfate were dissolved in water (5.0 mL). Triflic azide stock solution was added, followed by the addition of methanol (40 mL), to thereby obtain a homogeneous solution. The blue color reaction mixture was stirred vigorously at room temperature. Complete conversion of amine was indicated by the change of blue color to green. After stirring for 48 hours, TLC (EtOAc/MeOH 95:5) analysis indicated the completion of the reaction. The solvent was hereafter evaporated to dryness and the residue was subjected to column chromatography (EtOAc 100%).

$^1$H NMR (500 MHz, MeOD): 'Ring I': $\delta_H$=5.69 (d, 1H, J=3.7 Hz, H-1), 3.99 (ddd, 1H, J=9.9, 4.1, 2.6 Hz, H-5), 3.94 (dd, 1H, J=10.2, 9.1 Hz, H-3), 3.84 (dd, 1H, J=11.9, 2.3 Hz, H-6), 3.78 (dd, 1H, J=11.8, 4.4 Hz, H-6), 3.46 (dd, 1H, J=9.7, 9.3 Hz, H-4), 3.13 (dd, 1H, J=10.5, 3.7 Hz, H-2); 'Ring II': $\delta_H$=3.80 (t, 1H, J=8.8 Hz, H-5), 3.77-3.67 (m, 3H, H-1, H-3, H-4), 3.56 (t, 1H, J=9.6 Hz, H-6), 2.59-2.48 (m, 1H), 1.68 (dd, 1H, J=26.3, 12.7 Hz, H-2).

$^{13}$C NMR (125 MHz, MeOD): $\delta_C$=99.3 (C1'), 80.7, 77.8 (C5), 77.7 (C6), 73.9 (C5'), 72.4 (C3'), 71.6, 64.8 (C2'), 62.1 (C6'), 61.6, 60.9, 33.1 (C2).

MALDI TOFMS: calculated for $C_{12}H_{19}N_9O_7$ ([M+K]$^+$) m/e 440.3; measured m/e 440.2).

Preparation of 4',6'-O-benzylidene-1,2',3-triazido-paromamine (42: Compound 18 (1 gram, 2.49 mmol) was dissolved in dry DMF (20 mL) and Benzaldehyde dimethyl acetal (0.87 mL, 5.79 mmol) and a catalytic amount of CSA were added. The reaction mixture was stirred at 60° C. and the reaction progress was monitored by TLC (EtOAc 60%, Hexane 40%), which indicated the completion of the reaction after 2 hours. The reaction mixture was diluted with EtOAc and extracted with saturated aqueous solutions of NaHCO$_3$ and Brine. The combined organic layer was dried over MgSO$_4$, filtered and concentrated under reduced pressure. The crude product was purified by flash chromatography (EtOAc/hexane 1:1) to afford Compound 42 (1.0 gram, 8.3% yield).

$^1$H NMR (600 MHz, MeOD): 'Ring I': $\delta_H$=5.69 (d, 1H, J=3.5 Hz, H-1), 4.27 (dd, 1H, J$_1$=10.0, J$_2$=5.0 Hz, H-6), 4.20 (td, 1H, J$_1$=10.1, J$_2$=5.0 Hz, H-6), 4.15 (t, 1H, J=9.7 Hz, H-3), 3.81 (t, 1H, J=10.1 Hz, H-5), 3.59 (t, 1H, J=9.56 Hz, H-4), 3.31 (dd, 1H, J$_1$=10.4, J$_2$=4.6 Hz, H-2); 'Ring II': $\delta_H$=3.57 (t, 1H, J=8.2 Hz, H-5), 3.54-3.48 (m, 2H, H-3, H-4), 3.45 (ddd, 1H, J=14.7, 11.3, 5.5 Hz, H-1), 3.31 (t, 1H, J=9.7 Hz, H-6), 2.28 (dt, 1H, J$_1$=8.5, J$_2$=3.9 Hz, H-2eq), 1.46 (ddd, 1H, J$_1$=J$_2$=J$_3$=12.3 Hz, H-2ax); the additional peaks in the spectrum were identified as follow: 7.58-7.50 (m, 2H), 7.43-7.35 (m, 3H, Ar), 7.43-7.35 (m, 3H, Ar), 5.63 (s, 1H, PhCH).

$^{13}$C NMR (150 MHz, MeOD): $\delta_c$=139.10 (Ar), 129.98 (Ar), 129.07 (Ar), 127.56 (Ar), 103.14 (PhCH), 100.36 (C-1'), 83.06, 81.33, 77.82, 77.81, 69.85 (C-5'), 69.59 (C-6'), 65.23 (s), 64.58 (s), 61.76 (s), 60.95 (s), 33.21 (C-2).

MALDI TOFMS: calculated for C$_{19}$H$_{24}$N$_9$O$_7$ ([M+H]+) m/e 490.4; measured m/e 490.0.

Preparation of 4',6'—O-benzylidene-1,2',3-triazido-peracetylparomamine (43): Compound 42 (1.4 gram, 2.94 mmol) was dissolved in anhydrous pyridine (8 mL) and Acetic anhydride (1.4 mL, 14.8 mmol), and 4-DMAP (3.2 grams, 26.1 mmol) was added. The reaction progress was monitored by TLC, which indicated completion after 4 hours. The reaction mixture was diluted with EtOAc, and extracted with aqueous solution of HCl (2%), saturated aqueous NaHCO$_3$, and brine. The combined organic layers were dried over anhydrous MgSO$_4$ and concentrated. The crude product was purified by silica gel column chromatography (EtOAc/Hexane 4:6) to afford 43 (1.32 gram, 73% yield).

$^1$H NMR (600 MHz, MeOD): 'Ring I': $\delta_H$=5.57 (dd, 1H, J$_1$=10.3, J$_2$=9.6 Hz, H-3), 5.15 (d, 1H, J=3.2 Hz, H-1), 4.31 (dt, 2H, J$_j$=13.0, J$_2$=5.0 Hz, H-5, H-6), 3.73 (dd, 1H, J$_1$=14.4, J$_2$=5.6 Hz, H-6), 3.62 (t, 1H, J=9.3 Hz, H-4), 3.24 (dd, 1H, J$_1$=10.5, J$_2$=4.0 Hz, H-2); 'Ring II': $\delta_H$=5.17 (t, 1H, J=9.7 Hz, H-5), 4.92 (t, 1H, J=10.0 Hz, H-6), 3.74-3.56 (m, 2H, H-4, H-1), 3.46 (ddd, 1H, J$_1$=12.2, J$_2$=10.1, J$_3$=4.9 Hz, H-3), 2.43 (dt, 1H J$_1$=13.0, J$_2$=4.5 Hz, H-2), 1.59 (ddd, 1H, J$_j$=25.8, J$_2$=12.8 Hz, H-2); the additional peaks in the spectrum were identified as follow: $\delta_H$=7.44 (dt, J$_1$=5.0, J$_2$=3.0 Hz, 2H, Ar), 7.39-7.30 (m, 3H, Ar), 5.49 (s, 1H, PhCH).

$^{13}$C NMR (150 MHz, CDCl$_3$): =170.06 (C=O), 169.76 (C=O), 169.37 (C=O), 136.93 (Ar), 129.26 (Ar), 128.36 (Ar), 126.30 (Ar), 101.74 (PhCH), 100.22 (C-1'), 79.17 (C-4'), 78.72 (C-4), 74.27 (C-6), 73.72 (C-5), 68.69 (C-6'), 68.63 (C-3'), 63.51 (C-5'), 61.46 (C-2'), 58.29 (C-3), 57.68 (C-1), 31.77 (C-2), 20.87 (CH$_3$CO), 20.67 (CH$_3$CO), 20.64 (CH$_3$CO).

Preparation of (1S,2S,3R,4S,6R)-3-(2S,3R,4R,5S,6R)-4-acetoxy-3-azido-5-hydroxy-6-(hydroxymethyl)tetrahydro-2H-pyran-2-yl)oxy)-4,6-diazidocyclohexane-1,2-diyl diacetate (44): Compound 43 (1.32 gram, 2.14 mmol) was dissolved in mixture of AcOH/H$_2$O (5:1, 10 mL) and the solution was stirred at 60° C. overnight. After the reaction completion, as indicated by TLC, the aqueous acetic acid was removed by evaporation. The crude residue was dissolved in EtOAc, and extracted with saturated aqueous NaHCO$_3$, and brine. The combined organic layers were dried over anhydrous MgSO$_4$ and concentrated. The crude product was purified by silica gel column chromatography (EtOAc/Hexane 6:4) to afford 44 (771 mg, 68% yield).

$^1$H NMR (600 MHz, CDCl$_3$): 'Ring I': $\delta_H$=5.28 (t, 1H, J=9.9 Hz, H-3), 5.13 (d, 1H, J=3.6 Hz, H-1), 4.09 (d, 1H, J=10.0 Hz, H-4), 3.95-3.79 (m, 2H, H-6, H-6), 3.67 (t, 1H, J=9.1 Hz, H-5), 3.28 (dd, 1H, J$_1$=10.3, J$_2$=3.5 Hz, H-2); 'Ring II': $\delta_H$=5.12 (t, 1H, J=9.8 Hz, H-5), 4.91 (t, 1H, J=10.0 Hz, H-6), 3.73-3.67 (m, 1H, H-3), 3.63 (t, 1H, J=9.7 Hz, H-4), 3.52 (td, 1H, J=12.1, 4.6 Hz, H-1), 2.42 (dt, 1H, J$_1$=13.2, J 2=4.4 Hz, H-2), 1.59 (ddd, 1H, J$_1$=J$_2$=J$_3$=12.6 Hz, H-2)); the additional peaks in the spectrum were identified as follow: $\delta$=2.15 (s, 3H, CH$_3$C=O), 2.11-2.02 (m, 6H, CH$_3$C=O).

$^{13}$C NMR (150 MHz, CDCl$_3$): $\delta_c$=171.78 (C=O), 170.10 (C=O), 169.73 (C=O), 99.33 (C-1'), 78.79 (C-4), 74.21 (C-6), 73.68 (C-5), 73.03 (C-3'), 72.62 (C-4'), 69.45 (C-5'), 61.64 (C-6'), 61.02 (C-2'), 58.71 (C-1), 57.65 (C-3), 31.98 (C-2), 21.06 (CH$_3$CO), 20.72 (CH$_3$CO), 20.66 (CH$_3$CO).

Preparation of (1S,2S,3R,4S,6R)-3-(((2S,3R,4S)-4-acetoxy-3-azido-6-formyl-3,4-dihydro-2H-pyran-2-yl) oxy)-4,6-diazidocyclohexane-1,2-diyl diacetate (48): To a stirred solution of compound 47 (88 mg, 0.145 mmol) in CH$_2$Cl$_2$ (3 mL) at 0° C., DMP (123 mg, 0.289 mmol) was added in one portion and the resulting mixture was stirred at 0° C. for 40 minutes. Then the reaction mixture was allowed to reach room temperature and stirred for additional 3 hours. After completion of the reaction as indicated by TLC, Et$_3$N (0.2 mL) was added in one-pot at r.t. and mixture was stirred 30 minutes. Thereafter, the reaction mixture was diluted with EtOAc and washed with water, followed by brine. The combined organic layers were dried over anhydrous MgSO$_4$ and concentrated. The crude product was purified by silica gel column chromatography (EtOAc/Hexane 3:7) to afford 48 (50 mg, 68% yield).

$^1$H NMR (600 MHz, CDCl$_3$): 'Ring I': $\delta_H$=5.93 (d, 1H, J=2.6 Hz, H-4), 5.76 (dd, 1H, J$_1$=9.4, J$_2$=2.4 Hz, H-3), 5.38 (d, 1H, J=2.6 Hz, H-1), 3.71 (dd, 1H, J$_1$=9.4, J$_2$=2.7 Hz, H-2); 'Ring II': $\delta_H$=5.13 (t, 1H, J=9.9 Hz, H-5), 4.90 (t, 1H, J=10.0 Hz, H-6), 3.82 (t, 1H, J=9.8 Hz, H-4), 3.60 (ddd, 1H, J$_1$=12.6, J$_2$=10.2, J$_3$=4.6 Hz, H-3), 3.42 (ddd, 1H, J$_1$=12.6, J$_2$=10.0, J$_3$=4.6 Hz, H-3), 2.31 (dt, 1H, J$_1$=13.5, J$_2$=4.6 Hz, H-2), 1.49 (ddd, 1H, J$_1$=J$_2$=J$_3$=12.7 Hz, H-2); the additional peaks in the spectrum were identified as follow: $\delta$=9.24 (s, 1H, CHO), 2.14 (s, 3H, CH$_3$CO), 2.08 (s, 3H, CH$_3$CO), 2.06 (s, 3H, CH$_3$CO);

$^{13}$C NMR (150 MHz, CDCl$_3$): =185.12 (CHO), 170.01 (C=O), 169.87 (C=O), 169.48 (C=O), 148.79 (C-5'), 116.71 (C-4'), 98.98 (C-1'), 79.20 (C-4), 73.99 (C-6), 73.25 (C-5), 66.43 (C-3'), 59.14 (C-3), 58.50 (C-2'), 57.84 (C-1), 32.14 (C-2), 20.91 (CH$_3$CO), 20.69 (CH$_3$CO), 20.64 (CH$_3$CO).

Preparation of (1S,2S,3R,4S,6R)-34(2S,3R,4S)-4-acetoxy-3-azido-6-(hydroxymethyl)-3,4-dihydro-2H-pyran-2-yl) oxy)-4,6-diazidocyclohexane-1,2-diyl diacetate (49): To a stirred solution of aldehyde 48 (1.0 gram, 1.97 mmol) in dry MeOH (10 mL), cooled to 0° C., CeCl$_3$·7H$_2$O (734 mg, 1.97 mmol) and NaBH$_4$ (74 mg, 1.95 mmol) were added successively. The progress of the reaction was monitored by TLC (EtOAc/Hexane 2:3), which indicated completion after 1 hour. The MeOH was evaporated completely and H$_2$O was added. The aqueous layer was extracted with EtOAc. The combined organic layers were washed with brine, dried over MgSO$_4$, evaporated to dryness, and purified by column chromatography (silica gel, EtOAc/Hexane) to yield corresponding allyl alcohol 49 (960 mg, 96%).

$^1$H NMR (600 MHz, CDCl$_3$): 'Ring I': $\delta_H$=5.44 (d, 1H, J=5.9, H-3), 5.25 (d, 1H, J=2.4 Hz, H-1), 5.03 (d, 1H, J=2.7 Hz, H-4), 4.09-3.96 (m, 2H, H-6, H-6), 3.58 (dd, 1H, J, =7.0, J$_2$=2.5 Hz, H-2); 'Ring II': $\delta_H$=5.12 (t, 1H, J=9.9 Hz, H-5), 4.89 (t, 1H, J=10.0 Hz, H-6), 3.79 (t, 1H, J=9.8 Hz, H-4), 3.69-3.54 (m, 1H, H-1), 3.48 (ddd, 1H, =12.6, J$_2$=10.0, J$_3$=4.6 Hz, H-3), 2.30 (dt, 1H, =13.4, J$_2$=4.5 Hz, H-2eq), 1.44 (ddd, 1H, J, =J$_2$=J$_3$=12.8 Hz, H-2ax); The additional peaks in the spectrum were identified as follow: $\delta_H$=2.57 (brs, 1H, 6'-OH), 2.06 (s, 3H, CH$_3$), 2.04 (s, 6H, CH$_3$).

$^{13}$C NMR (150 MHz, CDCl$_3$): $\delta_C$=170.0 (CH$_3$—CO), 169.9 (CH$_3$—CO), 169.4 (CH$_3$—CO), 152.6 (C5'), 98.3 (C1'), 96.3 (C4'), 78.8 (C4), 73.9 (C6), 73.3 (C5), 66.6 (C3'), 61.7 (C6'), 59.3 (C3), 58.9 (C2'), 57.8 (C1), 32.3 (C2), 21.0 (CH$_3$), 20.6 (CH$_3$), 20.5 (CH$_3$).

Preparation of (1S,2R,3R,4S,6R)-4,6-diazido-3-(2S,3R,4S)-3-azido-4-hydroxy-6-(hydroxymethyl)-3,4-dihydro-2H-pyran-2-yl)oxy)cyclohexane-1,2-diol (50): To a stirred solution of alcohol 49 under argon atmosphere (960 mg, 1.88 mmol) in dry MeOH (15 mL), NaOMe (459 mg, 8.49 mmol) was added. The progress of the reaction was monitored by TLC (EtOAc/Hexane 3:2), which indicated completion after 6 hours. Then the reaction mixture was passed through a pad of silica gel column and the column was washed with MeOH. The combined organic layers were evaporated to dryness, and purified by column chromatography (silica gel, EtOAc/Hexane) to yield compound 50 (700 mg, 97%).

$^1$H NMR (500 MHz, MeOD): 'Ring I': $\delta_H$=5.80 (d, 1H, J=2.5 Hz, H-1), 5.03 (dt, 1H, J, =2.5, J$_2$=1.0 Hz, H-4), 4.47-4.39 (m, 1H, H-3), 4.06-3.96 (m, 2H, H-6), 3.42 (dd, 1H, J, =8.0, J$_2$=2.5 Hz, H-2); 'Ring II': $\delta_H$=3.61 (t, 1H, J=9.5 Hz, H-4), 3.52 (t, 1H, J=9.5 Hz, H-5), 3.46 (ddd, 1H, J, =12.5, J$_2$=9.5, J$_3$=4.5 Hz, H-3), 3.43-3.37 (m, 1H, H-1), 3.26 (t, 1H, J=9.5 Hz, H-6), 2.16 (dt, 1H, J, =12.5, J$_2$=4.5 Hz, H-2eq), 1.29 (ddd, 1H, J$_1$=J$_2$=J$_3$=12.5 Hz, H-2ax).

$^{13}$C NMR (125 MHz, MeOD): $\delta_C$=152.6, 100.5 (C4'), 99.6 (C1'), 81.7 (C4), 77.9 (C6), 77.6 (C5), 64.9 (C3'), 63.8 (C2'), 62.0 (C1), 61.9 (C6'), 61.6 (C3), 33.7 (C2).

MALDI TOFMS: calculated for C$_{12}$H$_{17}$N$_9$O$_6$ ([M+Na]+) m/e 406.3; measured m/e 406.3.

Preparation of (1S,2R,3R,4S,6R)-4,6-diamino-3-(((2S,3R,4S)-3-amino-4-hydroxy-6-(hydroxymethyl)-3,4-dihydro-2H-pyran-2-yl)oxy)cyclohexane-1,2-diol (NB154): To a stirred solution of Compound 50 (256 mg, 1.0 equiv.) in a mixture of THF (3.0 mL) and aqueous NaOH (1 mM, 5.0 mL), PMe$_3$ (1 M solution in THF, 0.55 mL, 7.8 equiv.) was added. The progress of the reaction was monitored by TLC [CH$_2$Cl$_2$/MeOH/H$_2$O/MeNH$_2$ (33% solution in EtOH), 10:15:6:15], which indicated completion after 3.5 hours. The reaction mixture was purified by flash chromatography on a short column of silica gel. The column was washed with the following solvents: THF (100 mL), CH$_2$Cl$_2$ (100 mL), EtOH (50 mL), and MeOH (100 mL). The product was then eluted with the mixture of 5% MeNH$_2$ solution (33% solution in EtOH) in 80% MeOH. Fractions containing the product were combined and evaporated under vacuum. The pure product was obtained by passing the above product through a short column of Amberlite CG50 (NH$_4^+$ form). First, the column was washed with water, then the product was eluted with a mixture of 10% NH$_4$OH in water to yield NB154 (184 mg, 90%).

For storage and biological tests, NB154 was converted to its sulfate salt form as follow: The free base form was dissolved in water, the pH was adjusted to 7 with H$_2$SO$_4$ (0.1 N) and lyophilized to afford the sulfate salt of NB154.

$^1$H NMR (500 MHz, MeOD): 'Ring I': $\delta_H$=5.40 (d, 1H, J=2.5 Hz, H-1), 4.98 (d, 1H, J=3.0 Hz, H-4), 4.06 (dd, 1H, J, =7.0, J$_2$=3.0 Hz, H-3), 4.01-3.91 (m, 2H, H-6), 2.92 (dd, 1H, J, =7.0, J$_2$=2.5 Hz, H-2); 'Ring II': $\delta_H$=3.41-3.35 (m, 2H, H-4, H-5), 3.09 (t, 1H, J=9.5 Hz, H-6), 2.76-2.70 (m, 1H, H-3), 2.66 (ddd, 1H, J, =12.5, J$_2$=10.0, J$_3$=4.5 Hz, H-1), 2.03 (dt, 1H, J$_1$=12.5, J$_2$=4.5 Hz, H-2eq), 1.24 (ddd, 1H, J$_1$=J$_2$=J$_3$=12.5 Hz, H-2ax).

$^{13}$C NMR (125 MHz, MeOD): $\delta_C$=152.6, 101.8 (C1'), 101.5 (C4'), 86.7, 78.8 (C6), 77.7, 68.0 (C3'), 62.5 (C6'), 55.6 (C2'), 52.4 (C3), 51.2 (C1), 36.6 (C2).

MALDI TOFMS: calculated for C$_{12}$H$_{23}$N$_3$O$_6$ ([M+H]$^+$) m/e 306.3; measured m/e 306.8.

Syntheses of NB158 and NB159:

NB158 and NB159 were prepared as depicted in Scheme 13.

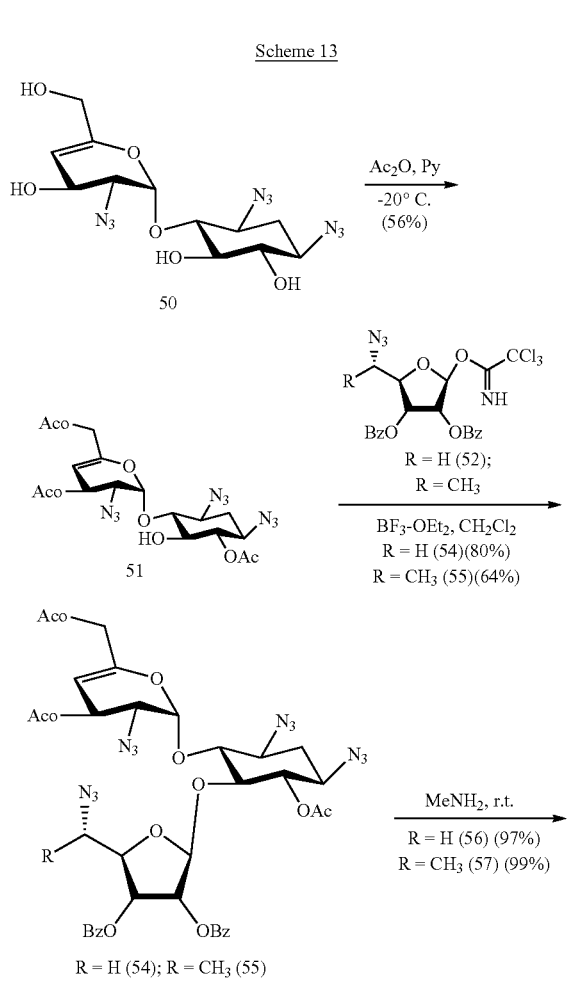

Scheme 13

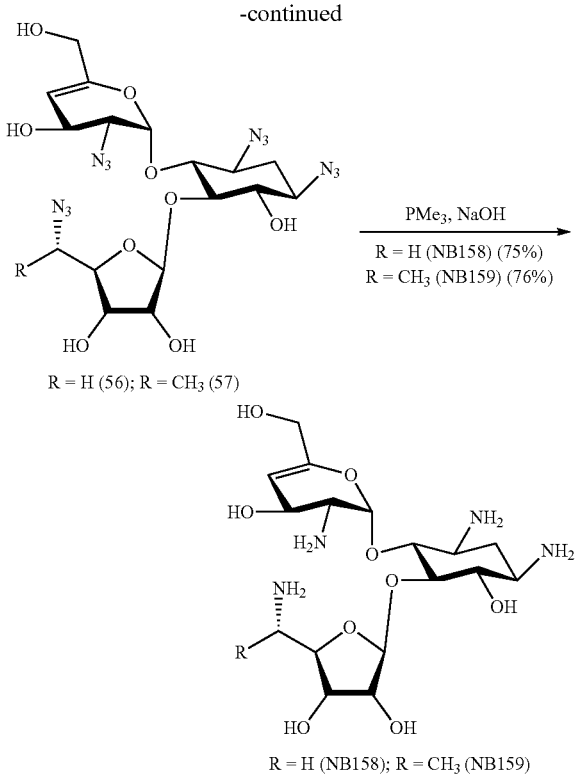

R = H (56); R = CH₃ (57)

R = H (NB158); R = CH₃ (NB159)

Briefly, the syntheses of pseudo-trisaccharides NB158 and NB159 were accomplished from the corresponding acceptor 51, which is obtained from regioselective acetylation of 50 at low temperature (−20° C.) using acetic anhydride in pyridine. Acceptor 51 upon glycosylation reaction with trichloroacetimidate donors 52 and 53 with catalytic amount of $BF_3OEt_2$ afforded the protected pseudo-trisaccharides 54 and 55 exclusively as corresponding β-anomers in excellent yields. The global ester deprotection of pseudo-trisaccharides 54 and 55 with methylamine and the Staudinger reaction to convert azides into corresponding amines resulted in Compounds NB158 and NB159.

Preparation of ((2S,3R,4S)-4-acetoxy-24(1R,2S,3S,4R,6S)-3-acetoxy-4,6-diazido-2-hydroxycyclohexyl)oxy)-3-azido-3,4-dihydro-2H-pyran-6-yl)methyl acetate (51): Compound 50 (700 mg, 1.82 mmol) was dissolved in anhydrous pyridine (8 mL) and cooled to −20° C. At this temperature, acetic anhydride (0.6 mL, 6.19 mmol) was added dropwise and the reaction was allowed to progress at −20° C. The reaction progress was monitored by TLC, which indicated completion after 17 hours. The reaction mixture was diluted with EtOAc, and extracted with aqueous solution of $NaHCO_3$, HCl (2%), saturated aqueous $NaHCO_3$, and brine. The combined organic layers were dried over anhydrous $MgSO_4$ and concentrated. The crude product was purified by silica gel column chromatography to afford 51 (520 mg, 56%).

¹H NMR (600 MHz, $CDCl_3$): 'Ring I': $δ_H$=5.62 (d, 1H, J=8.7, H-3), 5.59 (d, 1H, J=2.8 Hz, H-1), 5.03 (d, 1H, J=2.7 Hz, H-4), 4.52 (q, 2H, J=13.4 Hz, H-6, H-6), 3.77 (dd, 1H, J, =8.7, $J_2$=2.8 Hz, H-2); 'Ring II': $δ_H$=4.86 (t, 1H, J=9.9 Hz, H-6), 3.69 (td, 1H, $J_1$=9.5, $J_2$=4.3 Hz, H-5), 3.58 (t, 1H, J=9.5 Hz, H-4), 3.50 (ddd, 1H, $J_1$=12.6, $J_2$=10.0, $J_3$=4.6 Hz, H-1), 3.37 (ddd, 1H, $J_1$=12.6, $J_2$=9.8, $J_3$=4.6 Hz, H-3), 2.28 (dt, 1H, J, =13.5, $J_2$=4.6 Hz, H-2eq), 1.43 (ddd, 1H, J, =$J_2$=$J_3$=12.6 Hz, H-2ax); The additional peaks in the spectrum were identified as follow: $δ_H$=2.17 (s, 3H, $CH_3$), 2.12 (s, 3H, $CH_3$), 2.10 (s, 3H, $CH_3$).

¹³C NMR (150 MHz, $CDCl_3$): $δ_C$=170.9 ($CH_3$—CO), 170.4 ($CH_3$—CO), 170.4 ($CH_3$—CO), 148.2 (C5'), 99.1 (C4'), 98.8 (C1'), 83.1 (C4), 75.7 (C6), 74.7 (C5), 67.4 (C3'), 62.4 (C6'), 59.7 (C2'), 59.1 (C3), 58.0 (C1), 32.6 (C2), 21.1 ($CH_3$), 20.9 ($CH_3$), 20.9 ($CH_3$).

Preparation of Glycosylation product (54): Anhydrous $CH_2Cl_2$ (15 mL) was added to a powdered, flame-dried 4 Å molecular sieves (2.0 grams), followed by the addition of acceptor 51 (270 mg, 0.53 mmol) and donor 52 (1.115 gram, 2.11 mmol). The reaction mixture was stirred for 10 minutes at room temperature and was then cooled to −30° C. At this temperature, catalytic amount of $BF_3.Et_2O$ (0.1 ml) was added and the mixture was stirred at −30° C. and the reaction progress was monitored by TLC, which indicated the completion after 60 minutes. The reaction mixture was diluted with ethyl acetate and washed with saturated $NaHCO_3$ and brine. The combined organic layer was dried over $MgSO_4$, evaporated and subjected to column chromatography (EtOAc/Hexane) to obtain Compound 54 (370 mg) in 80% yield.

¹H NMR (600 MHz, $CDCl_3$): 'Ring I': $δ_H$=5.69 (d, 1H, J=2.3, H-1), 5.43 (dd, 1H, J, =6.4, $J_2$=4.0 Hz, H-3), 5.07 (d, 1H, J=3.3 Hz, H-4), 4.55 (q, 2H, J=13.3 Hz, H-6, H-6), 3.92 (dd, 1H, $J_1$=6.8, $J_2$=2.3 Hz, H-2); 'Ring II': $δ_H$=5.0 (t, 1H, J=10.1 Hz, H-6), 3.87 (t, 1H, J=9.4 Hz, H-5), 3.79 (t, 1H, J=9.6 Hz, H-4), 3.49 (ddd, 1H, $J_1$=12.2, $J_2$=10.0, $J_3$=4.3 Hz, H-1), 3.43 (ddd, 1H, $J_1$=12.1, $J_2$=9.8, $J_3$=4.5 Hz, H-3), 2.34-2.22 (m, 1H, H-2eq), 1.45 (ddd, 1H, $J_1$=$J_2$=$J_3$=12.7 Hz, H-2ax); 'Ring III': $δ_H$=5.56 (d, 1H, J=1.1 Hz, H-1), 5.55-5.53 (m, 1H, H-2), 5.44 (dd, 1H, $J_1$=6.8, $J_2$=5.3 Hz, H-3), 4.57-4.49 (m, 1H, H-4), 3.66 (dd, 1H, $J_1$=13.5, $J_2$=3.6 Hz, H-5), 3.56 (dd, 1H, $J_1$=13.3, $J_2$=6.0 Hz, H-5); The additional peaks in the spectrum were identified as follow: $δ_H$=7.93 (t, 2H, J=4.2 Hz, Ar), 7.88 (dd, 2H, $J_1$=8.3, $J_2$=1.2 Hz, Ar), 7.59-7.50 (m, 2H, Ar), 7.39 (t, 2H, J=7.9 Hz, Ar), 7.34 (t, 2H, J=7.9 Hz, Ar), 2.29 (s, 3H, $CH_3$), 2.10 (s, 3H, $CH_3$), 2.09 (s, 3H, $CH_3$).

¹³C NMR (150 MHz, $CDCl_3$): $δ_C$=170.3 ($CH_3$—CO), 170.1 ($CH_3$—CO), 170.0 ($CH_3$—CO), 165.5 ($C_6H_5$—CO), 165.2 ($C_6H_5$—CO), 149.3 (C5'), 133.8 (Ar), 133.7 (Ar), 129.7 (Ar), 129.7 (Ar), 129.7 (Ar), 128.8 (Ar), 128.7 (Ar), 128.6 (Ar), 128.5 (Ar), 107.5 (C1"), 97.9 (C1'), 97.8 (C4'), 80.8 (C4", C4), 78.9 (C5), 74.7 (C2"), 73.9 (C6), 71.7 (C3'), 66.8 (C3"), 62.3 (C6'), 59.8 (C3), 59.3 (C2'), 58.4 (C1), 52.7 (C5"), 32.5 (C2), 21.1 ($CH_3$), 20.9 ($CH_3$), 20.8 ($CH_3$).

Preparation of Compound 56: The glycosylation product 54 (370 mg, 0.422 mmol) was treated with a solution of $MeNH_2$ (33% solution in EtOH, 15 mL) and the reaction progress was monitored by TLC (EtOAc/MeOH 85:15), which indicated completion after 12 hours. The reaction mixture was evaporated to dryness and was subjected to column chromatography (MeOH/EtOAc 2:8) to obtain the corresponding completely unprotected perazido derivative 56 (237 mg) in 97% yield.

¹H NMR (600 MHz, MeOD): 'Ring I': $δ_H$=5.83 (d, 1H, J=2.5, H-1), 5.02 (dd, 1H, J, =1.8, $J_2$=1.1 Hz, H-4), 4.35 (dd, 1H, J, =4.4, $J_2$=2.4 Hz, H-3), 4.05-3.94 (m, 2H, H-6, H-6), 3.53 (dd, 1H, J, =7.6, $J_2$=4.2 Hz, H-2); 'Ring II': $δ_H$=3.70 (t, 1H, J=9.7 Hz, H-4), 3.62 (t, 1H, J=9.1 Hz, H-5), 3.49-3.41 (m, 1H, H-3), 3.39 (dt, 1H, $J_1$=9.8, $J_2$=4.9 Hz, H-1), 3.37-3.34 (m, 1H, H-6), 2.12 (dt, 1H, J, =13.0, $J_2$=4.5 Hz, H-2eq), 1.23 (ddd, 1H, J, =$J_2$=$J_3$=12.5 Hz, H-2ax); 'Ring III': $δ_H$=5.37 (d, 1H, J=1.3 Hz, H-1), 4.16 (dd, 1H, J, =4.7, $J_2$=1.3 Hz, H-2), 4.10 (dd, 1H, J, =7.7, $J_2$=4.2 Hz, H-3), 4.02 (dd, 1H, J$_1$=7.0, J$_2$=2.7 Hz, H-4), 3.59 (dd, 1H, J, =13.3, J$_2$=3.2 Hz, H-5), 3.50 (dd, 1H, J$_1$=13.2, J$_2$=6.4 Hz, H-5);

$^{13}$C NMR (150 MHz, MeOD): δ$_C$=152.8 (C5'), 111.1 (C1"), 100.1 (C4'), 98.8 (C1'), 83.9 (C5), 82.4 (C4"), 79.7 (C4), 77.5 (C6), 76.2 (C2"), 72.4 (C3"), 65.3 (C3'), 64.0 (C2'), 62.1 (C6'), 61.9 (C1), 61.7 (C3), 54.2 (C5"), 33.5 (C2).

Preparation of NB158: To a stirred solution of compound 56 (237 mg, 0.438 mmol) in a mixture of THF (3 mL) and aqueous NaOH (1 mM, 5 mL), PMe$_3$ (1 M solution in THF, 3.5 mL, 40.1 mmol) was added. The progress of the reaction was monitored by TLC [CH$_2$Cl$_2$/MeOH/H$_2$O/MeNH$_2$ (33% solution in EtOH), 10:15:6:15], which indicated completion after 3 hours. The reaction mixture was purified by flash chromatography on a short column of silica gel. The column was washed with the following solvents: THF (100 mL), CH$_2$Cl$_2$ (100 mL), EtOH (50 mL), and MeOH (100 mL). The product was then eluted with the mixture of 5% MeNH$_2$ solution (33% solution in EtOH) in 80% MeOH. Fractions containing the product were combined and evaporated under vacuum. The pure product was obtained by passing the above product through a short column of Amberlite CG50 (NH$_4$$^+$ form). First, the column was washed with water, then the product was eluted with a mixture of 10% NH$_4$OH in water to yield NB158 (138 mg, 75%).

For storage and biological tests, NB158 was converted to its sulfate salt form as follow: The free base form was dissolved in water, the pH was adjusted to 6.7 with H$_2$SO$_4$ (0.1 N) and lyophilized to afford the sulfate salt of NB158.

$^1$H NMR (600 MHz, MeOD): 'Ring I': δ$_H$=5.40 (d, 1H, J=2.0, H-1), 5.01 (d, 1H, J=3.7 Hz, H-4), 4.04 (t, 1H, J=5.3 Hz, H-3), 4.0 (s, 2H, H-6, H-6), 3.09 (dd, 1H, =5.1, J$_2$=1.9 Hz, H-2); 'Ring II': δ$_H$=3.57-3.50 (m, 2H, H-4, H-5), 3.19 (t, 1H, J=9.1 Hz, H-6), 2.79 (ddd, 1H, J$_1$=12.5, J$_2$=9.3, J$_3$=4.3 Hz, H-3), 2.67 (ddd, 1H, J$_1$=11.8, J$_2$=9.9, J$_3$=4.1 Hz, H-1), 2.04 (dt, 1H, J, =8.3, J$_2$=6.2 Hz, H-2eq), 1.24 (ddd, 1H, J, =J$_2$=J$_3$=12.3 Hz, H-2ax); 'Ring III': δ$_H$=5.29 (s, 1H, H-1), 4.14 (d, 1H, J=5.4 Hz, H-2), 4.06-4.02 (m, 1H, H-3), 3.92-3.87 (m, 1H, H-4), 2.98 (dd, 1H, J, =13.0, =4.4 Hz, H-5), 2.84 (dd, 1H, J, =12.9, J$_2$=8.4 Hz, H-5);

$^{13}$C NMR (150 MHz, MeOD): δ$_C$=153.4 (C5'), 110.6 (C1"), 100.5 (C4', C1'), 84.9 (C5), 84.45 (C4), 84.41 (C4"), 78.9 (C6), 76.3 (C2"), 72.8 (C3"), 67.8 (C3'), 62.3 (C6'), 55.0 (C2'), 52.5 (C1), 51.4 (C3), 45.4 (C5"), 37.2 (C2).

Preparation of Glycosylation product (55): Anhydrous CH$_2$Cl$_2$ (15 mL) was added to a powdered, flame-dried 4 Å molecular sieves (2.0 grams), followed by the addition of acceptor 51 (265 mg, 0.520 mmol) and donor 53 (1.12 gram, 2.06 mmol). The reaction mixture was stirred for 10 minutes at room temperature and was then cooled to −30° C. At this temperature, catalytic amount of BF$_3$.Et$_2$O (0.1 ml) was added and the mixture was stirred at −30° C. and the reaction progress was monitored by TLC, which indicated the completion after 60 minutes. The reaction mixture was diluted with ethyl acetate and washed with saturated NaHCO$_3$ and brine. The combined organic layer was dried over MgSO$_4$, evaporated and subjected to column chromatography (EtOAc/Hexane) to obtain Compound 55 (295 mg) in 64% yield.

$^1$H NMR (600 MHz, CDCl$_3$): 'Ring I': δ$_H$=5.69 (d, 1H, J=2.4, H-1), 5.42 (dd, 1H, J, =6.7, J$_2$=3.8 Hz, H-3), 5.06 (d, 1H, J=3.0 Hz, H-4), 4.54 (q, 2H, J=13.3 Hz, H-6, H-6), 3.96 (dd, 1H, J, =6.8, J$_2$=2.5 Hz, H-2); 'Ring II': δ$_H$=4.99 (t, 1H, J=9.9 Hz, H-6), 3.87 (t, 1H, J=9.5 Hz, H-5), 3.78 (t, 1H, J=9.5 Hz, H-4), 3.50 (ddd, 1H, J$_1$=12.6, J$_2$=10.1, J$_3$=4.6 Hz, H-1), 3.41 (ddd, 1H, J$_1$=12.5, J$_2$=9.7, J$_3$=4.6 Hz, H-3), 2.28 (dt, 1H, J, =13.2, J$_2$=4.6 Hz, H-2eq), 1.44 (ddd, 1H, J, =J$_2$=J$_3$=12.7 Hz, H-2ax); 'Ring III': δ$_H$=5.58 (s, 1H, H-1), 5.54 (d, 1H, J=4.9 Hz, H-2), 5.44 (dd, 1H, J$_1$=7.5, J$_2$=5.1 Hz, H-3), 4.31 (dd, 1H, J, =7.1, J$_2$=6.0 Hz, H-4), 3.67 (p, 1H, J=6.7 Hz, H-5), 1.31 (d, 3H, J=6.8 Hz, 6-CH$_3$); The additional peaks in the spectrum were identified as follow: δ$_H$=7.89 (ddt, 4H, J$_1$=14.3, J$_2$=8.4, J$_3$=1.4 Hz, Ar), 7.57-7.50 (m, 2H, Ar), 7.40-7.32 (m, 4H, Ar), 2.35 (s, 3H, CH$_3$), 2.10 (s, 3H, CH$_3$), 2.08 (s, 3H, CH$_3$).

$^{13}$C NMR (150 MHz, CDCl$_3$): δ$_C$=170.3 (CH$_3$—CO), 170.2 (CH$_3$—CO), 170.1 (CH$_3$—CO), 165.5 (C$_6$H$_5$—CO), 165.0 (C$_6$H$_5$—CO), 149.3 (C5'), 133.76 (Ar), 133.71 (Ar), 129.75 (Ar), 129.69 (Ar), 128.8 (Ar), 128.66 (Ar), 128.61 (Ar), 128.5 (Ar), 107.2 (C1"), 97.88 (C1'), 97.87 (C4'), 80.7 (C4"), 81.0 (C4), 78.2 (C5), 74.6 (C2"), 73.7 (C6), 71.9 (C3'), 66.9 (C3"), 62.3 (C6'), 59.7 (C3), 59.5 (C2'), 58.8 (C5"), 58.4 (C1), 32.5 (C2), 21.08 (CH$_3$), 21.01 (CH$_3$), 20.8 (CH$_3$), 15.6 (6"-CH$_3$).

Preparation of Compound 57: The glycosylation product 55 (295 mg, 0.331 mmol) was treated with a solution of MeNH$_2$ (33% solution in EtOH, 15 mL) and the reaction progress was monitored by TLC (EtOAc/MeOH 85:15), which indicated completion after 12 hours. The reaction mixture was evaporated to dryness and was subjected to column chromatography (MeOH/EtOAc 2:8) to obtain the corresponding completely unprotected perazido derivative 57 (180 mg) in 99% yield.

$^1$H NMR (600 MHz, MeOD): 'Ring I': δ$_H$=5.91 (d, 1H, J=2.6, H-1), 5.06 (d, 1H, J=2.3 Hz, H-4), 4.42 (ddt, 1H, J$_1$=8.0, J$_2$=2.7, J$_3$=1.4, Hz, H-3), 4.07-3.99 (m, 2H, H-6, H-6), 3.55 (dd, 1H, J, =7.9, J$_2$=3.6 Hz, H-2); 'Ring II': δ$_H$=3.74 (t, 1H, J=9.6 Hz, H-4), 3.66 (t, 1H, J=9.0 Hz, H-5), 3.47 (ddd, 2H, J$_1$=12.1, J$_2$=8.2, J$_3$=3.3 Hz, H-1, H-3), 3.42-3.40 (m, 1H, H-6), 2.17 (dt, 1H, J, =13.2, J$_2$=4.4 Hz, H-2eq), 1.28 (ddd, 1H, J, =J$_2$=J$_3$=12.3 Hz, H-2ax); 'Ring III': δ$_H$=5.41 (d, 1H, J=1.9 Hz, H-1), 4.22-4.18 (m, 2H, H-2, H-3), 3.81 (dd, 1H, J, =9.2, J$_2$=3.2 Hz, H-4), 3.72-3.66 (m, 1H, H-5), 1.40 (d, 3H, J=6.8 Hz, 6-CH$_3$);

$^{13}$C NMR (150 MHz, MeOD): δ$_C$=152.5 (C5'), 110.5 (C1"), 100.3 (C4'), 98.6 (C1'), 86.3 (C4"), 83.4 (C4), 79.4 (C4), 77.4 (C6), 76.2 (C2"), 72.6 (C3"), 65.3 (C3'), 64.0 (C2'), 62.1 (C6'), 61.9 (C1), 61.7 (C3), 60.6 (C5"), 33.5 (C2), 16.0 (6"-CH$_3$).

Preparation of NB159: To a stirred solution of Compound 57 (180 mg, 0.324 mmol) in a mixture of THF (3 mL) and aqueous NaOH (1 mM, 5 mL), PMe$_3$ (1 M solution in THF, 3.5 mL, 40.1 mmol) was added. The progress of the reaction was monitored by TLC [CH$_2$Cl$_2$/MeOH/H$_2$O/MeNH$_2$ (33% solution in EtOH), 10:15:6:15], which indicated completion after 3 hours. The reaction mixture was purified by flash chromatography on a short column of silica gel. The column was washed with the following solvents: THF (100 mL), CH$_2$Cl$_2$ (100 mL), EtOH (50 mL), and MeOH (100 mL). The product was then eluted with the mixture of 5% MeNH$_2$ solution (33% solution in EtOH) in 80% MeOH. Fractions containing the product were combined and evaporated under vacuum. The pure product was obtained by passing the above product through a short column of Amberlite CG50 (NH$_4$$^+$ form). First, the column was washed with water, then the product was eluted with a mixture of 10% NH$_4$OH in water to yield NB159 (110 mg, 76%).

For storage and biological tests, NB159 was converted to its sulfate salt form as follow: The free base form was dissolved in water, the pH was adjusted to 6.7 with H$_2$SO$_4$ (0.1 N) and lyophilized to afford the sulfate salt of NB159.

$^1$H NMR (600 MHz, MeOD): 'Ring I': δ$_H$=5.39 (s, 1H, H-1), 5.01 (d, 1H, J=3.4 Hz, H-4), 4.02 (t, 1H, J=4.0 Hz, H-3), 4.0 (d, 2H, J=2.7 H-6, H-6), 3.07 (d, 1H, J=6.2 Hz, H-2); 'Ring II': $\delta_H$=3.54 (dd, 2H, J, =20.3, $J_2$=10.7 Hz, H-4, H-5), 3.18 (t, 1H, J=9.3 Hz, H-6), 2.79 (ddd, 1H, $J_1$=12.8, $J_2$=6.9, $J_3$=4.0 Hz, H-3), 2.67 (ddd, 1H, $J_1$=9.6, $J_2$=5.1, $J_3$=3.9 Hz, H-1), 2.04 (dt, 1H, J, =13.1, $J_2$=4.3 Hz, H-2eq), 1.24 (ddd, 1H, J, =$J_2$=$J_3$=12.3 Hz, H-2ax); 'Ring III': $\delta_H$=5.29 (s, 1H, H-1), 4.11 (dd, 1H, $J_1$=14.7, $J_2$=6.2 Hz, H-2, H-3), 3.59-3.54 (m, 1H, H-4), 2.98 (t, 1H, J=5.8 Hz, H-5), 1.19 (d, 3H, J=7.9 Hz, 6-$CH_3$);

$^{13}$C NMR (150 MHz, MeOD): $\delta_C$=153.4 (C5'), 109.8 (C1"), 100.4 (C1'), 100.3 (C4'), 88.5 (C4"), 84.5 (C4), 84.0 (C5), 78.8 (C6), 76.4 (C2"), 72.9 (C3"), 67.8 (C3'), 62.4 (C6'), 55.0 (C2'), 52.6 (C1), 51.4 (C3), 51.3 (C5"), 37.2 (C2), 18.9 (6"-$CH_3$).

Readthrough Activity

Preliminary comparative in-vitro PTC suppression activity assays, performed essentially as described herein, showed that NB154 had readthrough activity almost 3.5 fold higher than paromamine and more or less similar activity as that of NB82.

Comparative in-vitro PTC suppression activity assays, performed essentially as described herein, further showed that NB158 and NB159 both exhibit a similar or slightly lower activity compared to their corresponding structurally related compounds NB30 and NB118.

However, the measured prokaryotic protein synthesis inhibition and subsequently the antibacterial activity of NB154, NB158 and NB159 are significantly lower than that of the corresponding paromamine, NB30, and NB118, as shown in Table 6 below, suggesting that these compounds are likely to exhibit extremely low toxicity.

TABLE 6

| Compound | Translation Inhibition | | Antibacterial activity MIC (µg/mL) | |
|---|---|---|---|---|
| | $IC_{50}^{Euk}$ (µM) | $IC_{50}^{Pro}$ (µM) | E. coli R477/100 | B. subtilis ATCC6633 |
| Paro. | 760 ± 79 | 14 ± 1.2 | — | — |
| NB154 | 375.94 ± 38.6 | 82.3 ± 11.93 | >384 | >384 |
| NB30 | 31 ± 4 | 0.45 ± 0.03 | 790 | 100 |
| NB158 | 70.7 ± 2.4 | 36.4 ± 3.5 | >192 | 192 |
| NB118 | 15.5 ± 1.3 | 1.9 ± 0.2 | 2659 | 83 |
| NB159 | 47.9 ± 3.3 | 134.5 ± 2.8 | >192 | 192 |

Example 7

Multi-Esterified Exemplary Compounds According to Some Embodiments of the Present Invention An additional chemical modification on previously described aminoglycosides was introduced with the aim of improving cellular permeability. This modification involved the multi esterification of two or more hydroxy groups of the aminoglycoside, to generate a pro-drug type compound. The rational of this strategy was (i) that attaching any hydrophobic R-group to the compound will improve its lipophylicity and as such increase the cell probability and uptake; (ii) that intracellular esterases will hydrolyze the pro-drug to regenerate the active drug; and (iii) that the pharmacokinetic properties of the desired pro-drug could be improved.

Initially, three multi-esterified derivatives of G418 were synthesized: the polybenzoate derivative, Bz-G418, polyisobutyrate derivative, iBut-G418, and polyacetate derivative, Ac-G418. Bz-NB124 was then also synthesized using the same synthetic protocol. Scheme 14 below Presents the chemical structures of these compounds.

Scheme 14

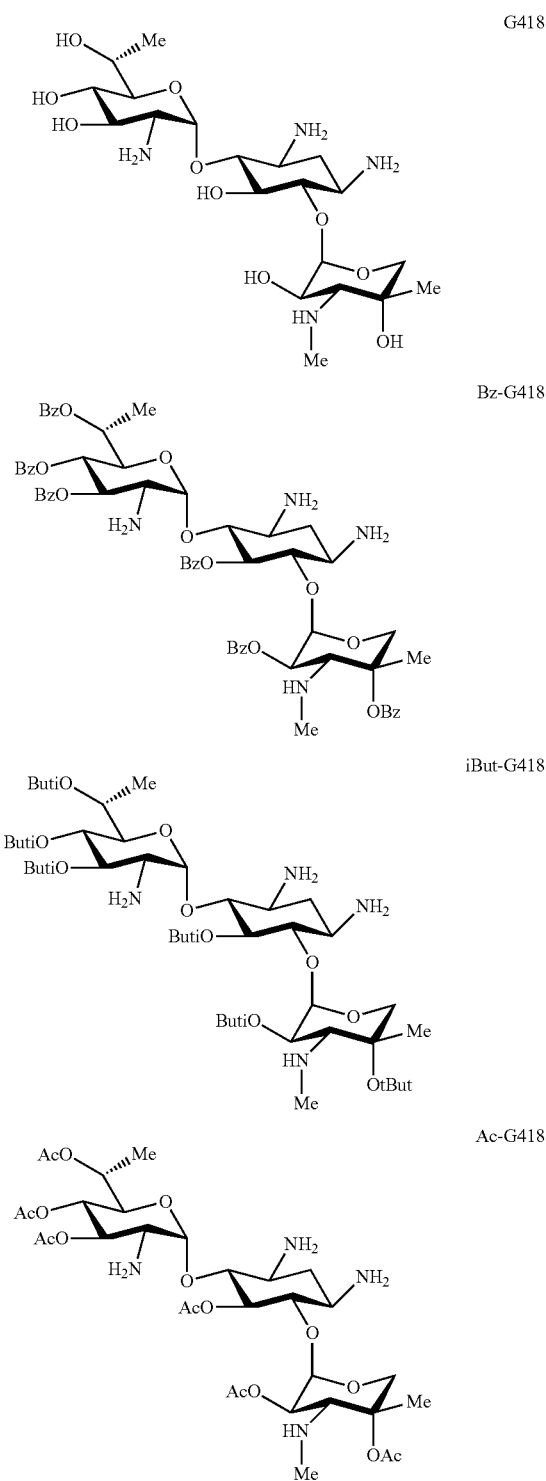

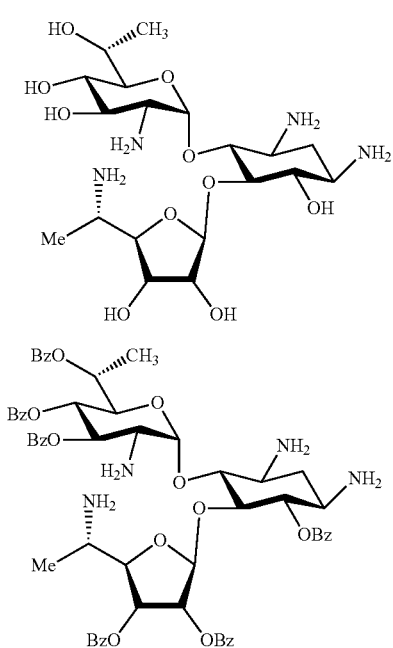

NB124

Bz-NB124

Syntheses of multi-esterified G418 Compounds:

Syntheses of the final compounds 63, 65 and 67 (Bz-G418, iBut-G418 and Ac-G418, respectively) were performed from the commercial G418 and are illustrated in Scheme 15.

Scheme 15

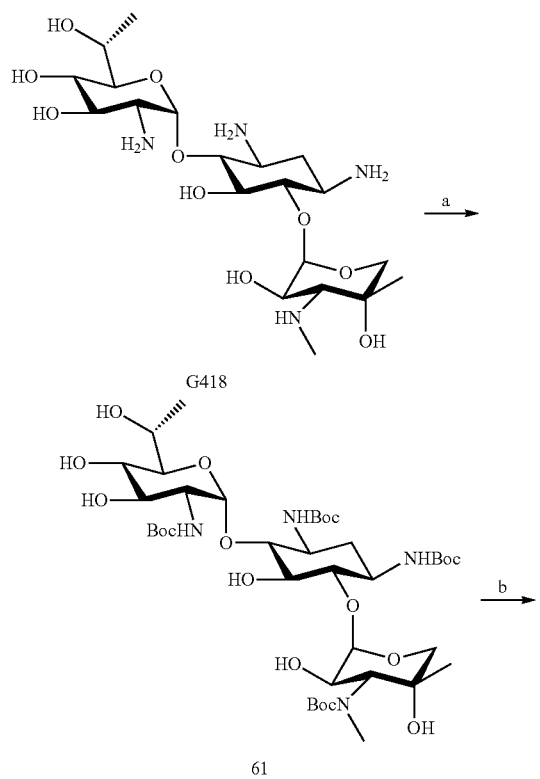

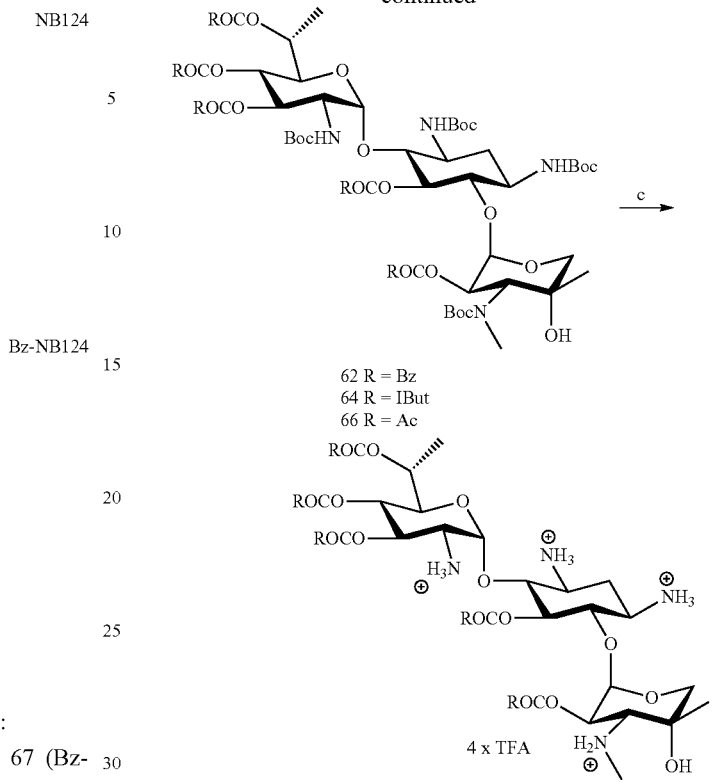

62 R = Bz
64 R = IBut
66 R = Ac

63 R = Bz
65 R = IBut
67 R = Ac

Reagents and conditions:
(a) Boc$_2$O, H$_2$O/MeOH, Et$_3$N, 50° C., 57%
(b) RCOCl, Py, 4-DMAP, 72%
(c) TFA, DCM, 72%.

First, G418 was subjected to Boc protection on its free amine groups to thereby obtain compound 61, which serves as an intermediate for later esterification derivatives and Boc deprotection steps via the TFA. The choice of the Boc protecting strategy is derived from the need to perform further selective deprotection without modifying the ester functional groups. The resulting final Compounds 63, 65 and 67 are converted to TFA-addition salts, which prevent the amines to react with the ester functionality.

Reaction of G418 and Di-tert-butyl dicarbonate yielded a mixture of per- and three-bocylated products, from which the per-bocylated product 61 was isolated via column chromatography. After the isolation of compound 61, the synthesis was divided to three different synthetic paths (see, Scheme 15). Esterification reactions of compound 61 with Benzoyl chloride, Acetyl chloride and Isobutyryl chloride were performed separately, to obtain the compounds 62, 64, and 66, respectively. Compound 62 was obtained upon heating the reaction mixture at 50° C. The esterification reaction was followed by removal of the Boc protecting groups by TFA, to thereby afford Compounds 63, 65 and 67. In all the obtained compounds the 4″ hydroxyl remained free, presumably due to a lower reactivity of the tertial hydroxyl.

Preparation of Compound 61: To a stirred solution of G418 (5 grams, 10.06 mmol) in 20 mL MeOH:H$_2$O (1:1), Et$_3$N (120 mmol) was added dropwise followed by addition of Di-tert-butyl dicarbonate (13.095 grams, 60 mmol). The reaction mixture was heated to 50° C. and allowed to stir overnight. The propagation of the reaction was monitored by TLC [MeOH/EtOAc, 1:9], which indicated completion after 24 hours. Thereafter, MeOH was evaporated and the remaining aqueous solution was extracted with EtOAc, washed with brine and dried over MgSO$_4$. Column chromatography of the residue (EtOAc/Hexane, 100% EtOAc) afforded Compound 1 as a white solid (3.96 grams, 57%).

$^1$H NMR (500 MHz, MeOD): δ=5.45 (d, 1H, J=9.6 Hz, H-1'), 5.21 (d, 1H, J=2.3 Hz, H-1"), 4.25-4.01 (m, 4H), 3.79 (dd, J=9.9, 2.8 Hz, 1H), 3.63 (t, J=8.4 Hz, 1H), 3.47 (m, 6H), 3.24-3.17 (m, 1H) 2.94 (s, 3H, NCH3-C3"), 2.14-1.92 (m, 1H, H-2), 1.44 (m, 4H, H-2, CH3-C4"), 1.24 (d, J=6.2 Hz, 3H). Additional peaks in the spectrum were identified as follow: δ 1.44 (m, 36H, Boc).

$^{13}$C NMR (126 MHz, MeOD): δ=159.30 (Carbamate), 159.03 (Carbamate), 158.62 (Carbamate), 158.05 (Carbamate), 100.08 (C-1"), 99.09 (C-1'), 82.33, 81.27 (ROC (CH$_3$)$_3$), 80.84 (ROC(CH$_3$)$_3$), 80.20 (ROC(CH$_3$)$_3$), 77.19 (ROC(CH$_3$)$_3$), 75.02, 74.71, 73.70, 73.52, 73.26, 71.08, 70.93, 68.70, 66.14, 61.53, 60.20, 59.00, 56.80, 28.85 (ROC (CH$_3$)$_3$), 28.84 (ROC(CH$_3$)$_3$), 28.84 (ROC(CH$_3$)$_3$), 28.83 (ROC(CH$_3$)$_3$), 28.83 (ROC(CH$_3$)$_3$), 28.82 (ROC(CH$_3$)$_3$), 28.79 (ROC(CH$_3$)$_3$), 28.74 (ROC(CH$_3$)$_3$), 22.58, 22.14.

MALDI TOFMS: calculated for C$_{40}$H$_{72}$N$_4$O$_{18}$ ([M+Na]+) m/e 919.48; measured m/e 919.79.

Preparation of Compound 62: Compound 61 (0.6 gram, 0.668 mmol) was dissolved in anhydrous pyridine (15 mL). The solution was cooled in an ice bath under stirring and benzoyl chloride (3 mL, 8.02 mmol) was added dropwise. The ice bath was removed, 4-DMAP (cat.) was added, and the reaction mixture was heated to 60° C. and left overnight. The progress of the reaction was monitored by TLC (EtOAc/Hexane 5:5). After completion of the reaction as indicated by TLC, the reaction mixture was diluted with EtOAc and washed with 5% HCl solution, NaHCO$_3$ and brine. The combined organic layer was dried over MgSO$_4$, evaporated and subsequently subjected to Column chromatography of the residue (EtOAc/Hexane, 4:6) to thereby afford Compound 62 as a white solid (0.687 gram, 72%).

$^1$H NMR (500 MHz, CDCl$_3$): 'Ring I': δ=5.49 (d, 1H, J=4.9 Hz, H-1), 4.89-4.77 (m, 2H, H-3, H-4), 4.69-4.31 (m, 1H, H-6), 4.01 (dd, 1H, J=9.8, 3.3 Hz, H-5), 3.72 (dd, 1H, J=11.4, 3.1 Hz, H-2), 1.57-0.63 (m, 3H, H-7). 'Ring II': δ=5.45 (dd, 1H, J=7.6, 3.5 Hz, H-4), 5.19 (dd, 1H, J=14.8, 4.8 Hz, H-5), 4.08-3.96 (m, 1H, H-6), 3.24-2.98 (m, 2H, H-1, H-3), 1.92-1.66 (m, 1H, H-2 eq), 0.57-0.63 (m, 1H, H-2 ax) 'Ring III': δ=5.47 (dd, 1H, J=7.9, 1.5 Hz, H-2), 5.32 (d, 1H, J=4.0 Hz, H-1), 4.43 (dd, 1H, J=11.6, 1.7 Hz, H-3), δ3.44 (d, 1H, J=12.9 Hz, H-5), 2.89 (s, 3H, NCH$_3$—C3"), 2.57 (d, 1H, J=13.2 Hz, H-5), 1.57-0.63 (m, 3H, CH$_3$—C4"). Additional peaks in the spectrum were identified as follow: δ=8.13-7.20 (m, 25H, Ph), 1.57-0.63 (m, 36H, Boc).

$^{13}$C NMR (126 MHz, CDCl$_3$): δ=165.83 (C=O), 165.75 (C=O), 165.34 (C=O), 165.12 (C=O), 165.07 (C=O), 155.00 (Carbamate), 154.84 (Carbamate), 154.73 (Carbamate), 154.67 (Carbamate), 133.76 (Ph), 133.66 (Ph), 133.58 (Ph), 133.41 (Ph), 133.38 (Ph), 133.22 (Ph), 133.12 (Ph), 132.95 (Ph), 132.90 (Ph), 130.15 (Ph), 130.03 (Ph), 129.99 (Ph), 129.96 (Ph), 129.90 (Ph), 129.77 (Ph), 129.41 (Ph), 129.30 (Ph), 128.79 (Ph), 128.75 (Ph), 128.67 (Ph), 128.61 (Ph), 128.54 (Ph), 128.32 (Ph), 128.23 (Ph), 128.03 (Ph), 98.12 (C-1"), 96.84 (C-1'), 80.18 (C-5), 79.88 (ROC (CH$_3$)$_3$), 79.76 (ROC(CH$_3$)$_3$), 79.52 (ROC(CH$_3$)$_3$), 79.44 ROC(CH$_3$)$_3$), 79.43 (ROC(CH$_3$)$_3$), 79.36 (C-6'), 78.54 (C-5') 75.84 (C-6), 73.03 (C-4'), 72.39 (C-2"), 70.75 (C-4'), 70.04 (C-3'), 69.05 (C-4) 69.20 (C-5"), 55.67 (s), 54.80 (C-3"), 53.37 (s), 52.89 (C-3), 52.50 (C-1), 49.15 (C-2'), 49.13 (s), 49.02 (s), 41.26 (NCH3-C3"), 31.54 (s), 30.32 (s), 29.62 (s), 28.44 (Boc), 28.21 (Boc), 28.20 (Boc), 28.18 (ROC(CH$_3$)$_3$), 28.15 (ROC(CH$_3$)$_3$), 28.09 (ROC(CH$_3$)$_3$), 28.02 (ROC(CH$_3$)$_3$), 27.89 (ROC(CH$_3$)$_3$), 27.88 (ROC (CH$_3$)$_3$), 27.86 (C-6'-CH$_3$), 22.29, 20.84 (C-4"-CH$_3$).

MALDI TOFMS: calculated for C$_{75}$H$_{92}$N$_4$O$_{23}$ ([M+Na]+) m/e 1440.55; measured m/e 1440.41.

Preparation of G418-Bz (63): Compound 62 (0.687 gram, 0.523 mmol) was dissolved in freshly distilled DCM (7 mL), cooled on ice bath and TFA (2 ml) was added dropwise. The reaction mixture was allowed to attain room temperature. Propagation of the reaction was monitored by TLC (Et$_3$N/MeOH 1:9), and indicated the completion of the reaction after 4 hours. The reaction mixture was thereafter evaporated to dryness to yield G418-Bz. For storage and biological tests, G418-Bz was dissolved in water and methanol and lyophilized to afford the TFA salt of G418-Bz (0.511 gram, 72%).

$^1$H NMR (500 MHz, MeOD): 'Ring I': δ=5.72 (dd, 1H, J=7.6, 4.8 Hz, H-3), 5.60 (dd, 1H, J=6.7, 6.0 Hz, H-4), 5.47 (bs, 1H, H-1), 5.40-5.36 (m, 1H, H-6), 4.47 (dd, 1H, J=5.9, 4.6 Hz, H-5), 3.76 (dd, 1H, J=3.7, 1.6 Hz, H-2), 1.35 (d, 3H, J=3.6 Hz, H-7). 'Ring II': δ=5.64 (d, 1H, J=8.1 Hz, H-5), 4.55 (s, 1H, H-4), 4.30 (s, 1H, H-6), δ3.86-3.67 (m, 2H, H-3, H-1) 2.55 (dt, 1H, J=12.5, 4.2 Hz, H-2 eq), 2.12 (q, 1H, J=12.8 Hz, H-2 ax). 'Ring III': δ=5.34 (dd, 1H, J=10.2, 3.3 Hz, H-2), 5.29 (d, 1H, J=4.1 Hz, H-1), 3.82 (d, 1H, J=10.3 Hz, H-3), δ 3.76 (d, 1H, J=15.1 Hz, H-5), 3.13 (d, 1H, J=12.2 Hz, H-5), δ 2.89 (s, 1H), 2.89 (s, 3H, NCH3-C3"), 1.26 (s, 3H, CH3-C4"). Additional peaks in the spectrum were identified as follow: δ=8.16 (d, 2H J=7.5 Hz, Ph), 8.03 (dd, 5H, J=16.4, 7.5 Hz, Ph), 7.93 (d, 2H, J=7.7 Hz, Ph), 7.70 (dd, 3H, J=13.9, 7.5 Hz, Ph), 7.57 (dt, 6H, J=12.2, 5.8 Hz, Ph), 7.47-7.25 (m, 10H, Ph).

$^{13}$C NMR (126 MHz, MeOD): δ=167.17 (C=O), 166.89 (C=O), 166.84 (C=O), 166.42 (C=O), 166.41 (C=O), 163.61 (TFA), 163.33 (TFA), 163.06 (TFA), 162.78 (TFA), 135.21 (Ph), 134.93 (Ph), 134.89 (Ph), 134.78 (Ph), 134.56 (Ph), 134.22 (Ph), 134.03 (Ph), 131.00 (Ph), 130.98 (Ph), 130.95 (Ph), 130.85 (Ph), 130.76 (Ph), 130.71 (Ph), 130.59 (Ph), 130.47 (Ph), 130.33 (Ph), 130.22 (Ph), 129.95 (Ph), 129.76 (Ph), 129.67 (Ph), 129.63 (Ph), 129.58 (Ph), 129.51 (Ph), 129.46 (Ph), 104.39 (C-1"), 99.84 (C-1'), 83.40 (C-5), 76.05 (C-5'), 71.73 (C-2"), 71.64 (C-3') 70.77 (C-5), 70.44 (C-6), 69.05 (C-4) 68.50 (C-4'), 63.51 (C-5"), 52.46 (C-3) 50.18 (C-3"), 50.10 (C-2'), 49.62 (C-1) 36.05 (NCH3-C3"), 29.15 (C-2), 22.27 (C-6'-CH$_3$), 16.94 (C-4"-CH$_3$).

MALDI TOFMS: calculated for C$_{55}$H$_{60}$N$_4$O$_{15}$ ([M+H]$^+$) m/e 1017.08; measured m/e 1018.18.

Preparation of Compound 64: Compound 61 (0.5 gram, 0.557 mmol) was dissolved in anhydrous pyridine (15 mL). The solution was cooled in an ice bath under stirring and isobutyryl chloride (0.7 ml, 6.684 mmol) was added dropwise. The ice bath was removed, 4-DMAP (cat.) was added, the reaction mixture was heated to 60° C. and left overnight. The Propagation of the reaction was monitored by TLC (EtOAc/Hexane 4:6). After the completion of the reaction as indicated by TLC, the reaction mixture was diluted with EtOAc and washed with 5% HCl solution, NaHCO$_3$ and brine. The combined organic layer was dried over MgSO$_4$ and evaporated. Column chromatography of the residue (EtOAc/Hexane, 3:7) afforded Compound 64 as a white solid (0.490, 75%).

$^1$H NMR (500 MHz, CDCl$_3$): 'Ring I': δ=5.27 (dd, 1H, J=11.8, 3.5 Hz, H-3), 5.05 (d, 1H, J=3.7 Hz, H-1), 5.00-4.96 (m, 2H, H-6, H-4), 4.59-4.54 (m, 1H, H-5), 3.27 (d, 1H, J=11.9 Hz, H-2), 1.45-1.01 (m, 3H, H-7). 'Ring II': δ=4.94

(dd, 1H, J=9.7, 8.3 Hz, H-5), 4.81-4.73 (m, 1H, H-6), 4.24-4.18 (m, 1H, H-4), 4.00-3.90 (m, 1H, H-1, H-3), 1.45-1.01 (m, 2H, H-2 eq, H-2 ax). 'Ring III': δ=4.98 (d, 1H, J=4.7 Hz, H-1), 4.89-4.85 (m, 1H, H-2), 3.55 (dd, 1H, J=11.4, 1.4 Hz, H-3), 3.38 (dd, 1H, J=4.0, 2.5 Hz, H-5), 3.32 (dd, 1H, J=13.6, 1.6 Hz, H-5), 2.96 (s, 3H, $NCH_3$—C3″), 1.45-1.01 (m, 3H, $CH_3$—C4″). Additional peaks in the spectrum were identified as follow: δ=6.76 (d, 1H, J=1.3 Hz, RNHCOOR), 5.85 (d, 1H, J=2.1 Hz, RNHCOOR), 5.83 (d, 1H, J=2.3 Hz, RNHCOOR), 5.72 (d, 1H, J=4.3 Hz, RNHCOOR), 1.45-1.01 (m, 71H, Boc, i-But).

$^{13}$C NMR (126 MHz, $CDCl_3$): δ=175.90 (C═O), 175.50 (C═O), 175.45 (C═O), 175.39 (C═O), 174.73 (C═O), 157.49 (Carbamate), 156.54 (Carbamate), 156.16 (Carbamate), 155.79 (Carbamate), 99.41 (C-1″), 99.01 (C-1′), 83.09 (s), 82.29 (s), 81.73 (C-6), 79.93 ($ROC(CH_3)_3$), 79.79 ($ROC(CH_3)_3$), 79.76 ($ROC(CH_3)_3$), 79.64 ($ROC(CH_3)_3$), 79.45 (C-4), 77.40 (s), 75.69 (s), 74.74 (C-5), 74.42 (s), 73.50 (s), 71.20 (C-6′), 71.10 (s), 70.59 (C-3″), 70.51 (s), 70.10 (C-5″), 69.73 (s), 69.05 (C-4), 68.98 (s), 68.91 (C-2″), 68.37 (C-4′), 67.47 (s), 67.25 (C-3′), 65.38 (C-2′), 55.72 (s), 54.52 (C-5′), 52.60 (s), 52.53 (d, J=17.3 Hz), 50.83 (C-3), 49.23 (C-1), 41.20 (N—$CH_3$), 34.17 (i-But), 34.10 (i-But), 34.04 (i-But), 33.98 (i-But), 33.74 (i-But), 29.91 (s), 29.61 (C-2), 28.40 (i-But), 28.36 (i-But), 28.34 (i-But), 28.30 (i-But), 28.26 (i-But), 28.18 (i-But), 22.90 (s), 18.83 ($ROC(CH_3)_3$), 18.73 ($ROC(CH_3)_3$), 18.72 ($ROC(CH_3)_3$), 18.61 ($ROC(CH_3)_3$), 18.58 ($ROC(CH_3)_3$), 18.49 ($ROC(CH_3)_3$), 18.34 (C-6′-$CH_3$), 17.91 (C-4″-$CH_3$).

MALDI TOFMS: calculated for $C_{60}H_{102}N_4O_{23}$ ([M+Na]+) m/e 1270.46; measured m/e 1270.42.

Preparation of G418-i-But (65): Compound 64 (0.490 gram, 0.42 mmol) was dissolved in freshly distilled DCM (10 mL), cooled on ice bath, TFA (2 mL) was added dropwise, and the reaction mixture was allowed to attain room temperature. Propagation of the reaction was monitored by TLC ($Et_3$N/MeOH 1:9), which indicated the completion of the reaction after 4 hours. The reaction mixture was evaporated to dryness to yield G418-i-But. For storage and biological tests, G418-i-But was dissolved in water and methanol and lyophilized to afford the TFA salt of G418-i-But. (0.408 gram, 78%).

$^1$H NMR (500 MHz, MeOD): 'Ring I': δ=5.38 (dd, 1H, J=8.8, 6.2 Hz, H-3), 5.25 (d, 1H, J=5.9 Hz, H-1), 5.23-5.16 (m, H, H-6), 5.07 (dd, 1H, J=6.6, 6.1 Hz, H-4), 4.09 (dd, 1H, J=6.0, 5.3 Hz, H-5), 3.62 (dd, 1H, J=4.6, 2.0 Hz, H-2), 1.31 (d, 3H, J=6.7 Hz, H-7). 'Ring II': δ=5.50 (dd, 1H, J=11.3, 7.3 Hz, H-5), 4.21-4.14 (m, 2H, H-4, H-6), 3.70 (m, 2H, H-1.H-3), 2.61-2.54 (m, 1H, H-2, eq), 2.17 (ddd, J=12.69, 1H, H-2,ax). 'Ring III': δ=5.29 (d, 1H, J=3.1 Hz, H-1), 5.21 (dd, 1H, J=8.8, 2.7 Hz, H-2), 3.66 (d, 1H, J=9.7 Hz, H-3), 3.74 (d, 1H, J=13.0 Hz, H-5), 3.45 (d, 1H, J=12.5 Hz, H-5), 2.88 (s, 3H, NCH3-C3″), 1.38 (s, 3H, CH3-C4″). Additional peaks in the spectrum were identified as follow: δ=1.21 (m, 35H, i-But).

$^{13}$C NMR (126 MHz, MeOD): δ=177.35 (C═O), 177.3 (C═O 177.19 (C═O), 176.83 (C═O), 176.67 (C═O), 163.22 (TFA), 162.94 (TFA), 162.66 (TFA), 162.38 (TFA), 121.44 (TFA), 119.12 (TFA), 116.80 (TFA), 114.47 (TFA), 97.77 (C-1″), 92.81 (C-1′), 81.81 (C-6), 77.48 (C-4), 76.61 (C-5′), 74.59 (C-5), 70.03 (C-3′), 69.71 (C-6′), 69.24 (C-5″), 69.05 (C-4), 68.27 (C-2″), 67.26 (C-4′), 63.62 (C-3″), 51.66 (C-2′), 50.29 (C-3), 49.86 (C-1), 35.56 (NCH3-C3″), 35.22 (i-But), 35.18 (i-But), 34.93 (i-But), 34.87 (i-But), 34.80 (i-But), 28.61 (C-2), 27.71 (s), 23.19 (s), 19.27 (i-But), 19.24 (i-But), 19.18 (i-But), 19.16 (i-But), 19.10 (i-But), 18.98 (i-But), 18.72 (i-But), 18.67 (C-6′-$CH_3$), 16.20 (C-4″-$CH_3$).

MALDI TOFMS: calculated for $C_{36}H_{63}N_4O_{13}$ ([M+$H_2$O]+) m/e 777.9; measured m/e 777.54.

Preparation of Compound 66: Compound 61 (0.3 gram, 0.334 mmol) was dissolved in anhydrous pyridine (8 mL). The solution was cooled in an ice bath under stirring and acetyl chloride (0.3 ml, 4.008 mmol) was added dropwise. The ice bath was removed, 4-DMAP (cat.) was added, and the reaction was heated to 60° C. and left overnight. The Progress of the reaction was monitored by TLC (EtOAc/Hexane 6.5:4.5). After completion of the reaction as indicated by TLC, the reaction mixture was diluted with EtOAc and washed with 5% HCl solution, $NaHCO_3$ and brine. The combined organic layer was dried over $MgSO_4$ and evaporated. Column chromatography of the residue (EtOAc/Hexane, 5:5) afforded Compound 66 as a white solid (0.25 gram, 68%).

$^1$H NMR (500 MHz, $CDCl_3$): 'Ring I': δ=5.38 (d, 1H, J=11.5 Hz, H-1), 5.20 (dd, 1H, J=2.4, 1.3 Hz, H-3), 4.60 (dd, 1H, J=11.4, 3.5 Hz, H-4), 4.45 (dd, 1H, J=11.8, 1.3 Hz, H-4), 4.14-4.09 (m, 1H, H-5), 3.31 (dd, 1H, J=12.4, 1.0 Hz, H-2), 1.46-1.20 (m, 3H, H-7). 'Ring II': δ=3.95-3.68 (m, 3H, H-4, H-5, H-6), 3.65-3.20 (m, 2H, H-1, H-3), 2.73-2.49 (m, 1H, H-2), 2.46-2.26 (m, 1H, H-2). 'Ring III': δ=5.20-5.18 (m, 2H, H-1, H-2), 4.18-4.12 (m, 1H, H-3), 3.80-3.73 (m, 1H, H-5), 3.57-3.51 (m, 1H, H-5), 2.94 (s, 3H, NCH3-C3″), 1.46-1.20 (m, 3H, CH3-C4″). Additional peaks in the spectrum were identified as follow: δ=6.74 (s, 1H, RNHCOOR), 5.90 (s, 1H, RNHCOOR), 5.88 (s, 1H, RNHCOOR), 5.52 (s, 2H, RNHCOOR), 2.13-1.92 (m, 12H, Ac), 1.47-1.21 (m, 36H, Boc).

$^{13}$C NMR (126 MHz, $CDCl_3$): δ=170.76 (C═O), 170.59 (C═O), 169.70 (C═O), 169.31 (C═O), 157.65 (Carbamate), 156.98 (Carbamate), 156.42 (Carbamate), 155.63 (Carbamate), 99.48 (C-1″), 98.39 (C-1′), 85.88 (C-6), 82.50 (C-4), 80.04 (s), 79.95 ($ROC(CH_3)_3$), 79.80 ($ROC(CH_3)_3$), 79.64 ($ROC(CH_3)_3$), 79.38 ($ROC(CH_3)_3$), 79.29 (s), 75.66 (C-5), 74.32 (s), 71.89 (C-3′), 70.58 (C-2′), 70.35 (C-5′), 70.32 (C-2″), 70.29 (C-3″), 69.05 (C-4), 68.70 (C-6′), 60.35 (C-5″), 54.37 (C-4′), 50.28 (C-3), 50.08 (C-1), 41.19 (N—$CH_3$), 30.50 (C-2), 28.38 ($ROC(CH_3)_3$), 28.34 ($ROC(CH_3)_3$), 28.29 ($ROC(CH_3)_3$), 28.27 ($ROC(CH_3)_3$), 28.21 ($ROC(CH_3)_3$), 28.14 ($ROC(CH_3)_3$), 22.93 (s), 21.70 (C-4″-$CH_3$), 20.82 (Ac), 20.72 (Ac), 20.70 (Ac), 20.63 (Ac), 14.13 (C-6′-$CH_3$).

MALDI TOFMS: calculated for $C_{48}H_{80}N_4O_{22}$ ([M+Na]+) m/e 1088.16; measured m/e 1088.27.

Preparation of G418-Ac (67): Compound 66 (0.25 gram, 0.23 mmol) was dissolved in freshly distilled DCM (5 mL), cooled on ice bath and TFA (1 mL) was added dropwise. The reaction mixture was allowed to attain room temperature. Propagation of the reaction was monitored by TLC ($Et_3$N/MeOH 1:9), which indicated the completion of the reaction after 4 hours. The reaction mixture was evaporated to dryness to yield G418-Ac. For storage and biological tests, G418-Ac was dissolved in water and methanol and lyophilized to afford the TFA salt of G418-Ac (0.19 gram, 73%).

$^1$H NMR (500 MHz, MeOD): 'Ring I': δ=5.28 (d, 1H, J=3.8 Hz, H-1), 5.08 (dd, 1H, J=10.5, 9.3 Hz, H-3), 4.67 (dd, 1H, J=10.0, 8.8 Hz, H-4), 4.62-4.60 (m, 1H, H-6), 4.02 (dd, 1H, J=10.0, 1.5 Hz, H-5), 3.40 (dd, 1H, J=10.9, 3.7 Hz, H-2), 0.89 (d, 3H J=6.1 Hz, H-7′).). 'Ring II': δ=3.82-3.77 (m, 3H, H-4, H-5, H-6), 3.56-3.46 (m, 2H, H-1, H-3), 2.52 (dd, 1H, J=8.0, 4.0 Hz, H-2), 2.00-1.90 (m, 1H, H-2). 'Ring III':

δ=5.28 (d, 1H, J=4.2 Hz, H-1), 5.14 (dd, 1H, J=11.2, 3.1 Hz, H-2), 3.66 (d, 1H, J=11.0 Hz, H-3), 3.90 (d, 1H, J=6.9 Hz, H-5), 3.56-3.46 (m, 1H, H-52.76), (s, 3H, NCH$_3$—C3"), 1.26 (s, 3H, CH$_3$—C4"). Additional peaks in the spectrum were identified as follow: δ=2.08 (s, 3H, Acetate), 2.00 (s, 3H, Acetate), 1.97 (s, 3H, Acetate), 1.97 (s, 3H, Acetate).

$^{13}$C NMR (126 MHz, MeOD): δ=171.65 (carbonyl), 171.43 (carbonyl), 171.09 (carbonyl), 162.93 (TFA), 162.64 (TFA), 162.36 (TFA), 162.05 (TFA), 121.33 (TFA), 119.00 (TFA), 116.68 (TFA), 114.36 (TFA), 99.35 (C-1'), 97.99 (C-1"), 84.02 (C-6), 83.43 (C-4), 75.15 (C-5), 73.17 (C-5'), 70.85 (C-6'), 70.62 (C-2"), 70.16 (C-3'), 69.57 (C-4'), 69.09 (C-5"), 69.05 (C-4), 62.74 (C-3"), 53.44 (C-2'), 49.87 (C-3), 49.73 (C-1), 35.81 (N—CH$_3$), 29.19 (C-2), 22.05 (C-4"-CH$_3$), 21.04 (Acetate), 20.96 (Acetate), 20.69 (Acetate), 20.50 (Acetate), 13.81 (C-7').

MALDI TOFMS: calculated for C$_{28}$H$_{48}$N$_4$O$_{14}$ ([M+Na]+) m/e 664.32; measured m/e 664.32.

Synthesis of Bz-NB124:

An exemplary multi-esterified form of NB124, featuring benzyl esters and also referred to herein as NB124-Bz ester or Bz-NB124 was prepared as depicted in Scheme 16 below.

Scheme 16

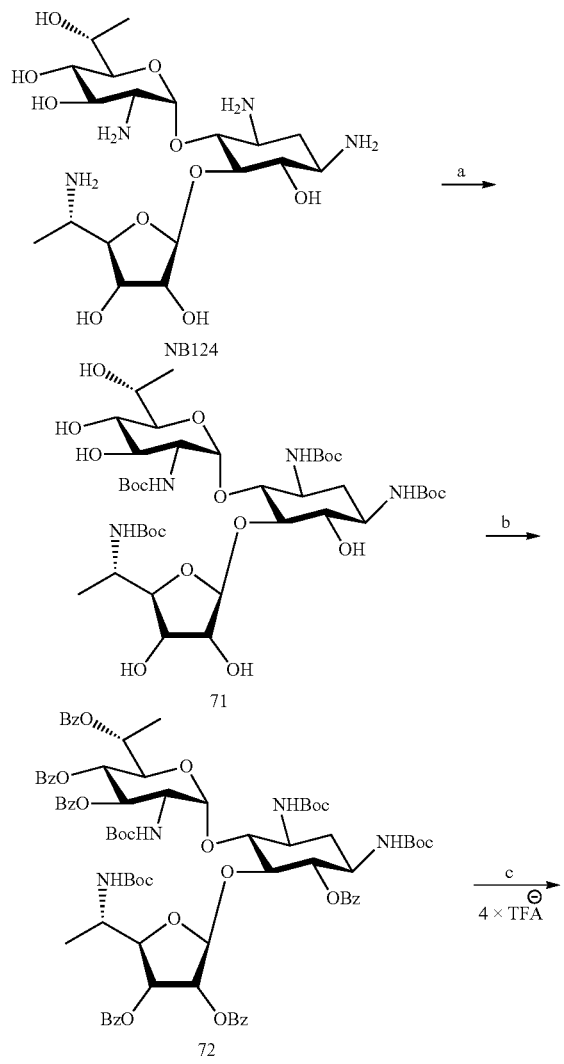

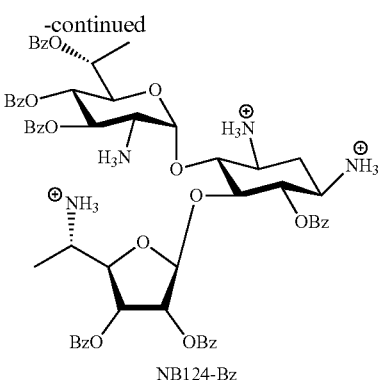

NB124-Bz

The starting material NB124 was synthesized by previously described [Kandasamy et al., J. Med. Chem. 2012]. NB124 as its free amine form was further modified by protecting all amines by Boc-protection yielding compound 71. Next, the secondary hydroxyls were converted to the corresponding benzoate esters, by treatment with benzoyl chloride, yielding compound 72. Finally, Boc-deprotection was performed by treatment with TFA, which resulted the desired compound NB124-Bz as the TFA salt.

Preparation of Compound 71: To a stirred solution of NB124 (0.5 gram, 1.036 mmol) in 10 mL MeOH:H$_2$O (1:1), Et$_3$N (8.289 mmol) was added dropwise followed by addition of Di-tert-butyl dicarbonate (4 grams, 18.648 mmol). The reaction was heated to 50° C. The propagation of the reaction was monitored by TLC [MeOH/EtOAc, 1:9], which indicated completion after 24 hours. Thereafter, MeOH was evaporated and the remaining aqueous solution was extracted with EtOAc, washed with brine and dried over MgSO$_4$. Column chromatography of the residue (EtOAc/Hexane, 100% EtOAc) afforded the Compound 71 as a white solid (0.580 gram, 60%).

$^1$H NMR (500 MHz, MeOD): δ=5.52 (s, 1H, H-1'), 5.16 (s, 1H, H-1"), 4.12 (m, 3H), 3.89 (dd, J=10.0, 3.0 Hz, 1H), 3.78 (d, J=6.3 Hz, 2H), 3.68-3.48 (m, 6H), 3.43 (dd, J=15.6, 7.4 Hz, 1H), 3.33-3.24 (m, 1H), 1.96 (d, J=15.6 Hz, 1H), 1.51-1.47 (m, 40H, Boc) 1.27 (dd, 6H, J=10.2, 4.0 Hz, C6'-CH$_3$, C5"-CH$_3$).

$^{13}$C NMR (126 MHz, MeOD): δ=157.27 (Carbamate), 157.03 (Carbamate), 156.85 (Carbamate), 156.78 (Carbamate), 109.99 (C-1"), 96.61 (C-1'), 86.23, 84.35, 82.32, 79.38, 78.78, 77.17, 74.09, 73.66, 72.83, 72.30, 70.49, 70.11, 69.28, 66.91, 62.86, 60.09, 55.20, 55.12, 51.03, 49.64, 34.47, 29.46, 29.31, 27.46 (Carbamate), 27.44 (Carbamate), 27.33 (Carbamate), 26.09, 26.07, 15.65, 13.04.

MALDI TOFMS: calculated for C$_{39}$H$_{70}$N$_4$O$_{18}$ ([M+Na]+) m/e 905.99; measured m/e 905.61.

Preparation of Compound 72: Compound 71 (0.195 gram, 0.129 mmol) was dissolved in anhydrous pyridine (8 mL). The solution was cooled in an ice bath under stirring and benzoyl chloride (0.2 ml, 1.552 mmol) was added dropwise. The ice bath was removed, 4-DMAP (cat.) was added, and the reaction was heated to 50° C. and left overnight. The Propagation of the reaction was monitored by TLC (EtOAc/Hexane 1:1). After completion of the reaction as indicated by TLC, the reaction mixture obtained was diluted with EtOAc and washed with 5% HCl solution, NaHCO$_3$ and brine. The combined organic layer was dried over MgSO$_4$ and evaporated. Column chromatography of the residue (EtOAc/Hexane, 1:1) afforded Compound 70 as a white solid (0.269 gram, 80%).

¹H NMR (500 MHz, CDCl₃): 'Ring I': δ=5.81 (d, 1H, J=4.1 Hz, H-1), 5.55 (dd, 1H J=10.5, 9.0 Hz, H-3), 5.49 (dd, 1H J=5.6, 4.3 Hz, H-4), 5.26-5.21 (m, 1H, H-6), 4.61 (dd, 1H, J=9.4, 2.1 Hz, H-5), 4.42 (dd, 1H, J=7.3, 1.1 Hz, H-2), 1.55 (d, 3H J=6.5 Hz, H-7). 'Ring II': δ=5.40 (dd, 1H, J=3.6, 2.0 Hz, H-4), 5.27 (dd, 1H, J=3.5, 1.4 Hz, H-5), 4.13-4.05 (m, 1H, H-6), 3.93-3.84 (m, 2H, H-1, H-3), 1.55 (dd, 1H, J=4.9, 1.1 Hz, H-2 eq), 1.24-1.20 (m, 1H, H-2 ax). 'Ring III': δ=5.39 (d, 1H, J=4.7 Hz, H-1), 5.28 (dd, 1H, J=12.8, 6.1 Hz, H-3), 5.10 (dd, 1H, J=9.5, 4.6 Hz, H-2), 3.76

3.64 (m, 1H, H-4), 1.55 (d, 1H, J=6.5 Hz, H-5), 1.22 (d, 3H, J=6.3 Hz, H-6). Additional peaks in the spectrum were identified as follow: δ=8.14-7.13 (m, 30H, Ph), 1.51 (s, 9H, Boc), 1.39 (s, 9H, Boc), 1.25 (s, 9H, Boc), 1.12 (s, 9H, Boc).

¹³C NMR (101 MHz, CDCl₃): δ=166.39 (C=O), 165.94 (C=O), 165.49 (C=O), 165.36 (C=O), 164.94 (C=O), 164.41 (C=O), 155.59 (Carbamate), 155.28 (Carbamate), 155.05 (Carbamate), 154.78 (Carbamate), 133.44 (Ph), 133.36 (Ph), 133.23 (Ph), 133.05 (Ph), 132.95 (Ph), 130.38 (Ph), 130.24 (Ph), 129.96 (Ph), 129.88 (Ph), 129.82 (Ph), 129.55 (Ph), 129.31 (Ph), 129.11 (Ph), 128.96 (Ph), 128.87 (Ph), 128.78 (Ph), 128.29 (Ph), 128.22 (Ph), 128.13 (Ph), 107.44 (C-1″), 97.30 (C-1′), 82.93 (C-6), 81.67, 80.03 (ROC(CH₃)₃), 79.56 (ROC(CH₃)₃), 79.40 (ROC(CH₃)₃), 79.19 (ROC(CH₃)₃), 78.32 (C-3), 75.77 (C-4), 75.68 (C-3″), 75.15 (C-5), 72.48 (C-4′), 70.02 (C-2″), 70.69 (C-6′), 70.07 (C-5′), 69.94 (C-3′), 60.33 (C-4″), 53.26 (C-2′), 50.2 (C-5″), 49.68 (C-3), 47.64 (C-1), 34.82 (C-2), 28.47 (ROC(CH₃)₃), 28.42 (ROC(CH₃)₃), 27.95 (ROC(CH₃)₃), 27.80 (ROC(CH₃)₃), 20.97 (C-7′), 17.73 (C-6″), 14.18 (C-6″).

MALDI TOFMS: calculated for $C_{81}H_{94}N_4O_{24}$ ([M+Na]+) m/e 1530.81; measured m/e 1530.81.

Preparation of NB124-Bz: Compound 72 (0.189 gram, 0.125 mmol) was dissolved in freshly distilled DCM (5 mL), cooled on ice bath and TFA (1 mL) was added dropwise. The reaction mixture was allowed to attain room temperature. Propagation of the reaction was monitored by TLC (Et₃N/MeOH 1:99), which indicated the completion of the reaction after 4 hours. The reaction mixture was evaporated to dryness to yield NB 124-Bz. For storage and biological tests, NB 124-Bz was dissolved in water and methanol and lyophilized to afford the TFA salt of NB 124-Bz (0.191 gram, 97%).

¹H NMR (500 MHz, MeOD): 'Ring I': δ=6.53 (d, 1H, J=3.8 Hz, H-1), 6.10 (dd, 1H J=10.6, 9.9 Hz, H-3), 5.76 (dd, 1H J=10.1, 9.2 Hz, H-4), 5.53-5.47 (m, 1H, H-5), 4.53 (dd, 1H, J=9.8, 3.9 Hz, H-5), 4.09 (d, 1H J=13.5 Hz, H-2), 1.46 (d, 3H, J=3.2 Hz, H-7). 'Ring II': δ=5.51 (dd, 1H, J=10.0, 8.6 Hz, H-4), 4.85-4.81 (m, 1H, H-5), 4.47 (dd, 1H, J=10.1, 8.2 Hz, H-6), 3.88-3.77 (m, 2H, H-1, H-3), 2.68-2.61 (m, 1H, H-2), 2.19-2.09 (m, 1H, H-2). 'Ring III': δ=5.77 (s, 1H, H-1), 5.50 (dd, 1H, J=8.8, 4.3 Hz, H-3), 5.40 (dd, 1H, J=3.5, 0.4 Hz, H-2), 4.10 (dd, 1H, J=10.0, 8.6 Hz, H-4), 3.52-3.46 (m, 1H, H-5), 0.96 (d, 3H, J=6.6 Hz, H-6). The additional peaks in the spectrum were identified as follow: δ=8.03-7.81 (m, Ph), 7.65-7.24 (m, Ph), 7.01 (m, Ph).

¹³C NMR (126 MHz, MeOD): δ=167.31 (C=O), 167.13 (C=O), 166.92 (C=O), 166.76 (C=O), 165.67 (C=O), 165.14 (C=O), 163.27 (TFA), 162.99 (TFA), 162.70 (TFA), 162.43 (TFA), 135.04 (Ph), 134.91 (Ph), 134.90 (Ph), 134.87 (Ph), 134.84 (Ph), 134.57 (Ph), 134.03 (Ph), 130.97 (Ph), 130.82 (Ph), 130.70 (Ph), 130.51 (Ph), 129.95 (Ph), 129.86 (Ph), 129.69 (Ph), 129.67 (Ph), 129.60 (Ph), 129.58 (Ph), 129.50 (Ph), 129.45 (Ph), 129.34 (Ph), 129.24 (Ph), 129.02 (Ph), 121.29 (TFA), 118.98 (TFA), 116.66 (TFA), 114.35 (TFA), 107.23 (C-1″), 92.70 (C-1′), 81.08 (C-5), 80.78 (C-2′), 76.93 (C-6), 76.76 (C-2″), 75.28 (C-4), 72.95 (C-3″), 72.48 (C-5′), 71.82 (C-3′), 71.48 (C-6′), 70.92 (C-4′), 53.85 (C-4″), 52.34 (C-5″), 50.26 (C-3), 50.04 (C-1), 29.28 (C-2), 16.61 (C-7′), 14.19 (C-6″).

MALDI TOFMS: calculated for $C_{61}H_{62}N_4O_{16}$ ([M+Na]+) m/e 1129.42; measured m/e 1129.42.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A compound represented by Formula I'b:

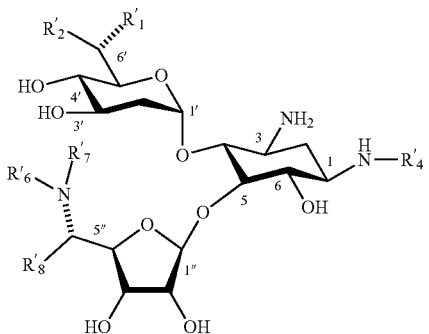

or a pharmaceutically acceptable salt thereof,
wherein:
the dashed line indicates an optional stereo-configuration of position 6' being an R configuration or an S configuration;
$R'_1$ is selected from hydroxyalkyl;
$R'_2$ is hydroxyl;
$R'_4$ is hydrogen;
$R'_6$ is hydrogen;
$R'_7$ is hydrogen; and
$R'_8$ is hydrogen or alkyl.

2. The compound of claim 1, wherein $R'_8$ is alkyl.

3. The compound of claim 1, wherein the alkyl is a methyl.

4. The compound of claim 1, wherein $R'_8$ is hydrogen.

5. The compound of claim 1, wherein the hydroxyalkyl is hydroxymethyl.

6. The compound of claim 1, having the following chemical formula:

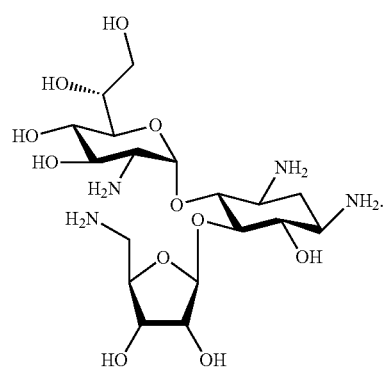

7. A pharmaceutical composition comprising the compound of claim 1 and a pharmaceutically acceptable carrier.

8. A method of treating a genetic disorder associated with a premature stop-codon mutation in a subject in need thereof, the method comprising administering to the subject a therapeutically effective amount of the compound of claim 1.

9. The method of claim 8, wherein said genetic disorder is selected from the group consisting of cystic fibrosis (CF), Duchenne muscular dystrophy (DMD), ataxia-telangiectasia, Hurler syndrome, hemophilia A, hemophilia B, Usher syndrome, Tay-Sachs, Becker muscular dystrophy (BMD), Congenital muscular dystrophy (CMD), Factor VII deficiency, Familial atrial fibrillation, Hailey-Hailey disease, McArdle disease, Mucopolysaccharidosis, Nephropathic cystinosis, Polycystic kidney disease, Rett syndrome, Spinal muscular atrophy (SMA), cystinosis, Severe epidermolysis bullosa, Dravet syndrome, X-linked nephrogenic diabetes insipidus (XNDI), X-linked retinitis pigmentosa and cancer.

10. A method of treating a genetic disorder associated with a premature stop-codon mutation in a subject in need thereof, the method comprising administering to the subject a therapeutically effective amount of the pharmaceutical composition of claim 7.

11. The method of claim 10, wherein said genetic disorder is selected from the group consisting of cystic fibrosis (CF), Duchenne muscular dystrophy (DMD), ataxia-telangiectasia, Hurler syndrome, hemophilia A, hemophilia B, Usher syndrome, Tay-Sachs, Becker muscular dystrophy (BMD), Congenital muscular dystrophy (CMD), Factor VII deficiency, Familial atrial fibrillation, Hailey-Hailey disease, McArdle disease, Mucopolysaccharidosis, Nephropathic cystinosis, Polycystic kidney disease, Rett syndrome, Spinal muscular atrophy (SMA), cystinosis, Severe epidermolysis bullosa, Dravet syndrome, X-linked nephrogenic diabetes insipidus (XNDI), X-linked retinitis pigmentosa and cancer.

* * * * *